United States Patent
Lee et al.

(10) Patent No.: US 10,196,396 B2
(45) Date of Patent: Feb. 5, 2019

(54) COMPOUNDS ANTAGONIZING A3 ADENOSINE RECEPTOR, METHOD FOR PREPARING THEM, AND MEDICAL-USE THEREOF

(71) Applicant: HANDOK INC., Seoul (KR)

(72) Inventors: Jin-Hwa Lee, Yongin-si (KR);
Seung-Yong Kim, Suwon-si (KR);
Do-Ran Kim, Seongnam-si (KR);
Koo-Hyeon Ahn, Daejeon (KR);
Gwi-Bin Lee, Seongnam-si (KR);
Doo-Seop Kim, Seoul (KR);
Hyun-Sook Hwang, Seoul (KR)

(73) Assignee: HANDOK INC., Seoul (KR)

(*) Notice: Subject to any disclaimer, the term of this patent is extended or adjusted under 35 U.S.C. 154(b) by 22 days.

(21) Appl. No.: 15/406,556

(22) Filed: Jan. 13, 2017

(65) Prior Publication Data
US 2017/0204101 A1 Jul. 20, 2017

Related U.S. Application Data

(60) Provisional application No. 62/278,897, filed on Jan. 14, 2016.

(51) Int. Cl.
| | | |
|---|---|---|
| *A01N 43/04* | (2006.01) | |
| *A61K 31/70* | (2006.01) | |
| *C07D 487/04* | (2006.01) | |
| *C07D 519/00* | (2006.01) | |
| *A61K 31/7068* | (2006.01) | |
| *A61K 31/7064* | (2006.01) | |
| *A61K 31/706* | (2006.01) | |

(52) U.S. Cl.
CPC ......... *C07D 487/04* (2013.01); *C07D 519/00* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 6,066,642 A | 5/2000 | Jacobson et al. | |
| 6,528,516 B1 | 3/2003 | Civan et al. | |
| 8,329,697 B2 * | 12/2012 | Garbaccio | C07D 487/04 514/249 |
| 8,426,411 B2 | 4/2013 | Wishart et al. | |
| 9,018,371 B2 | 4/2015 | Jeong et al. | |
| 2005/0256143 A1 | 11/2005 | Jeong et al. | |
| 2009/0258836 A1 | 10/2009 | Civan et al. | |
| 2013/0045943 A1 | 2/2013 | Caspi et al. | |

FOREIGN PATENT DOCUMENTS

| | | |
|---|---|---|
| EP | 0480713 A1 | 4/1992 |
| WO | 2004/026867 A2 | 4/2004 |
| WO | 2008/055711 A2 | 5/2008 |
| WO | 2009/108546 A1 | 9/2009 |
| WO | 2010/104027 A1 | 9/2010 |

OTHER PUBLICATIONS

Abbracchio et al., "G Protein-Dependent Activation of Phospholipase C by Adenosine A3 Receptors in Rat Brain", Molecular Pharmacology, 1995, vol. 48, pp. 1038-1045.
Bennis et al., "A new route to some enantiomerically pure substituted morpholines from D-ribono- and D-gulono-1, 4-lactones", Carbohydrate Research, 1994, vol. 264, pp. 33-44.
Yenil et al., "Synthesis and antimicrobial activities of two novel amino sugars derived from chloraloses", Carbohydrate Research, 2010, vol. 345, pp. 1617-1621.
Subrahmanyam et al., "Application of an Enyne Metathesis/Diels-Alder Cycloaddition Sequence: A New Versatile Approach to the Syntheses of C-Aryl Glycosides and Spiro-C-Aryl Glycosides", Chemistry European Journal, 2010, vol. 16, pp. 8545-8556.
Fredholm et al., "International Union of Pharmacology. XXV. Nomenclature and Classification of Adenosine Receptors", Pharmacological Reviews, 2001, vol. 53, No. 4, pp. 527-552.
Avila et al., "Knockout of A3 Adenosine Receptors Reduces Mouse Intraocular Pressure", Investigative Ophthalmology & Visual Science, 2002, vol. 43, No. 9, pp. 3021-3026.
Jeong et al., "N6-Substituted D-4'-Thioadenosine-5'-methyluronamides: Potent and Selective Agonists at the Human A3 Adenosine Receptor", Journal of Medicinal Chemistry, 2003, vol. 46, No. 18, pp. 3775-3777.
Gallos et al., "An Improved Approach to Chiral Cyclopentenone Building Blocks. Total Synthesis of Pentenomycin I and Neplanocin A", J. Org. Chem., 2005, vol. 70, No. 17, pp. 6884-6890.
Choi et al., "Preparative and Stereoselective Synthesis of the Versatile Intermediate for Carbocyclic Nucleosides: Effects of the Bulky Protecting Groups to Enforce Facial Selectivity", J. Org. Chem., 2004, vol. 69, No. 7, pp. 2634-2636.
Medeiros et al., "Medical Backgrounders: Glaucoma", Drugs of Today, 2002, vol. 38, No. 8, pp. 563-570.
Zeng et al., "Direct C-Glycosylation of Organotrifluoroborates with Glycosyl Fluorides and Its Application to the Total Synthesis of (+)-Varitriol," Organic Letters, 2011, vol. 13, No. 1, pp. 42-45.
Ramkumar et al., "The A3 Adenosine Receptor Is the Unique Adenosine Receptor Which Facilitates Release of Allergic Mediators in Mast Cells", The Journal of Biological Chemistry, 1993, vol. 268, No. 23, pp. 16887-16890.

(Continued)

*Primary Examiner* — Patrick T Lewis
(74) *Attorney, Agent, or Firm* — Knobbe Martens Olson & Bear LLP

(57) ABSTRACT

The present disclosure provides compounds useful in the amelioration, prevention or treatment of A3 adenosine receptor mediated diseases, such as glaucoma and glaucoma-related ocular disorders, having the structure of Formula I as defined in the detailed description; pharmaceutical compositions comprising at least one of the compounds; and methods for ameliorating, preventing or treating A3 adenosine receptor mediated diseases using the compound.

13 Claims, No Drawings

(56) References Cited

OTHER PUBLICATIONS

Schuman et al., "Short- and long-term safety of glaucoma drugs", Expert Opinion on Drug Safety, 2002, vol. 1, No. 2, pp. 181-194.
Moon et al., "Improved and alternative synthesis of D- and L-cyclopentenone derivatives, the versatile intermediates for the synthesis of carbocyclic nucleosides", Tetrahedron: Asymmetry, 2002, vol. 13, pp. 1189-1193.
Shih et al., "An efficient synthesis of L-allono-1, 4-lactone from 2,3:5,6-di-O-isopropylidene-D-mannono-1,4-lactone", Tetrahedron Letters, 2004, vol. 45, pp. 1789-1791.
Pal et al, "Structure-activity relationships of truncated adenosine derivatives as highly potent and selective human A3 adenosine receptor antagonists", Bioorganic & Medicinal Chemistry, 2009, vol. 17, No. 10, pp. 3733-3738.
International Search Report dated May 12, 2017 of corresponding PCT Application No. PCT/KR2017/000492—4 pages.

\* cited by examiner

COMPOUNDS ANTAGONIZING A3 ADENOSINE RECEPTOR, METHOD FOR PREPARING THEM, AND MEDICAL-USE THEREOF

FIELD

The present disclosure relates to novel heteroaryl-tetrahydrothiophene-3,4-diol, tetrahydrofuran-3,4-diol or cyclopentane-1,2-diol compounds which is effective as an A3 adenosine receptor antagonist, and medical uses of those compounds. The present disclosure also relates to methods for synthesizing those compounds.

BACKGROUND ART

G protein-coupled receptors (GPCRs) class is the largest family of cell-surface receptor which plays a crucial role in intracellular signal transduction. Adenosine receptors are part of the GPCR class, which belongs to the Class A or rhodopsin-like subfamily of GPCRs. Adenosine is a naturally occurring nucleoside, which exerts its biological effects by interacting with a family of adenosine receptors known as A1, A2a, A2b, and A3, which are involved in numerous physiological and pathophysiological processes (See Fredholm et al., Pharmacol. Rev. 2001, 53, 527-552).

Adenosine A1 and A2 receptor agonists, most derived from adenosine, have been intensively studied for use as hypotensive agents, therapeutics for mental illness and arrhythmia, lipid metabolism suppressant (therapeutics for diabetes) and neuroprotectives. On the other hand, their antagonists, derived from xanthine or in the form of two or more fused heterocyclic compounds, are developed as anti-asthmatics, anti-depressants, anti-arrhythmics, renal protectants, drugs for Parkinson's disease, and intelligence enhancers (See U.S. Pat. No. 9,018,371).

The function of the adenosine A3 receptor was the most recently identified, in contrast to the A1 and A2 receptors. The A3 receptor inhibited adenylyl cyclase, an enzyme that produces cAMP from ATP. Also, when activated by agonists, the A3 receptor was proven to mediate the activation of guanosine triphosphate-dependent phospholipase C, an enzyme which catalyzes the degradation of phosphatidyl inositol into inositol triphosphate and diacylglycerol (DAG) in the brain (See Ramkumar, V. et al., J. Biol. Chem., 1993, 268, 168871-168890; Abbracchio, M. P. et al., Mol. Pharmacol., 1995, 48, 1038-1045). On the other hand, the inactivation of A3 adenosine receptor causes the release of inflammation factors, such as histamine, from mast cells, bronchoconstriction, and the apoptosis of immune cells. Thus, A3 adenosine receptor agonists are under consideration in the treatment of cardiac and cerebral ischemia and cancer, while A3 adenosine receptor antagonists have been suggested to be useful as a potential treatment for glaucoma, inflammation and asthma (See U.S. Pat. Nos. 6,066,642 and 6,528,516 and WO 2008/055711).

Glaucoma remains one of the leading causes of irreversible blindness worldwide, afflicting approximately 70 million people. Elevated Intraocular Pressure (TOP) has been demonstrated as a major risk factor for the development and progression of glaucoma, through a number of well-conducted, prospective, randomized clinical trials that have provided overwhelming evidence that IOP reduction effectively slows the rate of development or progression of visual loss caused by glaucoma. However, available pharmacological and surgical therapies have limited efficacy and significant side effects (See Medeiros, F. A. et al., Drugs Today 2002, 38, 563-570). Most adverse effects associated with IOP-lowering medications are mild and ocular in nature; however, several of them are associated with systemic risks as well as serious ocular effects, especially following chronic use (See Schuman, J. S. et al., Expert Opin. Drug Saf 2002, 1, 181-194).

Adenosine levels have been found to be elevated in the aqueous humor of ocular hypertensive patients, and A3ARs are substantially upregulated on nonpigmented ciliary epithelial (NPE) cells in patients with pseudoexfoliation syndrome. The A3AR holds promise in glaucoma because knockout of the A3AR reduces IOP in the living mouse and A3AR antagonists have been shown to reduce IOP in rodents, rabbits, and both normal and glaucomatous monkey (See Avila et al., Investig. Ophthalmol. Vis. Sci., 2002, 43, 3021-3026). A3AR antagonists physiologically decrease inflow of aqueous humor by inhibiting Cl— channels of the NPE at the aqueous surface. It has also been observed that antagonists of A3AR are neuroprotective to oxygen and glucose deprived hippocampal tissue. A3AR are present on retinal ganglion cells and antagonists of the A3AR have the potential to be neuroprotective in patients with glaucoma.

Currently, none of the existing medical or surgical therapies protect the retina from degeneration in glaucoma.

SUMMARY

Therefore, one aspect of the present disclosure provides compounds, which are effective as an A3 adenosine receptor antagonist, useful for preventing, ameliorating or treating glaucoma, glaucoma-related ocular disorders, or inflammatory diseases.

Another aspect of the present disclosure provides a method for preparing such compounds.

Still another aspect of the present disclosure provides a pharmaceutical composition for preventing, ameliorating or treating glaucoma, glaucoma-related ocular disorders, and inflammatory diseases, comprising at least one of such compounds antagonizing an A3 adenosine receptor as an active ingredient. That is, still another aspect of the present disclosure provides a method for preventing, ameliorating or treating glaucoma, glaucoma-related ocular disorders, or inflammatory diseases, comprising administering a therapeutically effective amount of at least one of compounds according to embodiments of the present disclosure.

In one embodiment, there is provided a novel heteroaryl-tetrahydrothiophene-3,4-diol, tetrahydrofuran-3,4-diol or cyclopentane-1,2-diol compound of formula (I) below or a pharmaceutically acceptable salt thereof, which is effective as an A3 adenosine receptor antagonist, useful for preventing, ameliorating or treating glaucoma, glaucoma-related ocular disorders, and inflammatory diseases.

[Formula I]

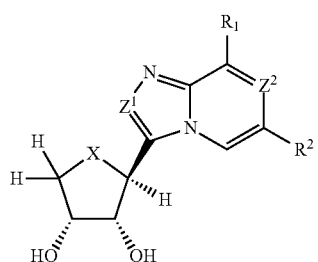

X is sulfur, oxygen or $CH_2$;

$Z^1$ and $Z^2$ are the same or different, and are each independently nitrogen or CH;

$R^1$ is halogen, $NR^3R^4$, $NR^3NR^3R^4$, $CR^3R^4R^5$, $OR^3$ or $SR^3$, wherein said $R^3$, $R^4$, and $R^5$ are each independently H, C1-6 alkyl, substituted C1-6 alkyl, C3-7 cycloalkyl, substituted C3-7 cycloalkyl, aryl, substituted aryl, heteroaryl, substituted heteroaryl, heterocycle, substituted heterocycle, heterocycloalkyl, substituted heterocycloalkyl, C2-6 alkynyl optionally substituted with aryl or heteroaryl, —C(=O)—C1-6 alkyl, —S(O)n-C1-6 alkyl, substituted —C(=O)—C1-6 alkyl, or substituted —S(O)n-C1-6 alkyl, and said n is 0, 1, or 2, and $R^2$ is H or halogen.

In another embodiment, there is provided a pharmaceutical composition comprising a compound of Formula I or a pharmaceutically acceptable salt thereof, and a pharmaceutically-acceptable carrier, excipient or diluent. In various embodiments, the pharmaceutical composition further comprises one or more additional pharmaceutically active compounds.

In yet another embodiment, there is provided a method for preventing, ameliorating or treating a condition comprising administering to a subject a therapeutically effective amount of a compound of Formula I or a pharmaceutical acceptable salt thereof, wherein the condition to be treated includes, but is not limited to, glaucoma or glaucoma-related ocular disorders. In various embodiments, the method comprises administering a combination of a compound of Formula I or a pharmaceutical acceptable salt thereof, and at least one additional pharmaceutically active compound.

In yet another embodiment, there is provided a method for preparing a compound of Formula I or a pharmaceutically acceptable salt thereof.

The compounds and the compositions above are more fully described in the detailed description that follows.

DETAILED DESCRIPTION OF EMBODIMENTS

The following description is merely exemplary in nature and is not intended to limit the present disclosure, application, or uses.

Definitions

The use of generic terms in the description of the compounds are herein defined for clarity.

This specification uses the terms "substituent", "radical", "group", "moiety", and "fragment" interchangeably.

As used herein, the singular forms "a" and "an" may include plural reference unless the context clearly dictates otherwise.

The number of carbon atoms in a hydrocarbyl substituent can be indicated by the prefix "CX-Y" where X is the minimum and Y is the maximum number of carbon atoms in the substituent.

As used herein, the term "alkyl", either alone or within other terms such as "haloalkyl" and "alkylaryl", refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "haloalkyl" refers to an alkyl moiety substituted with one or more halo groups. Examples of haloalkyl groups include —$CF_3$ and —$CHF_2$.

If a substituent is described as being "optionally substituted," the substituent may be either (1) not substituted or (2) substituted. If a substitutable position is not substituted, the default substituent is a hydrido radical.

As used herein, the term "substituted alkyl" refers to a straight or branched chain saturated hydrocarbon radical, which is optionally substituted with one or more substituents selected from the group consisting of C1-3 alkyl optionally having one to three fluorine substituents, C2-3 alkenyl, C2-3 alkynyl, C1-2 alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of C1-3 alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of C1-3 alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" or "cycloalkyl" refers to a non-aromatic cyclic hydrocarbon radical composed of three to seven carbon atoms. Five- to seven-membered rings may contain a double bond in the ring structure. In embodiments, "carbocycle" or "cycloalkyl" groups include, but are not limited to, cyclopropyl, cyclobutyl, cyclopentyl, cyclopentenyl, cyclohexyl, and cycloheptyl.

As used herein, the term "substituted carbocycle" or "substituted cycloalkyl" refers to a non-aromatic cyclic hydrocarbon radical composed by three to seven carbon atoms, which is optionally substituted with one or more substituents selected from the group consisting of C1-3 alkyl optionally having one to three fluorine substituents, C2-3 alkenyl, C2-3 alkynyl, C1-2 alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. In embodiments, optional substituents include substituted C1-3 alkyl, substituted C2-3 alkenyl, substituted C2-3 alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, SO2, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents. Examples of optional substituents are selected from the group consisting of substituted C1-3 alkyl, substituted C2-3 alkenyl, substituted C2-3 alkynyl, heteroaryl, heterocyclic, aryl, C1-3 alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, SO2, O, N, or N-oxide, optionally substituted with one or more substituents selected from the group which includes substituted C1-3 alkyl, substituted C2-3 alkenyl, substituted C2-3 alkynyl, heteroaryl, heterocyclic, aryl, C1-3 alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents. Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydrophthalazine-1,4-dionyl, and isoindole-1,3-dionyl.

As used herein, the term "alkoxy" refers to the group —ORa, where Ra is alkyl as defined above. In embodiments, alkoxy groups useful in embodiments of the present disclosure include, but are not limited to, methoxy, difluoromethoxy, trifluoromethoxy, ethoxy, n-propoxy, isopropoxy, n-butoxy and t-butoxy.

As used herein, the term "alkenyloxy" refers to the group —ORb, where Rb is alkenyl as defined above.

As used herein, the term "alkynyloxy" refers to the group —ORc, where Rc is alkynyl as defined above.

As used herein, the term "aralkoxy" refers to the group —ORaRd, wherein Ra is alkyl and Rd is aryl as defined above.

As used herein, the term "aryloxy" refers to the group —ORd, wherein Rd is aryl as defined above.

As used herein, the term "heteroaryloxy" refers to the group —ORe, where Re is heteroaryl as defined above.

As used herein, the term "mercapto" refers to the group —SH.

As used herein, the term "thio" refers to the group —SRf, wherein Rf is substituted alkyl, substituted carbocycle, aryl, heteroaryl or heterocyclic, as defined above.

As used herein, the term "sulfinyl" refers to the group —S—(O)Rf, wherein Rf is substituted alkyl, substituted carbocycle, aryl, heteroaryl or heterocyclic, as defined above.

As used herein, the term "sulfonyl" refers to the group —S(O)$_2$Rf, wherein Rf is substituted alkyl, substituted carbocycle, aryl, heteroaryl or heterocyclic, as defined above.

As used herein, the term "oxo" refers to the group =O.

As used herein, the term "hydroxyl" refers to the group —OH.

As used herein, the term "amino" refers to the group —NH$_2$. The amino group is optionally substituted with substituted alkyl, substituted carbocycle, aryl, heteroaryl or heterocyclic, as defined above.

As used herein, the term "cyano" refers to the group —CN.

As used herein, the term "aminosulfonyl" refers to the group —S(O)$_2$NH$_2$. The aminosulfonyl group is optionally substituted with substituted alkyl, substituted carbocycle, aryl, heteroaryl or heterocyclic, as defined above.

As used herein, the term "sulfonylamino" refers to the group —NHS(O)$_2$Rf wherein Rf is substituted alkyl, substituted carbocycle, aryl, heteroaryl or heterocyclic, as defined above.

As used herein, the term "carboxyamide" refers to the group —NHC(O)Rf wherein Rf is substituted alkyl, substituted carbocycle, aryl, heteroaryl or heterocyclic, as defined above.

As used herein, the term "carboxy" refers to the group —C(O)OH. The carboxy group is optionally substituted with substituted alkyl, substituted carbocycle, aryl, heteroaryl or heterocyclic, as defined above.

As used herein, the term "aminocarbonyl" refers to the group —C(O)NH2. The aminocarbonyl group is optionally substituted with substituted alkyl, substituted carbocycle, aryl, heteroaryl or heterocyclic, as defined above.

As used herein, the term "ureido" refers to the group —NHC(O)NHRg wherein Rg is hydrogen, alkyl, carbocycle or aryl as defined above.

As used herein, the term "guanidine" refers to the group —NHC(=NH)NH2.

As used herein, the term "acyl" refers to the group —C(O)Rh, wherein Rh is alkyl, carbocycle, or heterocyclic as defined herein.

As used herein, the term "aroyl" refers to the group —C(O)Rd, wherein Rd is aryl as defined herein.

As used herein, the term "heteroaroyl" refers to the group —C(O)Re, wherein Re is heteroaryl as defined herein.

As used herein, the term "acyloxy" refers to the group —OC(O)Rh, wherein Rh is alkyl, carbocycle, or heterocyclic as defined herein.

As used herein, the term "aroyloxy" refers to the group —OC(O)Rd, wherein Rd is aryl as defined herein.

As used herein, the term "heteroaroyloxy" refers to the group —OC(O)Re, wherein Re is heteroaryl as defined herein.

The term "pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

As used herein, the term "purified" means that when isolated, the isolate is greater than 90% pure, in one embodiment greater than 95% pure, in another embodiment greater than 99% pure and in another embodiment greater than 99.9% pure.

Compounds

One aspect of the present disclosure provides a compound of formula (I):

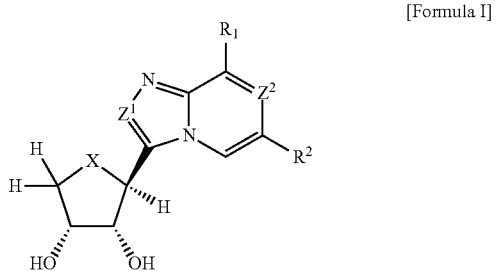

[Formula I]

or a pharmaceutically acceptable salt thereof, wherein:

X is sulfur, oxygen or $CH_2$;

$Z^1$ and $Z^2$ are the same or different, and are each independently nitrogen or CH;

$R^1$ is halogen, $NR^3R^4$, $NR^3NR^3R^4$, $CR^3R^4R^5$, $OR^3$ or $SR^3$, wherein said $R^3$, $R^4$, and $R^5$ are each independently H, C1-6 alkyl, substituted C1-6 alkyl, C3-7 cycloalkyl, substituted C3-7 cycloalkyl, aryl, substituted aryl, heteroaryl, substituted heteroaryl, heterocycle, substituted heterocycle, heterocycloalkyl, substituted heterocycloalkyl, C2-6 alkynyl optionally substituted with aryl or heteroaryl, —C(=O)—C1-6 alkyl, —S(O)n-C1-6 alkyl, substituted —C(=O)—C1-6 alkyl, or substituted —S(O)n-C1-6 alkyl, and said n is 0, 1, or 2, and $R^2$ is H or halogen.

In some embodiments, in the Formula I above,

X is sulfur, oxygen or $CH_2$;

$Z^1$ and $Z^2$ are the same or different, and are each independently nitrogen or CH;

$R^1$ is $NHR_3R_4$, $NR_3R_4$, $CCR_3R_4$, $NH((SO_2)R_3R_4$, $NH_2$, $N(CH_3)R_3R_4$, OH, $NH(NH)R_3R_4$, $R_3R_4$, $SR_3R_4$, $OR_3R_4$, $NHCOR_3R_4$, or $NH(SO_2)R_3R_4$, wherein $R_3$ is $(CRR')_n$, wherein R and R' are the same or different and are each independently H or $C_1$-$C_6$ alkyl, and n is 0, 1, 2 or 3; $R_4$ is substituted or unsubstituted phenyl, substituted or unsubstituted $C_1$-$C_6$ alkyl, substituted or unsubstituted $C_3$-$C_7$ cycloalkyl, substituted or unsubstituted heteroaryl selected from the group consisting of benzoimidazolyl, furanyl, imidazopyridinyl, indolyl, morpholinyl, piperidinyl, pyrazinyl, pyridinyl, pyrimidinyl, thiazolyl, thiophenyl, tetrazolyl, thiadiazolyl, oxadiazolyl, and oxazolyl, wherein the substituted compound is substituted with at least one selected from the group consisting of halogen, phenyl, phenoxy, cyano, $C_1$-$C_6$ alkyl, $C_1$-$C_6$ haloalkyl, $C_1$-$C_6$ alkoxy, $C_1$-$C_6$ haloalkoxyl, $C_3$-$C_7$ cycloalkyl, piperazinyl, morpholinyl, tetrazolyl, methylpiperazinyl, and $NR_aR_b$ wherein $R_a$ and $R_b$ are the same or different and are each independently hydrogen or $C_1$-$C_6$ alkyl, $COOR_c$ wherein $R_c$ is hydrogen or $C_1$-$C_6$ alkyl, and $CONR_dR_e$ wherein $R_d$ and $R_e$ are the same or different and are each independently hydrogen or $C_1$-$C_6$ alkyl; $R_3R_4$ may be 2-R''-substituted-cycloprop-1-yl or 1-R''-substituted-phenylcycloprop-1-yl, wherein R'' is phenyl, halophenyl or dihalophenyl; when $R_1$ is $NR_3R_4$, $R_3$ and $R_4$ may form a ring with the N in $NR_3R_4$;

$R^2$ is H or halogen.

One embodiment of the present disclosure is to provide a compound of formula (I-a):

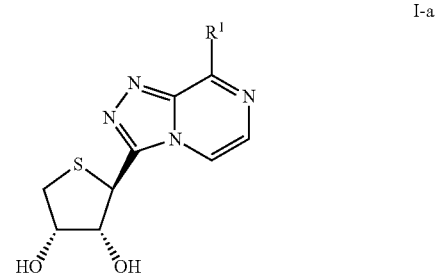

I-a or a pharmaceutically acceptable salt thereof, wherein $R^1$ has the same meanings as defined in Formula I.

Another embodiment of the present disclosure is to provide a compound of formula (I-b):

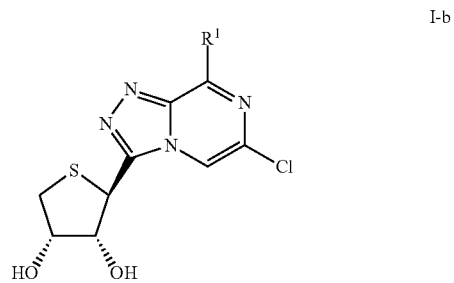

I-b or a pharmaceutically acceptable salt thereof, wherein $R^1$ has the same meanings as defined in Formula I.

Another embodiment of the present disclosure is to provide a compound of formula (I-c):

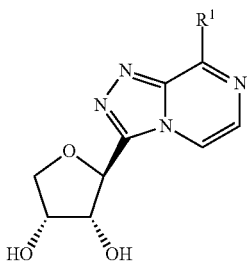

I-c or a pharmaceutically acceptable salt thereof, wherein $R^1$ has the same meanings as defined in Formula I.

A further embodiment of the present disclosure is to provide a compound of formula (I-d):

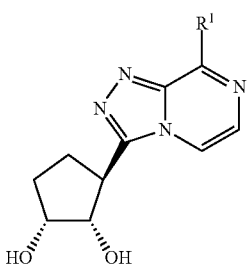

I-d or a pharmaceutically acceptable salt thereof, wherein $R^1$ has the same meanings as defined in Formula I.

A still another embodiment of the present disclosure is to provide a compound of formula (I-e):

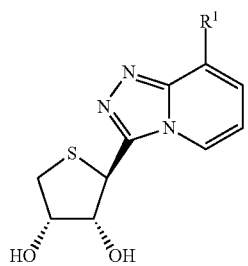

I-e or a pharmaceutically acceptable salt thereof, wherein $R^1$ has the same meanings as defined in Formula I.

An embodiment of the present disclosure also provides a compound of formula (II-a):

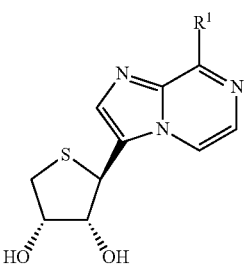

II-a or a pharmaceutically acceptable salt thereof, wherein $R^1$ has the same meanings as defined in Formula I.

A further embodiment of the present disclosure is to provide a compound of formula (II-b):

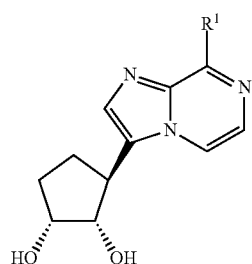

II-b or a pharmaceutically acceptable salt thereof, wherein $R^1$ has the same meanings as defined in Formula I.

Still another embodiment of the present disclosure is to provide a compound of formula (II-c):

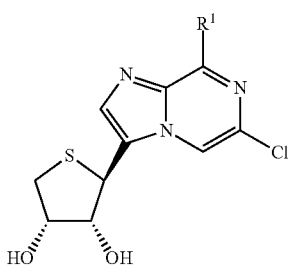

II-c or a pharmaceutically acceptable salt thereof, wherein $R^1$ has the same meanings as defined in Formula I.

A further embodiment of the present disclosure is to provide a compound of formula (II-d):

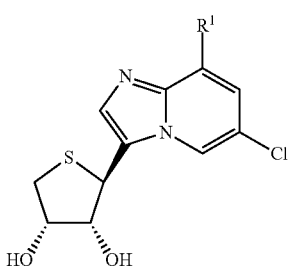

II-d or a pharmaceutically acceptable salt thereof, wherein $R^1$ has the same meanings as defined in Formula I.

Still another embodiment of the present disclosure is to provide a compound of formula (II-e):

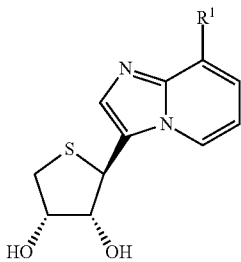

II-e or a pharmaceutically acceptable salt thereof, wherein R¹ has the same meanings as defined in Formula I.

Still another embodiment of the present disclosure is to provide a compound of formula (III-a):

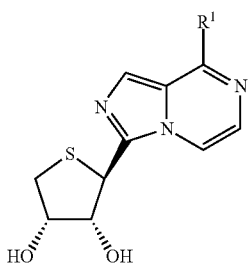

III-a or a pharmaceutically acceptable salt thereof, wherein R¹ has the same meanings as defined in Formula I.

Preferably, there is provided the compounds of the formula (I) wherein X is sulfur, oxygen or $CH_2$; $Z^1$ and $Z^2$ are the same or different, and are each independently nitrogen or CH; $R^1$ is $NR^3R^4$ or $CR^3R^4R^5$, wherein said $R^3$, $R^4$, and $R^5$ are each independently H, C1-6 alkyl, substituted C1-6 alkyl, C3-7 cycloalkyl, substituted C3-7 cycloalkyl, aryl, substituted aryl, heteroaryl, substituted heteroaryl, heterocycle, substituted heterocycle, heterocycloalkyl, substituted heterocycloalkyl, or C2-6 alkynyl optionally substituted with aryl or heteroaryl; and $R^2$ is H or halogen.

The compounds of the present disclosure have a high activity of A3 adenosine receptor antagonism, and are highly selective for an A3 adenosine receptors and less selective against other subtypes, e.g. A1 and A2a. In addition, the compounds of the present disclosure are highly soluble in water, and thus can be a good active ingredient for medicinal products for controlling intraocular pressure. The position and number of the atom N in the heteroaryl like the compounds of the present disclosure affects activity and selectivity of A3 adenosine receptor antagonism.

Preferably, the compounds of the present disclosure have the formula I or II as mentioned above. More preferably, in the formulas (I-a) and (II-a), $R^1$ has a bridge of —NH— instead of other bridges like —N═, —CH—, —S—, and —O—, and such compounds have higher activity of A3 adenosine receptor antagonism.

Preferably, in formulas (I) and (II), $R^3$ is halogen-substituted benzyl or phenethyl when $R^1$ is —$NHR^3$. When $R^3$ is a benzyl, preferably, the substituent is a small substituent, like halogen or methyl, positioned at the para.

Non-limiting examples of Formula I compounds include the following compounds and pharmaceutically acceptable salts thereof:

| No. | Compound Name |
|---|---|
| Compound 1 | (2S,3R,4S)-2-(8-((3-chlorobenzyl)amino)-[1,2,4]triazolo[4,3-a]pyrazine-3-yl)tetrahydrothiophene-3,4-diol |
| Compound 2 | (2S,3R,4S)-2-(8-(methylamino)-[1,2,4]triazolo[4,3-a]pyrazin-3-yl)tetrahydrothiophene-3,4-diol |
| Compound 3 | (2S,3R,4S)-2-(8-(piperidin-1-yl)-[1,2,4]triazolo[4,3-a]pyrazin-3-yl)tetrahydrothiophene-3,4-diol |
| Compound 4 | (2S,3R,4S)-2-(8-morpholino-[1,2,4]triazolo[4,3-a]pyrazin-3-yl)tetrahydrothiophene-3,4-diol |
| Compound 5 | (2S,3R,4S)-2-(8-(benzylamino)-[1,2,4]triazolo[4,3-a]pyrazin-3-yl)tetrahydrothiophene-3,4-diol |
| Compound 6 | (2S,3R,4S)-2-(8-((3-iodobenzyl)amino)-[1,2,4]triazolo[4,3-a]pyrazin-3-yl)tetrahydrothiophene-3,4-diol |
| Compound 7 | (2S,3R,4S)-2-(8-((cyclopropylmethyl)amino)-[1,2,4]triazolo[4,3-a]pyrazin-3-yl)tetrahydrothiophene-3,4-diol |
| Compound 8 | (2S,3R,4S)-2-(8-(cyclobutylamino)-[1,2,4]triazolo[4,3-a]pyrazin-3-yl)tetrahydrothiophene-3,4-diol |
| Compound 9 | (2S,3R,4S)-2-(8-((3-(trifluoromethyl)benzyl)amino)-[1,2,4]triazolo[4,3-a]pyrazin-3-yl)tetrahydrothiophene-3,4-diol |
| Compound 10 | (2S,3R,4S)-2-(8-((thiophen-3-ylmethyl)amino)-[1,2,4]triazolo[4,3-a]pyrazin-3-yl)tetrahydrothiophene-3,4-diol |
| Compound 11 | (2S,3R,4S)-2-(8-(phenethylamino)-[1,2,4]triazolo[4,3-a]pyrazin-3-yl)tetrahydrothiophene-3,4-diol |
| Compound 12 | (2S,3R,4S)-2-(8-((3-methylbenzyl)amino)-[1,2,4]triazolo[4,3-a]pyrazin-3-yl)tetrahydrothiophene-3,4-diol |
| Compound 13 | (2S,3R,4S)-2-(8-((3-fluorobenzyl)amino)-[1,2,4]triazolo[4,3-a]pyrazin-3-yl)tetrahydrothiophene-3,4-diol |
| Compound 14 | (2S,3R,4S)-2-(8-((3-(trifluoromethoxy)benzyl)amino)-[1,2,4]triazolo[4,3-a]pyrazin-3-yl)tetrahydrothiophene-3,4-diol |
| Compound 15 | (2S,3R,4S)-2-(8-((3-methoxybenzyl)amino)-[1,2,4]triazolo[4,3-a]pyrazin-3-yl)tetrahydrothiophene-3,4-diol |
| Compound 16 | 3-(((3-((2S,3R,4S)-3,4-dihydroxytetrahydrothiophen-2-yl)-[1,2,4]triazolo[4,3-a]pyrazin-8-yl)amino)methyl)benzonitrile |
| Compound 17 | (2S,3R,4S)-2-(8-((3-bromobenzyl)amino)-[1,2,4]triazolo[4,3-a]pyrazin-3-yl)tetrahydrothiophene-3,4-diol |
| Compound 18 | (2S,3R,4S)-2-(8-((cyclohexylmethyl)amino)-[1,2,4]triazolo[4,3-a]pyrazin-3-yl)tetrahydrothiophene-3,4-diol |
| Compound 19 | (2S,3R,4S)-2-(8-(cyclopentylamino)-[1,2,4]triazolo[4,3-a]pyrazin-3-yl)tetrahydrothiophene-3,4-diol |
| Compound 20 | (2S,3R,4S)-2-(8-(cyclohexylamino)-[1,2,4]triazolo[4,3-a]pyrazin-3-yl)tetrahydrothiophene-3,4-diol |
| Compound 21 | (2S,3R,4S)-2-(8-((pyridin-3-ylmethyl)amino)-[1,2,4]triazolo[4,3-a]pyrazin-3-yl)tetrahydrothiophene-3,4-diol 2,2,2-trifluoroacetic acid |
| Compound 22 | (2S,3R,4S)-2-(8-((pyridin-4-ylmethyl)amino)-[1,2,4]triazolo[4,3-a]pyrazin-3-yl)tetrahydrothiophene-3,4-diol 2,2,2-trifluoroacetic acid |
| Compound 23 | (2S,3R,4S)-2-(8-((furan-3-ylmethyl)amino)-[1,2,4]triazolo[4,3-a]pyrazin-3-yl)tetrahydrothiophene-3,4-diol |
| Compound 24 | (2S,3R,4S)-2-(8-((3-chlorophenethyl)amino)-[1,2,4]triazolo[4,3-a]pyrazin-3-yl)tetrahydrothiophene-3,4-diol |
| Compound 25 | (2S,3R,4S)-2-(8-((3-bromophenethyl)amino)-[1,2,4]triazolo[4,3-a]pyrazin-3-yl)tetrahydrothiophene-3,4-diol |
| Compound 26 | (2S,3R,4S)-2-(8-((3-fluorophenethyl)amino)-[1,2,4]triazolo[4,3-a]pyrazin-3-yl)tetrahydrothiophene-3,4-diol |
| Compound 27 | (2S,3R,4S)-2-(8-((2-phenylcyclopropyl)amino)-[1,2,4]triazolo[4,3-a]pyrazin-3-yl)tetrahydrothiophene-3,4-diol |
| Compound 28 | (2S,3R,4S)-2-(8-((2-(3-chlorophenyl)propan-2-yl)amino)-[1,2,4]triazolo[4,3-a]pyrazin-3-yl)tetrahydrothiophene-3,4-diol |

| No. | Compound Name |
|---|---|
| Compound 29 | (2S,3R,4S)-2-(8-((1-(3-chlorophenyl)cyclopropyl)amino)-[1,2,4]triazolo[4,3-a]pyrazin-3-yl)tetrahydrothiophene-3,4-diol |
| Compound 30 | (2S,3R,4S)-2-(8-((3-chlorophenyl)ethynyl)-[1,2,4]triazolo[4,3-a]pyrazin-3-yl)tetrahydrothiophene-3,4-diol |
| Compound 31 | (2S,3R,4S)-2-(8-(cyclopropylamino)-[1,2,4]triazolo[4,3-a]pyrazin-3-yl)tetrahydrothiophene-3,4-diol |
| Compound 32 | (2S,3R,4S)-2-(8-(isopentylamino)-[1,2,4]triazolo[4,3-a]pyrazin-3-yl)tetrahydrothiophene-3,4-diol |
| Compound 33 | (2S,3R,4S)-2-(8-((2-morpholinoethyl)amino)-[1,2,4]triazolo[4,3-a]pyrazin-3-yl)tetrahydrothiophene-3,4-diol |
| Compound 34 | 3-chloro-N-(3-((2S,3R,4S)-3,4-dihydroxytetrahydrothiophen-2-yl)-[1,2,4]triazolo[4,3-a]pyrazin-8-yl)benzenesulfonamide |
| Compound 35 | (2S,3R,4R)-2-(8-((3-chlorobenzyl)amino)-[1,2,4]triazolo[4,3-a]pyrazin-3-yl)tetrahydrofuran-3,4-diol |
| Compound 36 | (2S,3R,4S)-2-(8-((imidazo[1,2-a]pyridin-2-ylmethyl)amino)-[1,2,4]triazolo[4,3-a]pyrazin-3-yl)tetrahydrothiophene-3,4-diol |
| Compound 37 | (2S,3R,4S)-2-(8-amino-[1,2,4]triazolo[4,3-a]pyrazin-3-yl)tetrahydrothiophene-3,4-diol |
| Compound 38 | (2S,3R,4R)-2-(8-((3-iodobenzyl)amino)-[1,2,4]triazolo[4,3-a]pyrazin-3-yl)tetrahydrofuran-3,4-diol |
| Compound 39 | (2S,3R,4R)-2-(8-((3-chlorophenethyl)amino)-[1,2,4]triazolo[4,3-a]pyrazin-3-yl)tetrahydrofuran-3,4-diol |
| Compound 40 | 4-(((3-((2S,3R,4S)-3,4-dihydroxytetrahydrothiophen-2-yl)-[1,2,4]triazolo[4,3-a]pyrazin-8-yl)amino)methyl)-2-fluoro-N-methylbenzamide |
| Compound 41 | (2S,3R,4S)-2-(8-((4-methylpiperazin-1-yl)amino)-[1,2,4]triazolo[4,3-a]pyrazin-3-yl)tetrahydrothiophene-3,4-diol |
| Compound 42 | (2S,3R,4S)-2-(8-(morpholinoamino)-[1,2,4]triazolo[4,3-a]pyrazin-3-yl)tetrahydrothiophene-3,4-diol |
| Compound 43 | (2S,3R,4S)-2-(8-(((1S,2R)-2-phenylcyclopropyl)amino)-[1,2,4]triazolo[4,3-a]pyrazin-3-yl)tetrahydrothiophene-3,4-diol |
| Compound 44 | 2-chloro-4-(((3-((2S,3R,4S)-3,4-dihydroxytetrahydrothiophen-2-yl)-[1,2,4]triazolo[4,3-a]pyrazin-8-yl)amino)methyl)-N-methylbenzamide |
| Compound 45 | (2S,3R,4S)-2-(8-(((S)-1-(3-chlorophenyl)ethyl)amino)-[1,2,4]triazolo[4,3-a]pyrazin-3-yl)tetrahydrothiophene-3,4-diol |
| Compound 46 | (2S,3R,4S)-2-(8-(((R)-1-(3-chlorophenyl)ethyl)amino)-[1,2,4]triazolo[4,3-a]pyrazin-3-yl)tetrahydrothiophene-3,4-diol |
| Compound 47 | (2S,3R,4S)-2-(8-((2-chlorobenzyl)amino)-[1,2,4]triazolo[4,3-a]pyrazin-3-yl)tetrahydrothiophene-3,4-diol |
| Compound 48 | (2S,3R,4S)-2-(8-((4-chlorobenzyl)amino)-[1,2,4]triazolo[4,3-a]pyrazin-3-yl)tetrahydrothiophene-3,4-diol |
| Compound 49 | (2S,3R,4S)-2-(8-((4-iodobenzyl)amino)-[1,2,4]triazolo[4,3-a]pyrazin-3-yl)tetrahydrothiophene-3,4-diol |
| Compound 50 | (2S,3R,4S)-2-(8-((2-fluorophenethyl)amino)-[1,2,4]triazolo[4,3-a]pyrazin-3-yl)tetrahydrothiophene-3,4-diol |
| Compound 51 | (2S,3R,4S)-2-(8-((2-(piperidin-1-yl)ethyl)amino)-[1,2,4]triazolo[4,3-a]pyrazin-3-yl)tetrahydrothiophene-3,4-diol |
| Compound 52 | (2S,3R,4S)-2-(8-((2-(dimethylamino)ethyl)(methyl)amino)-[1,2,4]triazolo[4,3-a]pyrazin-3-yl)tetrahydrothiophene-3,4-diol |
| Compound 53 | (2S,3R,4S)-2-(8-hydroxy-[1,2,4]triazolo[4,3-a]pyrazin-3-yl)tetrahydrothiophene-3,4-diol |
| Compound 54 | (2S,3R,4S)-2-(8-(2-(3-chlorophenyl)hydrazinyl)-[1,2,4]triazolo[4,3-a]pyrazin-3-yl)tetrahydrothiophene-3,4-diol |
| Compound 55 | (2S,3R,4S)-2-(8-((3,5-dichlorobenzyl)amino)-[1,2,4]triazolo[4,3-a]pyrazin-3-yl)tetrahydrothiophene-3,4-diol |
| Compound 56 | (2S,3R,4S)-2-(8-((2,5-dichlorobenzyl)amino)-[1,2,4]triazolo[4,3-a]pyrazin-3-yl)tetrahydrothiophene-3,4-diol |
| Compound 57 | (2S,3R,4S)-2-(8-((thiophen-2-ylmethyl)amino)-[1,2,4]triazolo[4,3-a]pyrazin-3-yl)tetrahydrothiophene-3,4-diol |
| Compound 58 | (2S,3R,4S)-2-(8-((2,3-dichlorobenzyl)amino)-[1,2,4]triazolo[4,3-a]pyrazin-3-yl)tetrahydrothiophene-3,4-diol |
| Compound 59 | (2S,3R,4S)-2-(8-((3,4-dichlorobenzyl)amino)-[1,2,4]triazolo[4,3-a]pyrazin-3-yl)tetrahydrothiophene-3,4-diol |
| Compound 60 | (2S,3R,4S)-2-(8-((2,4-dichlorobenzyl)amino)-[1,2,4]triazolo[4,3-a]pyrazin-3-yl)tetrahydrothiophene-3,4-diol |
| Compound 61 | methyl 2-chloro-5-(((3-((2S,3R,4S)-3,4-dihydroxytetrahydrothiophen-2-yl)-[1,2,4]triazolo[4,3-a]pyrazin-8-yl)amino)methyl)benzoate |
| Compound 62 | (2S,3R,4S)-2-(8-((2-iodobenzyl)amino)-[1,2,4]triazolo[4,3-a]pyrazin-3-yl)tetrahydrothiophene-3,4-diol |
| Compound 63 | (2S,3R,4S)-2-(8-((3-chloro-4-fluorophenethyl)amino)-[1,2,4]triazolo[4,3-a]pyrazin-3-yl)tetrahydrothiophene-3,4-diol |
| Compound 64 | (2S,3R,4S)-2-(8-((4-fluorophenethyl)amino)-[1,2,4]triazolo[4,3-a]pyrazin-3-yl)tetrahydrothiophene-3,4-diol |
| Compound 65 | (2S,3R,4S)-2-(8-((3-chloro-4-fluorobenzyl)amino)-[1,2,4]triazolo[4,3-a]pyrazin-3-yl)tetrahydrothiophene-3,4-diol |
| Compound 66 | (2S,3R,4S)-2-(8-((2,6-dichlorobenzyl)amino)-[1,2,4]triazolo[4,3-a]pyrazin-3-yl)tetrahydrothiophene-3,4-diol |
| Compound 67 | (2S,3R,4S)-2-(8-((3-(4-methylpiperazin-1-yl)benzyl)amino)-[1,2,4]triazolo[4,3-a]pyrazin-3-yl)tetrahydrothiophene-3,4-diol |
| Compound 68 | (2S,3R,4S)-2-(8-((3-(dimethylamino)benzyl)amino)-[1,2,4]triazolo[4,3-a]pyrazin-3-yl)tetrahydrothiophene-3,4-diol |
| Compound 69 | (2S,3R,4S)-2-(8-((3-(1H-tetrazol-5-yl)benzyl)amino)-[1,2,4]triazolo[4,3-a]pyrazin-3-yl)tetrahydrothiophene-3,4-diol |
| Compound 70 | (2S,3R,4S)-2-(8-((2-(3-fluorophenyl)cyclopropyl)amino)-[1,2,4]triazolo[4,3-a]pyrazin-3-yl)tetrahydrothiophene-3,4-diol |
| Compound 71 | (2S,3R,4S)-2-(8-((2-(3-chlorophenyl)cyclopropyl)amino)-[1,2,4]triazolo[4,3-a]pyrazin-3-yl)tetrahydrothiophene-3,4-diol |
| Compound 72 | (2S,3R,4S)-2-(8-(((1R,2S)-2-phenylcyclopropyl)amino)-[1,2,4]triazolo[4,3-a]pyrazin-3-yl)tetrahydrothiophene-3,4-diol |
| Compound 73 | (2S,3R,4S)-2-(8-((2,3-difluorophenethyl)amino)-[1,2,4]triazolo[4,3-a]pyrazin-3-yl)tetrahydrothiophene-3,4-diol |
| Compound 74 | (2S,3R,4S)-2-(8-((2,4-difluorophenethyl)amino)-[1,2,4]triazolo[4,3-a]pyrazin-3-yl)tetrahydrothiophene-3,4-diol |
| Compound 75 | (2S,3R,4S)-2-(8-(((1R,2R)-2-phenylcyclopropyl)amino)-[1,2,4]triazolo[4,3-a]pyrazin-3-yl)tetrahydrothiophene-3,4-diol |
| Compound 76 | (2S,3R,4S)-2-(8-((2,5-difluorophenethyl)amino)-[1,2,4]triazolo[4,3-a]pyrazin-3-yl)tetrahydrothiophene-3,4-diol |
| Compound 77 | (2S,3R,4S)-2-(8-(3-chlorophenethyl)-[1,2,4]triazolo[4,3-a]pyrazin-3-yl)tetrahydrothiophene-3,4-diol |
| Compound 78 | (2S,3R,4S)-2-(8-((4-chloro-3-fluorophenethyl)amino)-[1,2,4]triazolo[4,3-a]pyrazin-3-yl)tetrahydrothiophene-3,4-diol |
| Compound 79 | methyl 5-(((3-((2S,3R,4S)-3,4-dihydroxytetrahydrothiophen-2-yl)-[1,2,4]triazolo[4,3-a]pyrazin-8-yl)amino)methyl)-2-fluorobenzoate |
| Compound 80 | (2S,3R,4S)-2-(8-((3-(piperazin-1-yl)benzyl)amino)-[1,2,4]triazolo[4,3-a]pyrazin-3-yl)tetrahydrothiophene-3,4-diol |

| No. | Compound Name |
|---|---|
| Compound 81 | (2S,3R,4S)-2-(8-((2,6-difluorophenethyl)amino)-[1,2,4]triazolo[4,3-a]pyrazin-3-yl)tetrahydrothiophene-3,4-diol |
| Compound 82 | (2S,3R,4S)-2-(8-((3,4-difluorophenethyl)amino)-[1,2,4]triazolo[4,3-a]pyrazin-3-yl)tetrahydrothiophene-3,4-diol |
| Compound 83 | (2S,3R,4S)-2-(8-((3,5-difluorophenethyl)amino)-[1,2,4]triazolo[4,3-a]pyrazin-3-yl)tetrahydrothiophene-3,4-diol |
| Compound 84 | (2S,3R,4S)-2-(8-(((1S,2R)-2-(3,4-difluorophenyl)cyclopropyl)amino)-[1,2,4]triazolo[4,3-a]pyrazin-3-yl)tetrahydrothiophene-3,4-diol |
| Compound 85 | (2S,3R,4S)-2-(8-((5-chloro-2-fluorobenzyl)amino)-[1,2,4]triazolo[4,3-a]pyrazin-3-yl)tetrahydrothiophene-3,4-diol |
| Compound 86 | (2S,3R,4S)-2-(8-((3-chloro-5-fluorobenzyl)amino)-[1,2,4]triazolo[4,3-a]pyrazin-3-yl)tetrahydrothiophene-3,4-diol |
| Compound 87 | (2S,3R,4S)-2-(8-((3-cyclopropylbenzyl)amino)-[1,2,4]triazolo[4,3-a]pyrazin-3-yl)tetrahydrothiophene-3,4-diol |
| Compound 88 | (2S,3R,4S)-2-(8-(([1,1'-biphenyl]-3-ylmethyl)amino)-[1,2,4]triazolo[4,3-a]pyrazin-3-yl)tetrahydrothiophene-3,4-diol |
| Compound 89 | (2S,3R,4S)-2-(8-((3-phenoxybenzyl)amino)-[1,2,4]triazolo[4,3-a]pyrazin-3-yl)tetrahydrothiophene-3,4-diol |
| Compound 90 | methyl3-(((3-((2S,3R,4S)-3,4-dihydroxytetrahydrothiophen-2-yl)-[1,2,4]triazolo[4,3-a]pyrazin-8-yl)amino)methyl)benzoate |
| Compound 91 | (2S,3R,4S)-2-(8-((3-morpholinobenzyl)amino)-[1,2,4]triazolo[4,3-a]pyrazin-3-yl)tetrahydrothiophene-3,4-diol |
| Compound 92 | (2S,3R,4S)-2-(8-((3-chlorobenzyl)thio)-[1,2,4]triazolo[4,3-a]pyrazin-3-yl)tetrahydrothiophene-3,4-diol |
| Compound 93 | (2S,3R,4S)-2-(8-((3-fluoro-4-(5-methyloxazol-2-yl)benzyl)amino)-[1,2,4]triazolo[4,3-a]pyrazin-3-yl)tetrahydrothiophene-3,4-diol |
| Compound 94 | (2S,3R,4S)-2-(8-((3-fluoro-4-(5-methylthiazol-2-yl)benzyl)amino)-[1,2,4]triazolo[4,3-a]pyrazin-3-yl)tetrahydrothiophene-3,4-diol |
| Compound 95 | (2S,3R,4S)-2-(8-((3-fluoro-4-(5-methyl-1,3,4-oxadiazol-2-yl)benzyl)amino)-[1,2,4]triazolo[4,3-a]pyrazin-3-yl)tetrahydrothiophene-3,4-diol |
| Compound 96 | (2S,3R,4S)-2-(8-((3-(2-methyl-2H-tetrazol-5-yl)benzyl)amino)-[1,2,4]triazolo[4,3-a]pyrazin-3-yl)tetrahydrothiophene-3,4-diol |
| Compound 97 | (2S,3R,4S)-2-(8-((3-fluoro-4-(5-methyl-1,3,4-thiadiazol-2-yl)benzyl)amino)-[1,2,4]triazolo[4,3-a]pyrazin-3-yl)tetrahydrothiophene-3,4-diol |
| Compound 98 | (2S,3R,4S)-2-(8-(((1S,2R)-2-(3-fluorophenyl)cyclopropyl)amino)-[1,2,4]triazolo[4,3-a]pyrazin-3-yl)tetrahydrothiophene-3,4-diol |
| Compound 99 | (2S,3R,4S)-2-(8-(((1S,2R)-2-(3-chlorophenyl)cyclopropyl)amino)-[1,2,4]triazolo[4,3-a]pyrazin-3-yl)tetrahydrothiophene-3,4-diol |
| Compound 100 | (2S,3R,4S)-2-(6-chloro-8-((3-chlorobenzyl)amino)-[1,2,4]triazolo[4,3-a]pyrazin-3-yl)tetrahydrothiophene-3,4-diol |
| Compound 101 | (2S,3R,4S)-2-(6-chloro-8-((2,5-dichlorobenzyl)amino)-[1,2,4]triazolo[4,3-a]pyrazin-3-yl)tetrahydrothiophene-3,4-diol |
| Compound 102 | (2S,3R,4S)-2-(6-chloro-8-((3,5-dichlorobenzyl)amino)-[1,2,4]triazolo[4,3-a]pyrazin-3-yl)tetrahydrothiophene-3,4-diol |
| Compound 103 | (2S,3R,4S)-2-(6-chloro-8-((5-chloro-2-fluorobenzyl)amino)-[1,2,4]triazolo[4,3-a]pyrazin-3-yl)tetrahydrothiophene-3,4-diol |
| Compound 104 | (2S,3R,4S)-2-(6-chloro-8-((4-fluorophenethyl)amino)-[1,2,4]triazolo[4,3-a]pyrazin-3-yl)tetrahydrothiophene-3,4-diol |
| Compound 105 | (2S,3R,4S)-2-(6-chloro-8-((3-fluorophenethyl)amino)-[1,2,4]triazolo[4,3-a]pyrazin-3-yl)tetrahydrothiophene-3,4-diol |
| Compound 106 | (2S,3R,4S)-2-(6-chloro-8-((3,4-difluorophenethyl)amino)-[1,2,4]triazolo[4,3-a]pyrazin-3-yl)tetrahydrothiophene-3,4-diol |
| Compound 107 | (2S,3R,4S)-2-(6-chloro-8-((4-chloro-3-fluorophenethyl)amino)-[1,2,4]triazolo[4,3-a]pyrazin-3-yl)tetrahydrothiophene-3,4-diol |
| Compound 108 | (2S,3R,4S)-2-(6-chloro-8-(((1S,2R)-2-phenylcyclopropyl)amino)-[1,2,4]triazolo[4,3-a]pyrazin-3-yl)tetrahydrothiophene-3,4-diol |
| Compound 109 | (2S,3R,4S)-2-(8-((3-chlorobenzyl)amino)imidazo[1,2-a]pyrazin-3-yl)tetrahydrothiophene-3,4-diol |
| Compound 110 | (2S,3R,4S)-2-(8-aminoimidazo[1,2-a]pyrazin-3-yl)tetrahydrothiophene-3,4-diol |
| Compound 111 | (2S,3R,4S)-2-(8-(methylamino)imidazo[1,2-a]pyrazin-3-yl)tetrahydrothiophene-3,4-diol |
| Compound 112 | (2S,3R,4S)-2-(8-((cyclopropylmethyl)amino)imidazo[1,2-a]pyrazin-3-yl)tetrahydrothiophene-3,4-diol |
| Compound 113 | (2S,3R,4S)-2-(8-(cyclobutylamino)imidazo[1,2-a]pyrazin-3-yl)tetrahydrothiophene-3,4-diol |
| Compound 114 | (2S,3R,4S)-2-(8-(cyclopropylamino)imidazo[1,2-a]pyrazin-3-yl)tetrahydrothiophene-3,4-diol |
| Compound 115 | (2S,3R,4S)-2-(8-(isopentylamino)imidazo[1,2-a]pyrazin-3-yl)tetrahydrothiophene-3,4-diol |
| Compound 116 | (2S,3R,4S)-2-(8-morpholinoimidazo[1,2-a]pyrazin-3-yl)tetrahydrothiophene-3,4-diol |
| Compound 117 | (2S,3R,4S)-2-(8-(piperidin-1-yl)imidazo[1,2-a]pyrazin-3-yl)tetrahydrothiophene-3,4-diol |
| Compound 118 | (2S,3R,4S)-2-(8-(4-benzylpiperidin-1-yl)imidazo[1,2-a]pyrazin-3-yl)tetrahydrothiophene-3,4-diol |
| Compound 119 | (2S,3R,4S)-2-(8-(4-(4-fluorobenzyl)piperazin-1-yl)imidazo[1,2-a]pyrazin-3-yl)tetrahydrothiophene-3,4-diol |
| Compound 120 | (2S,3R,4S)-2-(8-(benzylamino)imidazo[1,2-a]pyrazin-3-yl)tetrahydrothiophene-3,4-diol |
| Compound 121 | (2S,3R,4S)-2-(8-((3-methylbenzyl)amino)imidazo[1,2-a]pyrazin-3-yl)tetrahydrothiophene-3,4-diol |
| Compound 122 | (2S,3R,4S)-2-(8-((3-fluorobenzyl)amino)imidazo[1,2-a]pyrazin-3-yl)tetrahydrothiophene-3,4-diol |
| Compound 123 | (2S,3R,4S)-2-(8-((3-(trifluoromethyl)benzyl)amino)imidazo[1,2-a]pyrazin-3-yl)tetrahydrothiophene-3,4-diol |
| Compound 124 | (2S,3R,4S)-2-(8-((3-iodobenzyl)amino)imidazo[1,2-a]pyrazin-3-yl)tetrahydrothiophene-3,4-diol |
| Compound 125 | 4-(((3-((2S,3R,4S)-3,4-dihydroxytetrahydrothiophen-2-yl)imidazo[1,2-a]pyrazin-8-yl)amino)methyl)-2-fluoro-N-methylbenzamide |
| Compound 126 | 2-chloro-4-(((3-((2S,3R,4S)-3,4-dihydroxytetrahydrothiophen-2-yl)imidazo[1,2-a]pyrazin-8-yl)amino)methyl)-N-methylbenzamide |
| Compound 127 | (2S,3R,4S)-2-(8-((3-fluorophenethyl)amino)imidazo[1,2-a]pyrazin-3-yl)tetrahydrothiophene-3,4-diol |
| Compound 128 | (2S,3R,4S)-2-(8-(phenethylamino)imidazo[1,2-a]pyrazin-3-yl)tetrahydrothiophene-3,4-diol |
| Compound 129 | (2S,3R,4S)-2-(8-((2-phenylcyclopropyl)amino)imidazo[1,2-a]pyrazin-3-yl)tetrahydrothiophene-3,4-diol |
| Compound 130 | (2S,3R,4S)-2-(8-((thiophen-3-ylmethyl)amino)imidazo[1,2-a]pyrazin-3-yl)tetrahydrothiophene-3,4-diol |
| Compound 131 | (2S,3R,4S)-2-(8-((furan-3-ylmethyl)amino)imidazo[1,2-a]pyrazin-3-yl)tetrahydrothiophene-3,4-diol |
| Compound 132 | (2S,3R,4S)-2-(8-((3-bromobenzyl)amino)imidazo[1,2-a]pyrazin-3-yl)tetrahydrothiophene-3,4-diol |
| Compound 133 | (2S,3R,4S)-2-(8-(cyclopentylamino)imidazo[1,2-a]pyrazin-3-yl)tetrahydrothiophene-3,4-diol |
| Compound 134 | (2S,3R,4S)-2-(8-((pyridin-2-ylmethyl)amino)imidazo[1,2-a]pyrazin-3-yl)tetrahydrothiophene-3,4-diol |
| Compound 135 | (2S,3R,4S)-2-(8-((pyridin-3-ylmethyl)amino)imidazo[1,2-a]pyrazin-3-yl)tetrahydrothiophene-3,4-diol |
| Compound 136 | (2S,3R,4S)-2-(8-((pyridin-4-ylmethyl)amino)imidazo[1,2-a]pyrazin-3-yl)tetrahydrothiophene-3,4-diol |
| Compound 137 | (2S,3R,4S)-2-(8-((3-methoxybenzyl)amino)imidazo[1,2-a]pyrazin-3-yl)tetrahydrothiophene-3,4-diol |
| Compound 138 | (2S,3R,4S)-2-(8-(cyclohexylamino)imidazo[1,2-a]pyrazin-3-yl)tetrahydrothiophene-3,4-diol |
| Compound 139 | (2S,3R,4S)-2-(8-(cyclohexylmethyl)amino)imidazo[1,2-a]pyrazin-3-yl)tetrahydrothiophene-3,4-diol |

-continued

| No. | Compound Name |
|---|---|
| Compound 140 | (2S,3R,4S)-2-(8-((3-(trifluoromethoxy)benzyl)amino)imidazo[1,2-a]pyrazin-3-yl)tetrahydrothiophene-3,4-diol |
| Compound 141 | 3-(((3-((2S,3R,4S)-3,4-dihydroxytetrahydrothiophen-2-yl)imidazo[1,2-a]pyrazin-8-yl)amino)methyl)benzonitrile |
| Compound 142 | (2S,3R,4S)-2-(8-((pyrimidin-5-ylmethyl)amino)imidazo[1,2-a]pyrazin-3-yl)tetrahydrothiophene-3,4-diol |
| Compound 143 | (2S,3R,4S)-2-(8-((pyrazin-2-ylmethyl)amino)imidazo[1,2-a]pyrazin-3-yl)tetrahydrothiophene-3,4-diol |
| Compound 144 | (2S,3R,4S)-2-(8-((pyrimidin-2-ylmethyl)amino)imidazo[1,2-a]pyrazin-3-yl)tetrahydrothiophene-3,4-diol |
| Compound 145 | (2S,3R,4S)-2-(8-((pyrimidin-4-ylmethyl)amino)imidazo[1,2-a]pyrazin-3-yl)tetrahydrothiophene-3,4-diol |
| Compound 146 | (2S,3R,4S)-2-(8-((3-chlorophenethyl)amino)imidazo[1,2-a]pyrazin-3-yl)tetrahydrothiophene-3,4-diol |
| Compound 147 | (2S,3R,4S)-2-(8-((thiazol-4-ylmethyl)amino)imidazo[1,2-a]pyrazin-3-yl)tetrahydrothiophene-3,4-diol |
| Compound 148 | (2S,3R,4S)-2-(8-((thiazol-2-ylmethyl)amino)imidazo[1,2-a]pyrazin-3-yl)tetrahydrothiophene-3,4-diol |
| Compound 149 | (2S,3R,4S)-2-(8-((3-bromophenethyl)amino)imidazo[1,2-a]pyrazin-3-yl)tetrahydrothiophene-3,4-diol |
| Compound 150 | (2S,3R,4S)-2-(8-((2-morpholinoethyl)amino)imidazo[1,2-a]pyrazin-3-yl)tetrahydrothiophene-3,4-diol |
| Compound 151 | (2S,3R,4S)-2-(8-((1-(3-chlorophenyl)cyclopropyl)amino)imidazo[1,2-a]pyrazin-3-yl)tetrahydrothiophene-3,4-diol |
| Compound 152 | (2S,3R,4S)-2-(8-((2-(3-chlorophenyl)propan-2-yl)amino)imidazo[1,2-a]pyrazin-3-yl)tetrahydrothiophene-3,4-diol |
| Compound 153 | (2S,3R,4S)-2-(8-(((1H-benzo[d]imidazol-2-yl)methyl)amino)imidazo[1,2-a]pyrazin-3-yl)tetrahydrothiophene-3,4-diol hydrochloride |
| Compound 154 | (2S,3R,4S)-2-(8-((2-(piperidin-1-yl)ethyl)amino)imidazo[1,2-a]pyrazin-3-yl)tetrahydrothiophene-3,4-diol |
| Compound 155 | (2S,3R,4S)-2-(8-((3-chlorobenzyl)oxy)imidazo[1,2-a]pyrazin-3-yl)tetrahydrothiophene-3,4-diol |
| Compound 156 | (2S,3R,4S)-2-(8-(2-(dimethylamino)ethyl)(methyl)amino)imidazo[1,2-a]pyrazine-3-yl)tetrahydrothiophene-3,4-diol |
| Compound 157 | (2S,3R,4S)-2-(8-((thiazol-5-ylmethyl)amino)imidazo[1,2-a]pyrazin-3-yl)tetrahydrothiophene-3,4-diol |
| Compound 158 | 3-chloro-N-(3-((2S,3R,4S)-3,4-dihydroxytetrahydrothiophen-2-yl)imidazo[1,2-a]pyrazin-8-yl)benzamide |
| Compound 159 | (2S,3R,4S)-2-(8-((3-chlorophenyl)ethynyl)imidazo[1,2-a]pyrazin-3-yl)tetrahydrothiophene-3,4-diol |
| Compound 160 | (2S,3R,4S)-2-(8-(((R)-1-(3-chlorophenyl)ethyl)amino)imidazo[1,2-a]pyrazin-3-yl)tetrahydrothiophene-3,4-diol |
| Compound 161 | (2S,3R,4S)-2-(8-(((S)-1-(3-chlorophenyl)ethyl)amino)imidazo[1,2-a]pyrazin-3-yl)tetrahydrothiophene-3,4-diol |
| Compound 162 | (2S,3R,4S)-2-(8-(((1S,2R)-2-phenylcyclopropyl)amino)imidazo[1,2-a]pyrazin-3-yl)tetrahydrothiophene-3,4-diol |
| Compound 163 | (2S,3R,4S)-2-(8-((2-chlorobenzyl)amino)imidazo[1,2-a]pyrazin-3-yl)tetrahydrothiophene-3,4-diol |
| Compound 164 | (2S,3R,4S)-2-(8-((4-chlorobenzyl)amino)imidazo[1,2-a]pyrazin-3-yl)tetrahydrothiophene-3,4-diol |
| Compound 165 | (2S,3R,4S)-2-(8-((4-iodobenzyl)amino)imidazo[1,2-a]pyrazin-3-yl)tetrahydrothiophene-3,4-diol |
| Compound 166 | (2S,3R,4S)-2-(8-(((1H-indol-5-yl)methyl)amino)imidazo[1,2-a]pyrazin-3-yl)tetrahydrothiophene-3,4-diol |
| Compound 167 | 3-chloro-N-(3-((2S,3R,4S)-3,4-dihydroxytetrahydrothiophen-2-yl)imidazo[1,2-a]pyrazin-8-yl)benzenesulfonamide |
| Compound 168 | (2S,3R,4S)-2-(8-((2-iodobenzyl)amino)imidazo[1,2-a]pyrazin-3-yl)tetrahydrothiophene-3,4-diol |
| Compound 169 | (2S,3R,4S)-2-(8-((2-fluorophenethyl)amino)imidazo[1,2-a]pyrazin-3-yl)tetrahydrothiophene-3,4-diol |
| Compound 170 | (2S,3R,4S)-2-(8-((4-fluorophenethyl)amino)imidazo[1,2-a]pyrazin-3-yl)tetrahydrothiophene-3,4-diol |
| Compound 171 | Methyl 5-(((3-((2S,3R,4S)-3,4-dihydroxytetrahydrothiophen-2-yl)imidazo[1,2-a]pyrazin-8-yl)amino)methyl)-2-fluorobenzoate |
| Compound 172 | (2S,3R,4S)-2-(8-((3-chloro-4-fluorophenethyl)amino)imidazo[1,2-a]pyrazin-3-yl)tetrahydrothiophene-3,4-diol |
| Compound 173 | (2S,3R,4S)-2-(8-((3-(dimethylamino)benzyl)amino)imidazo[1,2-a]pyrazin-3-yl)tetrahydrothiophene-3,4-diol |
| Compound 174 | (2S,3R,4S)-2-(8-((3-(4-methylpiperazin-1-yl)benzyl)amino)imidazo[1,2-a]pyrazin-3-yl)tetrahydrothiophene-3,4-diol |
| Compound 175 | (2S,3R,4S)-2-(8-((2,3-dichlorobenzyl)amino)imidazo[1,2-a]pyrazin-3-yl)tetrahydrothiophene-3,4-diol |
| Compound 176 | (2S,3R,4S)-2-(8-((2,4-dichlorobenzyl)amino)imidazo[1,2-a]pyrazin-3-yl)tetrahydrothiophene-3,4-diol |
| Compound 177 | (2S,3R,4S)-2-(8-((2,5-dichlorobenzyl)amino)imidazo[1,2-a]pyrazin-3-yl)tetrahydrothiophene-3,4-diol |
| Compound 178 | (2S,3R,4S)-2-(8-((thiophen-2-ylmethyl)amino)imidazo[1,2-a]pyrazin-3-yl)tetrahydrothiophene-3,4-diol |
| Compound 179 | (2S,3R,4S)-2-(8-((2-(3-fluorophenyl)cyclopropyl)amino)imidazo[1,2-a]pyrazin-3-yl)tetrahydrothiophene-3,4-diol |
| Compound 180 | (2S,3R,4S)-2-(8-((2-(3-chlorophenyl)cyclopropyl)amino)imidazo[1,2-a]pyrazin-3-yl)tetrahydrothiophene-3,4-diol |
| Compound 181 | (2S,3R,4S)-2-(8-((3-(piperazin-1-yl)benzyl)amino)imidazo[1,2-a]pyrazin-3-yl)tetrahydrothiophene-3,4-diol |
| Compound 182 | Methyl2-chloro-5-(((3-((2S,3R,4S)-3,4-dihydroxytetrahydrothiophen-2-yl)imidazo[1,2-a]pyrazin-8-yl)amino)methyl)benzoate |
| Compound 183 | (2S,3R,4S)-2-(8-((3-chloro-4-fluorobenzyl)amino)imidazo[1,2-a]pyrazin-3-yl)tetrahydrothiophene-3,4-diol |
| Compound 184 | (2S,3R,4S)-2-(8-((3,5-dichlorobenzyl)amino)imidazo[1,2-a]pyrazin-3-yl)tetrahydrothiophene-3,4-diol |
| Compound 185 | (2S,3R,4S)-2-(8-((3,4-dichlorobenzyl)amino)imidazo[1,2-a]pyrazin-3-yl)tetrahydrothiophene-3,4-diol |
| Compound 186 | (2S,3R,4S)-2-(8-((2,6-dichlorobenzyl)amino)imidazo[1,2-a]pyrazin-3-yl)tetrahydrothiophene-3,4-diol |
| Compound 187 | 5-(((3-((2S,3R,4S)-3,4-dihydroxytetrahydrothiophen-2-yl)imidazo[1,2-a]pyrazin-8-yl)amino)methyl)-2-fluorobenzoic acid 2,2,2-trifluoroacetic acid |
| Compound 188 | 5-(((3-((2S,3R,4S)-3,4-dihydroxytetrahydrothiophen-2-yl)imidazo[1,2-a]pyrazin-8-yl)amino)methyl)-2-fluoro-N,N-dimethylbenzamide |
| Compound 189 | 2-chloro-5-(((3-((2S,3R,4S)-3,4-dihydroxytetrahydrothiophen-2-yl)imidazo[1,2-a]pyrazin-8-yl)amino)methyl)benzoic acid 2,2,2-trifluoroacetic acid |
| Compound 190 | 2-chloro-5-(((3-((2S,3R,4S)-3,4-dihydroxytetrahydrothiophen-2-yl)imidazo[1,2-a]pyrazin-8-yl)amino)methyl)-N,N-dimethylbenzamide |
| Compound 191 | (2S,3R,4S)-2-(8-((3-(1H-tetrazol-5-yl)benzyl)amino)imidazo[1,2-a]pyrazin-3-yl)tetrahydrothiophene-3,4-diol 2,2,2-trifluoroacetic acid |
| Compound 192 | (2S,3R,4S)-2-(8-((2,3-difluorophenethyl)amino)imidazo[1,2-a]pyrazin-3-yl)tetrahydrothiophene-3,4-diol |
| Compound 193 | (2S,3R,4S)-2-(8-((2,4-difluorophenethyl)amino)imidazo[1,2-a]pyrazin-3-yl)tetrahydrothiophene-3,4-diol |
| Compound 194 | (2S,3R,4S)-2-(8-((2,5-difluorophenethyl)amino)imidazo[1,2-a]pyrazin-3-yl)tetrahydrothiophene-3,4-diol |
| Compound 195 | (2S,3R,4S)-2-(8-((2,6-difluorophenethyl)amino)imidazo[1,2-a]pyrazin-3-yl)tetrahydrothiophene-3,4-diol |
| Compound 196 | (2S,3R,4S)-2-(8-((3,5-difluorophenethyl)amino)imidazo[1,2-a]pyrazin-3-yl)tetrahydrothiophene-3,4-diol |
| Compound 197 | (2S,3R,4S)-2-(8-((3,4-difluorophenethyl)amino)imidazo[1,2-a]pyrazin-3-yl)tetrahydrothiophene-3,4-diol |

| No. | Compound Name |
|---|---|
| Compound 198 | (2S,3R,4S)-2-(8-((4-chloro-3-fluorophenethyl)amino)imidazo[1,2-a]pyrazin-3-yl)tetrahydrothiophene-3,4-diol |
| Compound 199 | (2S,3R,4S)-2-(8-((3-chlorobenzyl)thio)imidazo[1,2-a]pyrazin-3-yl)tetrahydrothiophene-3,4-diol |
| Compound 200 | (2S,3R,4S)-2-(8-(((1R,2S)-2-phenylcyclopropyl)amino)imidazo[1,2-a]pyrazin-3-yl)tetrahydrothiophene-3,4-diol |
| Compound 201 | (2S,3R,4S)-2-(8-((3-chloro-5-fluorobenzyl)amino)imidazo[1,2-a]pyrazin-3-yl)tetrahydrothiophene-3,4-diol |
| Compound 202 | (2S,3R,4S)-2-(8-((3-cyclopropylbenzyl)amino)imidazo[1,2-a]pyrazin-3-yl)tetrahydrothiophene-3,4-diol |
| Compound 203 | (2S,3R,4S)-2-(8-((([1,1'-biphenyl]-3-ylmethyl)amino)imidazo[1,2-a]pyrazin-3-yl)tetrahydrothiophene-3,4-diol |
| Compound 204 | (2S,3R,4S)-2-(8-((3-phenoxybenzyl)amino)imidazo[1,2-a]pyrazin-3-yl)tetrahydrothiophene-3,4-diol |
| Compound 205 | methyl 3-(((3-((2S,3R,4S)-3,4-dihydroxytetrahydrothiophen-2-yl)imidazo[1,2-a]pyrazin-8-yl)amino)methyl)benzoate |
| Compound 206 | (2S,3R,4S)-2-(8-(3-chlorophenethyl)imidazo[1,2-a]pyrazin-3-yl)tetrahydrothiophene-3,4-diol |
| Compound 207 | (2S,3R,4S)-2-(8-(((1R,2R)-2-phenylcyclopropyl)amino)imidazo[1,2-a]pyrazin-3-yl)tetrahydrothiophene-3,4-diol |
| Compound 208 | (2S,3R,4S)-2-(8-((5-chloro-2-fluorobenzyl)amino)imidazo[1,2-a]pyrazin-3-yl)tetrahydrothiophene-3,4-diol |
| Compound 209 | (2S,3R,4S)-2-(8-(((1S,2R)-2-(3,4-difluorophenyl)cyclopropyl)amino)imidazo[1,2-a]pyrazin-3-yl)tetrahydrothiophene-3,4-diol |
| Compound 210 | (2S,3R,4S)-2-(8-((3-morpholinobenzyl)amino)imidazo[1,2-a]pyrazin-3-yl)tetrahydrothiophene-3,4-diol |
| Compound 211 | (2S,3R,4S)-2-(8-((3-fluoro-4-(5-methyloxazol-2-yl)benzyl)amino)imidazo[1,2-a]pyrazin-3-yl)tetrahydrothiophene-3,4-diol |
| Compound 212 | (2S,3R,4S)-2-(8-((3-fluoro-4-(5-methylthiazol-2-yl)benzyl)amino)imidazo[1,2-a]pyrazin-3-yl)tetrahydrothiophene-3,4-diol |
| Compound 213 | (2S,3R,4S)-2-(8-((3-fluoro-4-(5-methyl-1,3,4-oxadiazol-2-yl)benzyl)amino)imidazo[1,2-a]pyrazin-3-yl)tetrahydrothiophene-3,4-diol |
| Compound 214 | (2S,3R,4S)-2-(8-((3-(2-methyl-2H-tetrazol-5-yl)benzyl)amino)imidazo[1,2-a]pyrazin-3-yl)tetrahydrothiophene-3,4-diol |
| Compound 215 | (2S,3R,4S)-2-(8-(((1S,2R)-2-(3-fluorophenyl)cyclopropyl)amino)imidazo[1,2-a]pyrazin-3-yl)tetrahydrothiophene-3,4-diol |
| Compound 216 | (2S,3R,4S)-2-(8-(((1S,2R)-2-(3-chlorophenyl)cyclopropyl)amino)imidazo[1,2-a]pyrazin-3-yl)tetrahydrothiophene-3,4-diol |
| Compound 217 | (2S,3R,4S)-2-(6-chloro-8-((3-chlorobenzyl)amino)imidazo[1,2-a]pyrazin-3-yl)tetrahydrothiophene-3,4-diol |
| Compound 218 | (2S,3R,4S)-2-(8-((3-chlorobenzyl)amino)-[1,2,4]triazolo[4,3-a]pyridin-3-yl)tetrahydrothiophene-3,4-diol |
| Compound 219 | (2S,3R,4S)-2-(8-((3-chlorobenzyl)amino)imidazo[1,5-a]pyrazin-3-yl)tetrahydrothiophene-3,4-diol |
| Compound 220 | (2S,3R,4S)-2-(6-chloro-8-((3-chlorobenzyl)amino)imidazo[1,2-a]pyridin-3-yl)tetrahydrothiophene-3,4-diol |
| Compound 221 | (2S,3R,4S)-2-(8-((3-chlorobenzyl)amino)imidazo[1,2-a]pyridin-3-yl)tetrahydrothiophene-3,4-diol |
| Compound 222 | (1R,2S,3S)-3-(8-((3-chlorobenzyl)amino)imidazo[1,2-a]pyrazin-3-yl)cyclopentane-1,2-diol |
| Compound 223 | (1R,2S,3S)-3-(8-((3,5-dichlorobenzyl)amino)imidazo[1,2-a]pyrazin-3-yl)cyclopentane-1,2-diol |
| Compound 224 | (1R,2S,3S)-3-(8-((2,5-dichlorobenzyl)amino)imidazo[1,2-a]pyrazin-3-yl)cyclopentane-1,2-diol |
| Compound 225 | (1R,2S,3S)-3-(8-((5-chloro-2-fluorobenzyl)amino)imidazo[1,2-a]pyrazin-3-yl)cyclopentane-1,2-diol |
| Compound 226 | (1R,2S,3S)-3-(8-((4-fluorophenethyl)amino)imidazo[1,2-a]pyrazin-3-yl)cyclopentane-1,2-diol |
| Compound 227 | (1R,2S,3S)-3-(8-((3-fluorophenethyl)amino)imidazo[1,2-a]pyrazin-3-yl)cyclopentane-1,2-diol |
| Compound 228 | (1R,2S,3S)-3-(8-((3,4-difluorophenethyl)amino)imidazo[1,2-a]pyrazin-3-yl)cyclopentane-1,2-diol |
| Compound 229 | (1R,2S,3S)-3-(8-((3-chloro-4-fluorophenethyl)amino)imidazo[1,2-a]pyrazin-3-yl)cyclopentane-1,2-diol |
| Compound 230 | (1R,2S,3S)-3-(8-(((1S,2R)-2-phenylcyclopropyl)amino)imidazo[1,2-a]pyrazin-3-yl)cyclopentane-1,2-diol |
| Compound 231 | (1R,2S,3S)-3-(8-((4-chloro-3-fluorophenethyl)amino)imidazo[1,2-a]pyrazin-3-yl)cyclopentane-1,2-diol |
| Compound 232 | (1R,2S,3S)-3-(8-((3-chlorobenzyl)amino)-[1,2,4]triazolo[4,3-a]pyrazin-3-yl)cyclopentane-1,2-diol |
| Compound 233 | (1R,2S,3S)-3-(8-((3,5-dichlorobenzyl)amino)-[1,2,4]triazolo[4,3-a]pyrazin-3-yl)cyclopentane-1,2-diol |
| Compound 234 | (1R,2S,3S)-3-(8-((2,5-dichlorobenzyl)amino)-[1,2,4]triazolo[4,3-a]pyrazin-3-yl)cyclopentane-1,2-diol |
| Compound 235 | (1R,2S,3S)-3-(8-((5-chloro-2-fluorobenzyl)amino)-[1,2,4]triazolo[4,3-a]pyrazin-3-yl)cyclopentane-1,2-diol |
| Compound 236 | (1R,2S,3S)-3-(8-((4-fluorophenethyl)amino)-[1,2,4]triazolo[4,3-a]pyrazin-3-yl)cyclopentane-1,2-diol |
| Compound 237 | (1R,2S,3S)-3-(8-((3-fluorophenethyl)amino)-[1,2,4]triazolo[4,3-a]pyrazin-3-yl)cyclopentane-1,2-diol |
| Compound 238 | (1R,2S,3S)-3-(8-((3,4-difluorophenethyl)amino)-[1,2,4]triazolo[4,3-a]pyrazin-3-yl)cyclopentane-1,2-diol |
| Compound 239 | (1R,2S,3S)-3-(8-((3-chloro-4-fluorophenethyl)amino)-[1,2,4]triazolo[4,3-a]pyrazin-3-yl)cyclopentane-1,2-diol |
| Compound 240 | (1R,2S,3S)-3-(8-(((1S,2R)-2-phenylcyclopropyl)amino)-[1,2,4]triazolo[4,3-a]pyrazin-3-yl)cyclopentane-1,2-diol |
| Compound 241 | (1R,2S,3S)-3-(8-((4-chloro-3-fluorophenethyl)amino)-[1,2,4]triazolo[4,3-a]pyrazin-3-yl)cyclopentane-1,2-diol |

The compounds according to Formula I may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified, the structure is intended to encompass all individual stereoisomers and all mixtures thereof. Thus, compounds according to Formula I containing one or more chiral centers may be used as racemic mixtures, diastereomeric mixtures, enantiomerically enriched mixtures, diastereomerically enriched mixtures, or as enantiomerically and diastereomerically pure individual stereoisomers.

Individual stereoisomers of a compound according to Formula I which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into a diastereomeric salt, complex or derivative, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may contain an acidic functional group. In certain other embodiments, compounds according to Formula I may contain a basic functional group. Thus, the skilled artisan will appreciate that salts of the compounds according to Formula I may be prepared. Indeed, in embodiments of the invention, salts of the compounds according to Formula I may be preferable over the respective free base or free acid because, for example, such salts may impart greater stability or solubility to the molecule thereby facilitating formulation into a dosage form. Accordingly, embodiments of the invention are further directed pharmaceutically acceptable salts of the compounds according to Formula I. For a review on suitable salts see Berge et al, J. Pharm. Sci., 1977, 66, 1-19.

Acid salts: Suitable addition salts are formed from acids which form non-toxic salts and examples are hydrochloride, hydrobromide, hydroiodide, sulphate, bisulphate, nitrate, phosphate, hydrogen phosphate, acetate, maleate, malate, fumarate, malonate, lactate, tartrate, citrate, formate, gluconate, succinate, piruvate, oxalate, oxaloacetate, trifluoroacetate, saccharate, benzoate, methanesulphonate, ethanesulphonate, benzenesulphonate, p-toluenesulphonate, methanesulphonic, ethanesulphonic, p-toluenesulphonic, and isethionate.

Base salts: Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, the term "compounds according to embodiments of the invention" means both the compounds according to Formula I and salts thereof, including pharmaceutically acceptable salts. The term "a compound according to embodiments of the invention" also appears herein and refers to both a compound according to Formula I and its salts, including pharmaceutically acceptable salts.

The compounds according to embodiments of the invention may exist in solid or liquid form. In the solid state, the compounds according to embodiments of the invention may exist in crystalline or noncrystalline form, or as a mixture thereof. For compounds according to embodiments of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. Embodiments of the invention include all such solvates.

The skilled artisan will further appreciate that certain compounds according to embodiments of the invention that exist in crystalline form, including the various solvates thereof, may exhibit polymorphism (i.e. the capacity to occur in different crystalline structures). These different crystalline forms are typically known as "polymorphs." Embodiments of the invention include all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents used in making the compound, or by using different isolation or purification procedures. For example, changes in temperature, pressure, or solvent may result in polymorphs. In addition, one polymorph may spontaneously convert to another polymorph under certain conditions.

The compounds according to embodiments of the invention may exist in a form of prodrug. As used herein and unless specifically so stated otherwise, the term "prodrug" means a derivative that can hydrolyze, oxidize, or otherwise react under biological conditions (in vitro or in vivo) to provide an active compound according to embodiments of the prevent invention. Examples of prodrugs include, but are not limited to, derivatives and metabolites of compounds according to the present disclosure that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistiy and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

In another embodiment, there is provided a composition comprising a compound of Formula I or a pharmaceutically acceptable salt thereof. In yet another embodiment, there is provided a pharmaceutical composition comprising a therapeutically effective amount of a compound of Formula I or a pharmaceutically acceptable salt thereof, and a pharmaceutically acceptable carrier, excipient or diluent.

General Synthetic Schemes

Another aspect of the present disclosure is to provide a method of making compounds of Formula I or a pharmaceutically acceptable salt thereof.

The compounds of the present disclosure can be prepared using the methods illustrated in the general synthetic schemes and experimental procedures detailed below. These general synthetic schemes and experimental procedures are presented for purposes of illustration and are not intended to be limiting. The starting materials used to prepare the compounds of the present disclosure are commercially available or can be prepared using routine methods known in the art.

The diol intermediate 6 used in preparing the compound of formula (I) may be synthesized from commercially available D-Mannose disclosed in *J. Med. Chem.* 2003, 46, 3775-3777, and U.S. Pat. No. 9,018,371. To prepare the compound of formula I-a, I-b and I-e, oxidative cleavage of diol 6 with sodium periodate on wet silica at r.t for 3 h gave aldehyde 7 as shown in Scheme 1.
Scheme 1:
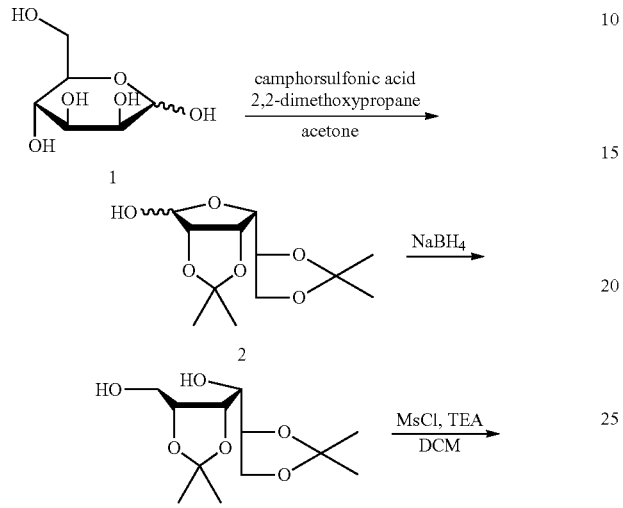
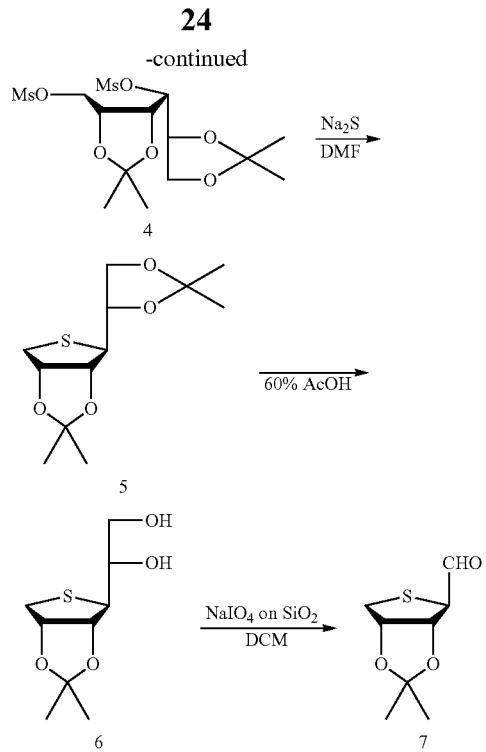
Scheme 2:
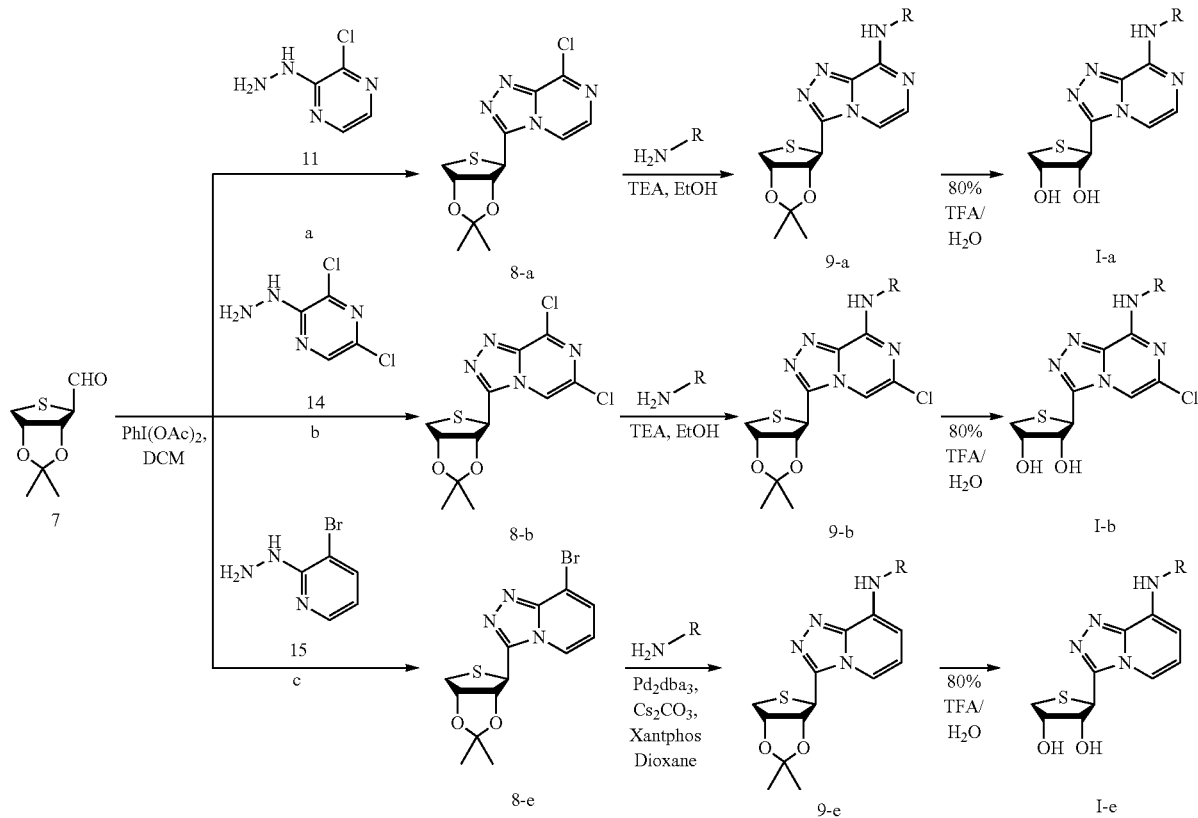

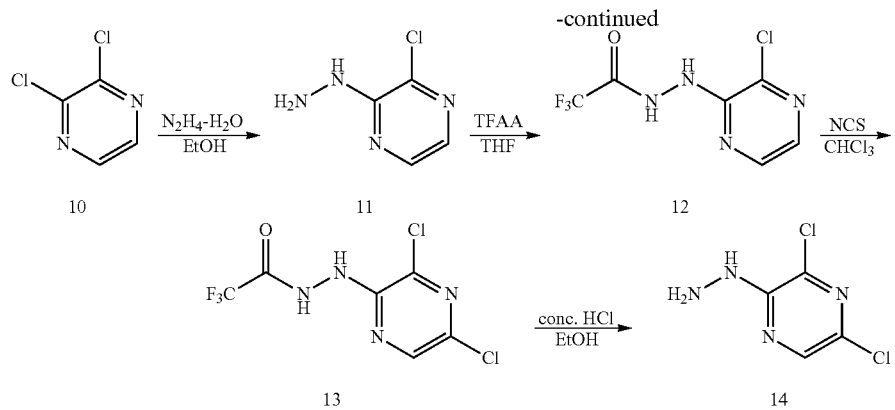

As shown in Scheme 2, cyclizing the resulting aldehyde 7 using hydrazine 11, 14, and 15, followed by addition PhI(OAC)$_2$ provides key intermediate 8-a, 8-b, and 8-e. In the case that hydrazine is 11 and 14; the heterocyclic triazopyrazine 8-a and 8-b can be treated with an amine derivative in the presence of triethylamine at 85° C. to provide compound 9-a and 9-b, which is then submitted to hydrolysis of the acetonide derivatives using 80% aqueous acetic acid to the final nucleosides I-a and I-b, respectively. In the case that hydrazine is 15; the heterocyclic triazopyridine 8-e can be treated with an amine derivative in the presence of Pd$_2$dba$_3$, Xantphos and Cs$_2$CO$_3$ at 110° C. to provide compound 9-e, which is then submitted to hydrolysis of the acetonide derivative using 80% aqueous trifluoroacetic acid to the final nucleoside I-e, respectively.

Scheme 3:

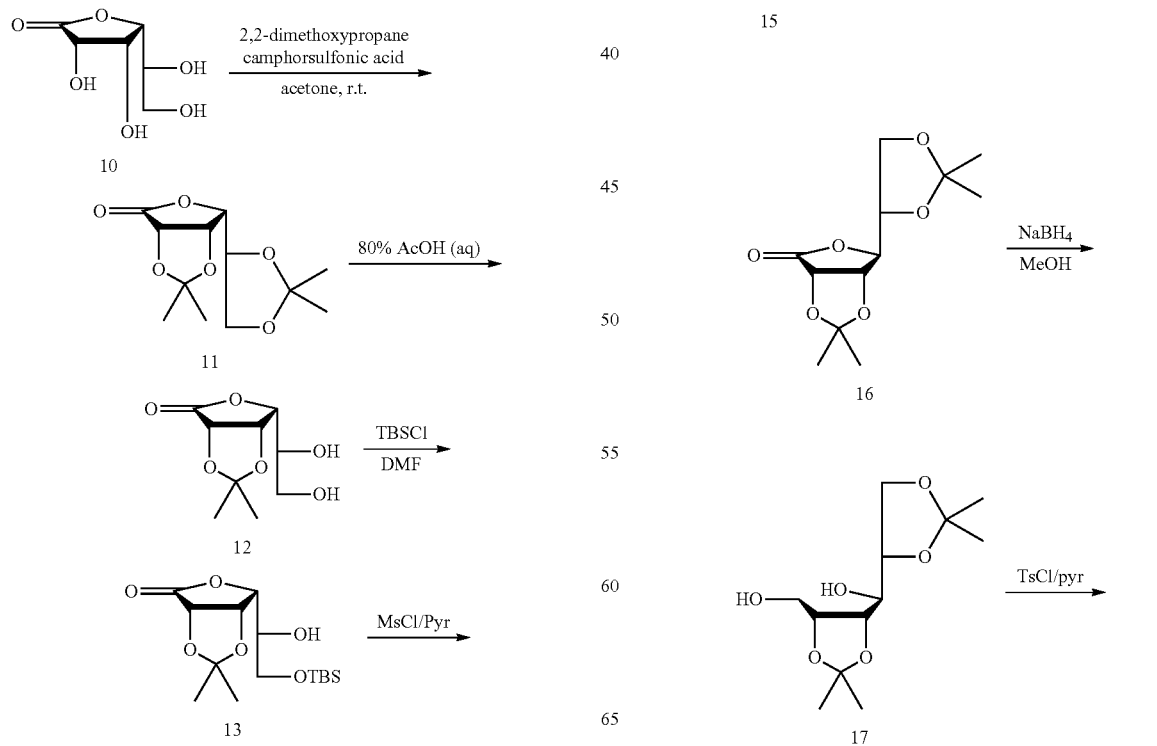

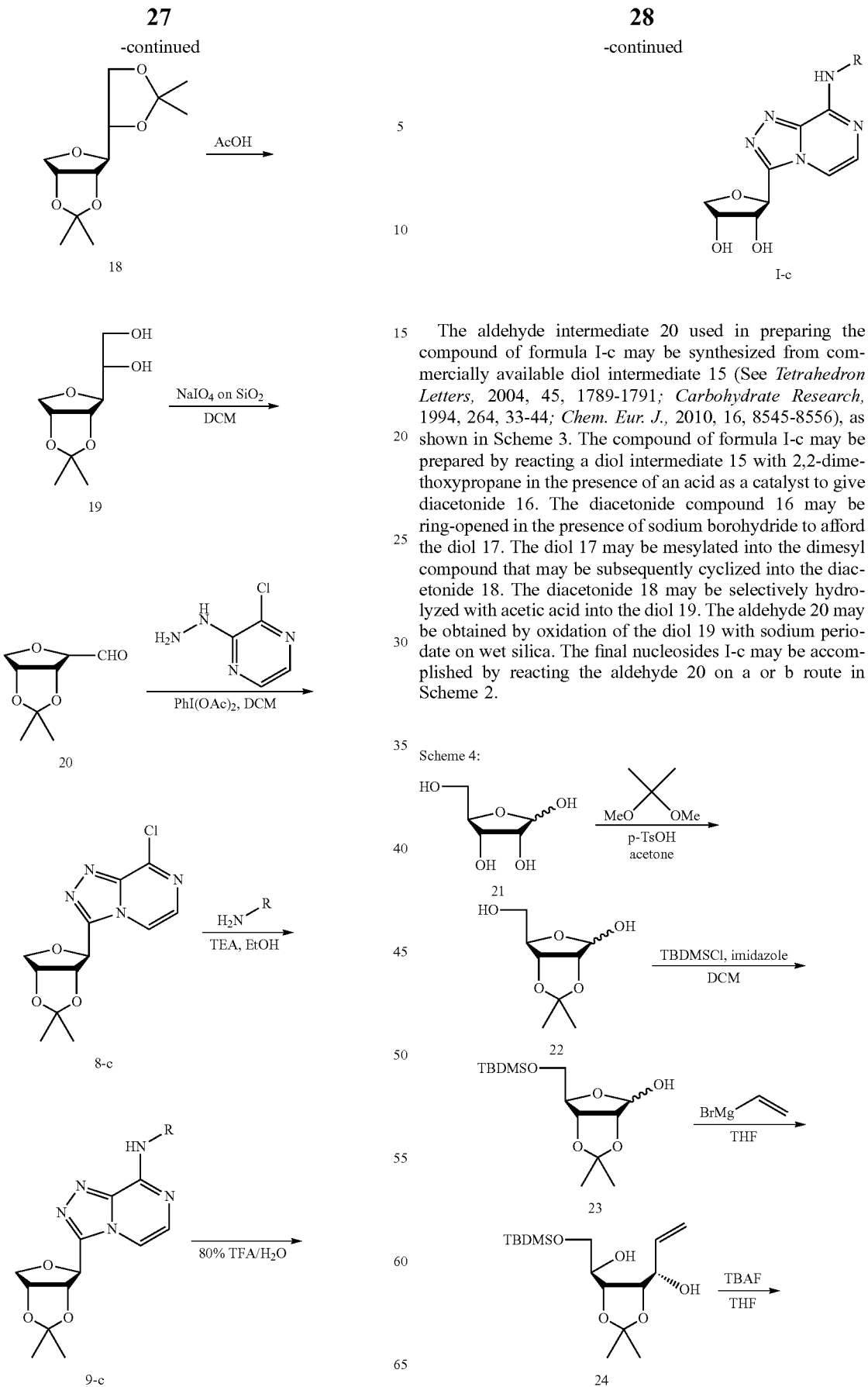

The aldehyde intermediate 20 used in preparing the compound of formula I-c may be synthesized from commercially available diol intermediate 15 (See *Tetrahedron Letters,* 2004, 45, 1789-1791; *Carbohydrate Research,* 1994, 264, 33-44; *Chem. Eur. J.,* 2010, 16, 8545-8556), as shown in Scheme 3. The compound of formula I-c may be prepared by reacting a diol intermediate 15 with 2,2-dimethoxypropane in the presence of an acid as a catalyst to give diacetonide 16. The diacetonide compound 16 may be ring-opened in the presence of sodium borohydride to afford the diol 17. The diol 17 may be mesylated into the dimesyl compound that may be subsequently cyclized into the diacetonide 18. The diacetonide 18 may be selectively hydrolyzed with acetic acid into the diol 19. The aldehyde 20 may be obtained by oxidation of the diol 19 with sodium periodate on wet silica. The final nucleosides I-c may be accomplished by reacting the aldehyde 20 on a or b route in Scheme 2.

Scheme 4:

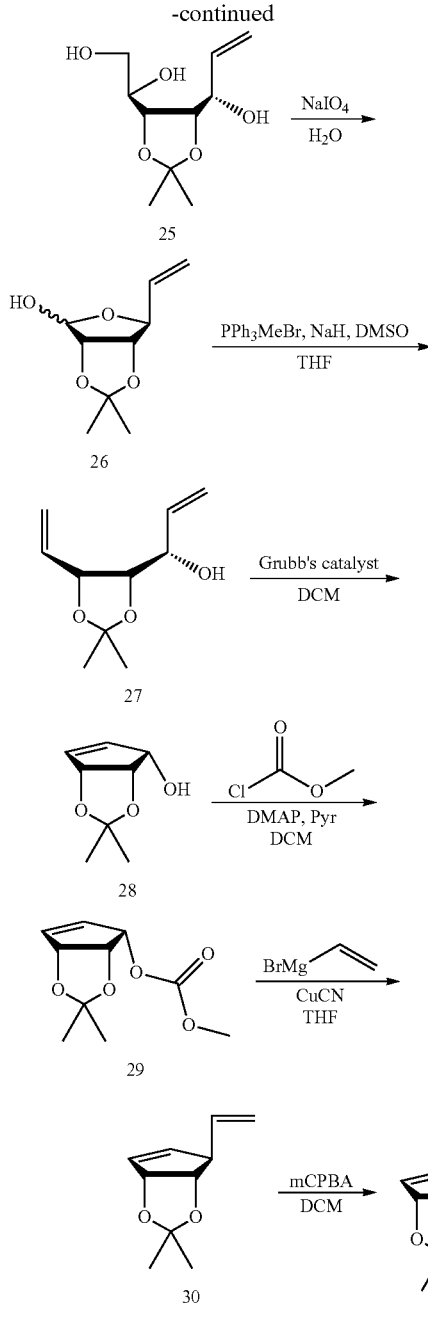

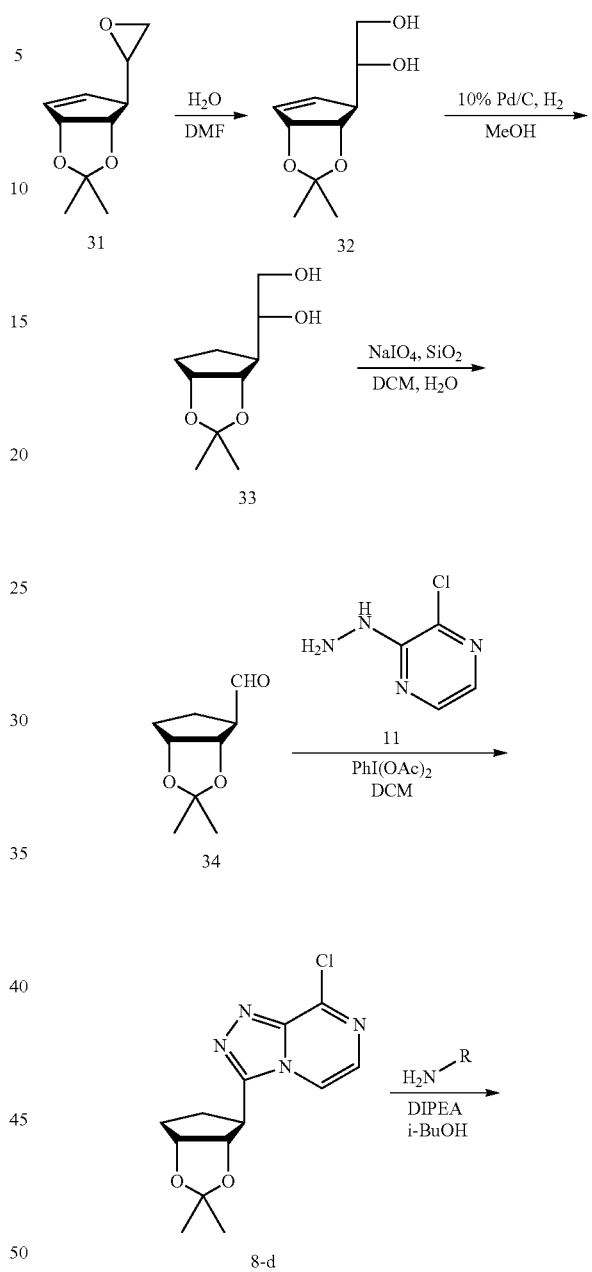

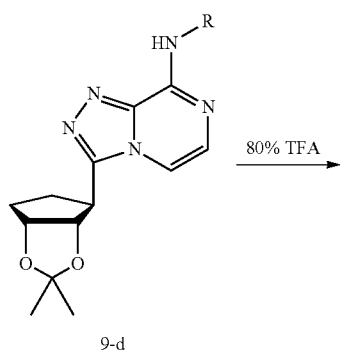

Cyclopentyl alcohol intermediate 28 used in preparing the compound of formula I-d and II-c may be described in *J. Org. Chem.*, 2005, 70(17), 6884-6890, *J. Org. Chem.*, 2004, 69(7), 2634-2636, *Tetrahedron* Asymmetry 13 (2002) 1189-1193. Protected cyclopentyl alcohol 28 may be acylated with methyl chloroformate to produce carbonate 29. Carbonate 29 may be reacted with vinyl magnesium bromide in the presence of copper(I) cyanide to provide the vinyl derivertive 30. Regioselective epoxidation of the terminal vinyl group may be achieved using mCPBA at low temperature to produce epoxide 31.

31

-continued

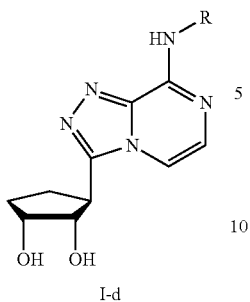

I-d

Epoxide 31 may be regioselectively reacted with H$_2$O under thermal conditions to give the unsaturated cyclopentyl diol 32. The unsaturated cyclopentyl diol 32 may be reacted with 10% palladium in the presence of hydrogen gas to provide the saturated cyclopentyl diol 33. The aldehyde 34 may be obtained by oxidation of the saturated cyclopentyl diol 33 with sodium periodate on wet silica. The final nucleosides I-d may be accomplished by reacting the aldehyde 20 on a or b route in Scheme 2.

Scheme 6:

32

-continued

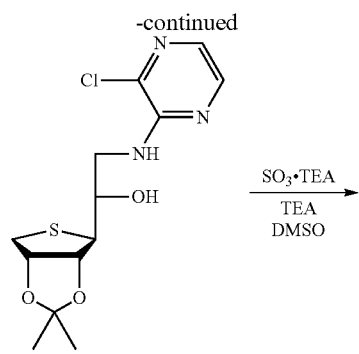

38

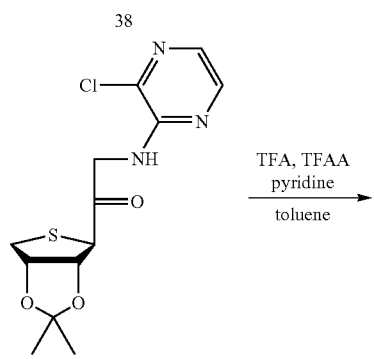

39

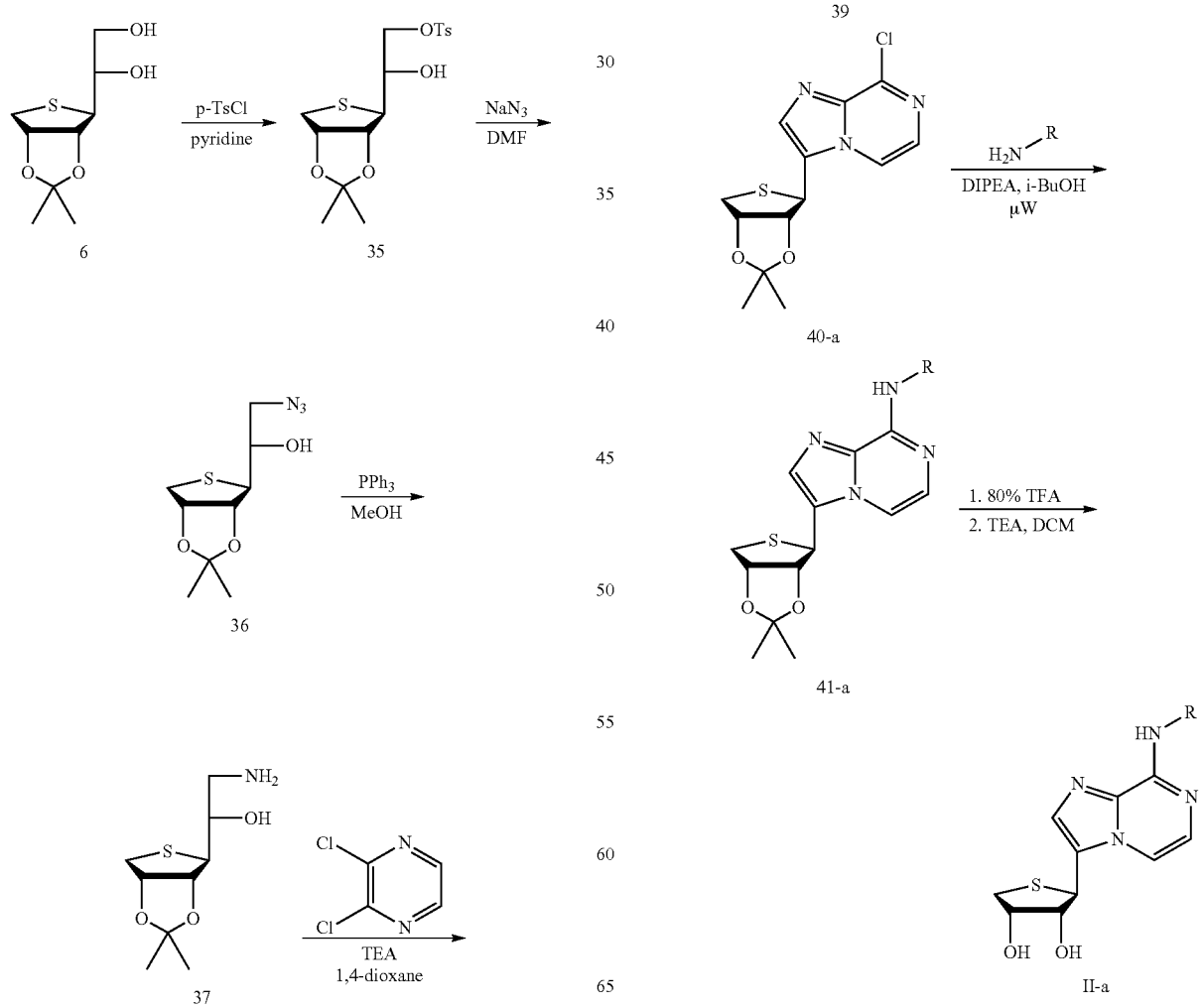

As shown in Scheme 6, the compound of formula II-a may be prepared by tosylating a diol intermediate 6 in the presence of pyridine to produce the tosylated compound 35. Treatment of the tosylated compound 35 with sodium azide at 120° C. provides an azide intermediate 36. The reduction of the azide intermediate 36 may be conducted using triphenylphosphine at 85° C. Amino alcohols 37 may be coupled with 2,3-dichloropyrazine at 110° C. to produce amino pyrazines 38. Sulfur trioxide pyridine complex oxidation of the secondary alcohol in pyrazines 38 yields the ketone 39 that may be subsequently cyclized in the presence of trifluoroacetic acid and trfiluoroacetic anhydride buffered by the presence of pyridine. These conditions provide the heterocyclic imidazopyrazine 40-a. (See *Carbohydrate Research*, 2010, 345, 1617-1621; EP0480713) The heterocyclic imidazopyrazine 40-a can be treated with an amine derivative in the presence of DIPEA with microwave irradiation to provide compound 41-a, which is then submitted to hydrolysis of the acetonide derivatives using 80% aqueous trifluoroacetic acid to the final nucleosides II-a, respectively.

Scheme 7:

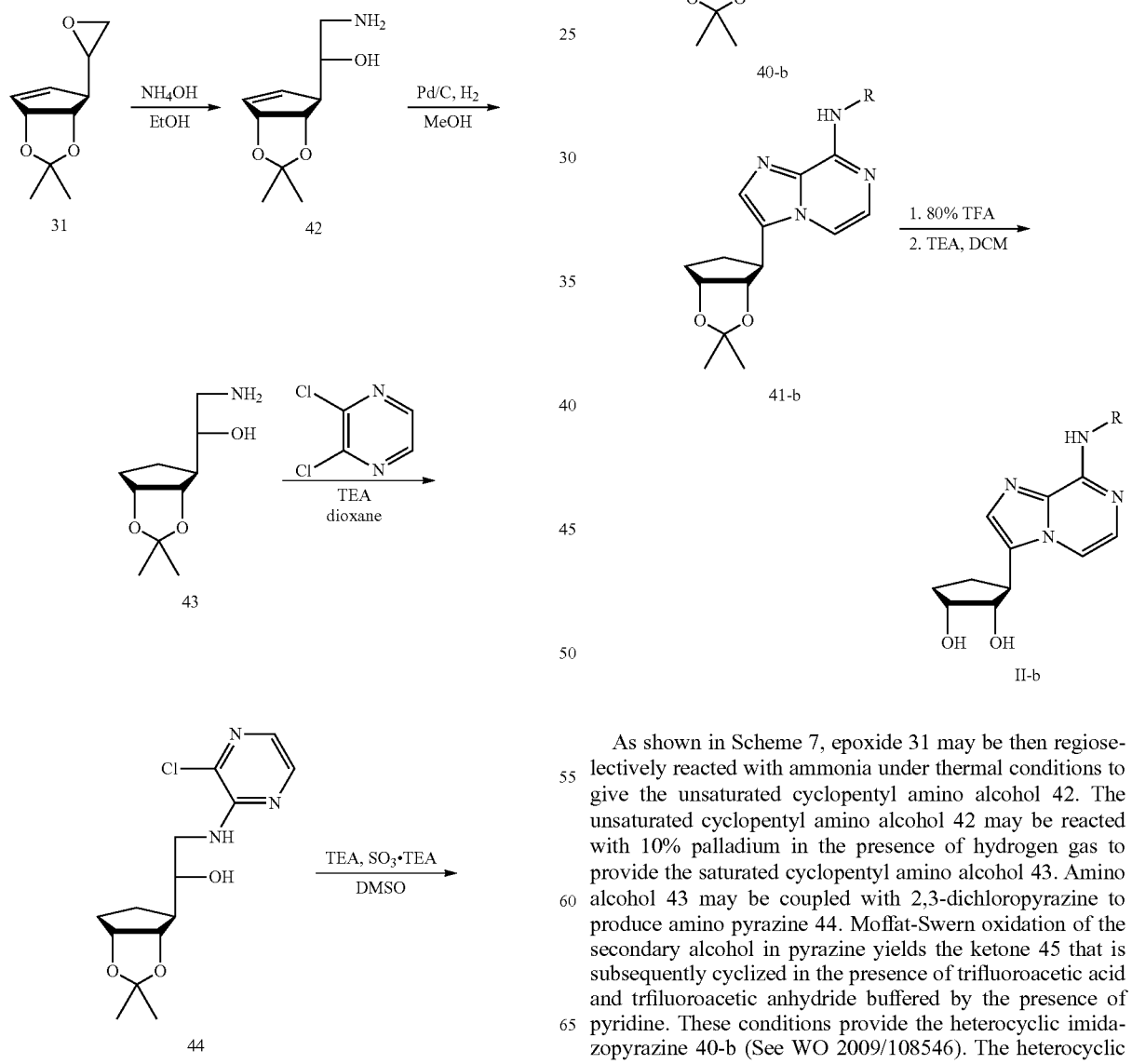

As shown in Scheme 7, epoxide 31 may be then regioselectively reacted with ammonia under thermal conditions to give the unsaturated cyclopentyl amino alcohol 42. The unsaturated cyclopentyl amino alcohol 42 may be reacted with 10% palladium in the presence of hydrogen gas to provide the saturated cyclopentyl amino alcohol 43. Amino alcohol 43 may be coupled with 2,3-dichloropyrazine to produce amino pyrazine 44. Moffat-Swern oxidation of the secondary alcohol in pyrazine yields the ketone 45 that is subsequently cyclized in the presence of trifluoroacetic acid and trfiluoroacetic anhydride buffered by the presence of pyridine. These conditions provide the heterocyclic imidazopyrazine 40-b (See WO 2009/108546). The heterocyclic imidazopyrazine 40-b can be treated with an amine derivative in the presence of DIPEA with heating to provide compound 41-b, which is then submitted to hydrolysis of the acetonide derivatives using 80% aqueous trifluoroacetic acid to the final nucleosides II-b, respectively.

Scheme 8:

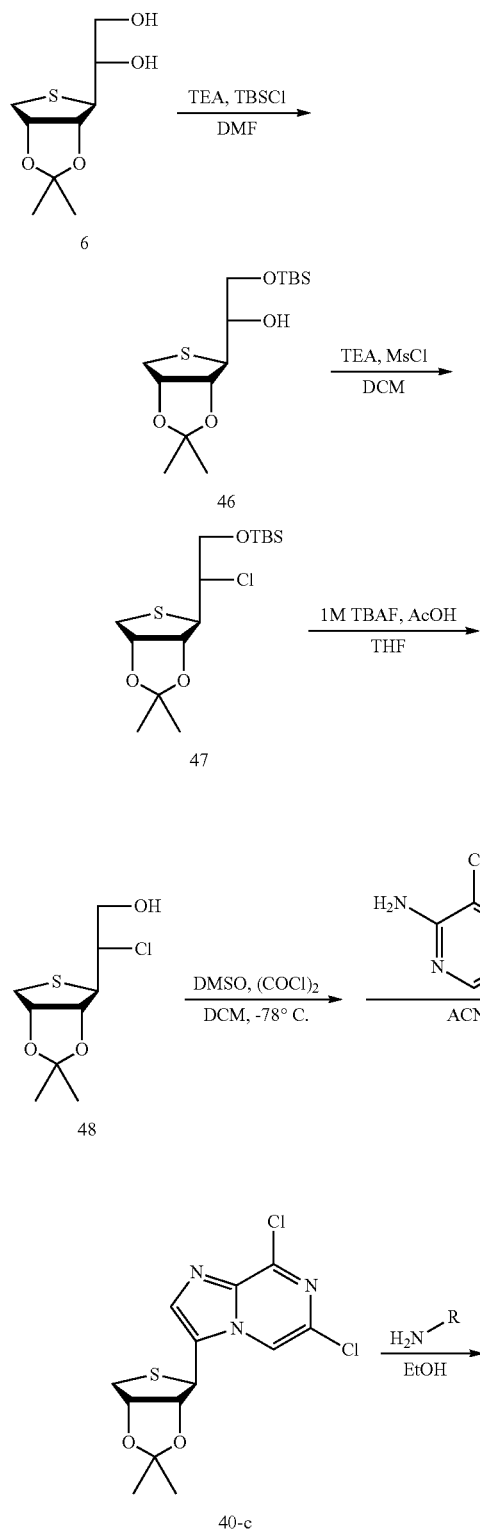

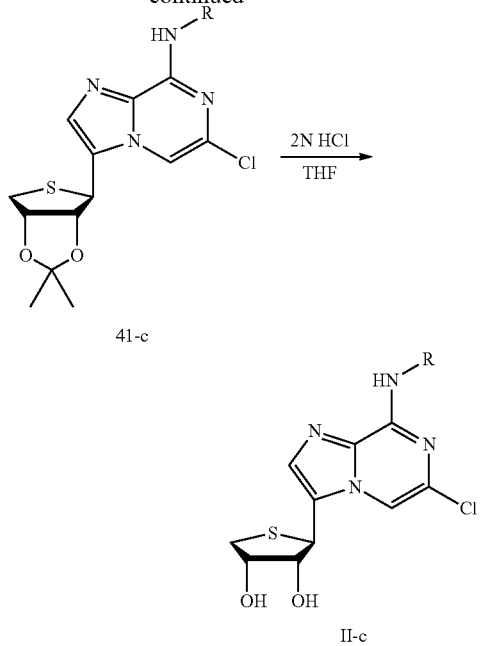

As shown in Scheme 8, the compound of formula II-c may be prepared by adding tert-butyldimethylsilyl chloride to a diol intermediate 6 in the presence of triethylamine to produce the protected compound 46. Treatment of the protected compound 46 with methanesulfonyl chloride in the presence of triethylamine provides a chloride intermediate 47. Moffat-Swern oxidation of the secondary alcohol 48 yields the ketone intermediate that may be subsequently cyclized in the presence of 2,3-dichloropyrazine. These conditions provide the heterocyclic imidazopyrazine 40-c. the heterocyclic triazopyrazine 40-c can be treated with an amine derivative to provide compound 41-c, which is then submitted to hydrolysis of the acetonide derivatives using 2N HCl to the final nucleosides II-c, respectively.

Scheme 9:

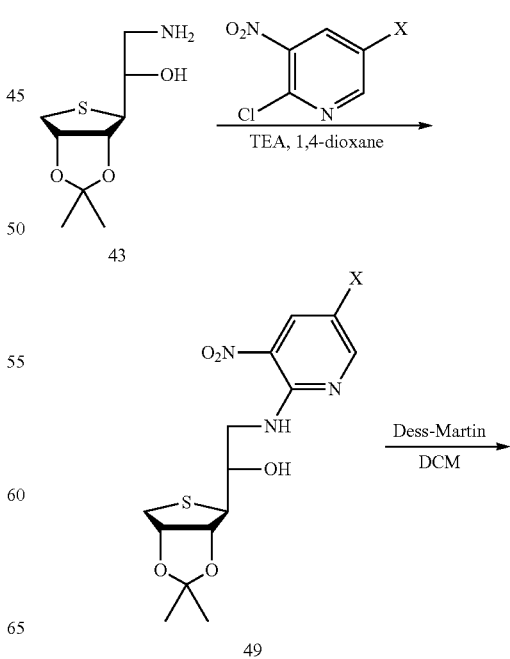

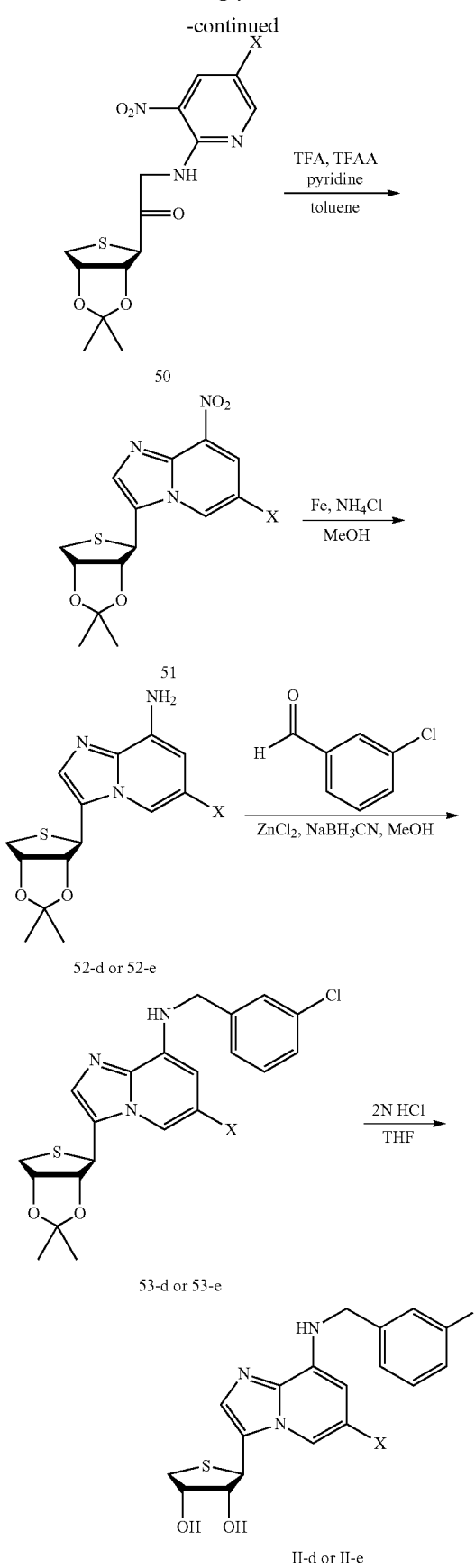

As shown in Scheme 9, amino alcohols 43 may be coupled with a 3-nitropyridine derivative at 110° C. to produce amino pyridines 49. Dess-Martin oxidation of the secondary alcohol in pyridines 49 yields the ketone 50 that may be subsequently cyclized in the presence of trifluoroacetic acid and trifluoroacetic anhydride buffered by the presence of pyridine. These conditions provide the heterocyclic imidazopyridine 51. The reduction of imidazopyridine 51 may be conducted using Fe in the presence of ammonium chloride at 85° C. (See *Org. Lett.*, 2011, 13, 42-45). Imidazopyridine 52-d or 52-e can be treated with sodium cyanoborohydride in the presence of an aldehyde derivative and zinc chloride at 85° C. to provide compound 53-d or 53-e (See WO2004/026867), which is then submitted to hydrolysis of the acetonide derivatives using 2N hydrochloric acid to the final nucleosides II-d or II-e, respectively.

Scheme 10:

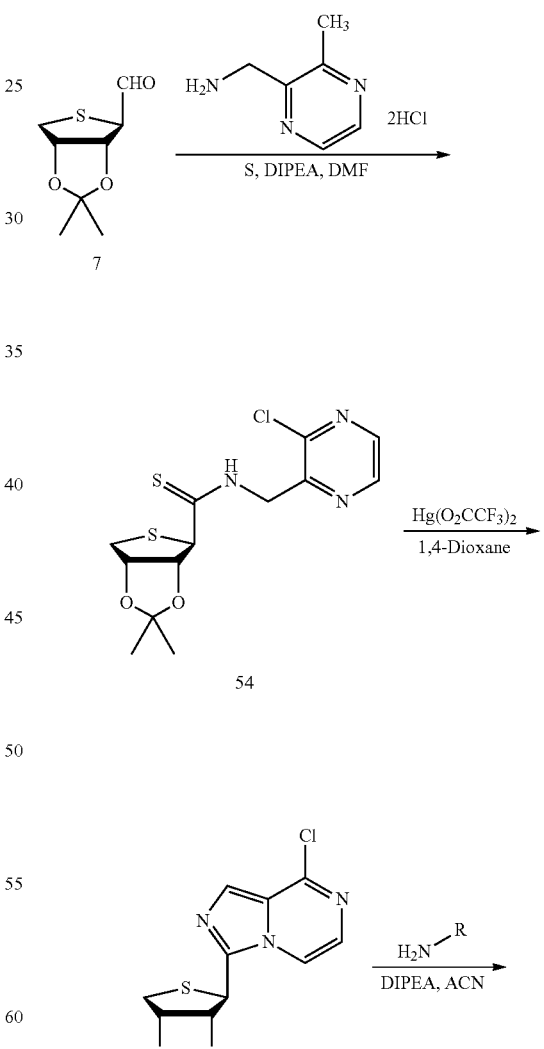

-continued

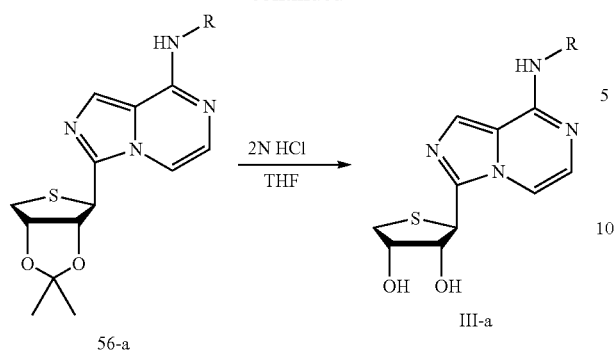

56-a

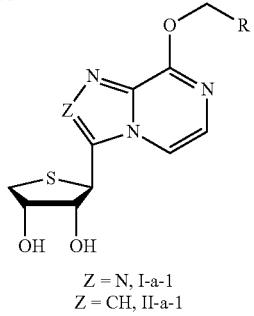

III-a

As shown in Scheme 10, aldehyde 7 may be coupled with (3-chloropyrazin-2-yl)methanamine 2HCl, DIPEA and sulfur to produce intermediate 54. Cyclizing intermediate 54 using $Hg(O_2CCF_3)_2$ provides key intermediate 55-a (See WO 2010/104027; U.S. Pat. No. 8,426,411). The heterocyclic imidazoopyrazine 55-a can be treated with an amine derivative in the presence of DIPEA at 70° C. to provide compound 56-a, which is then submitted to hydrolysis of the acetonide derivatives using 2N HCl to the final nucleosides III-a, respectively.

Scheme 11:

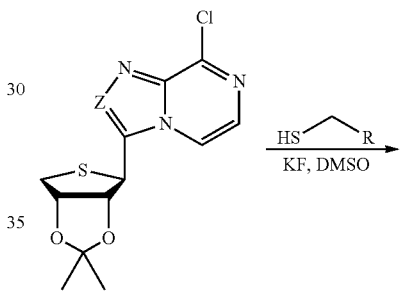

8-a
40-a

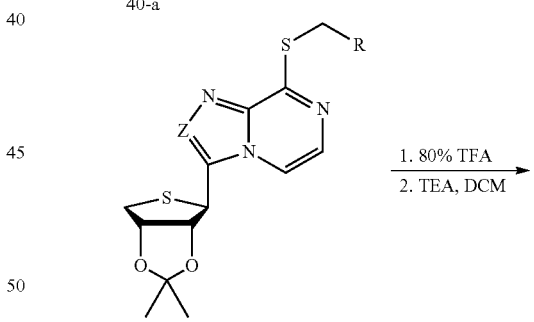

Z = N, 9-a-1
Z = CH, 41-a-1

-continued

Z = N, I-a-1
Z = CH, II-a-1

When the substituent $R^1$ is OR, Scheme 11 is taken for the synthesis of the final nucleosides I-a-1 or II-a-1. As seen in Scheme 11, the synthesis of the final nucleosides is accomplished by reacting the compound 8-a or 40-a with Buchwald-Hartwig Cross-Coupling agent to afford the compound 9-a-1 or 41-a-1 and reacting the compound 9-a-1 or 41-a-1 with 80% trifluoroacetic acid to afford the final nucleosides I-a-1 or II-a-1, respectively.

Scheme 12:

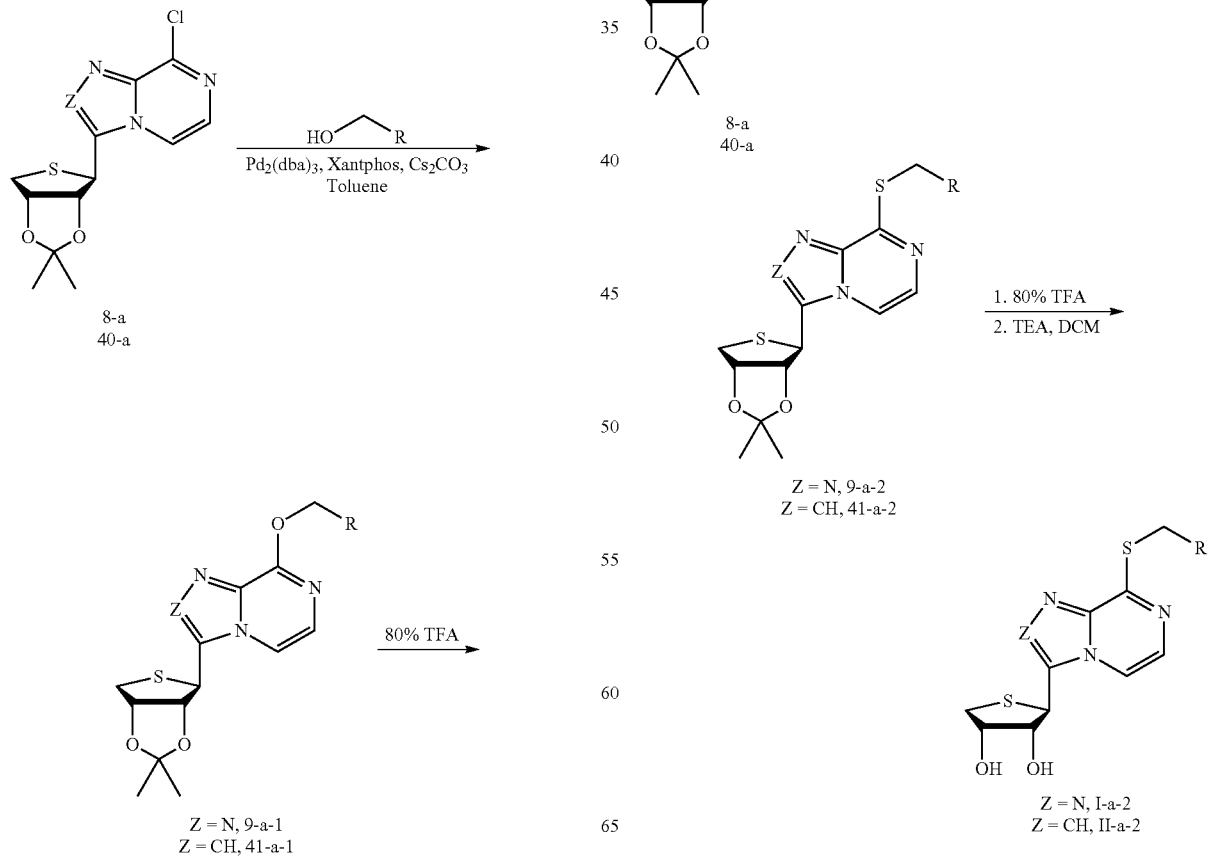

8-a
40-a

Z = N, 9-a-2
Z = CH, 41-a-2

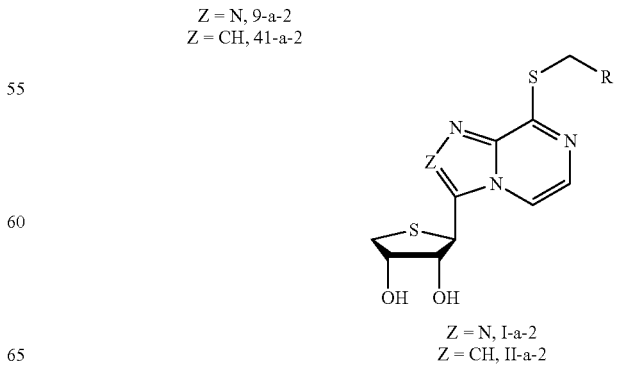

Z = N, I-a-2
Z = CH, II-a-2

When the substituent R[1] is SR, Scheme 12 is taken for the synthesis of the final nucleosides I-a-2 or II-a-2. As seen in Scheme 12, the synthesis of the final nucleosides is accomplished by reacting the compound 8-a or 40-a with KF to afford the compound 9-a-2 or 41-a-2 and reacting the compound 9-a-2 or 41-a-2 with 80% trifluoroacetic acid and then adding TEA to solution to afford the final nucleosides I-a-2 or II-a-2, respectively.

Scheme 13:

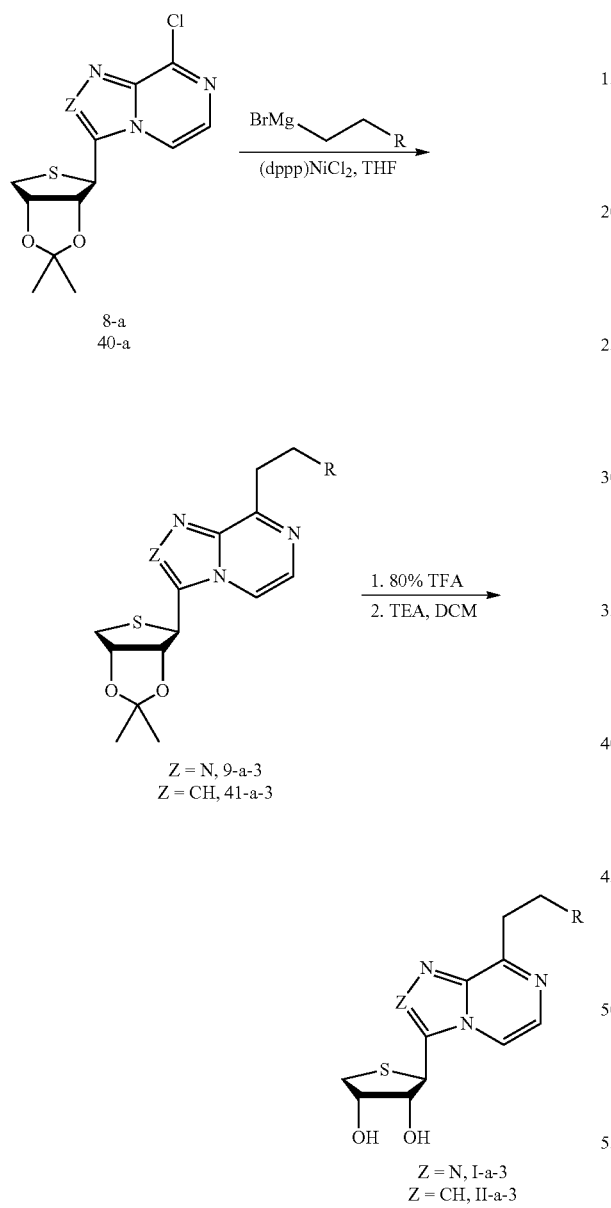

Scheme 14:

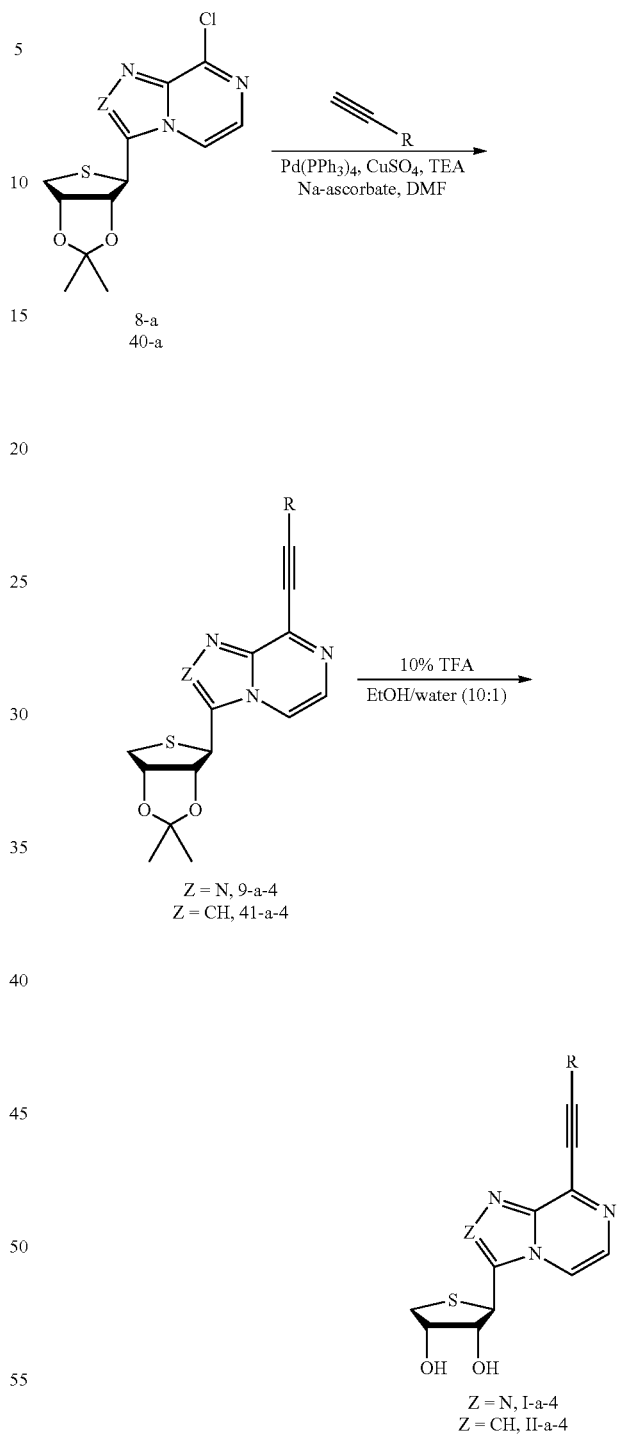

When the substituent R[1] is CH$_2$R, Scheme 13 is taken for the synthesis of the final nucleosides I-a-3 or II-a-3. As seen in Scheme 13, the synthesis of the final nucleosides is accomplished by reacting the compound 8-a or 40-a with Grignard agent to afford the compound 9-a-3 or 41-a-3 and reacting the compound 9-a-3 or 41-a-3 with 80% trifluoroacetic acid and then adding TEA to solution to afford the final nucleosides I-a-3 or II-a-3, respectively.

When the substituent R[1] is alkynyl R, Scheme 14 is taken for the synthesis of the final nucleosides I-a-4 or II-a-4. As seen in Scheme 14, synthesis of the final nucleosides is accomplished by reacting the compound 8-a or 40-a with Sonogashira Cross-Coupling agent to afford the compound 9-a-4 or 41-a-4 and reacting the compound 9-a-4 or 41-a-4 with 10% trifluoroacetic acid to afford the final nucleosides I-a-4 or II-a-4, respectively.

Scheme 15:

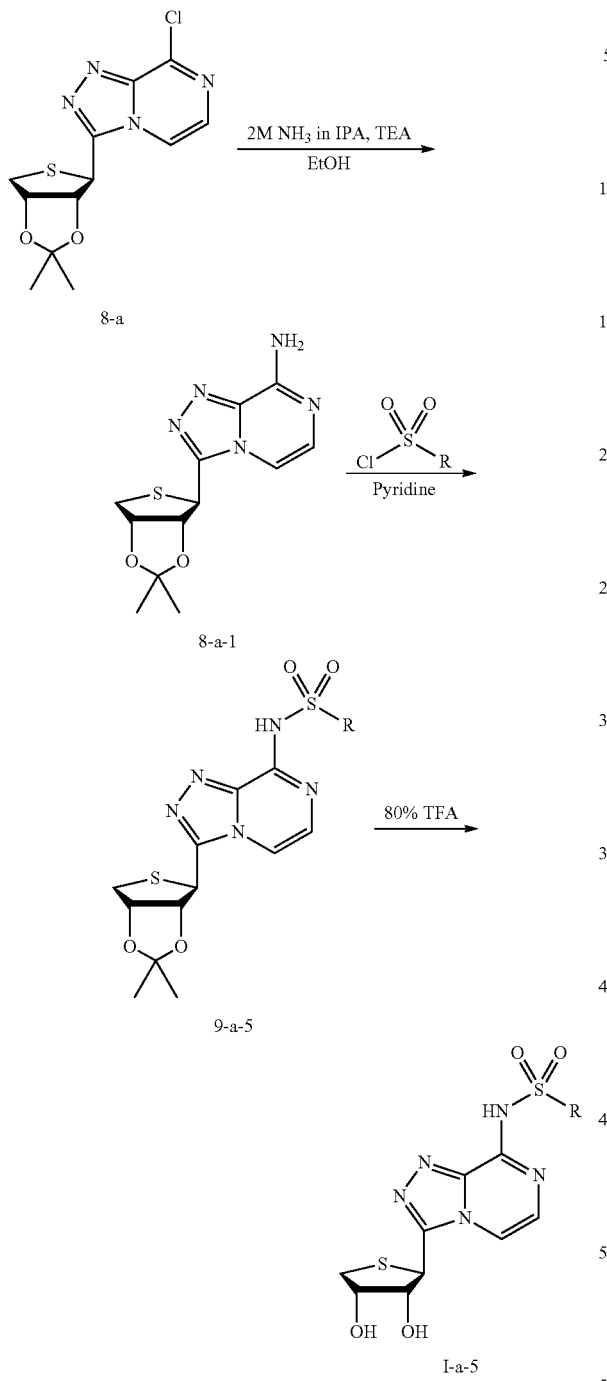

Scheme 16

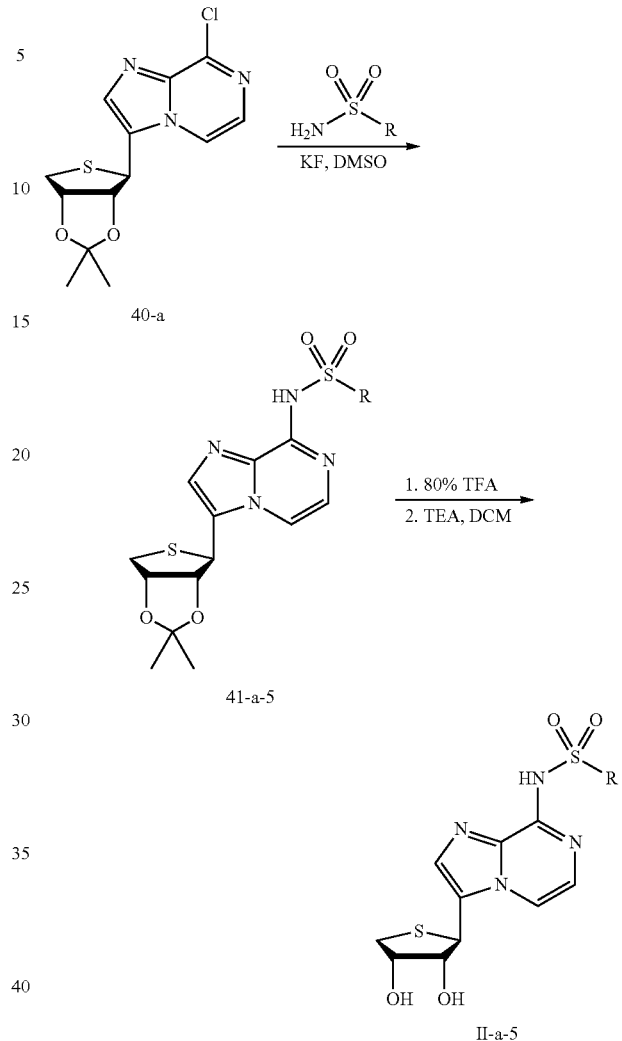

When the substituent R[1] is sulfonyl R[3], Scheme 16 is taken for the synthesis of the final nucleosides II-a-5. As seen in Scheme 16, synthesis of the final nucleosides is accomplished by reacting the compound 40-a with sulfonamide to afford the compound 41-a-5 and reacting the compound 41-a-5 with 80% trifluoroacetic acid and then adding TEA to solution to afford the final nucleosides II-a-5, respectively.

When the substituent R[1] is sulfonyl R, Scheme 15 is taken for the synthesis of the final nucleosides I-a-5. As seen in Scheme 15, synthesis of the final nucleosides is accomplished by reacting the compound 8-a with 2M NH3 in IPA to afford the compound 8-a-1, which may be coupled with sulfonyl chloride and reacting the compound 9-a-5 with 80% trifluoroacetic acid to afford the final nucleosides I-a-5, respectively.

Scheme 17

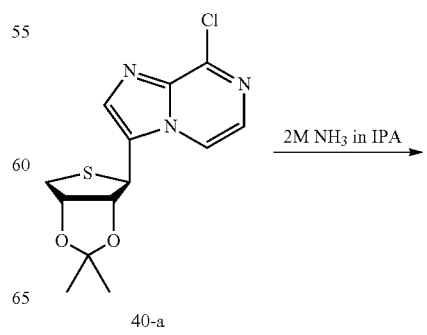

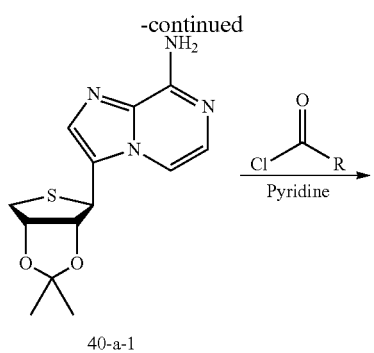

40-a-1

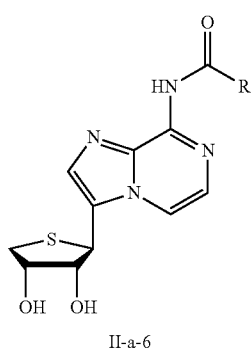

41-a-6

II-a-6

When the substituent R¹ is carbonyl R, Scheme 17 is taken for the synthesis of the final nucleosides II-a-6. As seen in Scheme 17, synthesis of the final nucleosides is accomplished by reacting the compound 40-a with 2M NH3 in IPA to afford the compound 40-a-1, which may be coupled with carbonyl chloride and reacting the compound 41-a-6 with 80% trifluoroacetic acid to afford the final nucleosides II-a-6, respectively.

Medical Uses and Methods of Treatment

The present disclosure further provides methods for treating a condition in a subject having or susceptible to having such a condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

1. Conditions

In some embodiments the conditions that can be treated in accordance with the present disclosure include, but are not limited to, glaucoma and glaucoma-related ocular disorders. That is, in another embodiment, there is provided a method for preventing, ameliorating or treating a condition comprising administering to a subject in need thereof a therapeutically effective amount of a compound of Formula I or pharmaceutically acceptable salt thereof, wherein the condition is selected from the group consisting of glaucoma or glaucoma-related ocular disorders. In another embodiment, the subject is a human. In another embodiment, the condition is glaucoma.

In some embodiments, there is provided a method for antagonizing an A3 adenosine receptor comprising contacting the cells with an effective amount of at lease one compound according to embodiments of the present disclosure. In another embodiment, the containing takes place in vivo.

2. Subjects

Suitable subjects to be treated according to embodiments of the present disclosure include mammalian subjects. Mammals according to embodiments of the present disclosure include, but are not limited to, human, canine, feline, bovine, caprine, equine, ovine, porcine, rodents, lagomorphs, primates, and the like, and encompass mammals in utero.

3. Administration and Dosing

The compounds of the present disclosure are generally administered in a therapeutically effective amount.

The compounds of the present disclosure can be administered by any suitable route in the form of a pharmaceutical composition adapted to such a route, and in a dose effective for the treatment intended. An effective dosage is typically in the range of about 0.0001 to about 100 mg per kg body weight per day, preferably about 0.01 to about 30 mg/kg/day, in single or divided doses. Depending on age, species and condition being treated, dosage levels below the lower limit of this range may be suitable. In other cases, still larger doses may be used without harmful side effects. Larger doses may also be divided into several smaller doses, for administration throughout the day. Typically, appropriate dosing will be determined using techniques known to one skilled in the art (see, for example, Remington: The Science and Practice of Pharmacy, Mack Publishing Co., 20th ed., 2000).

In certain embodiments, provided herein are methods for treating or preventing glaucoma and/or glaucoma-related ocular disorders in a subject comprising administering to said subject a therapeutically effective amount of at least one compound according to the present disclosure, A3 adenosine receptor antagonist. In more specific embodiments, provided herein are methods for treating glaucoma and/or glaucoma-related ocular disorders in a subject comprising administering to said subject an effective amount of said compound(s), wherein the compound(s) is administered by intravitreal injection. In certain embodiments, provided herein are methods for treating glaucoma and/or glaucoma-related ocular disorders in a subject comprising administering to said subject an effective amount of the compound, wherein the compound(s) is administered in liquid form at a concentrations of about 0.001 mg/mL to about 0.01 mg/mL, or about 0.005 mg/mL to about 0.05 mg/mL, or about 0.01 mg/mL to about 0.1 mg/mL, or about 0.05 mg/mL to about 0.5 mg/mL, or about 0.1 mg/mL to about 1.0 mg/mL, or about 0.5 mg/mL to about 5 mg/mL, or about 1.0 mg/mL to about 10 mg/mL, or about 2 mg/mL to about 10 mg/mL, or about 5.0 mg/mL to about 10 mg/mL, or about 5.0 mg/mL to about 15 mg/mL, or about 10 mg/mL to about 20 mg/mL. In certain specific embodiments, at least one compound according to the present disclosure is administered topically.

Pharmaceutical Compositions

For the treatment of the conditions referred to above, the compounds of described herein can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges and capsules, which can contain liquids, gels, or powders.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Non-limiting examples of disintegrants include sodium or calcium carboxymethyl cellulose, croscarmellose sodium, polyvinylpyrrolidone, hydroxypropyl cellulose, starch and the like.

Suitable lubricants, for use in a tablet, may be present in amounts from about 0.1% to about 5% by weight, and include stearic acid, $SiO_2$, calcium, zinc or magnesium stearate, sodium stearyl fumarate and the like.

Suitable binders, for use in a tablet, include gelatin, polyethylene glycol, sugars, gums, starch, hydroxypropyl cellulose, hydroxypropylmethyl cellulose, polyvinyl pyrrolidone, and the like.

Suitable diluents, for use in a tablet, include mannitol, xylitol, lactose, dextrose, sucrose, sorbitol, microcrystalline cellulose, and starch.

Suitable surface active agents and glidants, for use in a tablet, may be present in amounts from about 0.1% to about 3% by weight, and include polysorbate 80, sodium dodecyl sulfate, talc and silicon dioxide.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Ocular Administration

Disclosed herein are formulations comprising the disclosed compounds as topical ophthalmic solutions (eye drops), which are normally available as a sterile, isotonic (i.e., a pH of between about 3 and about 8, between about 4 to about 8, between about 7 to about 8, or about 7.4) solution, optionally further comprising a preservative. The term "eye drops" as used herein refers to a pharmaceutical liquid formulation which is administered in the form of drops on the external surface of the eye and which has a local effect on the posterior segment of the eye, including the choroids, retinal pigment epithelium, retina, macula, fovea, optic nerve and vitreous humor. Accordingly, in certain embodiments, a compound as disclosed herein may be combined with purified water and adjusted for physiological pH and isotonicity.

Examples of buffering agents to maintain or adjust pH include, but are not limited to, acetate buffers, citrate buffers, phosphate buffers and borate buffers. Examples of tonicity adjustors are sodium chloride, mannitol and glycerin.

The eye drop formulation is then optionally aliquoted into either a plurality of discrete, sterile disposable cartridges each of which is suitable for unit dosing, or a single cartridge for unit dosing. Such a single disposable cartridge may be, for example, a conical or cylindrical specific volume dispenser, with a container having side-walls squeezable in a radial direction to a longitudinal axis in order to dispense the container contents therefrom at one end of the container. Such disposable containers are currently used to dispense eye drops at 0.3 to 0.4 mL per unit dosing, and are ideally adaptable for the delivery of eye drops.

Ophthalmic eye-drop solutions may also be packaged in multi-dose form, for example, as a plastic bottle with an eye-dropper. In such formulations, preservatives are optionally added to prevent microbial contamination after opening of the container. Suitable preservatives include, but are not limited to: benzalkonium chloride, thimerosal, chlorobutanol, methylparaben, propylparaben, phenylethyl alcohol, edetate disodium, sorbic acid, polyquatemium-1, or other agents known to those skilled in the art, and all of which are contemplated for use in the present disclosure. Preservative-containing formulations may comprise from about 0.001 to about 1.0% weight/volume of the preservative.

In certain embodiments, polymers may be added to ophthalmic solutions in order to increase the viscosity of the vehicle, thereby prolonging contact of the solution with the cornea and enhancing bioavailability. In certain embodiments, such polymers are selected from cellulose derivatives (e.g., methylcellulose, hydroxyethylcellulose, hydroxypropylcellulose or carboxymethylcellulose), dextran 70, gelatin, polyols, glycerin, polyethylene glycol 300, polyethylene glycol 400, polysorbate 80, propylene glyclol, polyvinyl alcohol and povidone, or a combination thereof In certain embodiments ophthalmic solutions as disclosed herein may further comprise stabilizer/solubilizer such as a cyclodextrin. In certain such embodiments, the cyclodextrin is selected from α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin.

In certain embodiments, a compound as disclosed herein may be administered in a sustained release ophthalmic solution formulation.

In certain embodiments, the compound as disclosed herein may be administered through ocular drug delivery systems, such as, but not limited to, colloidal dosage forms, such as nanoparticles, nanomicelles, liposomes, microemulsions, bioadhesive gels and fibrin sealant-based approaches to sustain drug levels at the target site. Other ocular drug delivery systems include drug-eluting contact lenses, ultrasound-mediated drug delivery, ocular iontophoresis, and drug-coated microneedles.

In certain embodiments, the frequency of administration can vary greatly, depending on the needs of each subject and the severity of the disease to be treated, such administration may be from about once a week to about ten times a day, such as from about three times a week to about three times a day, or once or twice a day.

Combinations and Combination Therapy

The compounds of the present disclosure can be used, alone or in combination with other pharmaceutically active compounds, to treat conditions such as those previously described above. The compound(s) of the present disclosure and other pharmaceutically active compound(s) can be administered simultaneously (either in the same dosage form or in separate dosage forms) or sequentially. Accordingly, in one embodiment, the present disclosure comprises methods for treating a condition by administering to the subject a therapeutically-effective amount of one or more compounds of the present disclosure and one or more additional pharmaceutically active compounds.

In another embodiment, there is provided a pharmaceutical composition comprising one or more compounds of the present disclosure, one or more additional pharmaceutically active compounds, and a pharmaceutically acceptable carrier, excipient or diluent.

In another embodiment, the one or more additional pharmaceutically active compounds is selected from the group consisting of a prostaglandin analog, beta-adrenergic receptor antagonist, alpha-2-adrenergic agonist, carbonic anhydrase inhibitor, miotic agent, monoclonal antibody, corticosteroid, glucocorticoid, kinase inhibitor, cycloplegic and an antimetabolite, or a combination thereof.

In certain embodiments, the other medicament is laser therapy.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an A3 adenosine receptor antagonist as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In this way, there is provided a pharmaceutical composition for use in the prevention, amelioration or treatment of glaucoma or glaucoma-related ocular disorders comprising (a) the compound(s) according to embodiments of the present disclosure and (b) a therapeutically effective amount of an active pharmaceutical ingredient as mentioned above. In addition, there is provided a method for preventing, ameliorating or treating glaucoma or glaucoma-related ocular disorders comprising administering to a subject in need thereof (a) a therapeutically effective amount of a compound according to the present disclosure and (b) administering to a subject in need thereof a therapeutically effective amount of an active pharmaceutical ingredient as mentioned above.

Advantageous Effects

In one aspect, there is provided compounds, which are effective as an A3 adenosine receptor antagonist, useful for preventing, ameliorating or treating glaucoma, glaucoma-related ocular disorders, or inflammatory diseases. In another aspect, there is provided a method for preparing the compound(s) according to embodiments of the present disclosure. In yet another aspect, there is provided a pharmaceutical composition for preventing, ameliorating or treating glaucoma, glaucoma-related ocular disorders, and inflammatory diseases, comprising at least one of such compounds antagonizing an A3 adenosine receptor according to embodiments of the present disclosure as an active ingredient. In yet another aspect, there is provided a method for preventing, ameliorating or treating glaucoma, glaucoma-related ocular disorders, or inflammatory diseases, comprising administering a therapeutically effective amount of the compound(s) according to embodiments of the present disclosure. In yet another aspect, there is provided a method of antagonizing A3 adenosine receptor with the compound(s) according to embodiments of the present disclosure.

Hereinafter, embodiments of the present disclosure will further be described in detail. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

SYNTHETIC EXAMPLES

Some embodiments of the present disclosure were synthesized as follows:

Example 1: Synthesis of (2S,3R,4S)-2-(8-((3-chlorobenzyl)amino)-[1,2,4]triazolo[4,3-a]pyrazin-3-yl)tetrahydrothiophene-3,4-diol STEP1 Preparation of Compound (3aR,4R,6aS)-2,2-dimethyltetrahydrothieno[3,4-d][1,3]dioxole-4-carbaldehyde To a suspension of silica gel (20 g) in DCM (100 mL) was added a suspension of NaIO$_4$ (4.4 g, 20.4 mmol) in H$_2$O (5 mL) with constant stirring at room temperature. The mixture was cooled in an ice-bath and treated with a suspension of (S)-1-((3aR,4S,6aS)-2,2-dimethyltetrahydrothieno[3,4-d][1,3]dioxol-4-yl)ethane-1,2-diol (3 g, 13.6 mmol) in DCM and the progress of the reaction was monitored by TLC until disappearance of the starting material (4 h). The mixture was filtered through a pad of Celite, the cake was washed with DCM and concentrated in vacuo. The residue was purified by MPLC on SiO$_2$ (Hexanes:EtOAc=9:1 to 3:1) to give (3aR,4R,6aS)-2,2-dimethyltetrahydrothieno[3,4-d][1,3]dioxole-4-carbaldehyde (1.6 g, 62%) as a white solid.

$^1$H-NMR (CDCl$_3$, 400 MHz): δ 9.38 (s, 1H), 7.28 (s, 1H), 5.13 (d, J=5.5 Hz, 1H), 4.96-4.92 (m, 1H), 3.95 (s, 1H), 2.93-2.87 (m, 1H), 2.65 (dd, J=13.3, 4.1 Hz, 1H), 1.54 (s, 3H), 1.35 (s, 3H).

STEP2 Preparation of Compound 8-chloro-3-((3aR, 4S,6aS)-2,2-dimethyltetrahydrothieno[3,4-d][1,3]dioxol-4-yl)-[1,2,4]triazolo[4, 3-a]pyrazine To a solution of (3aR,4R,6aS)-2,2-dimethyltetrahydrothieno[3,4-d][1,3]dioxole-4-carbaldehyde (1.75 g, 9.3 mmol) in DCM (55 mL) was added 2-chloro-3-hydrazinylpyrazine (1.34 g, 9.3 mmol)(red suspension). The mixture was stirred at room temperature and monitored by TLC until disappearance of starting material (3 h). After cooled in ice-bath, the mixture was treated PhI(OAc)$_2$ (4.49 g, 13.94 mmol) and stirred for 4 h at room temperature. The reaction mixture was washed with sat. aq. NaHCO$_3$ solution and brine, dried over Na$_2$SO$_4$ and filtered. The organic layer was concentrated in vacuo to purified by MPLC on SiO$_2$ (Hexanes:EtOAc=9:1 to 1:1) to give 8-chloro-3-((3aR,4S,6aS)-2,2-dimethyltetrahydrothieno[3,4-d][1,3]dioxol-4-yl)-[1,2,4]triazolo[4, 3-a]pyrazine (28.6 g, 89%) as a yellow oil.

$^1$H-NMR (CDCl$_3$, 400 MHz): δ 7.85 (d, J=4.4 Hz, 1H), 7.75 (d, J=4.8 Hz, 1H), 6.55 (brs, 1H), 5.67 (d, J=5.6 Hz, 1H), 5.28 (m, 1H), 4.82 (t, J=4.4 Hz, 1H), 4.56 (s, 1H), 2.98 (d, J=2.8 Hz, 2H), 1.59 (s, 3H), 1.41 (s, 3H).

STEP3 Preparation of Compound N-(3-chlorobenzyl)-3-((3aR,4S,6aS)-2,2-dimethyltetrahydro thieno[3,4-d][1,3]dioxol-4-yl)-[1,2,4]triazolo[4,3-a]pyrazin-8-amine A solution of 8-chloro-3-((3aR,4S,6aS)-2,2-dimethyltetrahydrothieno[3,4-d][1,3]dioxol-4-yl)-[1,2,4]triazolo[4, 3-a]pyrazine (500 mg, 1.60 mmol), (3-chlorophenyl)methanamine (0.39 mL, 3.2 mmol) and TEA (0.68 mL, 4.8 mmol) in EtOH (8.0 mL) was stirred at 80° C. for 18 h. The reaction mixture was cooled to room temperature, diluted with DCM and washed with water and brine. The separated organic layer was dried over Na2SO4, filtered and concentrated in vacuo. The residue was purified by MPLC on SiO2 (2-5% MeOH in DCM) to give N-(3-chlorobenzyl)-3-((3aR,4S,6aS)-2,2-dimethyltetrahydrothieno[3,4-d][1,3]dioxol-4-yl)-[1,2,4]triazolo[4,3-a]pyrazin-8-amine (2.40 g, 90%) as a yellow oil.

$^1$H-NMR (CDCl3, 400 MHz): δ 7.41 (m, 2H), 7.27 (m, 3H), 7.24 (d, J=4.8 Hz, 1H), 5.75 (d, J=5.2 Hz, 1H), 5.31 (t, J=4.0 Hz, 1H), 4.62 (s, 1H), 2.95 (m, 2H), 1.59 (s, 3H), 1.42 (s, 3H).

STEP4 Preparation of Compound (2S,3R,4S)-2-(8-((3-chlorobenzyl)amino)-[1,2,4]triazolo[4,3-a]pyrazine-3-yl)tetrahydrothiophene-3,4-diol A solution of N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (2.40 g, 5.76 mmol) in 80% aq. TFA (46 mL) was stirred at room temperature for 1 h. The reaction mixture was concentrated in vacuo. The residue was diluted with DCM, and then TEA was added to the solution until pH 7. The mixture was stirred at room temperature for 10 min and concentrated in vacuo. The residue was purified by column chromatography on NH—SiO2 (EtOAc:MeOH=10:1) to give (2S,3R,4S)-2-(8-((3-chlorobenzyl)amino)-[1,2,4]triazolo[4,3-a]pyrazine-3-yl)tetrahydrothiophene-3,4-diol (1.95 g, 90%) as a white solid.

$^1$H-NMR (DMSO-d6, 400 MHz): δ 7.66 (d, J=5.2 Hz, 1H), 7.42-7.23 (m, 5H), 4.78 (s, 2H), 4.74 (dd, J=3.6, 8.0 Hz, 1H), 4.54 (dd, J=3.6, 7.6 Hz, 1H), 3.37 (dd, J=4.4, 11.2 Hz, 1H), 2.97 (dd, J=3.2, 11.2 Hz, 1H).

LC-MS MS(EI) for C16H16ClN5O2S [M+H]$^{+}$ (Calcd.: 377.85) Found: 378.2.

Example 2: Synthesis of (2S,3R,4S)-2-(8-(methylamino)-[1,2,4]triazolo[4,3-a]pyrazin-3-yl)tetrahydrothiophene-3,4-diol $^1$H-NMR (DMSO-d$_6$, 400 MHz): δ 8.14 (q, J=4.7 Hz, 1H), 7.66 (d, J=4.8 Hz, 1H), 7.30 (d, J=4.8 Hz, 1H), 5.42 (d, J=6.1 Hz, 1H), 5.31 (d, J=4.4 Hz, 1H), 4.76 (d, J=7.1 Hz, 1H), 4.66-4.60 (m, 1H), 4.44-4.38 (m, 1H), 3.25 (dt, J=10.6, 5.4 Hz, 1H), 2.95 (d, J=4.7 Hz, 3H), 2.82 (dd, J=10.7, 3.8 Hz, 1H).

LC-MS MS(EI) for C10H13N5O2S [M+H]$^{+}$ (Calcd.: 267.08) Found: 268.1.

Example 3: Synthesis of (2S,3R,4S)-2-(8-(piperidin-1-yl)-[1,2,4]triazolo[4,3-a]pyrazin-3-yl)tetrahydrothiophene-3,4-diol $^1$H-NMR (DMSO-d$_6$, 400 MHz): δ 7.70 (d, J=4.7 Hz, 1H), 7.34 (d, J=4.6 Hz, 1H), 5.37 (d, J=44.9 Hz, 2H), 4.77 (d, J=6.9 Hz, 1H), 4.66 (dd, J=6.8, 3.0 Hz, 1H), 4.42 (d, J=3.5 Hz, 1H), 4.22 (s, 4H), 3.23 (dd, J=10.6, 4.7 Hz, 1H), 2.83 (dd, J=10.6, 4.0 Hz, 1H), 1.68 (d, J=4.7 Hz, 2H), 1.60 (d, J=3.8 Hz, 4H).

LC-MS MS(EI) for C14H19N5O2S [M+H]$^{+}$ (Calcd.: 321.13) Found: 322.1.

Example 4: Synthesis of (2S,3R,4S)-2-(8-morpholino-[1,2,4]triazolo[4,3-a]pyrazin-3-yl)tetrahydrothiophene-3,4-diol $^1$H-NMR (DMSO-d$_6$, 400 MHz): δ 7.80 (d, J=4.7 Hz, 1H), 7.38 (d, J=4.7 Hz, 1H), 5.43 (d, J=6.0 Hz, 1H), 5.32 (d, J=4.3 Hz, 1H), 4.79 (d, J=7.0 Hz, 1H), 4.65 (td, J=6.3, 3.4 Hz, 1H), 4.45-4.36 (m, 1H), 4.22 (s, 4H), 3.80-3.66 (m, 4H), 3.24 (dd, J=10.7, 4.7 Hz, 1H), 2.83 (dd, J=10.6, 3.9 Hz, 1H).

LC-MS MS(EI) for C13H17N5O3S [M+H]$^{+}$ (Calcd.: 323.11) Found: 324.1.

Example 5: Synthesis of (2S,3R,4S)-2-(8-(benzylamino)-[1,2,4]triazolo[4,3-a]pyrazin-3-yl)tetrahydrothiophene-3,4-diol $^{1}$H-NMR (DMSO-d$_{6}$, 400 MHz): δ 8.76 (s, 1H), 7.68 (d, J=4.8 Hz, 1H), 7.41-7.17 (m, 6H), 5.42 (d, J=5.9 Hz, 1H), 5.31 (d, J=3.5 Hz, 1H), 4.77 (d, J=7.2 Hz, 1H), 4.68 (d, J=6.0 Hz, 2H), 4.65-4.58 (m, 1H), 4.46-4.37 (m, 1H), 3.25 (dd, J=10.6, 4.6 Hz, 1H), 2.82 (dd, J=10.7, 3.6 Hz, 1H).

LC-MS MS(EI) for C16H17N5O2S [M+H]$^{+}$ (Calcd.: 343.11) Found: 344.1.

Example 6: Synthesis of (2S,3R,4S)-2-(8-((3-iodobenzyl)amino)-[1,2,4]triazolo[4,3-a]pyrazin-3-yl)tetrahydrothiophene-3,4-diol $^{1}$H-NMR (DMSO-d$_{6}$, 400 MHz): δ 8.80 (t, J=6.1 Hz, 1H), 7.73 (s, 1H), 7.70 (d, J=4.8 Hz, 1H), 7.58 (d, J=7.8 Hz, 1H), 7.36 (d, J=7.7 Hz, 1H), 7.26 (d, J=4.8 Hz, 1H), 7.11 (t, J=7.8 Hz, 1H), 5.43 (d, J=5.9 Hz, 1H), 5.31 (d, J=4.3 Hz, 1H), 4.77 (d, J=7.2 Hz, 1H), 4.63 (d, J=6.5 Hz, 3H), 4.44-4.38 (m, 1H), 3.26 (dd, J=10.7, 4.6 Hz, 1H), 2.82 (dd, J=10.7, 3.7 Hz, 1H).

LC-MS MS(EI) for C16H16IN5O2S [M+H]$^{+}$ (Calcd.: 469.01) Found: 470.0.

Example 7: Synthesis of (2S,3R,4S)-2-(8-((cyclopropylmethyl)amino)-[1,2,4]triazolo[4,3-a]pyrazin-3-yl)tetrahydrothiophene-3,4-diol $^{1}$H-NMR (DMSO-d$_{6}$, 400 MHz): δ 8.23 (t, J=4.7 Hz, 1H), 7.65 (d, J=4.8 Hz, 1H), 7.27 (d, J=4.8 Hz, 1H), 5.42 (d, J=6.1 Hz, 1H), 5.31 (d, J=4.4 Hz, 1H), 4.76 (d, J=7.2 Hz, 1H), 4.63 (ddd, J=9.6, 6.7, 3.3 Hz, 1H), 4.44-4.37 (m, 1H), 3.25 (dd, J=10.7, 4.5 Hz, 1H), 2.82 (dd, J=10.7, 3.7 Hz, 1H), 1.27-1.12 (m, 2H), 0.47-0.38 (m, 2H), 0.31-0.23 (m, 2H).

LC-MS MS(EI) for C13H17N5O2S [M+H]$^{+}$ (Calcd.: 307.11) Found: 308.1.

Example 8: Synthesis of (2S,3R,4S)-2-(8-(cyclobutylamino)-[1,2,4]triazolo[4,3-a]pyrazin-3-yl)tetrahydrothiophene-3,4-diol $^{1}$H-NMR (DMSO-d$_{6}$, 400 MHz):) δ 8.40 (d, J=7.5 Hz, 2H), 7.65 (d, J=4.8 Hz, 2H), 7.26 (d, J=4.8 Hz, 2H), 5.41 (d, J=6.1 Hz, 2H), 5.30 (d, J=4.4 Hz, 2H), 4.76 (d, J=7.2 Hz, 2H), 4.69-4.54 (m, 4H), 4.45-4.36 (m, 2H), 3.25 (dd, J=10.6, 4.5 Hz, 2H), 2.81 (dd, J=10.6, 3.7 Hz, 2H), 2.23 (dd, J=13.2, 5.3 Hz, 5H), 2.20-2.08 (m, 4H), 1.75-1.60 (m, 4H).

LC-MS MS(EI) for C13H17N5O2S [M+H]$^{+}$ (Calcd.: 307.11) Found: 308.1.

Example 9: Synthesis of (2S,3R,4S)-2-(8-((3-(trifluoromethyl)benzyl)amino)-[1,2,4]triazolo[4,3-a]pyrazin-3-yl)tetrahydrothiophene-3,4-diol $^{1}$H-NMR (DMSO-d$_{6}$, 400 MHz): δ 8.87 (t, J=6.2 Hz, 1H), 7.76-7.69 (m, 2H), 7.66 (d, J=7.5 Hz, 1H), 7.56 (dt, J=15.3, 7.8 Hz, 2H), 7.26 (d, J=4.8 Hz, 1H), 5.42 (d, J=5.8 Hz, 1H), 5.31 (d, J=3.8 Hz, 1H), 4.77 (t, J=7.1 Hz, 3H), 4.63 (dd, J=9.0, 6.6 Hz, 1H), 4.44-4.38 (m, 1H), 3.25 (dd, J=10.6, 4.6 Hz, 1H), 2.82 (dd, J=10.7, 3.7 Hz, 1H).

LC-MS MS(EI) for C17H16F3N5O2S [M+H]$^{+}$ (Calcd.: 411.10) Found: 412.1.

Example 10: Synthesis of (2S,3R,4S)-2-(8-((thiophen-3-ylmethyl)amino)-[1,2,4]triazolo[4,3-a]pyrazin-3-yl)tetrahydrothiophene-3,4-diol $^{1}$H-NMR (DMSO-d$_{6}$, 400 MHz): δ 8.65 (t, J=6.3 Hz, 1H), 7.68 (d, J=4.7 Hz, 1H), 7.49-7.39 (m, 1H), 7.34-7.25 (m, 2H), 7.11 (d, J=4.2 Hz, 1H), 5.42 (d, J=5.6 Hz, 1H), 5.30 (d, J=3.3 Hz, 1H), 4.76 (d, J=7.2 Hz, 1H), 4.72-4.57 (m, 3H), 4.40 (s, 1H), 3.25 (dd, J=10.6, 4.4 Hz, 1H), 2.84-2.77 (m, 1H).

LC-MS MS(EI) for C14H15N5O2S2 [M+H]$^{+}$ (Calcd.: 349.07) Found: 350.1.

Example 11: Synthesis of (2S,3R,4S)-2-(8-(phenethylamino)-[1,2,4]triazolo[4,3-a]pyrazin-3-yl)tetrahydrothiophene-3,4-diol $^{1}$H-NMR (DMSO-d$_{6}$, 400 MHz): δ 8.22 (t, J=5.8 Hz, 1H), 7.67 (d, J=4.8 Hz, 1H), 7.34-7.22 (m, 5H), 7.22-7.16 (m, 1H), 5.42 (d, J=6.1 Hz, 1H), 5.31 (d, J=4.4 Hz, 1H), 4.76 (d, J=7.2 Hz, 1H), 4.66-4.59 (m, 1H), 4.44-4.37 (m, 1H), 3.70 (dd, J=13.6, 6.5 Hz, 2H), 3.25 (dd, J=10.7, 4.6 Hz, 1H), 2.94 (t, J=7.5 Hz, 2H), 2.82 (dd, J=10.6, 3.7 Hz, 1H).

LC-MS MS(EI) for C17H19N5O2S [M+H]$^{+}$ (Calcd.: 357.13) Found: 358.1.

Example 12: Synthesis of (2S,3R,4S)-2-(8-((3-methylbenzyl)amino)-[1,2,4]triazolo[4,3-a]pyrazin-3-yl)tetrahydrothiophene-3,4-diol $^{1}$H-NMR (DMSO-d$_{6}$, 400 MHz):) δ 8.72 (t, J=6.2 Hz, 1H), 7.68 (d, J=4.8 Hz, 1H), 7.26 (d, J=4.8 Hz, 1H), 7.15 (m, 3H), 7.02 (d, J=7.2 Hz, 1H), 5.43 (d, J=6.1 Hz, 1H), 5.32 (d, J=4.3 Hz, 1H), 4.77 (d, J=7.2 Hz, 1H), 4.69-4.60 (m, 3H), 4.44-4.38 (m, 1H), 3.26 (dd, J=10.7, 4.6 Hz, 1H), 2.82 (dd, J=10.7, 3.7 Hz, 1H), 2.26 (s, 3H).

LC-MS MS(EI) for C17H19N5O2S [M+H]$^{+}$ (Calcd.: 357.13) Found: 358.1.

Example 13: Synthesis of (2S,3R,4S)-2-(8-((3-fluorobenzyl)amino)-[1,2,4]triazolo[4,3-a]pyrazin-3-yl)tetrahydrothiophene-3,4-diol $^{1}$H-NMR (DMSO-d$_{6}$, 400 MHz): δ 8.77 (t, J=6.4 Hz, 1H), 7.67 (d, J=4.8 Hz, 1H), 7.30 (m, 1H), 7.22 (d, J=4.8 Hz, 1H), 7.18-7.09 (m, 2H), 7.00 (m, 1H), 5.40 (d, J=4.9 Hz, 1H), 5.28 (d, J=3.1 Hz, 1H), 4.74 (d, J=7.1 Hz, 1H), 4.65 (d, J=6.1 Hz, 2H), 4.59 (s, 1H), 4.37 (s, 1H), 3.22 (dd, J=10.7, 4.5 Hz, 1H), 2.78 (dd, J=10.6, 3.5 Hz, 1H).

LC-MS MS(EI) for C16H16FN5O2S [M+H]$^{+}$ (Calcd.: 361.10) Found: 362.1.

Example 14: Synthesis of (2S,3R,4S)-2-(8-((3-(trifluoromethoxy)benzyl)amino)-[1,2,4]triazolo[4,3-a]pyrazin-3-yl)tetrahydrothiophene-3,4-diol $^{1}$H-NMR (DMSO-d$_{6}$, 400 MHz): δ 8.84 (t, J=6.0 Hz, 1H), 7.71 (d, J=4.8 Hz, 1H), 7.47-7.32 (m, 3H), 7.26 (d, J=4.8 Hz, 1H), 7.21 (d, J=8.0 Hz, 1H), 5.43 (d, J=6.0 Hz, 1H), 5.32 (d, J=4.4 Hz, 1H), 4.78 (d, J=7.2 Hz, 1H), 4.72 (d, J=6.2 Hz, 2H), 4.66-4.59 (m, 1H), 4.46-4.37 (m, 1H), 3.26 (dd, J=10.6, 4.5 Hz, 1H), 2.82 (dd, J=10.7, 3.7 Hz, 1H).

LC-MS MS(EI) for C17H16F3N5O3S [M+H]⁺ (Calcd.: 427.09) Found: 428.1.

Example 15: Synthesis of (2S,3R,4S)-2-(8-((3-methoxybenzyl)amino)-[1,2,4]triazolo[4,3-a]pyrazin-3-yl)tetrahydrothiophene-3,4-diol ¹H-NMR (DMSO-d₆, 400 MHz): δ 8.72 (t, J=6.2 Hz, 1H), 7.68 (d, J=4.8 Hz, 1H), 7.26 (d, J=4.8 Hz, 1H), 7.20 (t, J=7.8 Hz, 1H), 6.95-6.89 (m, 2H), 6.81-6.75 (m, 1H), 5.42 (s, 1H), 5.31 (s, 1H), 4.77 (d, J=7.2 Hz, 1H), 4.69-4.59 (m, 3H), 4.41 (s, 1H), 3.71 (s, 3H), 3.26 (dd, J=10.7, 4.6 Hz, 1H), 2.82 (dd, J=10.6, 3.5 Hz, 1H).
LC-MS MS(EI) for C17H19N5O3S [M+H]⁺ (Calcd.: 373.12) Found: 374.1.

Example 16: Synthesis of 3-(((3-((2S,3R,4S)-3,4-dihydroxytetrahydrothiophen-2-yl)-[1,2,4]triazolo[4,3-a]pyrazin-8-yl)amino)methyl)benzonitrile ¹H-NMR (DMSO-d₆, 400 MHz): δ 8.83 (t, J=6.1 Hz, 1H), 7.79 (s, 1H), 7.70 (t, J=6.9 Hz, 3H), 7.52 (t, J=7.7 Hz, 1H), 7.26 (d, J=4.8 Hz, 1H), 5.42 (s, 1H), 5.32 (s, 1H), 4.78 (d, J=7.2 Hz, 1H), 4.72 (d, J=6.0 Hz, 2H), 4.63 (s, 1H), 4.41 (s, 1H), 3.26 (dd, J=10.6, 4.6 Hz, 1H), 2.82 (dd, J=10.7, 3.7 Hz, 1H).
LC-MS MS(EI) for C17H16N6O2S [M+H]⁺ (Calcd.: 368.11) Found: 369.1.

Example 17: Synthesis of (2S,3R,4S)-2-(8-((3-bromobenzyl)amino)-[1,2,4]triazolo[4,3-a]pyrazin-3-yl)tetrahydrothiophene-3,4-diol ¹H-NMR (DMSO-d₆, 400 MHz): δ 8.82 (t, J=6.1 Hz, 1H), 7.71 (d, J=4.8 Hz, 1H), 7.54 (s, 1H), 7.41 (d, J=7.9 Hz, 1H), 7.35 (d, J=7.9 Hz, 1H), 7.30-7.23 (m, 2H), 5.44 (d, J=6.0 Hz, 1H), 5.32 (d, J=4.4 Hz, 1H), 4.77 (d, J=7.2 Hz, 1H), 4.67 (d, J=6.1 Hz, 2H), 4.65-4.59 (m, 1H), 4.44-4.38 (m, 1H), 3.26 (dd, J=10.7, 4.5 Hz, 1H), 2.82 (dd, J=10.7, 3.7 Hz, 1H).
LC-MS MS(EI) for C16H16BrN5O2S [M+H]⁺ (Calcd.: 421.02) Found: 422.0.

Example 18: Synthesis of (2S,3R,4S)-2-(8-((cyclohexylmethyl)amino)-[1,2,4]triazolo[4,3-a]pyrazin-3-yl)tetrahydrothiophene-3,4-diol ¹H-NMR (DMSO-d₆, 400 MHz): δ 8.18 (t, J=6.0 Hz, 1H), 7.63 (d, J=4.8 Hz, 1H), 7.27 (d, J=4.8 Hz, 1H), 5.43 (d, J=6.0 Hz, 1H), 5.32 (d, J=4.3 Hz, 1H), 4.76 (d, J=7.2 Hz, 1H), 4.67-4.59 (m, 1H), 4.45-4.37 (m, 1H), 3.25 (dd, J=10.7, 4.6 Hz, 1H), 2.82 (dd, J=10.7, 3.7 Hz, 1H), 1.75-1.57 (m, 6H), 1.21-1.09 (m, 3H), 1.00-0.86 (m, 2H).
LC-MS MS(EI) for C16H23N5O2S [M+H]⁺ (Calcd.: 349.16) Found: 350.1.

Example 19: Synthesis of (2S,3R,4S)-2-(8-(cyclopentylamino)-[1,2,4]triazolo[4,3-a]pyrazin-3-yl)tetrahydrothiophene-3,4-diol ¹H-NMR (DMSO-d₆, 400 MHz): δ 8.04 (d, J=7.4 Hz, 1H), 7.64 (d, J=4.8 Hz, 1H), 7.28 (d, J=4.8 Hz, 1H), 5.42 (d, J=6.1 Hz, 1H), 5.31 (d, J=4.3 Hz, 1H), 4.76 (d, J=7.2 Hz, 1H), 4.68-4.54 (m, 1H), 4.50-4.33 (m, 2H), 3.25 (dd, J=10.6, 4.6 Hz, 1H), 2.82 (dd, J=10.7, 3.7 Hz, 1H), 2.01-1.85 (m, 2H), 1.76-1.59 (m, 4H), 1.59-1.48 (m, 2H).
LC-MS MS(EI) for C14H19N5O2S [M+H]⁺ (Calcd.: 321.13) Found: 322.1.

Example 20: Synthesis of (2S,3R,4S)-2-(8-(cyclohexylamino)-[1,2,4]triazolo[4,3-a]pyrazin-3-yl)tetrahydrothiophene-3,4-diol ¹H-NMR (DMSO-d₆, 400 MHz): δ 7.90 (d, J=8.2 Hz, 1H), 7.64 (d, J=4.8 Hz, 1H), 7.27 (d, J=4.8 Hz, 1H), 5.42 (d, J=6.0 Hz, 1H), 5.31 (d, J=4.3 Hz, 1H), 4.76 (d, J=7.2 Hz, 1H), 4.66-4.59 (m, 1H), 4.44-4.38 (m, 1H), 4.04 (s, 1H), 3.29-3.22 (m, 1H), 2.82 (dd, J=10.7, 3.7 Hz, 1H), 1.88 (d, J=12.2 Hz, 2H), 1.74 (d, J=13.1 Hz, 2H), 1.62 (d, J=12.4 Hz, 1H), 1.49-1.07 (m, 6H).
LC-MS MS(EI) for C15H21N5O2S [M+H]⁺ (Calcd.: 335.14) Found: 336.1.

Example 21: Synthesis of (2S,3R,4S)-2-(8-((pyridin-3-ylmethyl)amino)-[1,2,4]triazolo[4,3-a]pyrazin-3-yl)tetrahydrothiophene-3,4-diol 2,2,2-trifluoroacetic acid ¹H-NMR (DMSO-d₆, 400 MHz): δ 8.83 (t, J=6.2 Hz, 1H), 8.58 (d, J=1.7 Hz, 1H), 8.42 (dd, J=4.8, 1.5 Hz, 1H), 7.75 (d, J=7.9 Hz, 1H), 7.70 (d, J=4.8 Hz, 1H), 7.32 (dd, J=7.8, 4.7 Hz, 1H), 7.27 (d, J=4.8 Hz, 1H), 5.43 (d, J=6.1 Hz, 1H), 5.32 (d, J=4.3 Hz, 1H), 4.77 (d, J=7.2 Hz, 1H), 4.69 (d, J=6.2 Hz, 2H), 4.65-4.58 (m, 1H), 4.43-4.38 (m, 1H), 3.30-3.22 (m, 1H), 2.81 (dd, J=10.6, 3.6 Hz, 1H).
LC-MS MS(EI) for C15H16N6O2S [M+H]⁺ (Calcd.: 344.11) Found: 345.1.

Example 22: Synthesis of (2S,3R,4S)-2-(8-((pyridin-4-ylmethyl)amino)-[1,2,4]triazolo[4,3-a]pyrazin-3-yl)tetrahydrothiophene-3,4-diol 2,2,2-trifluoroacetic acid ¹H-NMR (DMSO-d₆, 400 MHz): δ 8.86 (t, J=6.3 Hz, 1H), 8.46 (dd, J=4.4, 1.6 Hz, 2H), 7.72 (d, J=4.8 Hz, 1H), 7.31 (d, J=5.9 Hz, 2H), 7.23 (d, J=4.8 Hz, 1H), 5.44 (d, J=6.1 Hz, 1H), 5.33 (d, J=4.3 Hz, 1H), 4.78 (d, J=7.2 Hz, 1H), 4.69 (d, J=6.0 Hz, 2H), 4.67-4.59 (m, 1H), 4.45-4.38 (m, 1H), 3.30-3.23 (m, 1H), 2.82 (dd, J=10.6, 3.6 Hz, 1H).
LC-MS MS(EI) for C15H16N6O2S [M+H]⁺ (Calcd.: 344.11) Found: 345.1.

Example 23: Synthesis of (2S,3R,4S)-2-(8-((furan-3-ylmethyl)amino)-[1,2,4]triazolo[4,3-a]pyrazin-3-yl)tetrahydrothiophene-3,4-diol ¹H-NMR (DMSO-d₆, 400 MHz): δ 8.49 (t, J=6.6 Hz, 1H), 7.67 (d, J=4.7 Hz, 1H), 7.55 (d, J=6.7 Hz, 2H), 7.29 (d, J=4.7 Hz, 1H), 6.48 (s, 1H), 5.40 (d, J=6.1 Hz, 1H), 5.29 (d, J=4.4 Hz, 1H), 4.76 (d, J=7.1 Hz, 1H), 4.65-4.58 (m, 1H), 4.49 (d, J=5.7 Hz, 2H), 4.43-4.36 (m, 1H), 3.24 (dd, J=10.6, 4.6 Hz, 1H), 2.81 (dd, J=10.3, 3.3 Hz, 1H).
LC-MS MS(EI) for C14H15N5O3S [M+H]⁺ (Calcd.: 333.09) Found: 334.1.

Example 24: Synthesis of (2S,3R,4S)-2-(8-((3-chlorophenethyl)amino)-[1,2,4]triazolo[4,3-a]pyrazin-3-yl)tetrahydrothiophene-3,4-diol ¹H-NMR (DMSO-d₆, 400 MHz): δ 8.26 (t, J=5.7 Hz, 1H), 7.67 (d, J=4.8 Hz, 1H), 7.34 (dd, J=5.0, 3.4 Hz, 1H), 7.32-7.28 (m, 2H), 7.28-7.19 (m, 2H), 5.43 (d, J=6.1 Hz, 1H), 5.32 (d, J=4.4 Hz, 1H), 4.76 (d, J=7.2 Hz, 1H), 4.66-4.59 (m, 1H), 4.43-4.37 (m, 1H), 3.71 (dd, J=12.6, 6.5 Hz, 2H), 3.25 (dd, J=10.6, 4.6 Hz, 1H), 2.96 (t, J=7.2 Hz, 2H), 2.82 (dd, J=10.7, 3.7 Hz, 1H).

LC-MS MS(EI) for $C_{17}H_{18}ClN_5O_2S$ $[M+H]^{+}$ (Calcd.: 391.09) Found: 392.1.

Example 25: Synthesis of (2S,3R,4S)-2-(8-((3-bromophenethyl)amino)-[1,2,4]triazolo[4,3-a]pyrazin-3-yl)tetrahydrothiophene-3,4-diol $^1$H-NMR (DMSO-$d_6$, 400 MHz): δ 8.26 (t, J=5.2 Hz, 1H), 7.67 (d, J=4.8 Hz, 1H), 7.48 (s, 1H), 7.40-7.35 (m, 1H), 7.30 (d, J=4.8 Hz, 1H), 7.24 (d, J=6.2 Hz, 2H), 5.43 (d, J=6.0 Hz, 1H), 5.32 (d, J=4.4 Hz, 1H), 4.76 (d, J=7.1 Hz, 1H), 4.65-4.59 (m, 1H), 4.45-4.36 (m, 1H), 3.70 (dd, J=12.9, 5.1 Hz, 2H), 3.25 (dd, J=10.6, 4.6 Hz, 1H), 2.95 (t, J=7.2 Hz, 2H), 2.81 (dd, J=10.6, 3.8 Hz, 1H).

LC-MS MS(EI) for $C_{17}H_{18}BrN_5O_2S$ $[M+H]^{+}$ (Calcd.: 435.04) Found: 436.0.

Example 26: Synthesis of (2S,3R,4S)-2-(8-((3-fluorophenethyl)amino)-[1,2,4]triazolo[4,3-a]pyrazin-3-yl)tetrahydrothiophene-3,4-diol $^1$H-NMR (DMSO-$d_6$, 400 MHz): δ 8.24 (t, J=5.6 Hz, 1H), 7.67 (d, J=4.8 Hz, 1H), 7.36-7.27 (m, 2H), 7.10 (t, J=7.7 Hz, 2H), 7.06-6.97 (m, 1H), 5.42 (d, J=6.1 Hz, 1H), 5.31 (d, J=4.4 Hz, 1H), 4.76 (d, J=7.2 Hz, 1H), 4.66-4.59 (m, 1H), 4.44-4.38 (m, 1H), 3.72 (dd, J=13.2, 6.7 Hz, 2H), 3.29-3.22 (m, 1H), 2.97 (t, J=7.2 Hz, 2H), 2.82 (dd, J=10.7, 3.8 Hz, 1H).

LC-MS MS(EI) for $C_{17}H_{18}FN_5O_2S$ $[M+H]^{+}$ (Calcd.: 375.12) Found: 376.1.

Example 27: Synthesis of (2S,3R,4S)-2-(8-((2-phenylcyclopropyl)amino)-[1,2,4]triazolo[4,3-a]pyrazin-3-yl)tetrahydrothiophene-3,4-diol $^1$H-NMR (DMSO-$d_6$, 400 MHz): δ 8.61 (s, 1H), 7.71 (d, J=4.8 Hz, 1H), 7.27 (dd, J=12.1, 6.0 Hz, 2H), 7.16 (d, J=6.6 Hz, 2H), 5.37 (s, 2H), 4.76 (d, J=7.2 Hz, 1H), 4.61 (dd, J=7.0, 3.0 Hz, 1H), 4.39 (dd, J=7.3, 3.8 Hz, 1H), 3.25 (dd, J=10.7, 4.6 Hz, 1H), 3.20-3.12 (m, 1H), 2.81 (dd, J=10.7, 3.7 Hz, 1H), 2.16-2.08 (m, 1H), 1.50 (dt, J=13.9, 4.7 Hz, 1H), 1.25 (dt, J=10.3, 5.0 Hz, 1H).

LC-MS MS(EI) for $C_{18}H_{19}N_5O_2S$ $[M+H]^{+}$ (Calcd.: 369.13) Found: 370.1.

Example 28: Synthesis of (2S,3R,4S)-2-(8-((2-(3-chlorophenyl)propan-2-yl)amino)-[1,2,4]triazolo[4,3-a]pyrazin-3-yl)tetrahydrothiophene-3,4-diol $^1$H-NMR (DMSO-$d_6$, 400 MHz): δ 7.99 (s, 1H), 7.64 (d, J=4.8 Hz, 1H), 7.42 (t, J=1.7 Hz, 1H), 7.38-7.34 (m, 1H), 7.28 (t, J=7.8 Hz, 1H), 7.24-7.20 (m, 1H), 7.08 (d, J=4.8 Hz, 1H), 5.51-5.30 (m, 2H), 4.77 (d, J=7.3 Hz, 1H), 4.61 (dd, J=7.2, 3.3 Hz, 1H), 4.42-4.37 (m, 1H), 3.26 (dd, J=10.8, 4.6 Hz, 1H), 2.81 (dd, J=10.7, 3.5 Hz, 1H), 1.78 (s, 6H).

LC-MS MS(EI) for $C_{18}H_{20}ClN_5O_2S$ $[M+H]^{+}$ (Calcd.: 405.10) Found: 406.1.

Example 29: Synthesis of (2S,3R,4S)-2-(8-((1-(3-chlorophenyl)cyclopropyl)amino)-[1,2,4]triazolo[4,3-a]pyrazin-3-yl)tetrahydrothiophene-3,4-diol $^1$H-NMR (DMSO-$d_6$, 400 MHz): δ 9.05 (s, 1H), 7.73 (d, J=4.8 Hz, 1H), 7.30-7.12 (m, 5H), 5.45 (d, J=5.0 Hz, 1H), 5.34 (d, J=3.8 Hz, 1H), 4.79 (d, J=7.3 Hz, 1H), 4.63 (s, 1H), 4.41 (s, 1H), 3.27 (dd, J=10.6, 4.4 Hz, 1H), 2.82 (dd, J=10.7, 3.6 Hz, 1H), 1.36 (s, 4H).

LC-MS MS(EI) for $C_{18}H_{18}ClN_5O_2S$ $[M+H]^{+}$ (Calcd.: 403.09) Found: 404.1.

Example 30: Synthesis of (2S,3R,4S)-2-(8-((3-chlorophenyl)ethynyl)-[1,2,4]triazolo[4,3-a]pyrazin-3-yl)tetrahydrothiophene-3,4-diol $^1$H-NMR (DMSO-$d_6$, 400 MHz):) δ 7.99-7.93 (m, 2H), 7.67-7.54 (m, 3H), 7.18 (d, J=5.2 Hz, 1H), 6.89 (s, 1H), 5.49 (d, J=6.0 Hz, 1H), 5.36 (d, J=4.4 Hz, 1H), 4.74 (d, J=7.2 Hz, 1H), 4.63-4.55 (m, 1H), 4.45-4.38 (m, 1H), 3.28-3.22 (m, 1H), 2.83 (dd, J=10.8, 3.5 Hz, 1H).

LC-MS MS(EI) for $C_{17}H_{13}ClN_4O_2S$ $[M+H]^{+}$ (Calcd.: 372.04) Found: 373.0.

Example 31: Synthesis of (2S,3R,4S)-2-(8-(cyclopropylamino)-[1,2,4]triazolo[4,3-a]pyrazin-3-yl)tetrahydrothiophene-3,4-diol $^1$H-NMR (DMSO-$d_6$, 400 MHz): δ 8.33 (d, J=4.0 Hz, 1H), 7.71 (d, J=4.8 Hz, 1H), 7.33 (d, J=4.8 Hz, 1H), 5.42 (d, J=6.1 Hz, 1H), 5.31 (d, J=4.4 Hz, 1H), 4.77 (d, J=7.2 Hz, 1H), 4.63 (ddd, J=7.2, 6.2, 3.2 Hz, 1H), 4.40 (dt, J=8.1, 4.0 Hz, 1H), 3.25 (dd, J=10.6, 4.5 Hz, 1H), 2.98-2.90 (m, 1H), 2.82 (dd, J=10.7, 3.7 Hz, 1H), 0.72 (d, J=7.3 Hz, 2H), 0.66 (d, J=3.8 Hz, 2H).

LC-MS MS(EI) for $C_{12}H_{15}N_5O_2S$ $[M+H]^{+}$ (Calcd.: 293.09) Found: 294.1.

Example 32: Synthesis of (2S,3R,4S)-2-(8-(isopentylamino)-[1,2,4]triazolo[4,3-a]pyrazin-3-yl)tetrahydrothiophene-3,4-diol $^1$H-NMR (DMSO-$d_6$, 400 MHz): δ 8.13 (t, J=5.8 Hz, 1H), 7.63 (d, J=4.8 Hz, 1H), 7.28 (d, J=4.8 Hz, 1H), 5.43 (d, J=5.9 Hz, 1H), 5.32 (d, J=4.0 Hz, 1H), 4.76 (d, J=7.2 Hz, 1H), 4.63 (td, J=6.6, 3.3 Hz, 1H), 4.45-4.37 (m, 1H), 3.48 (dd, J=13.5, 6.2 Hz, 2H), 3.25 (dd, J=10.6, 4.6 Hz, 1H), 2.82 (dd, J=10.7, 3.7 Hz, 1H), 1.62 (td, J=13.2, 6.6 Hz, 1H), 1.51 (dd, J=14.3, 7.0 Hz, 2H), 0.91 (d, J=6.6 Hz, 6H).

LC-MS MS(EI) for $C_{14}H_{21}N_5O_2S$ $[M+H]^{+}$ (Calcd.: 323.14) Found: 324.1.

Example 33: Synthesis of (2S,3R,4S)-2-(8-((2-morpholinoethyl)amino)-[1,2,4]triazolo[4,3-a]pyrazin-3-yl)tetrahydrothiophene-3,4-diol $^1$H-NMR (DMSO-$d_6$, 400 MHz): δ 7.95 (t, J=5.7 Hz, 2H), 7.67 (d, J=4.8 Hz, 2H), 7.29 (d, J=4.8 Hz, 2H), 5.44 (d, J=5.9 Hz, 2H), 5.33 (d, J=4.2 Hz, 2H), 4.77 (d, J=7.2 Hz, 2H), 4.63 (td, J=7.1, 3.4 Hz, 2H), 4.44-4.38 (m, 2H), 3.58 (dt, J=9.1, 5.5 Hz, 12H), 3.25 (dd, J=10.6, 4.6 Hz, 2H), 2.82 (dd, J=10.7, 3.7 Hz, 2H), 2.56 (t, J=6.7 Hz, 5H), 2.43 (d, J=3.8 Hz, 8H).

LC-MS MS(EI) for $C_{15}H_{22}N_6O_3S$ $[M+H]^{+}$ (Calcd.: 366.15) Found: 367.1.

Example 34: Synthesis of 3-chloro-N-(3-((2S,3R,4S)-3,4-dihydroxytetrahydrothiophen-2-yl)-[1,2,4]triazolo[4,3-a]pyrazin-8-yl)benzenesulfonamide $^1$H-NMR (DMSO-$d_6$, 400 MHz): δ 11.78 (s, 1H), 8.00 (t, J=1.7 Hz, 1H), 7.92 (d, J=7.9 Hz, 1H), 7.79 (d, J=5.2 Hz, 1H), 7.73 (d, J=7.7 Hz, 1H), 7.62 (t, J=7.8 Hz, 1H), 7.07 (d, J=5.0 Hz, 1H), 5.45 (d, J=5.8 Hz, 1H), 5.33 (d, J=4.0 Hz, 1H), 4.73 (d, J=7.0 Hz, 1H), 4.54 (td, J=6.5, 3.5 Hz, 1H), 4.40 (dd, J=7.2, 3.6 Hz, 1H), 3.23 (dd, J=10.6, 4.6 Hz, 1H), 2.81 (dd, J=10.7, 3.8 Hz, 1H).

LC-MS MS(EI) for C15H14ClN5O4S2 [M+H]+' (Calcd.: 427.02) Found: 428.0.

Example 35: Synthesis of (2S,3R,4R)-2-(8-((3-chlorobenzyl)amino)-[1,2,4]triazolo[4,3-a]pyrazin-3-yl)tetrahydrofuran-3,4-diol $^1$H-NMR (DMSO-d$_6$, 400 MHz): δ 8.70 (t, J=6.4 Hz, 1H), 7.72 (d, J=4.9 Hz, 1H), 7.40 (s, 1H), 7.37-7.25 (m, 3H), 7.18 (d, J=4.9 Hz, 1H), 5.49 (d, J=4.3 Hz, 1H), 5.31 (d, J=4.0 Hz, 1H), 5.20 (d, J=6.2 Hz, 1H), 4.70-4.63 (m, 2H), 4.46-4.36 (m, 1H), 4.29 (dd, J=8.7, 4.5 Hz, 1H), 3.95 (dd, J=8.2, 6.7 Hz, 1H), 3.87-3.80 (m, 1H).

LC-MS MS(EI) for C16H16ClN5O3 [M+H]+' (Calcd.: 361.09) Found: 362.1.

Example 36: Synthesis of (2S,3R,4S)-2-(8-((imidazo[1,2-a]pyridin-2-ylmethyl)amino)-[1,2,4]triazolo[4,3-a]pyrazin-3-yl)tetrahydrothiophene-3,4-diol $^1$H-NMR (DMSO-d$_6$, 400 MHz): δ 8.63-8.56 (m, 1H), 8.44 (dt, J=6.7, 1.0 Hz, 1H), 7.74-7.69 (m, 2H), 7.47 (dd, J=9.0, 0.7 Hz, 1H), 7.28 (d, J=4.8 Hz, 1H), 7.18 (ddd, J=9.1, 6.7, 1.3 Hz, 1H), 6.82 (td, J=6.8, 1.2 Hz, 1H), 5.54-5.47 (m, 1H), 5.38 (d, J=3.7, 1.9 Hz, 1H), 4.83-4.77 (m, 3H), 4.68-4.60 (m, 1H), 4.46-4.39 (m, 1H), 3.27 (dd, J=10.0, 3.9 Hz, 1H), 2.83 (dd, J=10.6, 3.7 Hz, 1H).

LC-MS MS(EI) for C17H17N7O2S [M+H]+' (Calcd.: 383.12) Found: 384.1.

Example 37: Synthesis of (2S,3R,4S)-2-(8-amino-[1,2,4]triazolo[4,3-a]pyrazin-3-yl)tetrahydrothiophene-3,4-diol $^1$H-NMR (DMSO-d$_6$, 400 MHz): δ 7.66 (d, J=4.8 Hz, 2H), 7.52 (s, 2H), 7.23 (d, J=4.8 Hz, 2H), 7.06 (dd, J=6.8, 2.9 Hz, 3H), 5.35 (d, J=6.4 Hz, 2H), 5.25 (d, J=3.3 Hz, 2H), 4.63 (d, J=7.6 Hz, 2H), 4.25 (dd, J=8.0, 3.9 Hz, 4H), 3.24 (d, J=10.8 Hz, 2H), 2.76 (dd, J=11.0, 2.5 Hz, 2H).

LC-MS MS(EI) for C9H11N5O2S [M+H]+' (Calcd.: 253.06) Found: 254.1.

Example 38: Synthesis of (2S,3R,4R)-2-(8-((3-iodobenzyl)amino)-[1,2,4]triazolo[4,3-a]pyrazin-3-yl)tetrahydrofuran-3,4-diol $^1$H-NMR (DMSO-d$_6$, 400 MHz): δ 8.68 (t, J=6.3 Hz, 1H), 7.75-7.69 (m, 2H), 7.58 (d, J=7.9 Hz, 1H), 7.37 (d, J=8.1 Hz, 1H), 7.18 (d, J=4.8 Hz, 1H), 7.11 (t, J=7.8 Hz, 1H), 5.49 (d, J=4.2 Hz, 1H), 5.28 (d, J=4.4 Hz, 1H), 5.17 (d, J=6.2 Hz, 1H), 4.68-4.60 (m, 2H), 4.41 (dd, J=11.9, 5.6 Hz, 1H), 4.29 (q, J=4.4 Hz, 1H), 3.95 (dd, J=8.1, 6.7 Hz, 1H), 3.88-3.80 (m, 1H).

LC-MS MS(EI) for C16H16IN5O3 [M+H]+' (Calcd.: 453.03) Found: 454.0.

Example 39: Synthesis of (2S,3R,4R)-2-(8-((3-chlorophenethyl)amino)-[1,2,4]triazolo[4,3-a]pyrazin-3-yl)tetrahydrofuran-3,4-diol $^1$H-NMR (DMSO-d$_6$, 400 MHz): δ 8.11 (t, J=5.7 Hz, 1H), 7.69 (d, J=4.9 Hz, 1H), 7.35 (t, J=1.7 Hz, 1H), 7.34-7.28 (m, 1H), 7.28-7.19 (m, 3H), 5.48 (d, J=4.2 Hz, 1H), 5.29 (d, J=4.4 Hz, 1H), 5.19 (d, J=6.3 Hz, 1H), 4.46-4.37 (m, 1H), 4.28 (q, J=4.4 Hz, 1H), 3.95 (dd, J=8.2, 6.7 Hz, 1H), 3.87-3.80 (m, 1H), 3.70 (dd, J=13.2, 7.0 Hz, 2H), 2.96 (t, J=7.2 Hz, 2H).

LC-MS MS(EI) for C17H18ClN5O3 [M+H]+' (Calcd.: 375.11) Found: 376.1.

Example 40: Synthesis of 4-(((3-((2S,3R,4S)-3,4-dihydroxytetrahydrothiophen-2-yl)-[1,2,4]triazolo[4,3-a]pyrazin-8-yl)amino)methyl)-2-fluoro-N-methylbenzamide $^1$H-NMR (DMSO-d$_6$, 400 MHz): δ 8.83 (t, J=6.1 Hz, 1H), 8.15 (s, 1H), 7.71 (d, J=4.8 Hz, 1H), 7.55 (t, J=7.8 Hz, 1H), 7.32-7.15 (m, 3H), 5.42 (d, J=6.1 Hz, 1H), 5.31 (d, J=4.4 Hz, 1H), 4.78 (d, J=7.2 Hz, 1H), 4.70 (d, J=6.1 Hz, 2H), 4.67-4.59 (m, 1H), 4.46-4.37 (m, 1H), 3.26 (dd, J=10.7, 4.5 Hz, 1H), 2.82 (dd, J=10.7, 3.7 Hz, 1H), 2.74 (d, J=4.6 Hz, 3H).

LC-MS MS(EI) for C18H19FN6O3S [M+H]+' (Calcd.: 418.12) Found: 419.1.

Example 41: Synthesis of (2S,3R,4S)-2-(8-((4-methylpiperazin-1-yl)amino)-[1,2,4]triazolo[4,3-a]pyrazin-3-yl)tetrahydrothiophene-3,4-diol $^1$H-NMR (DMSO-d$_6$, 400 MHz): δ 9.14 (s, 1H), 7.72 (d, J=4.8 Hz, 1H), 7.31 (d, J=4.8 Hz, 1H), 5.44 (d, J=5.8 Hz, 1H), 5.33 (d, J=4.0 Hz, 1H), 4.77 (d, J=7.2 Hz, 1H), 4.65-4.60 (m, 1H), 4.44-4.37 (m, 1H), 3.26 (dd, J=10.6, 4.6 Hz, 1H), 2.91 (t, J=4.9 Hz, 4H), 2.82 (dd, J=10.7, 3.7 Hz, 1H), 2.43 (s, 4H), 2.18 (s, 3H).

LC-MS MS(EI) for C14H21N7O2S [M+H]+' (Calcd.: 351.15) Found: 352.1.

Example 42: Synthesis of (2S,3R,4S)-2-(8-(morpholinoamino)-[1,2,4]triazolo[4,3-a]pyrazin-3-yl)tetrahydrothiophene-3,4-diol $^1$H-NMR (DMSO-d$_6$, 400 MHz): δ 9.26 (s, 1H), 7.74 (d, J=4.8 Hz, 1H), 7.32 (d, J=4.8 Hz, 1H), 5.45 (d, J=5.8 Hz, 1H), 5.34 (d, J=4.0 Hz, 1H), 4.78 (d, J=7.2 Hz, 1H), 4.66-4.58 (m, 1H), 4.45-4.37 (m, 1H), 3.73-3.64 (m, 4H), 3.26 (dd, J=10.7, 4.6 Hz, 1H), 2.96-2.88 (m, 4H), 2.82 (dd, J=10.7, 3.7 Hz, 1H).

LC-MS MS(EI) for C13H18N6O3S [M+H]+' (Calcd.: 338.12) Found: 339.1.

Example 43: Synthesis of (2S,3R,4S)-2-(8-(((1S,2R)-2-phenylcyclopropyl)amino)-[1,2,4]triazolo[4,3-a]pyrazin-3-yl)tetrahydrothiophene-3,4-diol $^1$H-NMR (DMSO-d$_6$, 400 MHz): δ 8.58 (d, J=4.4 Hz, 1H), 7.71 (d, J=4.8 Hz, 1H), 7.35-7.23 (m, 3H), 7.21-7.13 (m, 3H), 5.43 (d, J=6.1 Hz, 1H), 5.32 (d, J=4.3 Hz, 1H), 4.78 (d, J=7.2 Hz, 1H), 4.62 (td, J=7.0, 3.2 Hz, 1H), 4.44-4.38 (m, 1H), 3.26 (dd, J=10.7, 4.6 Hz, 1H), 3.22-3.14 (m, 1H), 2.82 (dd, J=10.7, 3.7 Hz, 1H), 2.17-2.08 (m, 1H), 1.57-1.48 (m, 1H), 1.31-1.21 (m, 1H).

LC-MS MS(EI) for C18H19N5O2S [M+H]+' (Calcd.: 369.13) Found: 370.1.

Example 44: Synthesis of 2-chloro-4-(((3-((2S,3R,4S)-3,4-dihydroxytetrahydrothiophen-2-yl)-[1,2,4]triazolo[4,3-a]pyrazin-8-yl)amino)methyl)-N-methylbenzamide $^1$H-NMR (DMSO-d$_6$, 400 MHz): δ 8.85 (t, J=6.0 Hz, 1H), 8.29 (q, J=4.6 Hz, 1H), 7.71 (d, J=4.9 Hz, 1H), 7.44 (s, 1H), 7.37-7.30 (m, 2H), 7.26 (d, J=4.8 Hz, 1H), 5.46 (s, 1H), 5.35 (s, 1H), 4.78 (d, J=7.2 Hz, 1H), 4.68 (d, J=6.2 Hz, 2H), 4.66-4.59 (m, 1H), 4.41 (s, 1H), 3.26 (dd, J=10.6, 4.6 Hz, 1H), 2.82 (dd, J=10.7, 3.7 Hz, 1H), 2.72 (d, J=4.6 Hz, 3H).
LC-MS MS(EI) for C18H19ClN6O3S [M+H]$^{+}$ (Calcd.: 434.09) Found: 435.1.

Example 45: Synthesis of (2S,3R,4S)-2-(8-(((S)-1-(3-chlorophenyl)ethyl)amino)-[1,2,4]triazolo[4,3-a]pyrazin-3-yl)tetrahydrothiophene-3,4-diol $^{1}$H-NMR (DMSO-d$_6$, 400 MHz): δ 8.70 (d, J=8.2 Hz, 1H), 7.67 (d, J=4.8 Hz, 1H), 7.53 (t, J=1.8 Hz, 1H), 7.43-7.37 (m, 1H), 7.32 (t, J=7.7 Hz, 1H), 7.28-7.21 (m, 2H), 5.45-5.36 (m, 2H), 5.31 (d, J=4.3 Hz, 1H), 4.76 (d, J=7.2 Hz, 1H), 4.65-4.58 (m, 1H), 4.44-4.37 (m, 1H), 3.26 (dd, J=10.7, 4.6 Hz, 1H), 2.82 (dd, J=10.7, 3.7 Hz, 1H), 1.55 (d, J=7.1 Hz, 3H).
LC-MS MS(EI) for C17H18ClN5O2S [M+H]$^{+}$ (Calcd.: 391.09) Found: 392.1.

Example 46: Synthesis of (2S,3R,4S)-2-(8-(((R)-1-(3-chlorophenyl)ethyl)amino)-[1,2,4]triazolo[4,3-a]pyrazin-3-yl)tetrahydrothiophene-3,4-diol $^{1}$H-NMR (DMSO-d$_6$, 400 MHz): δ 8.71 (d, J=8.2 Hz, 1H), 7.68 (d, J=4.8 Hz, 1H), 7.53 (s, 1H), 7.40 (d, J=7.6 Hz, 1H), 7.32 (t, J=7.8 Hz, 1H), 7.29-7.24 (m, 1H), 7.23 (d, J=4.8 Hz, 1H), 5.48-5.35 (m, 2H), 5.32 (d, J=4.3 Hz, 1H), 4.77 (d, J=7.2 Hz, 1H), 4.66-4.57 (m, 1H), 4.45-4.36 (m, 1H), 3.25 (dd, J=10.6, 4.5 Hz, 1H), 2.81 (dd, J=10.6, 3.6 Hz, 1H), 1.55 (d, J=7.1 Hz, 3H).
LC-MS MS(EI) for C17H18ClN5O2S [M+H]$^{+}$ (Calcd.: 391.09) Found: 392.1.

Example 47: Synthesis of (2S,3R,4S)-2-(8-((2-chlorobenzyl)amino)-[1,2,4]triazolo[4,3-a]pyrazin-3-yl)tetrahydrothiophene-3,4-diol $^{1}$H-NMR (DMSO-d$_6$, 400 MHz): δ 8.76 (t, J=6.1 Hz, 1H), 7.73 (d, J=4.8 Hz, 1H), 7.48-7.42 (m, 1H), 7.32-7.22 (m, 4H), 5.43 (d, J=6.1 Hz, 1H), 5.32 (d, J=4.4 Hz, 1H), 4.80 (d, J=7.2 Hz, 1H), 4.74 (d, J=6.1 Hz, 2H), 4.68-4.61 (m, 1H), 4.45-4.39 (m, 1H), 3.27 (dd, J=10.6, 4.6 Hz, 1H), 2.83 (dd, J=10.7, 3.7 Hz, 1H).
LC-MS MS(EI) for C16H16ClN5O2S [M+H]$^{+}$ (Calcd.: 377.07) Found: 378.1.

Example 48: Synthesis of (2S,3R,4S)-2-(8-((4-chlorobenzyl)amino)-[1,2,4]triazolo[4,3-a]pyrazin-3-yl)tetrahydrothiophene-3,4-diol $^{1}$H-NMR (DMSO-d$_6$, 400 MHz): δ 8.79 (t, J=6.2 Hz, 1H), 7.69 (d, J=4.8 Hz, 1H), 7.42-7.31 (m, 4H), 7.25 (d, J=4.8 Hz, 1H), 5.42 (d, J=6.0 Hz, 1H), 5.31 (d, J=4.2 Hz, 1H), 4.78 (d, J=7.2 Hz, 1H), 4.71-4.58 (m, 3H), 4.45-4.38 (m, 1H), 3.26 (dd, J=10.6, 4.6 Hz, 1H), 2.82 (dd, J=10.7, 3.7 Hz, 1H).
LC-MS MS(EI) for C16H16ClN5O2S [M+H]$^{+}$ (Calcd.: 377.07) Found: 378.1.

Example 49: Synthesis of (2S,3R,4S)-2-(8-((4-iodobenzyl)amino)-[1,2,4]triazolo[4,3-a]pyrazin-3-yl)tetrahydrothiophene-3,4-diol $^{1}$H-NMR (DMSO-d$_6$, 400 MHz):) δ 8.78 (t, J=6.3 Hz, 1H), 7.69 (d, J=4.8 Hz, 1H), 7.68-7.61 (m, 2H), 7.25 (d, J=4.8 Hz, 1H), 7.16 (d, J=8.4 Hz, 2H), 5.42 (d, J=6.1 Hz, 1H), 5.31 (d, J=4.3 Hz, 1H), 4.77 (d, J=7.2 Hz, 1H), 4.68-4.56 (m, 3H), 4.46-4.37 (m, 1H), 3.26 (dd, J=10.6, 4.6 Hz, 1H), 2.82 (dd, J=10.7, 3.7 Hz, 1H).
LC-MS MS(EI) for C16H16IN5O2S [M+H]$^{+}$ (Calcd.: 469.01) Found: 470.0.

Example 50: Synthesis of (2S,3R,4S)-2-(8-((2-fluorophenethyl)amino)-[1,2,4]triazolo[4,3-a]pyrazin-3-yl)tetrahydrothiophene-3,4-diol $^{1}$H-NMR (DMSO-d$_6$, 400 MHz): δ 8.25 (t, J=5.7 Hz, 1H), 7.67 (d, J=4.8 Hz, 1H), 7.31 (dd, J=11.0, 6.6 Hz, 2H), 7.28-7.22 (m, 1H), 7.19-7.07 (m, 2H), 5.44 (d, J=6.2 Hz, 1H), 5.33 (d, J=4.1 Hz, 1H), 4.77 (d, J=7.2 Hz, 1H), 4.66-4.59 (m, 1H), 4.45-4.38 (m, 1H), 4.10 (q, J=5.2 Hz, 2H), 3.72 (dt, J=12.5, 6.2 Hz, 2H), 3.25 (dd, J=10.8, 4.5 Hz, 1H), 2.99 (t, J=7.1 Hz, 2H), 2.82 (dd, J=10.6, 3.6 Hz, 1H).
LC-MS MS(EI) for C17H18FN5O2S [M+H]$^{+}$ (Calcd.: 375.12) Found: 376.1.

Example 51: Synthesis of (2S,3R,4S)-2-(8-((2-(piperidin-1-yl)ethyl)amino)-[1,2,4]triazolo[4,3-a]pyrazin-3-yl)tetrahydrothiophene-3,4-diol $^{1}$H-NMR (DMSO-d$_6$, 400 MHz): δ 7.87 (t, J=5.6 Hz, 1H), 7.66 (d, J=4.8 Hz, 1H), 7.29 (d, J=4.8 Hz, 1H), 5.45 (d, J=5.8 Hz, 1H), 5.33 (d, J=4.0 Hz, 1H), 4.77 (d, J=7.2 Hz, 1H), 4.63 (m, 1H), 4.41 (m, 1H), 3.57 (m, 2H), 3.25 (dd, J=10.6, 4.6 Hz, 1H), 2.82 (dd, J=10.6, 3.7 Hz, 1H), 2.38 (m, 5H), 1.54-1.32 (m, 7H).
LC-MS MS(EI) for C16H24N6O2S [M+H]$^{+}$ (Calcd.: 364.17) Found: 365.2.

Example 52: Synthesis of (2S,3R,4S)-2-(8-((2-(dimethylamino)ethyl)(methyl)amino)-[1,2,4]triazolo[4,3-a]pyrazin-3-yl)tetrahydrothiophene-3,4-diol $^{1}$H-NMR (DMSO-d$_6$, 400 MHz): δ 7.66 (d, J=4.7 Hz, 1H), 7.33 (d, J=4.7 Hz, 1H), 5.47 (d, J=5.7 Hz, 1H), 5.35 (d, J=4.0 Hz, 1H), 4.76 (d, J=6.9 Hz, 1H), 4.70-4.64 (m, 1H), 4.46-4.39 (m, 1H), 4.25 (s, 2H), 3.41 (s, 3H), 3.23 (dd, J=10.6, 4.7 Hz, 1H), 2.83 (dd, J=10.6, 4.0 Hz, 1H), 2.18 (s, 6H).
LC-MS MS(EI) for C14H22N6O2S [M+H]$^{+}$ (Calcd.: 338.15) Found: 339.1.

Example 53: Synthesis of (2S,3R,4S)-2-(8-hydroxy-[1,2,4]triazolo[4,3-a]pyrazin-3-yl)tetrahydrothiophene-3,4-diol $^{1}$H-NMR (DMSO-d$_6$, 400 MHz): δ 11.46 (s, 1H), 7.44 (d, J=5.8 Hz, 1H), 6.90 (d, J=5.8 Hz, 1H), 5.46 (s, 1H), 5.32 (s, 1H), 4.71 (d, J=7.0 Hz, 1H), 4.62-4.54 (m, 1H), 4.45-4.37 (m, 1H), 3.23 (dd, J=10.6, 4.7 Hz, 1H), 2.82 (dd, J=10.6, 3.9 Hz, 1H).
LC-MS MS(EI) for C9H10N4O3S [M+H]$^{+}$ (Calcd.: 254.05) Found: 255.0.

Example 54: Synthesis of (2S,3R,4S)-2-(8-(2-(3-chlorophenyl)hydrazinyl)-[1,2,4]triazolo[4,3-a]pyrazin-3-yl)tetrahydrothiophene-3,4-diol $^{1}$H-NMR (DMSO-d$_6$, 400 MHz): δ 10.01 (s, 1H), 8.74 (s, 1H), 7.93 (s, 1H), 7.79 (s, 1H), 7.70 (d, J=7.6 Hz, 1H), 7.26 (s, 1H), 6.79-6.64 (m, 1H), 5.47 (d, J=5.1 Hz, 1H), 5.33 (s, 1H), 4.81 (s, 1H), 4.66 (s, 1H), 4.42 (s, 1H), 3.31-3.24 (m, 1H), 2.83 (dd, J=10.7, 3.7 Hz, 1H).

LC-MS MS(EI) for C15H15ClN6O2S [M+H]⁺¹ (Calcd.: 378.07) Found: 380.0.

Example 55: Synthesis of (2S,3R,4S)-2-(8-((3,5-dichlorobenzyl)amino)-[1,2,4]triazolo[4,3-a]pyrazin-3-yl)tetrahydrothiophene-3,4-diol ¹H-NMR (DMSO-d₆, 400 MHz): δ 8.83 (t, J=6.1 Hz, 1H), 7.73 (d, J=4.8 Hz, 1H), 7.47 (t, J=1.9 Hz, 1H), 7.40 (d, J=1.9 Hz, 2H), 7.27 (d, J=4.8 Hz, 1H), 5.42 (d, J=6.0 Hz, 1H), 5.31 (d, J=4.4 Hz, 1H), 4.78 (d, J=7.2 Hz, 1H), 4.67 (d, J=6.1 Hz, 2H), 4.65-4.60 (m, 1H), 4.44-4.38 (m, 1H), 3.26 (dd, J=10.7, 4.6 Hz, 1H), 2.82 (dd, J=10.7, 3.7 Hz, 1H).
LC-MS MS(EI) for C16H15Cl2N5O2S [M+H]⁺¹ (Calcd.: 411.03) Found: 412.0.

Example 56: Synthesis of (2S,3R,4S)-2-(8-((2,5-dichlorobenzyl)amino)-[1,2,4]triazolo[4,3-a]pyrazin-3-yl)tetrahydrothiophene-3,4-diol ¹H-NMR (DMSO-d₆, 400 MHz): δ 8.80 (t, J=6.0 Hz, 1H), 7.75 (d, J=4.8 Hz, 1H), 7.51 (d, J=8.5 Hz, 1H), 7.36 (dd, J=8.5, 2.6 Hz, 1H), 7.32 (d, J=2.6 Hz, 1H), 7.26 (d, J=4.8 Hz, 1H), 5.44 (d, J=6.0 Hz, 1H), 5.32 (d, J=4.3 Hz, 1H), 4.80 (d, J=7.2 Hz, 1H), 4.72 (d, J=6.0 Hz, 2H), 4.68-4.60 (m, 1H), 4.46-4.40 (m, 1H), 3.27 (dd, J=10.7, 4.6 Hz, 1H), 2.83 (dd, J=10.7, 3.7 Hz, 1H).
LC-MS MS(EI) for C16H15Cl2N5O2S [M+H]⁺¹ (Calcd.: 411.03) Found: 412.0.

Example 57: Synthesis of (2S,3R,4S)-2-(8-((thiophen-2-ylmethyl)amino)-[1,2,4]triazolo[4,3-a]pyrazin-3-yl)tetrahydrothiophene-3,4-diol ¹H-NMR (DMSO-d₆, 400 MHz): δ 8.79 (t, J=6.1 Hz, 1H), 7.72 (d, J=4.8 Hz, 1H), 7.36-7.31 (m, 2H), 7.04 (dd, J=3.4, 1.2 Hz, 1H), 6.94 (dd, J=5.1, 3.4 Hz, 1H), 5.44 (d, J=6.0 Hz, 1H), 5.32 (d, J=4.3 Hz, 1H), 4.83 (d, J=6.4 Hz, 2H), 4.78 (d, J=7.2 Hz, 1H), 4.66-4.59 (m, 1H), 4.45-4.38 (m, 1H), 3.26 (dd, J=10.7, 4.6 Hz, 1H), 2.82 (dd, J=10.7, 3.7 Hz, 1H).
LC-MS MS(EI) for C14H15N5O2S2 [M+H]⁺¹ (Calcd.: 349.07) Found: 350.1.

Example 58: Synthesis of (2S,3R,4S)-2-(8-((2,3-dichlorobenzyl)amino)-[1,2,4]triazolo[4,3-a]pyrazin-3-yl)tetrahydrothiophene-3,4-diol ¹H-NMR (DMSO-d₆, 400 MHz): δ 8.82 (t, J=5.6 Hz, 1H), 7.72 (d, J=4.8 Hz, 1H), 7.57-7.49 (m, 1H), 7.32-7.20 (m, 3H), 5.45 (d, J=5.8 Hz, 1H), 5.33 (d, J=4.0 Hz, 1H), 4.78 (d, J=7.1 Hz, 1H), 4.73 (d, J=5.6 Hz, 2H), 4.66-4.58 (m, 1H), 4.44-4.37 (m, 1H), 3.25 (dd, J=10.7, 4.7 Hz, 1H), 2.81 (dd, J=10.8, 3.5 Hz, 1H).
LC-MS MS(EI) for C16H15Cl2N5O2S [M+H]⁺¹ (Calcd.: 411.03) Found: 412.0.

Example 59: Synthesis of (2S,3R,4S)-2-(8-((3,4-dichlorobenzyl)amino)-[1,2,4]triazolo[4,3-a]pyrazin-3-yl)tetrahydrothiophene-3,4-diol ¹H-NMR (DMSO-d₆, 400 MHz): δ 8.82 (t, J=6.0 Hz, 1H), 7.71 (d, J=4.8 Hz, 1H), 7.60 (s, 1H), 7.56 (d, J=8.3 Hz, 1H), 7.34 (d, J=8.3 Hz, 1H), 7.26 (d, J=4.8 Hz, 1H), 5.45 (d, J=5.8 Hz, 1H), 5.33 (d, J=3.8 Hz, 1H), 4.78 (d, J=7.2 Hz, 1H), 4.70-4.59 (m, 3H), 4.45-4.38 (m, 1H), 3.26 (dd, J=10.7, 4.5 Hz, 1H), 2.82 (dd, J=10.7, 3.5 Hz, 1H).

LC-MS MS(EI) for C16H15Cl2N5O2S [M+H]⁺¹ (Calcd.: 411.03) Found: 412.0.

Example 60: Synthesis of (2S,3R,4S)-2-(8-((2,4-dichlorobenzyl)amino)-[1,2,4]triazolo[4,3-a]pyrazin-3-yl)tetrahydrothiophene-3,4-diol ¹H-NMR (DMSO-d₆, 400 MHz): δ 8.78 (t, J=5.9 Hz, 1H), 7.72 (d, J=4.8 Hz, 1H), 7.60 (d, J=1.9 Hz, 1H), 7.33 (dd, J=8.3, 1.9 Hz, 1H), 7.29 (d, J=8.3 Hz, 1H), 7.23 (d, J=4.8 Hz, 1H), 5.44 (d, J=6.3 Hz, 1H), 5.33 (d, J=3.8 Hz, 1H), 4.78 (d, J=7.3 Hz, 1H), 4.68 (d, J=5.9 Hz, 2H), 4.66-4.59 (m, 1H), 4.43-4.37 (m, 1H), 3.25 (dd, J=10.5, 4.5 Hz, 1H), 2.81 (dd, J=10.5, 3.5 Hz, 1H).
LC-MS MS(EI) for C16H15Cl2N5O2S [M+H]⁺¹ (Calcd.: 411.03) Found: 412.0.

Example 61: Synthesis of methyl 2-chloro-5-(((3-((2S,3R,4S)-3,4-dihydroxytetrahydrothiophen-2-yl)-[1,2,4]triazolo[4,3-a]pyrazin-8-yl)amino)methyl)benzoate ¹H-NMR (DMSO-d₆, 400 MHz): δ 8.86 (t, J=6.4 Hz, 1H), 7.81 (d, J=1.9 Hz, 1H), 7.71 (d, J=4.9 Hz, 1H), 7.53 (dt, J=14.3, 5.2 Hz, 2H), 7.26 (d, J=4.8 Hz, 1H), 5.44 (d, J=5.9 Hz, 1H), 5.33 (d, J=4.1 Hz, 1H), 4.78 (d, J=7.2 Hz, 1H), 4.69 (d, J=6.1 Hz, 2H), 4.62 (td, J=6.5, 3.3 Hz, 1H), 4.45-4.38 (m, 1H), 3.26 (dd, J=10.6, 4.6 Hz, 1H), 2.82 (dd, J=10.6, 3.7 Hz, 1H).
LC-MS MS(EI) for C18H18ClN5O4S [M+H]⁺¹ (Calcd.: 435.08) Found: 436.1.

Example 62: Synthesis of (2S,3R,4S)-2-(8-((2-iodobenzyl)amino)-[1,2,4]triazolo[4,3-a]pyrazin-3-yl)tetrahydrothiophene-3,4-diol ¹H-NMR (DMSO-d₆, 400 MHz): δ 8.77 (t, J=6.0 Hz, 1H), 7.87 (dd, J=7.8, 1.1 Hz, 1H), 7.73 (d, J=4.8 Hz, 1H), 7.35-7.28 (m, 1H), 7.25 (d, J=4.8 Hz, 1H), 7.20 (d, J=6.3 Hz, 1H), 7.01 (td, J=7.7, 1.6 Hz, 1H), 5.44 (d, J=6.1 Hz, 1H), 5.32 (d, J=4.4 Hz, 1H), 4.80 (d, J=7.2 Hz, 1H), 4.69-4.61 (m, 1H), 4.58 (d, J=6.0 Hz, 2H), 4.47-4.38 (m, 1H), 3.27 (dd, J=10.6, 4.5 Hz, 1H), 2.83 (dd, J=10.7, 3.7 Hz, 1H).
LC-MS MS(EI) for C16H16IN5O2S [M+H]⁺¹ (Calcd.: 469.01) Found: 470.0.

Example 63: Synthesis of (2S,3R,4S)-2-(8-((3-chloro-4-fluorophenethyl)amino)-[1,2,4]triazolo[4,3-a]pyrazin-3-yl)tetrahydrothiophene-3,4-diol ¹H-NMR (DMSO-d₆, 400 MHz): δ 8.23 (d, J=5.7 Hz, 1H), 7.67 (d, J=4.8 Hz, 1H), 7.49 (dd, J=7.3, 2.1 Hz, 1H), 7.34-7.28 (m, 2H), 7.28-7.22 (m, 1H), 5.43 (d, J=6.0 Hz, 1H), 5.32 (d, J=4.4 Hz, 1H), 4.76 (d, J=7.2 Hz, 1H), 4.63 (dd, J=11.2, 5.0 Hz, 1H), 4.44-4.38 (m, 1H), 3.71 (dd, J=13.1, 6.8 Hz, 2H), 3.25 (dd, J=10.7, 4.6 Hz, 1H), 2.95 (t, J=6.9 Hz, 2H), 2.82 (dd, J=10.7, 3.8 Hz, 1H).
LC-MS MS(EI) for C17H17ClFN5O2S [M+H]⁺¹ (Calcd.: 409.08) Found: 410.1.

Example 64: Synthesis of (2S,3R,4S)-2-(8-((4-fluorophenethyl)amino)-[1,2,4]triazolo[4,3-a]pyrazin-3-yl)tetrahydrothiophene-3,4-diol ¹H-NMR (DMSO-d₆, 400 MHz): δ 8.21 (t, J=5.6 Hz, 1H), 7.67 (d, J=4.8 Hz, 1H), 7.32-7.25 (m, 3H), 7.16-7.05 (m, 2H), 5.43 (d, J=6.0 Hz, 1H), 5.32 (d, J=4.3 Hz, 1H), 4.77 (d, J=7.2 Hz, 1H), 4.68-4.59 (m, 1H), 4.46-4.38 (m, 1H), 3.69 (m, 2H), 3.25 (dd, J=10.6, 4.6 Hz, 1H), 2.94 (t, J=7.3 Hz, 2H), 2.82 (dd, J=10.7, 3.7 Hz, 1H).

LC-MS MS(EI) for C17H18FN5O2S [M+H]+ (Calcd.: 375.12) Found: 376.1.

Example 65: Synthesis of (2S,3R,4S)-2-(8-((3-chloro-4-fluorobenzyl)amino)-[1,2,4]triazolo[4,3-a]pyrazin-3-yl)tetrahydrothiophene-3,4-diol $^1$H-NMR (DMSO-d$_6$, 400 MHz):) δ 8.80 (t, J=6.3 Hz, 1H), 7.71 (d, J=4.8 Hz, 1H), 7.56 (dd, J=7.2, 1.6 Hz, 1H), 7.40-7.30 (m, 2H), 7.27 (d, J=4.8 Hz, 1H), 5.42 (d, J=6.1 Hz, 1H), 5.31 (d, J=4.3 Hz, 1H), 4.78 (d, J=7.2 Hz, 1H), 4.69-4.60 (m, 3H), 4.44-4.38 (m, 1H), 3.26 (dd, J=10.7, 4.6 Hz, 1H), 2.82 (dd, J=10.7, 3.7 Hz, 1H).

LC-MS MS(EI) for C16H15ClFN5O2S [M+H]+ (Calcd.: 395.06) Found: 396.1.

Example 66: Synthesis of (2S,3R,4S)-2-(8-((2,6-dichlorobenzyl)amino)-[1,2,4]triazolo[4,3-a]pyrazin-3-yl)tetrahydrothiophene-3,4-diol $^1$H-NMR (DMSO-d$_6$, 400 MHz): δ 8.42 (t, J=4.5 Hz, 1H), 7.73 (d, J=4.8 Hz, 1H), 7.54-7.45 (m, 2H), 7.42-7.33 (m, 2H), 5.44 (s, 1H), 5.32 (s, 1H), 4.88 (d, J=4.5 Hz, 2H), 4.78 (d, J=7.2 Hz, 1H), 4.63 (s, 1H), 4.41 (s, 1H), 3.26 (dd, J=10.7, 4.6 Hz, 1H), 2.82 (dd, J=10.7, 3.7 Hz, 1H).

LC-MS MS(EI) for C16H15Cl2N5O2S [M+H]+ (Calcd.: 411.03) Found: 412.1.

Example 67: Synthesis of (2S,3R,4S)-2-(8-((3-(4-methylpiperazin-1-yl)benzyl)amino)-[1,2,4]triazolo[4,3-a]pyrazin-3-yl)tetrahydrothiophene-3,4-diol $^1$H-NMR (DMSO-d$_6$, 400 MHz): δ 8.65 (t, J=6.2 Hz, 1H), 7.68 (d, J=4.8 Hz, 1H), 7.27 (d, J=4.8 Hz, 1H), 7.15-7.08 (m, 1H), 6.98 (s, 1H), 6.82-6.73 (m, 2H), 5.42 (d, J=6.1 Hz, 1H), 5.30 (d, J=4.4 Hz, 1H), 4.77 (d, J=7.2 Hz, 1H), 4.68-4.58 (m, 3H), 4.46-4.37 (m, 1H), 3.26 (dd, J=10.7, 4.6 Hz, 1H), 3.15-3.05 (m, 4H), 2.82 (dd, J=10.7, 3.7 Hz, 1H), 2.47-2.39 (m, 4H), 2.21 (s, 3H).

LC-MS MS(EI) for C21H27N7O2S [M+H]+ (Calcd.: 441.19) Found: 442.2.

Example 68: Synthesis of (2S,3R,4S)-2-(8-((3-(dimethylamino)benzyl)amino)-[1,2,4]triazolo[4,3-a]pyrazin-3-yl)tetrahydro thiophene-3,4-diol $^1$H-NMR (DMSO-d$_6$, 400 MHz): δ 8.64 (t, J=6.2 Hz, 1H), 7.67 (d, J=4.8 Hz, 1H), 7.27 (d, J=4.8 Hz, 1H), 7.13-7.04 (m, 1H), 6.77 (s, 1H), 6.64 (d, J=7.7 Hz, 1H), 6.58 (dd, J=8.0, 2.2 Hz, 1H), 5.43 (d, J=6.0 Hz, 1H), 5.31 (d, J=4.3 Hz, 1H), 4.77 (d, J=7.2 Hz, 1H), 4.70-4.56 (m, 3H), 4.47-4.37 (m, 1H), 3.26 (dd, J=10.7, 4.6 Hz, 1H), 2.85 (s, 6H), 2.82 (dd, J=10.7, 3.7 Hz, 1H).

LC-MS MS(EI) for C18H22N6O2S [M+H]+ (Calcd.: 386.15) Found: 387.1.

Example 69: Synthesis of (2S,3R,4S)-2-(8-((3-(1H-tetrazol-5-yl)benzyl)amino)-[1,2,4]triazolo[4,3-a]pyrazin-3-yl)tetrahydrothiophene-3,4-diol $^1$H-NMR (DMSO-d$_6$, 400 MHz): δ 8.87 (t, J=6.2 Hz, 1H), 8.10-8.01 (m, 1H), 7.88 (dt, J=6.9, 1.8 Hz, 1H), 7.71 (d, J=4.8 Hz, 1H), 7.58-7.48 (m, 2H), 7.27 (d, J=4.8 Hz, 1H), 5.43 (d, J=4.5 Hz, 1H), 5.31 (s, 1H), 4.88-4.72 (m, 3H), 4.69-4.58 (m, 1H), 4.47-4.35 (m, 1H), 3.26 (dd, J=10.6, 4.6 Hz, 1H), 2.82 (dd, J=10.7, 3.7 Hz, 1H).

LC-MS MS(EI) for C17H17N9O2S [M+H]+ (Calcd.: 411.12) Found: 412.1.

Example 70: Synthesis of (2S,3R,4S)-2-(8-((2-(3-fluorophenyl)cyclopropyl)amino)-[1,2,4]triazolo[4,3-a]pyrazin-3-yl)tetrahydrothiophene-3,4-diol $^1$H-NMR (DMSO-d$_6$, 400 MHz): δ 8.56 (d, J=4.3 Hz, 1H), 7.68 (d, J=4.8 Hz, 1H), 7.39-7.21 (m, 2H), 7.03-6.89 (m, 3H), 5.38 (d, J=6.0 Hz, 1H), 5.27 (d, J=4.2 Hz, 1H), 4.74 (d, J=7.2 Hz, 1H), 4.66-4.52 (m, 1H), 4.45-4.32 (m, 1H), 3.22 (dd, J=10.7, 4.5 Hz, 1H), 3.19-3.08 (m, 1H), 2.78 (dd, J=10.7, 3.7 Hz, 1H), 2.16-2.05 (m, 1H), 1.60-1.47 (m, 1H), 1.34-1.24 (m, 1H).

LC-MS MS(EI) for C18H18FN5O2S [M+H]+ (Calcd.: 387.12) Found: 388.1.

Example 71: Synthesis of (2S,3R,4S)-2-(8-((2-(3-chlorophenyl)cyclopropyl)amino)-[1,2,4]triazolo[4,3-a]pyrazin-3-yl)tetrahydrothiophene-3,4-diol $^1$H-NMR (DMSO-d$_6$, 400 MHz): δ 8.56 (d, J=4.2 Hz, 1H), 7.68 (d, J=4.8 Hz, 1H), 7.30-7.23 (m, 2H), 7.23-7.16 (m, 2H), 7.10 (d, J=7.6 Hz, 1H), 5.38 (d, J=6.0 Hz, 1H), 5.27 (d, J=4.0 Hz, 1H), 4.74 (d, J=7.2 Hz, 1H), 4.64-4.55 (m, 1H), 4.41-4.33 (m, 1H), 3.22 (dd, J=10.7, 4.5 Hz, 1H), 3.18-3.09 (m, 1H), 2.78 (dd, J=10.7, 3.6 Hz, 1H), 2.13-2.05 (m, 1H), 1.58-1.49 (m, 1H), 1.33-1.25 (m, 1H).

LC-MS MS(EI) for C18H18ClN5O2S [M+H]+, (Calcd.: 403.09) Found: 404.1.

Example 72: Synthesis of (2S,3R,4S)-2-(8-(((1R,2S)-2-phenylcyclopropyl)amino)-[1,2,4]triazolo[4,3-a]pyrazin-3-yl)tetrahydrothiophene-3,4-diol $^1$H-NMR (DMSO-d$_6$, 400 MHz): δ 8.57 (d, J=4.4 Hz, 3H), 7.71 (d, J=4.8 Hz, 3H), 7.33-7.24 (m, 9H), 7.21-7.13 (m, 9H), 5.42 (d, J=6.1 Hz, 3H), 5.31 (d, J=4.3 Hz, 3H), 4.78 (d, J=7.2 Hz, 3H), 4.68-4.60 (m, 3H), 4.45-4.38 (m, 3H), 3.26 (dd, J=10.7, 4.6 Hz, 3H), 3.22-3.13 (m, 3H), 2.82 (dd, J=10.7, 3.6 Hz, 3H), 2.17-2.08 (m, 3H), 1.57-1.48 (m, 3H), 1.31-1.21 (m, 4H).

LC-MS MS(EI) for C18H19N5O2S [M+H]+, (Calcd.: 369.13) Found: 370.1.

Example 73: Synthesis of (2S,3R,4S)-2-(8-((2,3-difluorophenethyl)amino)-[1,2,4]triazolo[4,3-a]pyrazin-3-yl)tetrahydrothiophene-3,4-diol $^1$H-NMR (DMSO-d$_6$, 400 MHz): δ 8.30-8.26 (1H, m), 7.67 (1H, d, J=4.8 Hz), 7.30 (1H, d, J=4.0 Hz), 7.27-7.25 (1H, m), 7.12-7.11 (2H, m), 5.42 (1H, d, J=6.0 Hz), 5.30 (1H, d, J=4.4 Hz), 4.77 (1H, d, J=7.2 Hz), 4.63 (1H, s), 4.41 (1H, s), 3.75-3.73 (2H, m), 3.25 (1H, dd, J=10.4, 4.4 Hz), 3.04 (2H, t, J=6.6 Hz), 2.82 (1H, dd, J=11.6, 4.0 Hz).

LC-MS MS(EI) for C17H17F2N5O2S [M+H]+ (Calcd.: 393.11) Found: 394.3.

Example 74: Synthesis of (2S,3R,4S)-2-(8-((2,4-difluorophenethyl)amino)-[1,2,4]triazolo[4,3-a]pyrazin-3-yl)tetrahydrothiophene-3,4-diol $^1$H-NMR (DMSO-d$_6$, 400 MHz): δ 8.26-8.22 (1H, m), 7.66 (1H, d, J=4.8 Hz), 7.35 (1H, q, J=8.0 Hz), 7.29 (1H, d, J=4.8 Hz), 7.19-7.14 (1H, m), 7.02-6.98 (1H, m), 5.41 (1H, d, J=6.0 Hz), 5.30 (1H, d, J=4.4 Hz), 4.76 (1H, d, J=6.8 Hz), 4.65-4.61 (1H, m), 4.41 (1H, s), 3.71-3.69 (2H, m), 3.25 (1H, dd, J=11.8, 5.4 Hz), 2.96 (2H, t, J=7.0 Hz), 2.82 (1H, dd, J=10.8, 3.6 Hz).

LC-MS MS(EI) for C17H17F2N5O2S [M+H]+ (Calcd.: 393.11) Found: 394.3.

Example 75: Synthesis of (2S,3R,4S)-2-(8-(((1R, 2R)-2-phenylcyclopropyl)amino)-[1,2,4]triazolo[4,3-a]pyrazin-3-yl)tetrahydrothiophene-3,4-diol $^1$H-NMR (DMSO-d$_6$, 400 MHz): δ 8.30-8.24 (1H, m), 7.60 (1H, t, J=4.4 Hz), 7.24-7.21 (3H, m), 7.11-7.10 (2H, m), 7.04-6.98 (1H, m), 5.41-5.39 (1H, m), 5.29 (1H, d, J=3.6 Hz), 4.70 (1H, d, J=7.2 Hz), 4.59 (1H, s), 4.37 (1H, s), 3.22 (1H, d, J=10.8 Hz), 2.79 (1H, d, J=12.4 Hz), 2.32-2.28 (1H, m), 1.58-1.56 (1H, m), 1.37-1.35 (1H, m). *A proton would be overlapped with H$_2$O peak at 3.40 ppm.

LC-MS MS(EI) for C18H19N5O2S [M+H]+ (Calcd.: 369.13) Found: 370.2.

Example 76: Synthesis of (2S,3R,4S)-2-(8-((2,5-difluorophenethyl)amino)-[1,2,4]triazolo[4,3-a]pyrazin-3-yl)tetrahydrothiophene-3,4-diol $^1$H-NMR (DMSO-d$_6$, 400 MHz): δ 8.26-8.22 (1H, m), 7.63 (1H, d, J=4.4 Hz), 7.26 (1H, d, J=4.8 Hz), 7.18-7.12 (2H, m), 7.06-7.02 (1H, m), 5.38 (1H, d, J=5.6 Hz), 5.26 (1H, s), 4.73 (1H, d, J=7.2 Hz), 4.62-4.58 (1H, m), 4.37 (1H, brs), 3.70-3.68 (2H, m), 3.21 (1H, dd, J=10.8, 4.4 Hz), 2.95 (2H, t, J=7.0 Hz), 2.78 (1H, dd, J=10.6, 3.4 Hz).

LC-MS MS(EI) for C17H17F2N5O2S [M+H]+ (Calcd.: 393.11) Found: 394.3.

Example 77: Synthesis of (2S,3R,4S)-2-(8-(3-chlorophenethyl)-[1,2,4]triazolo[4,3-a]pyrazin-3-yl)tetrahydrothiophene-3,4-diol $^1$H-NMR (DMSO-d$_6$, 400 MHz): δ 8.45 (1H, d, J=4.8 Hz), 7.84 (1H, d, J=5.2 Hz), 7.38 (1H, s), 7.33-7.29 (1H, m), 7.26-7.24 (2H, m), 5.45 (1H, d, J=6.0 Hz), 5.34 (1H, d, J=4.0 Hz), 4.90 (1H, d, J=6.8 Hz), 4.64 (1H, brs), 4.24 (1H, brs), 3.52 (2H, t, J=7.6 Hz), 3.30-3.27 (1H, m), 3.22 (2H, t, J=7.8 Hz), 2.84 (1H, dd, J=10.8, 3.2 Hz).

LC-MS MS(EI) for C17H17ClN4O2S [M+H]+ (Calcd.: 376.08) Found: 377.3.

Example 78: Synthesis of (2S,3R,4S)-2-(8-((4-chloro-3-fluorophenethyl)amino)-[1,2,4]triazolo[4,3-a]pyrazin-3-yl)tetrahydrothiophene-3,4-diol $^1$H-NMR (DMSO-d$_6$, 400 MHz): δ 8.19 (s, 1H), 7.63 (d, J=3.8 Hz, 1H), 7.43 (t, J=8.0 Hz, 1H), 7.28 (dd, J=12.8, 7.7 Hz, 2H), 7.08 (d, J=7.7 Hz, 1H), 5.41 (d, J=4.4 Hz, 1H), 5.29 (d, J=4.3 Hz, 1H), 4.72 (d, J=7.0 Hz, 1H), 4.62-4.55 (m, 1H), 4.41-4.34 (m, 1H), 3.68 (dd, J=13.0, 6.9 Hz, 2H), 3.24-3.18 (m, 1H), 2.93 (t, J=6.8 Hz, 2H), 2.78 (dd, J=9.9, 3.6 Hz, 1H).

LC-MS MS(EI) for C17H17ClFN5O2S [M+H]+, (Calcd.: 409.08) Found: 410.1.

Example 79: Synthesis of methyl 5-(((3-((2S,3R, 4S)-3,4-dihydroxytetrahydrothiophen-2-yl)-[1,2,4] triazolo[4,3-a]pyrazin-8-yl)amino)methyl)-2-fluorobenzoate $^1$H-NMR (DMSO-d$_6$, 400 MHz): δ 8.85-8.77 (m, 1H), 7.86 (d, J=5.3 Hz, 1H), 7.66 (d, J=4.3 Hz, 1H), 7.64-7.58 (m, 1H), 7.28-7.20 (m, 1H), 5.41 (d, J=6.1 Hz, 1H), 5.29 (d, J=4.9 Hz, 1H), 4.74 (d, J=6.9 Hz, 1H), 4.65 (s, 1H), 4.59 (d, J=4.9 Hz, 1H), 4.37 (s, 1H), 3.79 (s, 2H), 3.22 (dd, J=11.5, 4.3 Hz, 1H), 2.78 (dd, J=11.0, 3.8 Hz, 1H).

LC-MS MS(EI) for C18H18FN5O4S [M+H]+, (Calcd.: 419.11) Found: 420.1.

Example 80: Synthesis of (2S,3R,4S)-2-(8-((3-(piperazin-1-yl)benzyl)amino)-[1,2,4]triazolo[4,3-a] pyrazin-3-yl)tetrahydrothiophene-3,4-diol $^1$H-NMR (DMSO-d$_6$, 400 MHz): δ 8.64 (t, J=6.3 Hz, 1H), 8.58-8.31 (m, 2H), 7.65 (d, J=4.8 Hz, 1H), 7.22 (d, J=4.8 Hz, 1H), 7.13 (t, J=7.8 Hz, 1H), 6.97 (s, 1H), 6.81 (d, J=7.9 Hz, 2H), 5.38 (d, J=6.1 Hz, 1H), 5.28 (d, J=4.3 Hz, 1H), 4.73 (d, J=7.1 Hz, 1H), 4.59 (t, J=7.7 Hz, 3H), 4.44-4.34 (m, 2H), 4.06 (dd, J=11.2, 5.2 Hz, 1H), 3.26-3.18 (m, 5H), 3.14 (dd, J=12.4, 4.8 Hz, 5H), 2.79 (dd, J=10.7, 3.7 Hz, 1H).

LC-MS MS(EI) for C20H25N7O2S [M+H]+, (Calcd.: 427.18) Found: 428.2.

Example 81: Synthesis of (2S,3R,4S)-2-(8-((2,6-difluorophenethyl)amino)-[1,2,4]triazolo[4,3-a] pyrazin-3-yl)tetrahydrothiophene-3,4-diol $^1$H-NMR (DMSO-d$_6$, 400 MHz): δ 8.31-8.30 (1H, m), 7.66 (1H, d, J=4.8 Hz), 7.34-7.28 (2H, m), 7.03 (2H, t, J=5.2 Hz), 5.42 (1H, d, J=5.6 Hz), 5.30 (1H, d, J=4.4 Hz), 4.76 (1H, d, J=6.8 Hz), 4.66-4.62 (1H, m), 4.41 (1H, brs), 3.70-3.68 (2H, m), 3.25 (1H, dd, J=10.8, 4.8 Hz), 3.02 (2H, t, J=6.6 Hz), 2.83 (1H, dd, J=11.0, 3.4 Hz).

LC-MS MS(EI) for C17H17F2N5O2S [M+H]+, (Calcd.: 393.11) Found: 394.3.

Example 82: Synthesis of (2S,3R,4S)-2-(8-((3,4-difluorophenethyl)amino)-[1,2,4]triazolo[4,3-a] pyrazin-3-yl)tetrahydrothiophene-3,4-diol $^1$H-NMR (DMSO-d$_6$, 400 MHz): δ 8.24-8.22 (1H, m), 7.67 (1H, d, J=4.8 Hz), 7.36-7.29 (3H, m), 7.09 (1H, brs), 5.42 (1H, d, J=6.4 Hz), 5.30 (1H, d, J=4.4 Hz), 4.76 (1H, d, J=6.8 Hz), 4.63 (1H, brs), 4.41 (1H, brs), 3.72-3.70 (2H, m), 3.25 (1H, dd, J=11.0, 4.6 Hz), 2.95 (2H, t, J=7.0 Hz), 2.84-2.81 (1H, m).

LC-MS MS(EI) for C17H17F2N5O2S [M+H]+, (Calcd.: 393.11) Found: 394.3.

Example 83: Synthesis of (2S,3R,4S)-2-(8-((3,5-difluorophenethyl)amino)-[1,2,4]triazolo[4,3-a] pyrazin-3-yl)tetrahydrothiophene-3,4-diol $^1$H-NMR (DMSO-d$_6$, 400 MHz): δ 8.26-8.22 (1H, m), 7.67 (1H, d, J=4.8 Hz), 7.36-7.29 (1H, d, J=4.4 Hz), 7.06-7.00 (3H, m), 5.42 (1H, d, J=6.4 Hz), 5.30 (1H, d, J=4.0 Hz), 4.76 (1H, d, J=7.2 Hz), 4.63 (1H, brs), 4.41 (1H, brs), 3.74-3.73 (2H, m), 3.25 (1H, dd, J=10.4, 4.4 Hz), 2.99 (2H, t, J=6.8 Hz), 2.84-2.81 (1H, dd, J=10.6, 3.4 Hz).

LC-MS MS(EI) for C17H17F2N5O2S [M+H]+, (Calcd.: 393.11) Found: 394.3.

Example 84: Synthesis of (2S,3R,4S)-2-(8-(((1S, 2R)-2-(3,4-difluorophenyl)cyclopropyl)amino)-[1,2, 4]triazolo[4,3-a]pyrazin-3-yl)tetrahydrothiophene-3, 4-diol $^1$H-NMR (DMSO-d$_6$, 400 MHz): δ 8.59 (1H, d, J=4.0 Hz), 7.72 (1H, d, J=4.8 Hz), 7.36-7.24 (3H, m), 7.07 (1H, brs), 5.42 (1H, d, J=5.6 Hz), 5.31 (1H, d, J=4.4 Hz), 4.78 (1H, d, J=7.6 Hz), 4.61 (1H, brs), 4.42-4.41 (1H, m), 3.26 (1H, dd, J=10.6, 4.2 Hz), 3.14-3.13 (1H, m), 2.82 (1H, dd, J=10.6, 3.4 Hz), 2.14 (1H, brs), 1.56-1.51 (1H, m), 1.33-1.29 (1H, m).
LC-MS MS(EI) for $C_{18}H_{17}F_2N_5O_2S$ [M+H]+, (Calcd.: 405.11) Found: 406.3.

Example 85: Synthesis of (2S,3R,4S)-2-(8-((5-chloro-2-fluorobenzyl)amino)-[1,2,4]triazolo[4,3-a]pyrazin-3-yl)tetrahydrothiophene-3,4-diol $^1$H-NMR (DMSO-d$_6$, 400 MHz): δ 8.77 (1H, t, J=5.8 Hz), 7.74 (1H, d, J=4.4 Hz), 7.39-7.34 (2H, m), 7.29-7.23 (2H, m), 5.30 (1H, d, J=5.6 Hz), 5.31 (1H, d, J=4.4 Hz), 4.79 (1H, d, J=7.2 Hz), 4.72 (2H, d, J=6.0 Hz), 4.66-4.64 (1H, m), 4.42 (1H, brs), 3.27 (1H, dd, J=10.8, 4.8 Hz), 2.83 (1H, dd, J=10.8, 3.6 Hz).
LC-MS MS(EI) for $C_{16}H_{15}ClFN_5O_2S$ [M+H]+, (Calcd.: 395.06) Found: 396.2.

Example 86: Synthesis of (2S,3R,4S)-2-(8-((3-chloro-5-fluorobenzyl)amino)-[1,2,4]triazolo[4,3-a]pyrazin-3-yl)tetrahydrothiophene-3,4-diol $^1$H-NMR (DMSO-d$_6$, 400 MHz): δ 8.82 (1H, t, J=5.8 Hz), 7.72 (1H, d, J=5.2 Hz), 7.28-7.26 (3H, m), 7.18 (1H, d, J=9.2 Hz), 5.42 (1H, d, J=6.0 Hz), 5.30 (1H, d, J=4.4 Hz), 4.78 (1H, d, J=7.2 Hz), 4.69 (2H, d, J=5.6 Hz), 4.65-4.63 (1H, m), 4.42 (1H, brs), 3.26 (1H, dd, J=10.6, 4.6 Hz), 2.82 (1H, dd, J=10.6, 3.4 Hz).
LC-MS MS(EI) for $C_{16}H_{15}ClFN_5O_2S$ [M+H]+, (Calcd.: 395.06) Found: 396.2.

Example 87: Synthesis of (2S,3R,4S)-2-(8-((3-cyclopropylbenzyl)amino)-[1,2,4]triazolo[4,3-a]pyrazin-3-yl)tetrahydrothiophene-3,4-diol $^1$H-NMR (DMSO-d$_6$, 400 MHz): δ 8.71-8.66 (1H, m), 7.68 (1H, d, J=4.8 Hz), 7.26 (1H, d, J=4.8 Hz), 7.17-7.10 (3H, m), 6.90 (1H, d, J=7.2 Hz), 5.41 (1H, d, J=5.6 Hz), 5.30 (1H, d, J=3.6 Hz), 4.77 (1H, d, J=7.2 Hz), 4.64-4.63 (3H, m), 4.41 (1H, brs), 3.26 (1H, dd, J=11.2, 4.4 Hz), 2.84-2.81 (1H, m), 1.86-1.85 (1H, m), 0.91 (2H, d, J=8.4 Hz), 0.62-0.61 (2H, m).
LC-MS MS(EI) for $C_{19}H_{21}N_5O_2S$ [M+H]+, (Calcd.: 383.14) Found: 384.3.

Example 88: Synthesis of (2S,3R,4S)-2-(8-(([1,1'-biphenyl]-3-ylmethyl)amino)-[1,2,4]triazolo[4,3-a]pyrazin-3-yl)tetrahydrothiophene-3,4-diol $^1$H-NMR (DMSO-d$_6$, 400 MHz): δ 8.80 (1H, t, J=6.2 Hz), 7.69-7.70 (2H, m), 7.62 (2H, d, J=7.6 Hz), 7.52-7.37 (6H, m), 7.29 (1H, d, J=4.8 Hz), 5.42 (1H, d, J=5.6 Hz), 5.31 (1H, d, J=4.0 Hz), 4.79-4.77 (3H, m), 4.64 (1H, brs), 4.42 (1H, brs), 3.26 (1H, dd, J=10.4, 4.4 Hz), 2.83 (1H, dd, J=10.8, 3.2 Hz).
LC-MS MS(EI) for $C_{22}H_{21}N_5O_2S$ [M+H]+, (Calcd.: 419.50) Found: 420.3.

Example 89: Synthesis of (2S,3R,4S)-2-(8-((3-phenoxybenzyl)amino)-[1,2,4]triazolo[4,3-a]pyrazin-3-yl)tetrahydrothiophene-3,4-diol $^1$H-NMR (DMSO-d$_6$, 400 MHz): δ 8.75 (1H, t, J=5.8 Hz), 7.69 (1H, d, J=4.4 Hz), 7.37-7.29 (3H, m), 7.25 (1H, d, J=4.4 Hz), 7.13-7.09 (2H, m), 7.00-6.96 (3H, m), 6.85 (1H, d, J=8.0 Hz), 5.43 (1H, d, J=5.6 Hz), 5.31 (1H, d, J=4.4 Hz), 4.78 (1H, d, J=7.2 Hz), 4.67-4.65 (3H, m), 4.42-4.40 (1H, m), 3.26 (1H, dd, J=10.6, 4.6 Hz), 2.83 (1H, dd, J=10.8, 3.2 Hz).
LC-MS MS(EI) for $C_{22}H_{21}N_5O_3S$ [M+H]+, (Calcd.: 435.50) Found: 436.3.

Example 90: Synthesis of methyl 3-(((3-((2S,3R,4S)-3,4-dihydroxytetrahydrothiophen-2-yl)-[1,2,4]triazolo[4,3-a]pyrazin-8-yl)amino)methyl)benzoate $^1$H-NMR (DMSO-d$_6$, 400 MHz): δ 8.90-8.84 (1H, m), 7.98 (1H, s), 7.82 (1H, d, J=7.6 Hz), 7.70 (1H, d, J=4.8 Hz), 7.64 (1H, d, J=8.0 Hz), 7.46 (1H, t, J=7.6 Hz), 7.26 (1H, d, J=4.4 Hz), 5.42 (1H, d, J=6.0 Hz), 5.30 (1H, d, J=4.4 Hz), 4.78 (1H, d, J=6.8 Hz), 4.74 (1H, d, J=6.4 Hz), 4.63 (1H, brs), 4.41 (1H, brs), 3.83 (3H, s), 3.26 (1H, dd, J=10.8, 4.4 Hz), 2.82 (1H, dd, J=10.8, 3.6 Hz).
LC-MS MS(EI) for $C_{18}H_{19}N_5O_4S$ [M+H]+, (Calcd.: 401.12) Found: 402.3.

Example 91: Synthesis of (2S,3R,4S)-2-(8-((3-morpholinobenzyl)amino)-[1,2,4]triazolo[4,3-a]pyrazin-3-yl)tetrahydrothiophene-3,4-diol $^1$H-NMR (DMSO-d$_6$, 400 MHz): δ 8.66 (1H, t, J=6.6 Hz), 7.68 (1H, d, J=4.8 Hz), 7.27 (1H, d, J=4.8 Hz), 7.14 (1H, t, J=8.0 Hz), 6.98 (1H, s), 6.79 (2H, d, J=7.6 Hz), 5.42 (1H, d, J=5.6 Hz), 5.30 (1H, d, J=4.4 Hz), 4.77 (1H, d, J=7.2 Hz), 4.63 (1H, d, J=4.4 Hz), 4.42-4.40 (3H, m), 3.72 (4H, t, J=4.4 Hz), 3.26 (1H, dd, J=10.6, 4.2 Hz), 3.06 (4H, t, J=4.4 Hz), 2.83 (1H, dd, J=11.2, 3.2 Hz).
LC-MS MS(EI) for $C_{20}H_{24}N_6O_3S$ [M+H]+, (Calcd.: 428.51) Found: 429.3.

Example 92: Synthesis of (2S,3R,4S)-2-(8-((3-chlorobenzyl)thio)-[1,2,4]triazolo[4,3-a]pyrazin-3-yl)tetrahydrothiophene-3, 4-diol $^1$H-NMR (DMSO-d$_6$, 400 MHz): δ 8.35 (1H, d, J=4.8 Hz), 7.81 (1H, d, J=4.8 Hz), 7.56 (1H, s), 7.45 (1H, d, J=6.8 Hz), 7.38-7.32 (2H, m), 5.44 (1H, d, J=6.0 Hz), 5.34 (1H, d, J=3.2 Hz), 4.87 (1H, d, J=7.2 Hz), 4.61 (3H, s), 4.41 (1H, s), 3.28-3.27 (1H, m), 2.83 (1H, dd, J=10.8, 2.8 Hz).
LC-MS MS(EI) for $C_{16}H_{15}ClN_4O_2S_2$ [M+H]+, (Calcd.: 394.03) Found: 395.2.

Example 93: Synthesis of (2S,3R,4S)-2-(8-((3-fluoro-4-(5-methyloxazol-2-yl)benzyl)amino)-[1,2,4]triazolo[4,3-a]pyrazin-3-yl)tetrahydrothiophene-3,4-diol $^1$H-NMR (DMSO-d$_6$, 400 MHz): δ 8.85 (1H, t, J=6.6 Hz), 7.89 (1H, t, J=8.0 Hz), 7.72 (1H, d, J=4.4 Hz), 7.34-7.26 (3H, m), 7.02 (1H, s), 5.42 (1H, d, J=6.0 Hz), 5.31 (1H, d, J=4.4 Hz), 4.79 (1H, d, J=7.2 Hz), 4.74 (2H, d, J=5.2 Hz), 4.69-4.63 (1H, m), 4.49-4.41 (1H, m), 3.26 (1H, dd, J=10.6, 3.8 Hz), 2.83 (1H, dd, J=11.0, 3.4 Hz), 2.37 (3H, s).
LC-MS MS(EI) for $C_{20}H_{19}FN_6O_3S$ [M+H]+, (Calcd.: 442.12) Found: 443.2.

Example 94: Synthesis of (2S,3R,4S)-2-(8-((3-fluoro-4-(5-methylthiazol-2-yl)benzyl)amino)-[1,2,4]triazolo[4,3-a]pyrazin-3-yl)tetrahydrothiophene-3, 4-diol $^1$H-NMR (DMSO-d$_6$, 400 MHz): δ 8.85 (1H, t, J=6.8 Hz), 8.09 (1H, t, J=8.0 Hz), 7.72 (1H, d, J=4.8 Hz), 7.67 (1H, s), 7.36-7.31 (2H, m), 7.27 (1H, d, J=4.8 Hz), 5.42 (1H, d, J=5.6 Hz), 5.31 (1H, d, J=4.4 Hz), 4.78 (1H, d, J=7.6 Hz), 4.73 (2H, d, J=5.6 Hz), 4.66-4.63 (1H, m), 4.42-4.41 (1H, m), 3.26 (1H, dd, J=10.6, 4.2 Hz), 2.82 (1H, dd, J=10.8, 3.6 Hz).

*Protons from CH₃ were overlapped with DMSO peak at 2.5 ppm.

LC-MS MS(EI) for C20H19FN6O2S2 [M+H]+, (Calcd.: 458.10) Found: 459.2.

Example 95: Synthesis of (2S,3R,4S)-2-(8-((3-fluoro-4-(5-methyl-1,3,4-oxadiazol-2-yl)benzyl)amino)-[1,2,4]triazolo[4,3-a]pyrazin-3-yl)tetrahydrothiophene-3,4-diol $^1$H-NMR (DMSO-$d_6$, 400 MHz): δ 8.92-8.85 (1H, m), 7.93 (1H, t, J=7.8 Hz), 7.73 (1H, d, J=4.4 Hz), 7.43-7.37 (2H, m), 7.26 (1H, d, J=5.2 Hz), 5.43 (1H, d, J=5.6 Hz), 5.32 (1H, d, J=3.6 Hz), 4.80-4.76 (3H, m), 4.63 (1H, brs), 4.42 (1H, brs), 3.28 (1H, dd, J=11.0, 4.2 Hz), 2.84-2.81 (1H, m), 2.58 (3H, s).

LC-MS MS(EI) for C19H18FN7O3S [M+H]+, (Calcd.: 443.12) Found: 444.2.

Example 96: Synthesis of (2S,3R,4S)-2-(8-((3-(2-methyl-2H-tetrazol-5-yl)benzyl)amino)-[1,2,4]triazolo[4,3-a]pyrazin-3-yl)tetrahydrothiophene-3,4-diol $^1$H-NMR (DMSO-$d_6$, 400 MHz): δ 8.91 (1H, t, J=7.0 Hz), 8.08 (1H, s), 7.91 (1H, d, J=7.2 Hz), 7.70 (1H, d, J=4.8 Hz), 7.52-7.47 (2H, m), 7.27 (1H, d, J=4.8 Hz), 5.43 (1H, d, J=5.6 Hz), 5.31 (1H, d, J=4.4 Hz), 4.79-4.77 (3H, m), 4.65-4.62 (1H, m), 4.41 (4H, s), 3.26 (1H, dd, J=4.2 Hz), 2.82 (1H, dd, J=10.4, 2.4 Hz).

LC-MS MS(EI) for C18H19N9O2S [M+H]+, (Calcd.: 425.14) Found: 426.2.

Example 97: Synthesis of (2S,3R,4S)-2-(8-((3-fluoro-4-(5-methyl-1,3,4-thiadiazol-2-yl)benzyl)amino)-[1,2,4]triazolo[4,3-a]pyrazin-3-yl)tetrahydrothiophene-3,4-diol $^1$H-NMR (DMSO-$d_6$, 400 MHz): δ 8.88-8.84 (1H, m), 8.16 (1H, t, J=7.6 Hz), 7.72 (1H, d, J=4.8 Hz), 7.43-7.37 (2H, m), 7.26 (1H, d, J=5.2 Hz), 5.42 (1H, d, J=5.2 Hz), 5.31 (1H, s), 4.80-4.75 (3H, m), 4.63 (1H, brs), 4.42 (1H, brs), 3.28-3.24 (1H, m), 2.83 (1H, dd, J=11.0, 3.4 Hz), 2.79 (3H, s).

LC-MS MS(EI) for C19H18FN7O2S2 [M+H]+, (Calcd.: 459.09) Found: 460.2.

Example 98: Synthesis of (2S,3R,4S)-2-(8-(((1S,2R)-2-(3-fluorophenyl)cyclopropyl)amino)-[1,2,4]triazolo[4,3-a]pyrazin-3-yl)tetrahydrothiophene-3,4-diol $^1$H-NMR (DMSO-$d_6$, 400 MHz): δ 8.60 (1H, d, J=4.0 Hz), 7.25 (1H, d, J=4.8 Hz), 7.34-7.28 (2H, m), 7.04-6.97 (3H, m), 5.43 (1H, d, J=6.0 Hz), 5.32 (1H, d, J=4.4 Hz), 4.78 (1H, d, J=7.2 Hz), 4.64-4.62 (1H, m), 4.41 (1H, brs), 3.26 (1H, dd, J=10.8, 4.4 Hz), 3.17-3.16 (1H, m), 2.82 (1H, dd, J=10.4, 3.2 Hz), 2.14 (1H, brs), 1.59-1.54 (1H, m), 1.35-1.30 (1H, m).

LC-MS MS(EI) for C18H18FN5O2S [M+H]+, (Calcd.: 387.12) Found: 388.2.

Example 99: Synthesis of (2S,3R,4S)-2-(8-(((1S,2R)-2-(3-chlorophenyl)cyclopropyl)amino)-[1,2,4]triazolo[4,3-a]pyrazin-3-yl)tetrahydrothiophene-3,4-diol $^1$H-NMR (DMSO-$d_6$, 400 MHz): δ 8.61 (1H, d, J=3.6 Hz), 7.73 (1H, d, J=4.8 Hz), 7.32-7.30 (2H, m), 7.29-7.22 (2H, m), 7.15 (1H, d, J=7.6 Hz), 5.43 (1H, d, J=6.0 Hz), 5.32 (1H, d, J=4.0 Hz), 4.78 (1H, d, J=7.2 Hz), 4.63 (1H, brs), 4.41 (1H, brs), 3.26 (1H, dd, J=10.6, 4.6 Hz), 3.09 (1H, brs), 2.82 (1H, dd, J=11.0, 3.4 Hz), 2.13 (1H, brs), 1.58-1.56 (1H, m), 1.36-1.32 (1H, m).

LC-MS MS(EI) for C18H18ClN5O2S [M+H]+, (Calcd.: 403.09) Found: 404.2.

Example 100: Synthesis of (2S,3R,4S)-2-(6-chloro-8-((3-chlorobenzyl)amino)-[1,2,4]triazolo[4,3-a]pyrazin-3-yl)tetrahydrothiophene-3,4-diol

STEP1 Preparation of 2-chloro-3-hydrazinylpyrazine

To a solution of 2,3-dichloropyrazine (10.0 g, 67.1 mmol) in EtOH (224 mL) was added hydrazine hydrate (6.72 g, 134 mmol) at room temperature. The reaction mixture was refluxed for 3 hours. A precipitated solid was collected by filtration, washed with EtOH and dried under vacuum to afford 2-chloro-3-hydrazinylpyrazine (7.80 g, 80%) as an orange solid.

$^1$H-NMR (DMSO-$d_6$, 400 MHz): δ 8.30 (1H, brs), 8.07 (1H, d, J=2.4 Hz), 7.57 (1H, d, J=2.8 Hz), 4.34 (2H, brs).

STEP2 Preparation of N'-(3-chloropyrazin-2-yl)-2,2,2-trifluoroacetohydrazide To a solution of 2-chloro-3-hydrazinylpyrazine (4.50 g, 31.1 mmol) in THF (104 mL) was dropwise added TFAA (5.72 mL, 40.5 mmol) at 0° C. The reaction mixture was stirred at room temperature for 1 hour and quenched with water. The mixture was extracted DCM, washed with water, dried over Na2SO4, filtered and concentrated in vacuo to afford N'-(3-chloropyrazin-2-yl)-2,2,2-trifluoroacetohydrazide (2.76 g, 37%) as a yellow solid, which was used for the next reaction without further purification.

$^1$H-NMR (DMSO-$d_6$, 400 MHz): δ 11.6 (1H, s), 9.47 (1H, s), 8.18 (1H, d, J=2.8 Hz), 7.88 (1H, d, J=2.4 Hz).

STEP3 Preparation of N'-(3,5-dichloropyrazin-2-yl)-2,2,2-trifluoroacetohydrazide To a solution N'-(3-chloropyrazin-2-yl)-2,2,2-trifluoroacetohydrazide (2.76 g, 11.5 mmol) in CHCl3 (38 mL) was added NCS (2.30 g, 17.2 mmol) at 0° C. The reaction mixture was stirred at room temperature for 2 hours, diluted with water and extracted DCM. The separated organic layer was washed with water, dried over Na2SO4, filtered and concentrated in vacuo. The residue was purified by column chromatography on SiO2 (Hexanes:EtOAc=5:1) to afford N'-(3,5-dichloropyrazin-2-yl)-2,2,2-trifluoroacetohydrazide (1.50 g, 48%) as a yellow solid.

$^1$H-NMR (DMSO-$d_6$, 400 MHz): δ 11.7 (1H, s), 9.67 (1H, s), 8.35 (1H, s).

STEP4 Preparation of 3,5-dichloro-2-hydrazinylpyrazine

To a solution of N'-(3,5-dichloropyrazin-2-yl)-2,2,2-trifluoroacetohydrazide (1.50 g, 5.45 mmol) in EtOH (27 mL)

was added conc. HCl (3.31 mL, 109 mmol) at room temperature. The reaction mixture was stirred at 80° C. for 4 hours. After neutralization with saturated aq. Na2CO3, the mixture was extracted with EtOAc. The separated organic layer was washed with water, dried over Na2SO4, filtered and concentrated in vacuo. The residue was purified by column chromatography on NH—SiO2 (Hexanes:EtOAc=5:1) to give 3,5-dichloro-2-hydrazinylpyrazine (900 mg, 92%) as a yellow solid.

$^1$H-NMR (DMSO-d$_6$, 400 MHz): δ 8.54 (1H, brs), 8.20 (1H, s), 4.40 (2H, brs).

STEP4 Preparation of 6,8-dichloro-3-((3aR,4S,6aS)-2,2-dimethyltetrahydrothieno[3,4-d][1,3]dioxol-4-yl)-[1,2,4]triazolo[4,3-a]pyrazine A mixture of (3aR,4R,6aS)-2,2-dimethyltetrahydrothieno[3,4-d][1,3]dioxole-4-carbaldehyde (850 mg, 4.52 mmol) and 3,5-dichloro-2-hydrazinylpyrazine (889 mg, 4.97 mmol) in DCM (45 mL) was stirred at room temperature for 1 hour and cooled to 0° C. After addition of PhI(OAc)2 (2.18 g, 6.77 mmol) at 0° C., the reaction mixture was stirred at room temperature for 3 hours, and then washed with saturated aq. NaHCO3 and brine. The separated organic layer was dried over Na2SO4, filtered and concentrated in vacuo. The residue was purified by column chromatography on SiO2 (Hexanes:EtOAc=3:1) to give 6,8-dichloro-3-((3aR,4S,6aS)-2,2-dimethyltetrahydrothieno[3,4-d][1,3]dioxol-4-yl)-[1,2,4]triazolo[4,3-a]pyrazine (493 mg, 31%) as a yellow solid.

$^1$H-NMR (CDCl$_3$, 400 MHz): δ 7.95 (1H, s), 5.73 (1H, d, J=4.4 Hz), 5.30 (1H, s), 4.60 (1H, s), 3.02 (1H, d, J=13.2 Hz), 2.92 (1H, dd, J=13.2, 3.6 Hz), 1.59 (3H, s), 1.42 (3H, s).

STEP5 Preparation of 6-chloro-N-(3-chlorobenzyl)-3-((3aR,4S,6aS)-2,2-dimethyltetrahydrothieno[3,4-d][1,3]dioxol-4-yl)-[1,2,4]triazolo[4,3-a]pyrazin-8-amine A mixture of 6,8-dichloro-3-((3aR,4S,6aS)-2,2-dimethyltetrahydrothieno[3,4-d][1,3]dioxol-4-yl)-[1,2,4]triazolo[4,3-a]pyrazine (50.0 mg, 0.144 mmol), (3-chlorophenyl)methanamine (24.0 mg, 0.173 mmol) and DIPEA (30.0 μL, 0.173 mmol) in EtOH (2.0 mL) was stirred at room temperature for 18 hours. After concentration in vacuo, the residue was diluted with EtOAc and washed with water and brine. The separated organic layer was dried over Na2SO4, filtered and concentrated in vacuo. The residue was purified by column chromatography on NH—SiO2 (Hexanes:EtOAc=1:1) to give 6-chloro-N-(3-chlorobenzyl)-3-((3aR,4S,6aS)-2,2-dimethyltetrahydrothieno[3,4-d][1,3]dioxol-4-yl)-[1,2,4]triazolo[4,3-a]pyrazin-8-amine (50.0 mg, 77%) as a yellow oil.

$^1$H-NMR (CDCl$_3$, 400 MHz): δ 7.40 (1H, brs), 7.30-7.29 (4H, m), 6.85 (1H, brs), 5.64 (1H, d, J=5.2 Hz), 5.25 (1H, brs), 4.90-4.80 (2H, m), 4.51 (1H, s), 3.00-2.97 (2H, m), 1.56 (3H, s), 1.40 (3H, s).

STEP6 Preparation of (2S,3R,4S)-2-(6-chloro-8-((3-chlorobenzyl)amino)-[1,2,4]triazolo[4,3-a]pyrazin-3-yl)tetrahydrothiophene-3,4-diol A solution of 6-chloro-N-(3-chlorobenzyl)-3-((3aR,4S,6aS)-2,2-dimethyltetrahydrothieno[3,4-d][1,3]dioxol-4-yl)-[1,2,4]triazolo[4,3-a]pyrazin-8-amine (50.0 mg, 0.111 mmol) in 80% TFA (0.111 mL, 0.111 mmol) was stirred at room temperature for 30 min. After concentration in vacuo, the residue was diluted with DCM, and then TEA was added to the solution until pH 7. The mixture was stirred at room temperature for 20 min and concentrated in vacuo. The residue was purified by column chromatography on NH—SiO2 (EtOAc:MeOH=10:1) to give (2S,3R,4S)-2-(6-chloro-8-((3-chlorobenzyl)amino)-[1,2,4]triazolo[4,3-a]pyrazin-3-yl)tetrahydrothiophene-3,4-diol (30.0 mg, 65%) as a white solid.

$^1$H-NMR (DMSO-d$_6$, 400 MHz): δ 9.34-9.28 (1H, m), 7.92 (1H, s), 7.43 (1H, s), 7.38-7.32 (3H, m), 5.42 (1H, d, J=5.2 Hz), 5.30 (1H, d, J=4.0 Hz), 4.78 (1H, d, J=7.2 Hz), 4.65 (2H, d, J=4.8 Hz), 4.55 (1H, brs), 4.40 (1H, brs), 3.27 (1H, dd, J=10.6, 4.2 Hz), 2.82-2.80 (1H, m).

LC-MS MS(EI) for C16H15Cl2N5O2S [M+H]+, (Calcd.: 411.03) Found: 412.1.

Example 101: Synthesis of (2S,3R,4S)-2-(6-chloro-8-((2,5-dichlorobenzyl)amino)-[1,2,4]triazolo[4,3-a]pyrazin-3-yl)tetrahydrothiophene-3,4-diol $^1$H-NMR (DMSO-d$_6$, 400 MHz): δ 9.29 (1H, s), 7.96 (1H, s), 7.52 (1H, d, J=8.4 Hz), 7.43-7.38 (2H, m), 5.43 (1H, d, J=5.6 Hz), 5.30 (1H, d, J=4.8 Hz), 4.79 (1H, d, J=7.2 Hz), 4.71-4.69 (2H, m), 4.58-4.55 (1H. m), 4.43-4.40 (1H. m), 3.27 (1H, dd, J=10.6, 4.6 Hz), 2.82 (1H, dd, J=10.6, 3.4 Hz).

LC-MS MS(EI) for C16H14Cl3N5O2S [M+H]+, (Calcd.: 444.99) Found: 448.1.

Example 102: Synthesis of (2S,3R,4S)-2-(6-chloro-8-((3,5-dichlorobenzyl)amino)-[1,2,4]triazolo[4,3-a]pyrazin-3-yl)tetrahydrothiophene-3,4-diol $^1$H-NMR (DMSO-d$_6$, 400 MHz): δ 9.30 (1H, t, J=3.4 Hz), 7.95 (1H, s), 7.50 (1H, s), 7.43 (2H, s), 5.42 (1H, d, J=5.2 Hz), 5.30 (1H, d, J=2.8 Hz), 4.78 (1H, d, J=7.2 Hz), 4.65 (2H, d, J=4.8 Hz), 4.56-4.54 (1H, m), 4.41-4.39 (1H, m), 3.27 (1H, dd, J=10.8, 4.4 Hz), 2.82 (1H, dd, J=10.4, 3.6 Hz).

LC-MS MS(EI) for C16H14Cl3N5O2S [M+H]+, (Calcd.: 444.99) Found: 448.0.

Example 103: Synthesis of (2S,3R,4S)-2-(6-chloro-8-((5-chloro-2-fluorobenzyl)amino)-[1,2,4]triazolo[4,3-a]pyrazin-3-yl)tetrahydrothiophene-3,4-diol $^1$H-NMR (DMSO-d$_6$, 400 MHz): δ 9.29 (1H, brs), 7.95 (1H, s), 7.46-7.45 (1H, m), 7.39-7.37 (1H, m), 7.27 (1H, t, J=9.2 Hz), 5.42 (1H, d, J=5.6 Hz), 5.30 (1H, d, J=4.4 Hz), 4.79 (1H, d, J=7.2 Hz), 4.68-4.67 (2H, m), 4.56 (1H, brs), 4.41 (1H, brs), 3.27 (1H, dd, J=10.6, 4.6 Hz), 2.81 (1H, dd, J=10.2, 3.8 Hz).

LC-MS MS(EI) for C16H14Cl2FN5O2S [M+H]+, (Calcd.: 429.02) Found: 430.1.

Example 104: Synthesis of (2S,3R,4S)-2-(6-chloro-8-((4-fluorophenethyl)amino)-[1,2,4]triazolo[4,3-a]pyrazin-3-yl)tetrahydrothiophene-3,4-diol $^1$H-NMR (DMSO-d$_6$, 400 MHz): δ 8.81 (1H, t, J=4.8 Hz), 7.88 (1H, s), 7.31-7.28 (2H, m), 7.11 (2H, t, J=9.0 Hz), 5.42 (1H, d, J=5.6 Hz), 5.30 (1H, d, J=4.0 Hz), 4.77 (1H, d, J=6.8 Hz), 4.58-4.54 (1H, m), 4.42-4.37 (1H, m), 3.68-3.62 (2H, m), 3.26 (1H, dd, J=10.5, 4.1 Hz), 2.94 (2H, t, J=6.8 Hz), 2.81 (1H, dd, J=10.3, 4.2 Hz).

LC-MS MS(EI) for C17H17ClFN5O2S [M+H]+, (Calcd.: 409.08) Found: 410.2.

Example 105: Synthesis of (2S,3R,4S)-2-(6-chloro-8-((3-fluorophenethyl)amino)-[1,2,4]triazolo[4,3-a]pyrazin-3-yl)tetrahydrothiophene-3,4-diol $^1$H-NMR (DMSO-$d_6$, 400 MHz): δ 8.83-8.80 (1H, m), 7.88 (1H, s), 7.35-7.30 (1H, m), 7.14-7.09 (2H, m), 7.02 (1H, t, J=8.6 Hz), 5.43 (1H, d, J=5.6 Hz), 5.30 (1H, d, J=4.4 Hz), 4.77 (1H, d, J=6.4 Hz), 4.55 (1H, brs), 4.40 (1H, brs), 3.70-3.68 (2H, m), 3.25 (1H, dd, J=10.6, 4.6 Hz), 2.98 (2H, t, J=7.0 Hz), 2.81 (1H, dd, J=10.4, 4.0 Hz).
LC-MS MS(EI) for C17H17ClFN5O2S [M+H]+, (Calcd.: 409.08) Found: 410.2.

Example 106: Synthesis of (2S,3R,4S)-2-(6-chloro-8-((3,4-difluorophenethyl)amino)-[1,2,4]triazolo[4,3-a]pyrazin-3-yl)tetrahydrothiophene-3,4-diol $^1$H-NMR (DMSO-$d_6$, 400 MHz): δ 8.88 (1H, s), 7.94 (1H, s), 7.45-7.35 (2H, m), 7.18-7.13 (1H, m), 5.48 (1H, d, J=6.4 Hz), 5.37 (1H, d, J=4.4 Hz), 4.83 (1H, d, J=6.8 Hz), 4.62-4.61 (1H, m), 4.47-4.46 (1H, m), 3.75-3.73 (2H, m), 3.32 (1H, dd, J=13.2, 4.4 Hz), 3.01 (2H, t, J=4.8 Hz),), 2.87 (1H, d, J=8.0 Hz).
LC-MS MS(EI) for C17H16ClF2N5O2S [M+H]+, (Calcd.: 427.07) Found: 428.1.

Example 107: Synthesis of (2S,3R,4S)-2-(6-chloro-8-((4-chloro-3-fluorophenethyl)amino)-[1,2,4]triazolo[4,3-a]pyrazin-3-yl)tetrahydrothiophene-3,4-diol $^1$H-NMR (DMSO-$d_6$, 400 MHz): δ 8.82-8.76 (1H, m), 7.84 (1H, s), 7.44 (1H, d, J=8.0 Hz), 7.32 (1H, d, J=10.8 Hz), 7.09 (1H, d, J=8.0 Hz), 5.39 (1H, d, J=6.0 Hz), 5.26 (1H, d, J=4.4 Hz), 4.73 (1H, d, J=6.8 Hz), 4.54-4.50 (1H, m), 4.37-4.36 (1H, m), 3.66-3.65 (2H, m), 3.22 (1H, dd, J=10.4, 4.4 Hz), 2.93 (2H, t, J=6.8 Hz), 2.78 (1H, dd, J=10.4, 3.6 Hz).
LC-MS MS(EI) for C17H16C12FN5O2S [M+H]+, (Calcd.: 443.04) Found: 444.1.

Example 108: Synthesis of (2S,3R,4S)-2-(6-chloro-8-(((1S,2R)-2-phenylcyclopropyl)amino)-[1,2,4]triazolo[4,3-a]pyrazin-3-yl)tetrahydrothiophene-3,4-diol $^1$H-NMR (DMSO-$d_6$, 400 MHz): δ 9.13 (1H, s), 7.93 (1H, s), 7.31-7.18 (4H, m), 5.43 (1H, d, J=5.6 Hz), 5.30 (1H, d, J=4.0 Hz), 4.79 (1H, d, J=7.2 Hz), 4.58-4.53 (1H, m), 4.42-4.38 (1H, m), 3.26 (1H, dd, J=12.8, 6.0 Hz), 3.12-3.06 (1H, m), 2.81 (1H, dd, J=11.2, 3.2 Hz), 2.23-2.17 (1H, m), 1.49-1.46 (1H, m), 1.34-1.32 (1H, m). *A proton was not observed.
LC-MS MS(EI) for C18H18ClN5O2S [M+H]+, (Calcd.: 403.09) Found: 404.1.

Example 109: Synthesis of (2S,3R,4S)-2-(8-((3-chlorobenzyl)amino)imidazo[1,2-a]pyrazin-3-yl)tetrahydrothiophene-3,4-diol

STEP1 Preparation of (S)-2-((3aR,4S,6aS)-2,2-dimethyltetrahydrothieno[3,4-d][1,3]dioxol-4-yl)-2-hydroxyethyl 4-methylbenzenesulfonate To a solution of (S)-1-((3aR,4S,6aS)-2,2-dimethyltetrahydrothieno[3,4-d][1,3]dioxol-4-yl)ethane-1,2-diol (19.0 g, 86.0 mmol) in pyridine (108 mL) was added dropwise a solution of p-TsCl (21.38 g, 112 mmol) in pyridine (50 mL) at 0° C. The reaction mixture was stirred at room temperature for 18 h and poured onto ice-water. The mixture was extracted with DCM twice. The combined organic layers were dried over Na$_2$SO$_4$, filtered and concentrated in vacuo. The residue was purified by column chromatography on SiO$_2$ (Hexanes:EtOAc=7:1 to 3:1) to give (S)-2-((3aR,4S,6aS)-2,2-dimethyltetrahydrothieno[3,4-d][1,3]dioxol-4-yl)-2-hydroxyethyl4-methylbenzene sulfonate (28.6 g, 89%) as a yellow oil.
$^1$H-NMR (CDCl$_3$, 400 MHz): δ 7.80 (d, J=8.8 Hz, 2H), 7.37 (d, J=8.4 Hz, 2H), 4.90 (dd, J=5.2, 4.0 Hz, 1H), 4.78 (dd, J=5.6, 1.2 Hz, 1H), 4.14-4.08 (m, 2H), 3.99 (dd, J=14.4, 8.0 Hz, 1H), 3.32 (brs, 1H), 3.18 (dd, J=12.4, 4.8 Hz, 1H), 2.84 (d, J=12.4 Hz, 1H), 2.48-2.44 (m, 4H), 1.50 (s, 3H), 1.31 (s, 3H).

STEP2 Preparation of (S)-2-azido-1-((3aR,4S,6aS)-2,2-dimethyltetrahydrothieno[3,4-d][1,3]dioxol-4-yl)ethanol To a solution of (S)-2-((3aR,4S,6aS)-2,2-dimethyltetrahydrothieno[3,4-d][1,3]dioxol-4-yl)-2-hydroxyethyl 4-methylbenzenesulfonate (28.6 g, 76.0 mmol) in DMF (219 mL) was added sodium azide (24.9 g, 382 mmol) at room temperature. The reaction mixture was stirred at 120° C. for 3 h, cooled to room temperature and partitioned between EtOAc and water. The separated organic layer was dried over Na$_2$SO$_4$, filtered and concentrated in vacuo. The residue was purified by column chromatography on SiO$_2$ (Hexanes:EtOAc=5:1 to 2:1) to give (S)-2-azido-1-((3aR,4S,6aS)-2,2-dimethyltetrahydrothieno[3,4-d][1,3]dioxol-4-yl)ethanol (17.8 g, 95%) as a colorless oil.
$^1$H-NMR (CDCl$_3$, 400 MHz): δ 4.93 (td, J=5.5, 1.7 Hz, 1H), 4.74 (dd, J=5.8, 1.8 Hz, 1H), 3.84-3.89 (m, 1H), 3.49-3.37 (m, 3H), 3.17 (dd, J=12.6, 5.0 Hz, 1H), 2.91 (dd, J=12.4, 2.0 Hz, 1H), 2.37 (d, J=5.6 Hz, 1H), 1.53 (s, 3H), 1.33 (s, 3H).

STEP3 Preparation of (S)-2-amino-1-((3aR,4S,6aS)-2,2-dimethyltetrahydrothieno[3,4-d][1,3]dioxol-4-yl)ethanol To a solution of (S)-2-azido-1-((3aR,4S,6aS)-2,2-dimethyltetrahydrothieno[3,4-d][1,3]dioxol-4-yl)ethanol (17.8 g, 72.6 mmol) in MeOH (363 mL) was added triphenylphosphine (28.5 g, 109 mmol) at room temperature. The reaction mixture was refluxed for 2 h and then concentrated in vacuo. The residue was purified by column chromatography on SiO$_2$ (EtOAc only to EtOAc:MeOH=10:1) and then the obtained solid was recrystallized from petroleum ether and EtOAc, and collected by filtration. The filtered solid was washed with petroleum ether and dried under vacuum to give (S)-2-amino-1-((3aR,4S,6aS)-2,2-dimethyltetrahydrodrothieno[3,4-d][1,3]dioxol-4-yl)ethanol (8.63 g, 54%) as a white solid.
$^1$H-NMR (CDCl$_3$, 400 MHz): δ 4.94 (t, J=4.4 Hz, 1H), 4.79 (d, J=7.2 Hz, 1H), 3.69-3.65 (m, 1H), 3.31 (d, J=3.2 Hz, 1H), 3.21 (dd, J=12.4, 5.2 Hz, 1H), 2.89-2.85 (m, 2H), 2.76 (dd, J=12.8, 8.0 Hz, 1H), 1.87 (brs, 2H), 1.53 (s, 3H), 1.33 (s, 3H).

STEP4 Preparation of (S)-2-((3-chloropyrazin-2-yl)amino)-1-((3aR,4S,6aS)-2,2-dimethyltetrahydrothieno[3,4-d][1,3]dioxol-4-yl)ethanol To a solution of (S)-2-amino-1-((3aR,4S,6aS)-2,2-dimethyltetrahydrothieno[3,4-d][1,3]dioxol-4-yl)ethanol (8.63 g, 39.4 mmol) in 1,4-dioxane (131 mL) were added 2,3-dichloro pyrazine (17.6 g, 118 mmol) and TEA (27.4 mL, 197 mmol) at room temperature. The reaction mixture was stirred at 110° C. for 24 h and concentrated in vacuo. The residue was dissolved in DCM and washed with water. The organic layer was dried over $Na_2SO_4$, filtered and concentrated in vacuo. The residue was purified by column chromatography on $SiO_2$ (Hexanes:EtOAc=3:1) to give (S)-2-((3-chloropyrazin-2-yl)amino)-1-((3aR,4S,6aS)-2,2-dimethyltetrahydrothieno[3,4-d][1,3]dioxol-4-yl)ethanol (11.0 g, 84%) as a colorless oil.

$^1$H-NMR (CDCl$_3$, 400 MHz): δ 7.91 (d, J=2.8 Hz, 1H), 7.63 (d, J=2.8 Hz, 1H), 5.65 (t, J=6.0 Hz, 1H), 4.95 (td, J=5.6, 1.9 Hz, 1H), 4.77 (dd, J=5.6, 2.4 Hz, 1H), 3.97-3.93 (m, 1H) 3.73 (ddd, J=14.4, 6.8, 3.2 Hz, 1H), 3.63-3.57 (m, 1H), 3.55 (d, J=4.8 Hz, 1H), 3.41 (dd, J=5.2, 2.0 Hz, 1H), 3.21 (dd, J=12.4, 5.6 Hz, 1H), 2.92 (dd, J=12.8, 1.6 Hz, 1H), 1.54 (s, 3H), 1.34 (s, 3H).

STEP5 Preparation of 2-((3-chloropyrazin-2-yl)amino)-1-((3aR,4R,6aS)-2,2-dimethyltetrahydrothieno[3,4-d][1,3]dioxol-4-yl)ethanone To a solution of (S)-2-((3-chloropyrazin-2-yl)amino)-1-((3aR,4S,6aS)-2,2-dimethyltetrahydro thieno[3,4-d][1,3]dioxol-4-yl)ethanol (11.0 g, 33.2 mmol) and TEA (38.9 mL, 279 mmol) in DMSO (39 mL) was added triethylamine-sulfur trioxide complex (9.01 g, 49.7 mmol) at 0° C. The reaction mixture was stirred room temperature for 1 h and then partitioned between EtOAc and water. The separated organic layer was dried over $Na_2SO_4$, filtered and concentrated in vacuo. The residue was purified by column chromatography on $SiO_2$ (Hexanes:EtOAc=5:1 to 3:1) to give 2-((3-chloropyrazin-2-yl)amino)-1-((3aR,4R,6aS)-2,2-dimethyltetrahydrothieno[3,4-d][1,3]dioxol-4-yl)ethanone (7.03 g, 64%) as a white solid.

$^1$H-NMR (CDCl$_3$, 400 MHz): δ 7.94 (d, J=2.8 Hz, 1H), 7.69 (d, J=2.8 Hz, 1H), 5.97 (brs, 1H), 5.05-5.00 (m, 2H), 4.73 (dd, J=19.2, 5.2 Hz, 1H), 4.33 (dd, J=19.4, 5.0 Hz, 1H), 4.01 (s, 1H), 2.95-2.86 (m, 2H), 1.52 (s, 3H), 1.34 (s, 3H).

STEP6 Preparation of 8-chloro-3-((3aR,4S,6aS)-2,2-dimethyltetrahydrothieno[3,4-d][1,3]dioxol-4-yl)imidazo[1,2-a]pyrazine To a solution of 2-((3-chloropyrazin-2-yl)amino)-1-((3aR,4R,6aS)-2,2-dimethyltetrahydrothieno[3,4-d][1,3]dioxol-4-yl)ethanone (7.03 g, 21.3 mmol) in toluene (142 mL) were added pyridine (20.7 mL, 256 mmol) followed by TFA (11.5 mL, 149 mmol) at 0° C. After being stirred for 30 min at room temperature, the mixture was cooled to 0° C. and then TFAA (21.1 mL, 149 mmol) was added to it. The resulting reaction mixture was stirred at room temperature for 3 h. After concentration in vacuo, the residue was dissolved in DCM, washed with water and brine, dried over $Na_2SO_4$, filtered and concentrated in vacuo. The residue was purified by column chromatography on $SiO_2$ (Hexanes:EtOAc=3:1 to 1:1) and then the obtained solid was recrystallized from petroleum ether and EtOAc and collected by filtration. The filtered solid was washed with petroleum ether and dried under vacuum to give 8-chloro-3-((3aR,4S,6aS)-2,2-dimethyltetrahydrothieno[3,4-d][1,3]dioxol-4-yl)imidazo[1,2-a]pyrazine (5.25 g, 79%) as a white solid.

$^1$H-NMR (CDCl$_3$, 400 MHz): δ 8.01 (d, J=4.4 Hz, 1H), 7.79 (d, J=4.8 Hz, 1H), 7.63 (s, 1H), 5.15-5.09 (m, 2H), 4.59 (s, 1H), 3.11-3.00 (m, 2H), 1.61 (s, 3H), 1.40 (s, 3H).

STEP7 Preparation of N-(3-chlorobenzyl)-3-((3aR,4S,6aS)-2,2-dimethyltetrahydrothieno[3,4-d][1,3]dioxol-4-yl)imidazo[1,2-a]pyrazin-8-amine A mixture of 8-chloro-3-((3aR,4S,6aS)-2,2-dimethyltetrahydrothieno[3,4-d][1,3]dioxol-4-yl)imidazo[1,2-a]pyrazine (500 mg, 1.60 mmol), (3-chlorophenyl)methanamine (0.236 mL, 1.92 mmol) and DIPEA (0.700 mL, 4.01 mmol) in i-BuOH (8.0 mL) was subjected to microwave irradiation at 170° C. for 4 h. (The reaction was repeated 4 times in same scale). The combined reaction mixture was cooled to room temperature, diluted with EtOAc and washed with water and brine. The separated organic layer was dried over $Na_2SO_4$, filtered and concentrated in vacuo. The residue was purified by column chromatography on NH—$SiO_2$ (Hexanes:EtOAc=1:1) to give N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (2.40 g, 90%) as a yellow oil.

$^1$H-NMR (CDCl$_3$, 400 MHz): δ 7.44 (d, J=4.8 Hz, 1H), 7.39-7.40 (m, 2H), 7.26-7.25 (m, 4H), 6.32-6.24 (m, 1H), 5.10-5.05 (m, 2H), 4.78 (d, J=6.4 Hz, 2H), 4.55 (s, 1H), 3.05-3.04 (m, 2H), 1.60 (s, 3H), 1.38 (s, 3H).

STEP8 Preparation of (2S,3R,4S)-2-(8-((3-chlorobenzyl)amino)imidazo[1,2-a]pyrazin-3-yl)tetrahydrothiophene-3,4-diol A solution of N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (2.40 g, 5.76 mmol) in 80% aq. TFA (46 mL) was stirred at room temperature for 1 h. The reaction mixture was concentrated in vacuo. The residue was diluted with DCM, and then TEA was added to the solution until pH 7. The mixture was stirred at room temperature for 10 min and concentrated in vacuo. The residue was purified by column chromatography on NH—$SiO_2$ (EtOAc:MeOH=10:1) to give (2S,3R,4S)-2-(8-((3-chlorobenzyl)amino)imidazo[1,2-a]pyrazin-3-yl)tetrahydrothiophene-3,4-diol (1.95 g, 90%) as a white solid.

$^1$H-NMR (DMSO-d$_6$, 400 MHz): δ 8.14 (t, J=6.4 Hz, 1H), 7.66 (d, J=4.8 Hz, 1H), 7.52 (s, 1H), 7.38 (s, 1H), 7.32-7.26 (m, 4H), 5.32 (d, J=6.4 Hz, 1H), 5.23 (d, J=4.0 Hz, 1H), 4.66-4.63 (m, 3H), 4.28-4.22 (m, 2H), 3.24 (dd, J=10.8, 4.0 Hz, 1H), 2.77 (dd, J=8.6, 4.6 Hz, 1H).

LC-MS MS(EI) for C17H17ClN4O2S [M+H]$^{+}$ (Calcd.: 376.86) Found: 377.2.

Example 110: Synthesis of (2S,3R,4S)-2-(8-aminoimidazo[1,2-a]pyrazin-3-yl)tetrahydrothiophene-3,4-diol $^1$H-NMR (DMSO-d$_6$, 400 MHz): δ 7.70 (d, J=4.9 Hz, 1H), 7.57 (s, 1H), 7.39 (s, 2H), 7.24 (d, J=4.9 Hz, 1H), 5.36 (d, J=5.5 Hz, 1H), 5.26 (s, 1H), 4.65 (d, J=7.8 Hz, 1H), 4.25 (d, J=11.5 Hz, 2H), 3.24 (dd, J=10.9, 4.3 Hz, 2H), 2.76 (dd, J=11.0, 2.4 Hz, 1H).

LC-MS MS(EI) for C10H12N4O2S [M+H]$^{+}$ (Calcd.: 252.07) Found: 253.1.

Example 111: Synthesis of (2S,3R,4S)-2-(8-(methylamino)imidazo[1,2-a]pyrazin-3-yl)tetrahydrothiophene-3,4-diol $^1$H-NMR (DMSO-d$_6$, 400 MHz): δ 7.61 (d, J=4.8 Hz, 1H), 7.49-7.42 (m, 2H), 7.30 (d, J=4.7 Hz, 1H), 5.34 (d, J=6.3 Hz, 1H), 5.25 (d, J=3.7 Hz, 1H), 4.63 (d, J=7.7 Hz, 1H), 4.25 (dd, J=11.2, 3.9 Hz, 2H), 3.23 (dd, J=10.9, 4.3 Hz, 1H), 2.92 (d, J=4.8 Hz, 3H), 2.76 (dd, J=10.9, 2.5 Hz, 1H).
LC-MS MS(EI) for C11H14N4O2S [M+H]⁺' (Calcd.: 266.08) Found: 267.1.

Example 112: Synthesis of (2S,3R,4S)-2-(8-((cyclopropylmethyl)amino)imidazo[1,2-a]pyrazin-3-yl)tetrahydrothiophene-3,4-diol ¹H-NMR (DMSO-d₆, 400 MHz): δ 7.61 (d, J=4.7 Hz, 1H), 7.51-7.41 (m, 2H), 7.28 (d, J=4.7 Hz, 1H), 5.29 (d, J=37.6 Hz, 2H), 4.63 (d, J=7.7 Hz, 1H), 4.26 (s, 2H), 3.31 (d, J=6.4 Hz, 2H), 3.23 (dd, J=10.9, 4.4 Hz, 1H), 2.76 (dd, J=10.9, 2.5 Hz, 1H), 1.22-1.11 (m, 1H), 0.45-0.37 (m, 2H), 0.31-0.22 (m, 2H).
LC-MS MS(EI) for C14H18N4O2S [M+H]⁺' (Calcd.: 306.12) Found: 307.1.

Example 113: Synthesis of (2S,3R,4S)-2-(8-(cyclobutylamino)imidazo[1,2-a]pyrazin-3-yl)tetrahydrothiophene-3,4-diol ¹H-NMR (DMSO-d₆, 400 MHz): δ 7.64-7.58 (m, 2H), 7.48 (s, 1H), 7.27 (d, J=4.7 Hz, 1H), 5.30 (d, J=32.7 Hz, 2H), 4.61 (dd, J=15.0, 7.9 Hz, 2H), 4.25 (d, J=6.7 Hz, 2H), 3.23 (dd, J=10.9, 4.4 Hz, 1H), 2.75 (dd, J=10.9, 2.6 Hz, 1H), 2.29-2.19 (m, 2H), 2.19-2.06 (m, 2H), 1.72-1.56 (m, 2H).
LC-MS MS(EI) for C14H18N4O2S [M+H]⁺' (Calcd.: 306.12) Found: 307.1.

Example 114: Synthesis of (2S,3R,4S)-2-(8-(cyclopropylamino)imidazo[1,2-a]pyrazin-3-yl)tetrahydrothiophene-3,4-diol ¹H-NMR (DMSO-d₆, 400 MHz): δ 7.66 (d, J=4.7 Hz, 1H), 7.57 (d, J=3.8 Hz, 1H), 7.46 (s, 1H), 7.34 (d, J=4.7 Hz, 1H), 5.34 (d, J=6.1 Hz, 1H), 5.25 (d, J=3.3 Hz, 1H), 4.63 (d, J=7.7 Hz, 1H), 4.24 (dd, J=10.7, 3.8 Hz, 2H), 3.23 (dd, J=10.9, 4.2 Hz, 1H), 2.89 (td, J=7.1, 3.6 Hz, 1H), 2.76 (dd, J=10.9, 2.4 Hz, 1H), 0.74-0.65 (m, 2H), 0.65-0.58 (m, 2H).
LC-MS MS(EI) for C13H16N4O2S [M+H]⁺' (Calcd.: 292.10) Found: 293.1.

Example 115: Synthesis of (2S,3R,4S)-2-(8-(isopentylamino)imidazo[1,2-a]pyrazin-3-yl)tetrahydrothiophene-3,4-diol ¹H-NMR (DMSO-d₆, 400 MHz): δ 7.59 (d, J=4.8 Hz, 1H), 7.46 (s, 1H), 7.37 (t, J=5.9 Hz, 1H), 7.28 (d, J=4.7 Hz, 1H), 5.36 (d, J=5.0 Hz, 1H), 5.29 (d, J=11.3 Hz, 1H), 4.62 (d, J=7.6 Hz, 1H), 4.29-4.21 (m, 2H), 3.46 (dd, J=14.2, 6.2 Hz, 2H), 3.23 (dd, J=10.8, 4.4 Hz, 1H), 2.75 (dd, J=10.9, 2.6 Hz, 1H), 1.62 (dt, J=13.2, 6.6 Hz, 1H), 1.50 (dd, J=14.3, 7.0 Hz, 2H), 0.90 (d, J=6.6 Hz, 6H).
LC-MS MS(EI) for C15H22N4O2S [M+H]⁺' (Calcd.: 322.15) Found: 323.1.

Example 116: Synthesis of (2S,3R,4S)-2-(8-morpholinoimidazo[1,2-a]pyrazin-3-yl)tetrahydrothiophene-3,4-diol ¹H-NMR (DMSO-d₆, 400 MHz): δ 7.78 (d, J=4.6 Hz, 1H), 7.56 (s, 1H), 7.40 (d, J=4.6 Hz, 1H), 5.38 (d, J=5.6 Hz, 1H), 5.27 (d, J=3.5 Hz, 1H), 4.65 (d, J=7.5 Hz, 1H), 4.27 (d, J=4.5 Hz, 2H), 4.18-4.12 (m, 4H), 3.76-3.69 (m, 4H), 3.23 (dd, J=10.8, 4.4 Hz, 1H), 2.77 (dd, J=10.8, 2.6 Hz, 1H).
LC-MS MS(EI) for C14H18N4O3S [M+H]⁺' (Calcd.: 322.11) Found: 323.1.

Example 117: Synthesis of (2S,3R,4S)-2-(8-(piperidin-1-yl)imidazo[1,2-a]pyrazin-3-yl)tetrahydrothiophene-3,4-diol ¹H-NMR (DMSO-d₆, 400 MHz): δ 7.68 (d, J=4.6 Hz, 1H), 7.53 (s, 1H), 7.36 (d, J=4.5 Hz, 1H), 5.30 (t, J=20.3 Hz, 2H), 4.63 (d, J=7.6 Hz, 1H), 4.26 (d, J=5.8 Hz, 2H), 4.22-4.06 (m, 4H), 3.22 (dd, J=10.8, 4.4 Hz, 1H), 2.77 (dd, J=10.8, 2.6 Hz, 1H), 1.73-1.62 (m, 2H), 1.58 (d, J=4.0 Hz, 4H).
LC-MS MS(EI) for C15H20N4O2S [M+H]⁺' (Calcd.: 320.13) Found: 321.1.

Example 118: Synthesis of (2S,3R,4S)-2-(8-(4-benzylpiperidin-1-yl)imidazo[1,2-a]pyrazin-3-yl)tetrahydrothiophene-3,4-diol ¹H-NMR (DMSO-d₆, 400 MHz): δ 7.69 (d, J=4.6 Hz, 2H), 7.52 (s, 2H), 7.36 (d, J=4.5 Hz, 2H), 7.31-7.24 (m, 4H), 7.19 (dd, J=7.3, 2.9 Hz, 6H), 5.43-5.30 (m, 6H), 5.25 (d, J=1.9 Hz, 2H), 4.63 (d, J=7.6 Hz, 2H), 4.26 (s, 4H), 3.22 (dd, J=10.9, 4.5 Hz, 2H), 2.95 (t, J=11.7 Hz, 4H), 2.76 (dd, J=10.8, 2.6 Hz, 2H), 1.85 (s, 2H), 1.65 (d, J=11.2 Hz, 4H), 1.29-1.14 (m, 5H).
LC-MS MS(EI) for C22H26N4O2S [M+H]⁺' (Calcd.: 410.18) Found: 411.2.

Example 119: Synthesis of (2S,3R,4S)-2-(8-(4-(4-fluorobenzyl)piperazin-1-yl)imidazo[1,2-a]pyrazin-3-yl)tetrahydrothiophene-3,4-diol ¹H-NMR (DMSO-d₆, 400 MHz): δ 7.74 (d, J=4.6 Hz, 1H), 7.54 (s, 1H), 7.37 (dd, J=7.8, 5.2 Hz, 3H), 7.16 (t, J=8.9 Hz, 2H), 5.31 (d, J=42.1 Hz, 2H), 4.64 (d, J=7.6 Hz, 1H), 4.26 (s, 2H), 4.18 (s, 4H), 3.50 (s, 2H), 3.22 (dd, J=10.8, 4.4 Hz, 1H), 2.76 (dd, J=10.8, 2.6 Hz, 1H).
LC-MS MS(EI) for C21H24FN5O2S [M+H]⁺' (Calcd.: 429.16) Found: 430.2.

Example 120: Synthesis of (2S,3R,4S)-2-(8-(benzylamino)imidazo[1,2-a]pyrazin-3-yl)tetrahydrothiophene-3,4-diol ¹H-NMR (DMSO-d₆, 400 MHz): δ 8.04 (t, J=6.3 Hz, 3H), 7.64 (d, J=4.8 Hz, 4H), 7.50 (s, 4H), 7.36-7.31 (m, 8H), 7.31-7.24 (m, 12H), 7.23-7.16 (m, 4H), 5.30 (d, J=38.9 Hz, 6H), 4.65 (t, J=8.1 Hz, 12H), 4.26 (s, 8H), 3.24 (dd, J=10.9, 4.4 Hz, 4H), 2.76 (dd, J=10.9, 2.4 Hz, 4H).
LC-MS MS(EI) for C17H18N4O2S [M+H]⁺' (Calcd.: 342.12) Found: 343.1.

Example 121: Synthesis of (2S,3R,4S)-2-(8-((3-methylbenzyl)amino)imidazo[1,2-a]pyrazin-3-yl)tetrahydrothiophene-3,4-diol ¹H-NMR (DMSO-d₆, 400 MHz): δ 7.99 (t, J=6.3 Hz, 1H), 7.63 (d, J=4.8 Hz, 1H), 7.50 (s, 1H), 7.26 (d, J=4.7 Hz, 1H), 7.14 (p, J=7.5 Hz, 3H), 7.01 (d, J=7.2 Hz, 1H), 5.33 (d, J=5.7 Hz, 1H), 5.24 (s, 1H), 4.67-4.60 (m, 3H), 4.26 (s, 2H), 3.24 (dd, J=10.9, 4.4 Hz, 1H), 2.76 (dd, J=10.9, 2.4 Hz, 1H), 2.26 (s, 3H).
LC-MS MS(EI) for C18H20N4O2S [M+H]⁺' (Calcd.: 356.13) Found: 357.1.

Example 122: Synthesis of (2S,3R,4S)-2-(8-((3-fluorobenzyl)amino)imidazo[1,2-a]pyrazin-3-yl)tetrahydrothiophene-3,4-diol $^1$H-NMR (DMSO-d$_6$, 400 MHz): δ 8.13 (t, J=6.4 Hz, 1H), 7.65 (d, J=4.8 Hz, 1H), 7.52 (s, 1H), 7.33 (td, J=7.9, 6.2 Hz, 1H), 7.26 (d, J=4.7 Hz, 1H), 7.15 (dd, J=16.8, 9.0 Hz, 2H), 7.02 (td, J=8.3, 1.9 Hz, 1H), 5.34 (d, J=6.0 Hz, 1H), 5.24 (s, 1H), 4.71-4.62 (m, 3H), 4.26 (t, J=5.4 Hz, 2H), 3.24 (dd, J=10.8, 4.4 Hz, 1H), 2.76 (dd, J=10.9, 2.5 Hz, 1H).
LC-MS MS(EI) for C17H17FN4O2S [M+H]$^{+}$ (Calcd.: 360.11) Found: 361.1.

Example 123: Synthesis of (2S,3R,4S)-2-(8-((3-(trifluoromethyl)benzyl)amino)imidazo[1,2-a]pyrazin-3-yl)tetrahydrothiophene-3,4-diol $^1$H-NMR (DMSO-d$_6$, 400 MHz): δ 8.22 (t, J=6.3 Hz, 1H), 7.71 (s, 1H), 7.65 (t, J=5.9 Hz, 2H), 7.61-7.49 (m, 3H), 7.26 (d, J=4.7 Hz, 1H), 5.33 (d, J=6.4 Hz, 1H), 5.24 (d, J=3.7 Hz, 1H), 4.73 (d, J=6.3 Hz, 2H), 4.64 (d, J=7.7 Hz, 1H), 4.25 (dd, J=10.9, 4.3 Hz, 2H), 3.24 (dd, J=10.9, 4.3 Hz, 1H), 2.76 (dd, J=10.9, 2.5 Hz, 1H).
LC-MS MS(EI) for C18H17F3N4O2S [M+H]$^{+}$ (Calcd.: 410.10) Found: 411.1.

Example 124: Synthesis of (2S,3R,4S)-2-(8-((3-iodobenzyl)amino)imidazo[1,2-a]pyrazin-3-yl)tetrahydrothiophene-3,4-diol $^1$H-NMR (DMSO-d$_6$, 400 MHz): δ 8.13 (t, J=6.2 Hz, 1H), 7.72 (s, 1H), 7.65 (d, J=4.8 Hz, 1H), 7.57 (d, J=7.2 Hz, 1H), 7.52 (s, 1H), 7.35 (d, J=7.2 Hz, 1H), 7.26 (d, J=4.4 Hz, 1H), 7.10 (t, J=7.6 Hz, 1H), 5.33 (d, J=6.4 Hz, 1H), 5.24 (d, J=3.2 Hz, 1H), 4.65-4.61 (m, 3H), 4.27-4.24 (m, 2H), 3.24 (dd, J=10.6, 4.6 Hz, 1H), 2.76 (dd, J=10.8, 2.0 Hz, 1H).
LC-MS MS(EI) for C17H17IN4O2S [M+H]$^{+}$ (Calcd.: 468.01) Found: 469.0.

Example 125: Synthesis of 4-(((3-((2S,3R,4S)-3,4-dihydroxytetrahydrothiophen-2-yl)imidazo[1,2-a]pyrazin-8-yl)amino)methyl)-2-fluoro-N-methylbenzamide $^1$H-NMR (DMSO-d$_6$, 400 MHz): δ 8.15 (dt, J=8.7, 4.7 Hz, 2H), 7.66 (d, J=4.8 Hz, 1H), 7.57-7.51 (m, 2H), 7.25 (d, J=4.7 Hz, 1H), 7.20 (dd, J=13.6, 6.2 Hz, 2H), 5.33 (d, J=6.3 Hz, 1H), 5.24 (d, J=3.1 Hz, 1H), 4.66 (dd, J=13.3, 6.9 Hz, 3H), 4.29-4.22 (m, 2H), 3.25 (d, J=11.0 Hz, 1H), 2.80-2.71 (m, 4H).
LC-MS MS(EI) for C19H20FN5O3S [M+H]$^{+}$ (Calcd.: 417.13) Found: 418.1.

Example 126: Synthesis of 2-chloro-4-(((3-((2S,3R,4S)-3,4-dihydroxytetrahydrothiophen-2-yl)imidazo[1,2-a]pyrazin-8-yl)amino)methyl)-N-methylbenzamide $^1$H-NMR (DMSO-d$_6$, 400 MHz): δ 8.28-8.24 (m, 1H), 8.19 (t, J=6.2 Hz, 1H), 7.65 (d, J=4.8 Hz, 1H), 7.52 (s, 1H), 7.42 (s, 1H), 7.34-7.30 (m, 2H), 7.25 (d, J=4.4 Hz, 1H), 5.33 (d, J=6.4 Hz, 1H), 5.24 (d, J=4.0 Hz, 1H), 4.65-4.63 (m, 3H), 4.27-4.24 (m, 2H), 3.24 (d, J=10.8, 4.0 Hz, 1H), 2.78 (dd, J=13.2, 2.4 Hz, 1H), 2.72 (d, J=4.8 Hz, 3H).
LC-MS MS(EI) for C19H20ClN5O3S [M+H]$^{+}$ (Calcd.: 433.10) Found: 434.1.

Example 127: Synthesis of (2S,3R,4S)-2-(8-((3-fluorophenethyl)amino)imidazo[1,2-a]pyrazin-3-yl)tetrahydrothiophene-3,4-diol $^1$H-NMR (DMSO-d$_6$, 400 MHz): δ 7.63 (t, J=4.8 Hz, 1H), 7.50-7.47 (m, 2H), 7.35-7.29 (m, 2H), 7.10-7.08 (m, 2H), 7.02 (t, J=8.4 Hz, 1H), 5.33 (d, J=6.0 Hz, 1H), 5.24 (d, J=3.2 Hz, 1H), 4.63 (d, J=7.6 Hz, 1H), 4.27-4.22 (m, 2H), 3.69 (q, J=6.6 Hz, 2H), 3.24 (dd, J=11.2, 4.4 Hz, 1H), 2.96 (t, J=7.4 Hz, 2H), 2.76 (dd, J=11.0, 2.2 Hz, 1H).
LC-MS MS(EI) for C18H19FN4O2S [M+H]$^{+}$ (Calcd.: 374.12) Found: 375.1.

Example 128: Synthesis of (2S,3R,4S)-2-(8-(phenethylamino)imidazo[1,2-a]pyrazin-3-yl)tetrahydrothiophene-3,4-diol $^1$H-NMR (DMSO-d$_6$, 400 MHz): δ 7.62 (d, J=4.8 Hz, 1H), 7.48-7.41 (m, 2H), 7.33-7.29 (m, 2H), 7.29-7.23 (m, 3H), 7.22-7.16 (m, 1H), 5.34 (d, J=6.4 Hz, 1H), 5.25 (d, J=3.8 Hz, 1H), 4.63 (d, J=7.7 Hz, 1H), 4.26 (d, J=4.5 Hz, 2H), 3.72-3.64 (m, 2H), 3.23 (dd, J=10.8, 4.3 Hz, 1H), 2.93 (t, J=7.4 Hz, 2H), 2.76 (dd, J=10.9, 2.5 Hz, 1H).
LC-MS MS(EI) for C18H20N4O2S [M+H]$^{+}$ (Calcd.: 356.13) Found: 357.1.

Example 129: Synthesis of (2S,3R,4S)-2-(8-((2-phenylcyclopropyl)amino)imidazo[1,2-a]pyrazin-3-yl)tetrahydrothiophene-3,4-diol $^1$H-NMR (DMSO-d$_6$, 400 MHz): δ 7.86 (d, J=3.6 Hz, 1H), 7.66 (d, J=5.2 Hz, 1H), 7.49 (s, 1H), 7.30-7.25 (m, 3H), 7.18-7.16 (m, 3H), 5.33 (d, J=6.0 Hz, 1H), 5.23 (d, J=2.8 Hz, 1H), 4.64 (d, J=6.8 Hz, 1H), 4.29-4.21 (m, 2H), 3.24 (dd, J=7.6, 1.6 Hz, 1H), 3.16-3.13 (m, 1H), 2.76 (dd, J=11.2, 4.0 Hz, 1H), 2.10-2.04 (m, 1H), 1.52-1.46 (m, 1H), 1.29-1.20 (m, 1H).
LC-MS MS(EI) for C19H20N4O2S [M+H]$^{+}$ (Calcd.: 368.13) Found: 369.1.

Example 130: Synthesis of (2S,3R,4S)-2-(8-((thiophen-3-ylmethyl)amino)imidazo[1,2-a]pyrazin-3-yl)tetrahydrothiophene-3,4-diol $^1$H-NMR (DMSO-d$_6$, 400 MHz): δ 2.75 (1H, dd, J=11.6, 2.4 Hz), 3.24 (1H, dd, J=10.8, 4.0 Hz), 4.24-4.27 (2H, m), 4.64 (3H, d, J=5.6 Hz), 5.24 (1H, d, J=4.0 Hz), 5.33 (1H, d, J=6.4 Hz), 7.11 (1H, d, J=5.2 Hz), 7.26-7.28 (1H, m), 7.29 (1H, d, J=4.4 Hz), 7.43 (1H, dd, J=4.6, 3.0 Hz), 7.49 (1H, s), 7.64 (1H, d, J=4.8 Hz), 7.92 (1H, t, J=6.4 Hz).
LC-MS MS(EI) for C15H16N4O2S2 [M+H]$^{+}$ (Calcd.: 348.07) Found: 349.1.

Example 131: Synthesis of (2S,3R,4S)-2-(8-((furan-3-ylmethyl)amino)imidazo[1,2-a]pyrazin-3-yl)tetrahydrothiophene-3,4-diol $^1$H-NMR (DMSO-d$_6$, 400 MHz): δ 2.76 (1H, dd, J=11.0, 2.2 Hz), 3.23 (1H, dd, J=11.0, 3.8 Hz), 4.23-4.27 (2H, m), 4.48 (2H, d, J=6.4 Hz), 4.64 (1H, d, J=7.2 Hz), 5.24 (1H, d, J=4.0 Hz), 5.33 (1H, d, J=6.4 Hz), 6.49 (1H, s), 7.31 (1H, d, J=4.8 Hz), 7.48 (1H, s), 7.55 (2H, s), 7.64 (1H, d, J=4.4 Hz), 7.75 (1H, t, J=6.2 Hz).
LC-MS MS(EI) for C15H16N4O3S [M+H]$^{+}$ (Calcd.: 332.09) Found: 333.2.

Example 132: Synthesis of (2S,3R,4S)-2-(8-((3-bromobenzyl)amino)imidazo[1,2-a]pyrazin-3-yl)tetrahydrothiophene-3,4-diol $^1$H-NMR (DMSO-d$_6$, 400 MHz): δ 2.76 (1H, dd, J=10.8, 2.0 Hz), 3.24 (1H, dd, J=10.4, 4.4 Hz), 4.24-4.26 (2H, m), 4.65 (3H, d, J=6.0 Hz), 5.24 (1H, d, J=3.6 Hz), 5.34 (1H, d, J=6.0 Hz), 7.23-7.27 (2H, m), 7.34 (1H, d, J=7.6 Hz), 7.40 (1H, d, J=8.0 Hz), 7.52-7.53 (2H, m), 7.66 (1H, d, J=4.8 Hz), 8.15 (1H, t, J=6.4 Hz).
LC-MS MS(EI) for C17H17BrN4O2S [M+H]$^{+\prime}$ (Calcd.: 420.03) Found: 423.2.

Example 133: Synthesis of (2S,3R,4S)-2-(8-(cyclopentylamino)imidazo[1,2-a]pyrazin-3-yl)tetrahydrothiophene-3,4-diol $^1$H-NMR (DMSO-d$_6$, 400 MHz): δ 1.53-1.64 (4H, m), 1.69-1.72 (2H, m), 1.92-1.98 (2H, m), 2.76 (1H, dd, J=10.8, 2.4 Hz), 3.23 (1H, dd, J=10.8, 4.0 Hz), 4.22-4.26 (2H, m), 4.37-4.44 (1H, m), 4.63 (1H, d, J=7.6 Hz), 5.23 (1H, d, J=4.0 Hz), 5.33 (1H, d, J=6.4 Hz), 7.16 (1H, d, J=7.2 Hz), 7.29 (1H, d, J=4.4 Hz), 7.47 (1H, s), 7.61 (1H, d, J=4.4 Hz).
LC-MS MS(EI) for C15H20N4O2S [M+H]$^{+\prime}$ (Calcd.: 320.13) Found: 321.2.

Example 134: Synthesis of (2S,3R,4S)-2-(8-((pyridin-2-ylmethyl)amino)imidazo[1,2-a]pyrazin-3-yl)tetrahydrothiophene-3,4-diol $^1$H-NMR (DMSO-d$_6$, 400 MHz): δ 2.74 (1H, d, J=11.2 Hz), 3.23 (1H, dd, J=10.6, 4.2 Hz), 4.25 (2H, s), 4.64 (1H, d, J=8.0 Hz), 4.73 (2H, d, J=6.0 Hz), 5.24 (1H, d, J=2.8 Hz), 5.34 (1H, d, J=5.6 Hz), 7.21-7.28 (3H, m), 7.52 (1H, s), 7.64-7.71 (2H, m), 8.00 (1H, dt, J=6.0 Hz), 8.49 (1H, d, J=4.4 Hz).
LC-MS MS(EI) for C16H17N5O2S [M+H]$^{+\prime}$ (Calcd.: 343.11) Found: 344.3.

Example 135: Synthesis of (2S,3R,4S)-2-(8-((pyridin-3-ylmethyl)amino)imidazo[1,2-a]pyrazin-3-yl)tetrahydrothiophene-3,4-diol $^1$H-NMR (DMSO-d$_6$, 400 MHz): δ 2.75 (1H, dd, J=10.8, 2.4 Hz), 3.23 (1H, dd, J=11.0, 4.2 Hz), 4.24-4.26 (2H, m), 4.63-4.68 (3H, m), 5.23 (1H, d, J=4.0 Hz), 5.32 (1H, d, J=6.4 Hz), 7.27 (1H, d, J=4.8 Hz), 7.30 (1H, dd, J=8.2, 5.0 Hz), 7.51 (1H, s), 7.66 (1H, d, J=4.8 Hz), 7.72-7.74 (1H, m), 8.16 (1H, t, J=6.0 Hz), 8.41 (1H, dd, J=5.0, 1.8 Hz), 8.57 (1H, d, J=1.6 Hz).
LC-MS MS(EI) for C16H17N5O2S [M+H]$^{+\prime}$ (Calcd.: 343.11) Found: 344.2.

Example 136: Synthesis of (2S,3R,4S)-2-(8-((pyridin-4-ylmethyl)amino)imidazo[1,2-a]pyrazin-3-yl)tetrahydrothiophene-3,4-diol $^1$H-NMR (DMSO-d$_6$, 400 MHz): δ 2.76 (1H, dd, J=10.2, 3.0 Hz), 3.24 (1H, dd, J=10.6, 4.2 Hz), 4.25-4.28 (2H, m), 4.64-4.68 (3H, m), 5.24 (1H, d, J=4.0 Hz), 5.34 (1H, d, J=6.4 Hz), 7.24 (1H, d, J=4.8 Hz), 7.29 (2H, d, J=5.6 Hz), 7.54 (1H, s), 7.67 (1H, d, J=4.8 Hz), 8.19 (1H, t, J=6.0 Hz), 8.44-8.46 (2H, m).
LC-MS MS(EI) for C16H17N5O2S [M+H]$^{+\prime}$ (Calcd.: 343.11) Found: 344.3.

Example 137: Synthesis of (2S,3R,4S)-2-(8-((3-methoxybenzyl)amino)imidazo[1,2-a]pyrazin-3-yl)tetrahydrothiophene-3,4-diol $^1$H-NMR (DMSO-d$_6$, 400 MHz): δ 2.72-2.75 (1H, d, J=10.8 Hz), 3.22 (1H, dd, J=10.8, 4.0 Hz), 3.68 (3H, s), 4.22-4.25 (2H, m), 4.60-4.63 (3H, m), 5.22 (1H, d, J=3.2 Hz), 5.31 (1H, d, J=6.4 Hz), 6.75 (1H, d, J=7.2 Hz), 6.88 (1H, d, J=7.2 Hz), 6.89 (1H, s), 7.17 (1H, t, J=7.6 Hz), 7.24 (1H, d, J=4.8 Hz), 7.49 (1H, s), 7.62 (1H, d, J=4.4 Hz), 7.99 (1H, t, J=10.0 Hz).
LC-MS MS(EI) for C18H20N4O3S [M+H]$^{+\prime}$ (Calcd.: 372.13) Found: 373.2.

Example 138: Synthesis of (2S,3R,4S)-2-(8-(cyclohexylamino)imidazo[1,2-a]pyrazin-3-yl)tetrahydrothiophene-3,4-diol $^1$H-NMR (DMSO-d$_6$, 400 MHz): δ 1.14-1.20 (1H, m), 1.25-1.39 (4H, m), 1.57-1.61 (1H, m), 1.70-1.73 (2H, m), 1.86-1.90 (2H, m), 2.74 (1H, d, J=11.6 Hz), 3.21 (1H, dd, J=11.2, 4.0 Hz), 3.81-4.00 (1H, m), 4.23-4.24 (2H, m), 4.61 (1H, d, J=7.2 Hz), 5.21 (1H, d, J=4.0 Hz), 5.30 (1H, d, J=6.8 Hz), 7.01 (1H, d, J=8.4 Hz), 7.26 (1H, d, J=4.4 Hz), 7.44 (1H, s), 7.58 (1H, d, J=4.4 Hz).
LC-MS MS(EI) for C16H22N4O2S [M+H]$^{+\prime}$ (Calcd.: 334.15) Found: 335.2.

Example 139: Synthesis of (2S,3R,4S)-2-(8-((cyclohexylmethyl)amino)imidazo[1,2-a]pyrazin-3-yl)tetrahydrothiophene-3,4-diol $^1$H-NMR (DMSO-d$_6$, 400 MHz): δ 0.89-0.92 (2H, m), 1.12-1.65 (3H, m), 1.59-1.70 (6H, m), 2.74 (1H, d, J=11.2 Hz), 3.21 (1H, dd, J=11.0, 3.8 Hz), 3.26-3.28 (2H, m), 4.23-4.24 (2H, m), 4.60 (1H, d, J=7.6 Hz), 5.31 (1H, s), 5.32 (1H, d, J=6.4 Hz), 7.25 (1H, d, J=4.4 Hz), 7.38 (1H, t, J=6.2 Hz), 7.44 (1H, s), 7.56 (1H, d, J=4.8 Hz).
LC-MS MS(EI) for C17H24N4O2S [M+H]$^{+\prime}$ (Calcd.: 348.16) Found: 349.3.

Example 140: Synthesis of (2S,3R,4S)-2-(8-((3-(trifluoromethoxy)benzyl)amino)imidazo[1,2-a]pyrazin-3-yl)tetrahydrothiophene-3,4-diol $^1$H-NMR (DMSO-d$_6$, 400 MHz): δ 2.76 (1H, dd, J=10.6, 2.2 Hz), 3.24 (1H, dd, J=10.8, 4.0 Hz), 4.24-4.27 (2H, m), 4.65 (1H, d, J=7.6 Hz), 4.69 (2H, d, J=6.0 Hz), 5.24 (1H, d, J=4.0 Hz), 5.33 (1H, d, J=6.0 Hz), 7.20 (1H, d, J=8.0 Hz), 7.26 (1H, d, J=4.8 Hz), 7.32 (1H, s), 7.37 (1H, d, J=8.0 Hz), 7.42 (1H, t, J=8.0 Hz), 7.52 (1H, s), 7.66 (1H, d, J=5.2 Hz), 8.18 (1H, t, J=6.2 Hz).
LC-MS MS(EI) for C18H17F3N4O3S [M+H]$^{+\prime}$ (Calcd.: 426.10) Found: 427.2.

Example 141: Synthesis of 3-(((3-((2S,3R,4S)-3,4-dihydroxytetrahydrothiophen-2-yl)imidazo[1,2-a]pyrazin-8-yl)amino)methyl)benzonitrile $^1$H-NMR (DMSO-d$_6$, 400 MHz): δ 2.76 (1H, dd, J=11.0, 1.8 Hz), 3.24 (1H, dd, J=10.6, 3.8 Hz), 4.23-4.27 (2H, m), 4.64 (1H, d, J=7.2 Hz), 4.70 (2H, d, J=6.4 Hz), 5.24 (1H, d, J=3.6 Hz), 5.33 (1H, d, J=6.4 Hz), 7.26 (1H, d, J=4.8 Hz), 7.49-7.53 (2H, m), 7.66-7.69 (3H, m), 7.77 (1H, s), 8.19 (1H, t, J=6.4 Hz).

LC-MS MS(EI) for C18H17N5O2S [M+H]⁺ (Calcd.: 367.11) Found: 368.2.

Example 142: Synthesis of (2S,3R,4S)-2-(8-((pyrimidin-5-ylmethyl)amino)imidazo[1,2-a]pyrazin-3-yl)tetrahydrothiophene-3,4-diol ¹H-NMR (DMSO-d₆, 400 MHz): δ 2.75 (1H, dd, J=10.4, 2.0 Hz), 3.24 (1H, dd, J=10.8, 3.6 Hz), 4.24-4.28 (2H, m), 4.63-4.67 (3H, m), 5.23 (1H, d, J=3.6 Hz), 5.33 (1H, d, J=6.4 Hz), 7.29 (1H, d, J=5.2 Hz), 7.52 (1H, s), 7.68 (1H, d, J=4.8 Hz), 8.22 (1H, t, J=6.0 Hz), 8.79 (2H, s), 9.04 (1H, s).
LC-MS MS(EI) for C15H16N6O2S [M+H]⁺ (Calcd.: 344.11) Found: 345.2.

Example 143: Synthesis of (2S,3R,4S)-2-(8-((pyrazin-2-ylmethyl)amino)imidazo[1,2-a]pyrazin-3-yl)tetrahydrothiophene-3, 4-diol ¹H-NMR (DMSO-d₆, 400 MHz): δ 2.76 (1H, dd, J=10.8, 2.4 Hz), 3.25 (1H, dd, J=10.6, 4.2 Hz), 4.25-4.28 (2H, m), 4.65 (1H, d, J=8.0 Hz), 4.81 (2H, d, J=6.4 Hz), 5.24 (1H, d, J=3.2 Hz), 5.34 (1H, d, J=6.0 Hz), 7.25 (1H, d, J=4.4 Hz), 7.54 (1H, s), 7.68 (1H, d, J=4.4 Hz), 8.12 (1H, t, J=6.0 Hz), 8.50 (1H, d, J=2.4 Hz), 8.57 (1H, d, J=2.4 Hz), 8.58 (1H, s).
LC-MS MS(EI) for C15H16N6O2S [M+H]⁺ (Calcd.: 344.11) Found: 345.2.

Example 144: Synthesis of (2S,3R,4S)-2-(8-((pyrimidin-2-ylmethyl)amino)imidazo[1,2-a]pyrazin-3-yl)tetrahydrothiophene-3,4-diol ¹H-NMR (DMSO-d₆, 400 MHz): δ 2.76 (1H, d, J=10.8 Hz), 3.25 (1H, dd, J=11.2, 4.0 Hz), 4.23-4.30 (2H, m), 4.66 (1H, d, J=8.0 Hz), 4.84 (2H, d, J=6.0 Hz), 5.25 (1H, d, J=3.6 Hz), 5.35 (1H, d, J=6.8 Hz), 7.23 (1H, d, J=4.8 Hz), 7.38 (1H, t, J=5.0 Hz), 7.53 (1H, s), 7.66 (1H, d, J=5.2 Hz), 7.77 (1H, t, J=4.8 Hz), 8.76 (2H, d, J=4.8 Hz).
LC-MS MS(EI) for C15H16N6O2S [M+H]⁺ (Calcd.: 344.11) Found: 345.3.

Example 145: Synthesis of (2S,3R,4S)-2-(8-((pyrimidin-4-ylmethyl)amino)imidazo[1,2-a]pyrazin-3-yl)tetrahydrothiophene-3,4-diol ¹H-NMR (DMSO-d₆, 400 MHz): δ 2.76 (1H, dd, J=11.4, 1.0 Hz), 3.25 (1H, dd, J=11.8, 4.6 Hz), 4.25-4.29 (2H, m), 4.66 (1H, d, J=8.0 Hz), 4.72 (2H, d, J=5.6 Hz), 5.26 (1H, d, J=3.6 Hz), 5.35 (1H, d, J=6.4 Hz), 7.23 (1H, d, J=4.8 Hz), 7.36 (1H, d, J=5.2 Hz), 7.56 (1H, s), 7.69 (1H, d, J=4.8 Hz), 8.15 (1H, t, J=4.4 Hz), 8.66 (1H, d, J=5.2 Hz), 9.09 (1H, s).
LC-MS MS(EI) for C15H16N6O2S [M+H]⁺ (Calcd.: 344.11) Found: 345.2.

Example 146: Synthesis of (2S,3R,4S)-2-(8-((3-chlorophenethyl)amino)imidazo[1,2-a]pyrazin-3-yl)tetrahydrothiophene-3,4-diol ¹H-NMR (DMSO-d₆, 400 MHz): δ 2.76 (1H, dd, J=14.8, 6.0 Hz), 2.95 (2H, t, J=7.0 Hz), 3.23 (1H, dd, J=11.0, 3.8 Hz), 3.69 (2H, q, J=6.8 Hz), 4.25-4.26 (2H, m), 4.63 (1H, d, J=7.6 Hz), 5.23 (1H, d, J=3.6 Hz), 5.33 (1H, d, J=6.8 Hz), 7.21-7.24 (1H, m), 7.26 (1H, s), 7.29-7.34 (3H, m), 7.47 (1H, s), 7.48-7.51 (1H, m), 7.63 (1H, d, J=4.8 Hz).
LC-MS MS(EI) for C18H19ClN4O2S [M+H]⁺ (Calcd.: 390.09) Found: 391.3.

Example 147: Synthesis of (2S,3R,4S)-2-(8-((thiazol-4-ylmethyl)amino)imidazo[1,2-a]pyrazin-3-yl)tetrahydrothiophene-3,4-diol ¹H-NMR (DMSO-d₆, 400 MHz): δ 2.74 (1H, d, J=11.2 Hz), 3.22 (1H, dd, J=10.6, 3.8 Hz), 4.25-4.26 (2H, m), 4.63 (1H, d, J=7.6 Hz), 4.79 (2H, d, J=6.0 Hz), 5.23 (1H, d, J=3.6 Hz), 5.32 (1H, d, J=6.4 Hz), 7.26 (1H, d, J=4.4 Hz), 7.34 (1H, s), 7.50 (1H, s), 7.65 (1H, d, J=4.8 Hz), 7.90 (1H, t, J=6.0 Hz), 9.02 (1H, s).
LC-MS MS(EI) for C14H15N5O2S2 [M+H]⁺ (Calcd.: 349.07) Found: 350.2.

Example 148: Synthesis of (2S,3R,4S)-2-(8-((thiazol-2-ylmethyl)amino)imidazo[1,2-a]pyrazin-3-yl)tetrahydrothiophene-3,4-diol ¹H-NMR (DMSO-d₆, 400 MHz): δ 2.76 (1H, dd, J=10.6, 2.2 Hz), 3.25 (1H, dd, J=10.2, 3.8 Hz), 4.25-4.28 (2H, m), 4.66 (1H, d, J=8.0 Hz), 4.92 (2H, d, J=6.4 Hz), 5.24 (1H, d, J=3.6 Hz), 5.35 (1H, d, J=6.4 Hz), 7.31 (1H, d, J=4.8 Hz), 7.54 (1H, d, J=3.6 Hz), 7.55 (1H, s), 7.71 (1H, d, J=3.2 Hz), 7.72 (1H, d, J=5.2 Hz), 8.35 (1H, t, J=5.8 Hz).
LC-MS MS(EI) for C14H15N5O2S2 [M+H]⁺ (Calcd.: 349.07) Found: 350.2.

Example 149: Synthesis of (2S,3R,4S)-2-(8-((3-bromophenethyl)amino)imidazo[1,2-a]pyrazin-3-yl)tetrahydrothiophene-3,4-diol ¹H-NMR (DMSO-d₆, 400 MHz): δ 2.75 (1H, d, J=9.2, 3.2 Hz), 2.94 (2H, t, J=7.0 Hz), 3.23 (1H, dd, J=11.6, 5.2 Hz), 3.65-3.71 (2H, m), 4.23-4.27 (2H, m), 4.63 (1H, d, J=7.6 Hz), 5.23 (1H, d, J=4.0 Hz), 5.33 (1H, d, J=5.6 Hz), 7.24-7.26 (2H, m), 7.31 (1H, d, J=4.8 Hz), 7.38-7.39 (1H, m), 7.47-7.49 (3H, m), 7.63 (1H, d, J=4.8 Hz).
LC-MS MS(EI) for C18H19BrN4O2S [M+H]⁺ (Calcd.: 434.04) Found: 435.1.

Example 150: Synthesis of (2S,3R,4S)-2-(8-((2-morpholinoethyl)amino)imidazo[1,2-a]pyrazin-3-yl)tetrahydrothiophene-3,4-diol ¹H-NMR (DMSO-d₆, 400 MHz): δ 2.42 (4H, brs), 2.50-2.56 (2H, m), 2.75 (1H, dd, J=8.6, 4.6 Hz), 3.23 (1H, dd, J=11.0, 5.0 Hz), 3.54-3.58 (6H, m), 4.23-4.26 (2H, m), 4.63 (1H, d, J=7.6 Hz), 5.23 (1H, d, J=4.0 Hz), 5.32 (1H, d, J=6.4 Hz), 7.18-7.30 (1H, m), 7.29 (1H, d, J=5.2 Hz), 7.47 (1H, s), 7.62 (1H, d, J=4.8 Hz).
LC-MS MS(EI) for C16H23N5O3S [M+H]⁺ (Calcd.: 365.15) Found: 366.2.

Example 151: Synthesis of (2S,3R,4S)-2-(8-((1-(3-chlorophenyl)cyclopropyl)amino)imidazo[1,2-a]pyrazin-3-yl)tetrahydrothiophene-3,4-diol ¹H-NMR (DMSO-d₆, 400 MHz): δ 1.36 (4H, s), 2.75 (1H, dd, J=10.8, 2.0 Hz), 3.24 (1H, dd, J=11.2, 4.0 Hz), 4.24-4.27 (2H, m), 4.65 (1H, d, J=7.2 Hz), 5.23 (1H, d, J=3.6 Hz), 5.33 (1H, d, J=6.0 Hz), 7.13-7.27 (5H, m), 7.53 (1H, s), 7.68 (1H, d, J=5.2 Hz), 8.37 (1H, s).
LC-MS MS(EI) for C19H19ClN4O2S [M+H]⁺ (Calcd.: 402.09) Found: 403.3.

Example 152: Synthesis of (2S,3R,4S)-2-(8-((2-(3-chlorophenyl)propan-2-yl)amino)imidazo[1,2-a]pyrazin-3-yl)tetrahydrothiophene-3,4-diol ¹H-NMR (DMSO-d₆, 400 MHz): δ 1.74 (6H, s), 2.72 (1H, d, J=12.0 Hz), 3.20 (1H, dd, J=11.2, 3.6 Hz), 4.19-4.22 (2H, m), 4.60 (1H, d, J=7.6 Hz), 5.20 (1H, d, J=3.6 Hz), 5.30 (1H, d, J=6.4 Hz), 7.06 (1H, d, J=4.4 Hz), 7.13 (1H, s), 7.17 (1H, d, J=7.6 Hz), 7.24 (1H, t, J=7.6 Hz), 7.32 (1H, d, J=7.6 Hz), 7.38 (1H, s), 7.49 (1H, s), 7.58 (1H, d, J=4.8 Hz).

LC-MS MS(EI) for C19H21ClN4O2S [M+H]+ (Calcd.: 404.11) Found: 405.1.

Example 153: Synthesis of (2S,3R,4S)-2-(8-(((1H-benzo[d]imidazol-2-yl)methyl)amino)imidazo[1,2-a]pyrazin-3-yl)tetrahydrothiophene-3,4-diol hydrochloride $^1$H-NMR (DMSO-d$_6$, 400 MHz): δ 2.78 (1H, dd, J=9.2, 2.0 Hz), 3.26 (1H, dd, J=11.6, 4.4 Hz), 4.26-4.28 (4H, m), 4.70 (2H, d, J=8.0 Hz), 5.13 (2H, s), 7.26 (1H, d, J=4.8 Hz), 7.52 (2H, dd, J=5.8, 3.0 Hz), 7.66 (1H, s), 7.74 (2H, dd, J=6.0, 3.2 Hz), 7.82 (1H, d, J=4.8 Hz), 8.55 (1H, brs).

LC-MS MS(EI) for C18H19ClN6O2S [M+H]+ (Calcd.: 382.12) Found: 383.2.

Example 154: Synthesis of (2S,3R,4S)-2-(8-((2-(piperidin-1-yl)ethyl)amino)imidazo[1,2-a]pyrazin-3-yl)tetrahydrothiophene-3,4-diol $^1$H-NMR (DMSO-d$_6$, 400 MHz): δ 1.18-1.40 (2H, m), 1.48-1.49 (4H, m), 2.38 (4H, s), 2.50-2.52 (2H, m), 2.76 (1H, dd, J=10.6, 2.2 Hz), 3.23 (1H, dd, J=11.2, 4.0 Hz), 3.53 (2H, q, J=6.3 Hz), 4.25-4.26 (2H, m), 4.63 (1H, d, J=7.6 Hz), 5.23 (1H, d, J=4.0 Hz), 5.33 (1H, d, J=6.4 Hz), 7.12 (1H, t, J=5.4 Hz), 7.29 (1H, d, J=4.8 Hz), 7.47 (1H, s), 7.62 (1H, d, J=4.8 Hz).

LC-MS MS(EI) for C17H25N5O2S [M+H]+ (Calcd.: 363.17) Found: 364.2.

Example 155: Synthesis of (2S,3R,4S)-2-(8-((3-chlorobenzyl)oxy)imidazo[1,2-a]pyrazin-3-yl)tetrahydrothiophene-3,4-diol $^1$H-NMR (DMSO-d$_6$, 400 MHz): δ 2.77 (1H, dd, J=10.8, 2.0 Hz), 3.27 (1H, dd, J=11.2, 4.4 Hz), 4.25-4.28 (2H, m), 4.72 (1H, d, J=10.0 Hz), 5.27 (1H, d, J=3.6 Hz), 5.37 (1H, d, J=6.4 Hz), 5.55 (2H, s), 7.43-7.46 (4H, m), 7.58 (1H, s), 7.65 (1H, s), 8.14 (1H, d, J=5.2 Hz).

LC-MS MS(EI) for C17H16ClN3O3S [M+H]+ (Calcd.: 377.06) Found: 378.2.

Example 156: Synthesis of (2S,3R,4S)-2-(8-((2-(dimethylamino)ethyl)(methyl)amino)imidazo[1,2-a]pyrazine-3-yl)tetrahydrothiophene-3,4-diol $^1$H-NMR (DMSO-d$_6$, 400 MHz): δ 2.18 (6H, s), 2.76 (1H, dd, J=10.4, 2.4 Hz), 3.22 (1H, dd, J=11.0, 3.8 Hz), 3.38 (3H, s), 4.26-4.29 (4H, m), 4.62 (1H, d, J=7.6 Hz), 5.24 (1H, d, J=4.0 Hz), 5.34 (1H, d, J=6.0 Hz), 7.34 (1H, d, J=4.0 Hz), 7.52 (1H, s), 7.62 (1H, d, J=4.8 Hz). *Two protons were overlapped with DMSO peak at 2.5 ppm.

LC-MS MS(EI) for C15H23N5O2S [M+H]+ (Calcd.: 337.16) Found: 338.2.

Example 157: Synthesis of (2S,3R,4S)-2-(8-((thiazol-5-ylmethyl)amino)imidazo[1,2-a]pyrazin-3-yl)tetrahydrothiophene-3,4-diol $^1$H-NMR (DMSO-d$_6$, 400 MHz): δ 2.76 (1H, dd, J=11.4, 3.0 Hz), 3.24 (1H, dd, J=10.8, 4.0 Hz), 4.24-4.26 (2H, m), 4.64 (1H, d, J=7.6 Hz), 4.84 (2H, d, J=6.4 Hz), 5.23 (1H, d, J=4.0 Hz), 5.33 (1H, d, J=6.4 Hz), 7.35 (1H, d, J=4.8 Hz), 7.50 (1H, s), 7.69 (1H, d, J=4.4 Hz), 7.80 (1H, s), 8.15 (1H, t, J=6.4 Hz), 8.89 (1H, s).

LC-MS MS(EI) for C14H15N5O2S2 [M+H]+ (Calcd.: 349.07) Found: 350.1.

Example 158: Synthesis of 3-chloro-N-(3-((2S,3R,4S)-3,4-dihydroxytetrahydrothiophen-2-yl)imidazo[1,2-a]pyrazin-8-yl)benzamide $^1$H-NMR (DMSO-d$_6$, 400 MHz): δ 2.77 (1H, dd, J=11.2, 2.0 Hz), 3.29-3.32 (1H, m), 4.25-4.35 (2H, m), 4.80 (1H, d, J=8.80 Hz), 5.30 (1H, d, J=3.6 Hz), 5.43 (1H, d, J=6.0 Hz), 7.60 (1H, t, J=5.2 Hz), 7.72 (1H, d, J=8.4 Hz), 7.76 (2H, s), 7.98 (1H, brs), 8.08 (1H, s), 8.42 (1H, brs), 11.04 (1H, brs).

LC-MS MS(EI) for C17H15ClN4O3S [M+H]+ (Calcd.: 390.06) Found: 391.2.

Example 159: Synthesis of (2S,3R,4S)-2-(8-((3-chlorophenyl)ethynyl)imidazo[1,2-a]pyrazin-3-yl)tetrahydrothiophene-3,4-diol $^1$H-NMR (DMSO-d$_6$, 400 MHz): δ 2.79 (1H, d, J=11.2, Hz), 3.30-3.32 (1H, m), 4.26-4.32 (2H, m), 4.83 (1H, d, J=8.0 Hz), 5.31 (1H, d, J=4.0 Hz), 5.41 (1H, d, J=6.8 Hz), 7.54 (1H, t, J=7.8 Hz), 7.62 (1H, d, J=8.4 Hz), 7.67 (1H, d, J=8.0 Hz), 7.76 (1H, s), 7.90 (1H, s), 7.98 (1H, d, J=4.4 Hz), 8.60 (1H, d, J=4.4 Hz).

LC-MS MS(EI) for C18H14ClN3O2S [M+H]+ (Calcd.: 371.05) Found: 372.2.

Example 160: Synthesis of (2S,3R,4S)-2-(8-(((R)-1-(3-chlorophenyl)ethyl)amino)imidazo[1,2-a]pyrazin-3-yl)tetrahydrothiophene-3,4-diol $^1$H-NMR (DMSO-d$_6$, 400 MHz): δ 1.54 (3H, d, J=7.2 Hz), 2.75 (1H, dd, J=11.8, 2.6 Hz), 3.23 (1H, dd, J=10.8, 4.0 Hz), 4.24-4.27 (2H, m), 4.63 (1H, d, J=7.2 Hz), 5.22 (1H, d, J=4.0 Hz), 5.32 (1H, d, J=6.4 Hz), 5.37 (1H, t, J=7.2 Hz), 7.23 (1H, d, J=4.8 Hz), 7.25 (1H, s), 7.31 (1H, t, J=7.6 Hz), 7.39 (1H, d, J=7.6 Hz), 7.52 (2H, s), 7.63 (1H, d, J=4.8 Hz), 7.93 (1H, t, J=8.4 Hz).

LC-MS MS(EI) for C18H19ClN4O2S [M+H]+ (Calcd.: 390.09) Found: 432.1.

Example 161: Synthesis of (2S,3R,4S)-2-(8-(((S)-1-(3-chlorophenyl)ethyl)amino)imidazo[1,2-a]pyrazin-3-yl)tetrahydrothiophene-3,4-diol $^1$H-NMR (DMSO-d$_6$, 400 MHz): δ 1.54 (3H, d, J=7.2 Hz), 2.75 (1H, dd, J=10.8, 2.0 Hz), 3.23 (1H, dd, J=11.0, 4.2 Hz), 4.22-4.26 (2H, m), 4.63 (1H, d, J=8.0 Hz), 5.22 (1H, d, J=4.0 Hz), 5.32 (1H, d, J=6.8 Hz), 5.37 (1H, t, J=7.2 Hz), 7.23 (1H, d, J=4.4 Hz), 7.24 (1H, d, J=7.6 Hz), 7.31 (1H, t, J=7.8 Hz), 7.39 (1H, d, J=7.6 Hz), 7.52 (2H, s), 7.62 (1H, d, J=4.8 Hz), 7.94 (1H, t, J=8.4 Hz).

LC-MS MS(EI) for C18H19ClN4O2S [M+H]+ (Calcd.: 390.09) Found: 391.1.

Example 162: Synthesis of (2S,3R,4S)-2-(8-(((1S,2R)-2-phenylcyclopropyl)amino)imidazo[1,2-a]pyrazin-3-yl)tetrahydrothiophene-3,4-diol $^1$H-NMR (DMSO-d$_6$, 400 MHz): δ 1.23 (1H, q, J=6.4 Hz), 1.46-1.50 (1H, m), 2.01-2.10 (1H, m), 2.76 (1H, dd, J=13.4, 2.6 Hz), 3.12-3.13 (1H, m), 3.24 (1H, dd, J=11.4, 3.4 Hz), 4.22-4.28 (2H, m), 4.64 (1H, d, J=7.2 Hz), 5.23 (1H, d, J=3.6 Hz), 5.32 (1H, d, J=6.8 Hz), 7.12-7.18 (3H, m), 7.25-7.30 (3H, m), 7.49 (1H, s), 7.67 (1H, d, J=4.8 Hz), 7.85 (1H, d, J=4.8 Hz).
LC-MS MS(EI) for C19H20N4O2S [M+H]+ (Calcd.: 368.13) Found: 369.3.

Example 163: Synthesis of (2S,3R,4S)-2-(8-((2-chlorobenzyl)amino)imidazo[1,2-a]pyrazin-3-yl)tetrahydrothiophene-3,4-diol $^1$H-NMR (DMSO-d$_6$, 400 MHz): δ 2.76 (1H, d, J=11.6 Hz), 3.25 (1H, dd, J=11.2, 4.4 Hz), 4.27 (2H, brs), 4.66 (1H, d, J=8.0 Hz), 4.72 (2H, d, J=6.4 Hz), 5.25 (1H, d, J=3.6 Hz), 5.34 (1H, d, J=6.4 Hz), 7.24-7.26 (4H, m), 7.44 (1H, t, J=3.6 Hz), 7.55 (1H, s), 7.67 (1H, d, J=4.8 Hz), 8.04 (1H, t, J=5.2 Hz).
LC-MS MS(EI) for C17H17ClN4O2S [M+H]+ (Calcd.: 376.08) Found: 377.2.

Example 164: Synthesis of (2S,3R,4S)-2-(8-((4-chlorobenzyl)amino)imidazo[1,2-a]pyrazin-3-yl)tetrahydrothiophene-3,4-diol $^1$H-NMR (DMSO-d$_6$, 400 MHz): δ 2.76 (1H, dd, J=11.0, 2.2 Hz), 3.24 (1H, dd, J=10.6, 4.2 Hz), 4.22-4.28 (2H, m), 4.64 (3H, J=6.4 Hz), 5.24 (1H, d, J=3.2 Hz), 5.33 (1H, d, J=6.0 Hz), 7.25 (1H, d, J=4.4 Hz), 7.32-7.36 (4H, m), 7.51 (1H, s), 7.64 (1H, d, J=4.8 Hz), 8.11 (1H, d, J=6.2 Hz).
LC-MS MS(EI) for C17H17ClN4O2S [M+H]+ (Calcd.: 376.08) Found: 377.2.

Example 165: Synthesis of (2S,3R,4S)-2-(8-((4-iodobenzyl)amino)imidazo[1,2-a]pyrazin-3-yl)tetrahydrothiophene-3,4-diol $^1$H-NMR (DMSO-d$_6$, 400 MHz): δ 2.75 (1H, dd, J=11.2, 2.4 Hz), 3.24 (1H, dd, J=10.2, 4.6 Hz), 4.24-4.25 (2H, m), 4.60 (2H, d, J=6.4 Hz), 4.64 (1H, d, J=8.0 Hz), 5.23 (1H, d, J=4.0 Hz), 5.33 (1H, d, J=6.8 Hz), 7.14 (2H, d, J=8.4 Hz), 7.25 (1H, d, J=4.8 Hz), 7.51 (1H, s), 7.64 (2H, d, J=8.4 Hz), 7.64 (1H, d, J=4.8 Hz), 8.10 (1H, t, J=6.4 Hz).
LC-MS MS(EI) for C17H17IN4O2S [M+H]+ (Calcd.: 468.01) Found: 469.1.

Example 166: Synthesis of (2S,3R,4S)-2-(8-(((1H-indol-5-yl)methyl)amino)imidazo[1,2-a]pyrazin-3-yl)tetrahydrothiophene-3,4-diol $^1$H-NMR (DMSO-d$_6$, 400 MHz): δ 2.7 (1H, dd, J=9.8, 3.0 Hz), 3.23 (1H, dd, J=10.8, 4.4 Hz), 4.22-4.28 (2H, m), 4.63 (1H, d, J=6.4 Hz), 4.72 (2H, d, J=6.0 Hz), 5.23 (1H, s), 5.33 (1H, d, J=6.4 Hz), 6.35 (1H, s), 7.12 (1H, d, J=6.8 Hz), 7.27-7.31 (3H, m), 7.48 (2H, s), 7.62 (1H, d, J=4.8 Hz), 7.85 (1H, t, J=6.6 Hz), 10.97 (1H, s).
LC-MS MS(EI) for C19H19N5O2S [M+H]+ (Calcd.: 381.13) Found: 382.2.

Example 167: Synthesis of 3-chloro-N-(3-((2S,3R,4S)-3,4-dihydroxytetrahydrothiophen-2-yl)imidazo[1,2-a]pyrazin-8-yl)benzenesulfonamide $^1$H-NMR (DMSO-d$_6$, 400 MHz): δ 2.75 (1H, dd, J=10.2, 2.6 Hz), 3.24 (1H, dd, J=10.6, 4.2 Hz), 4.19 (1H, d, J=6.8 Hz), 4.25 (1H, m), 4.63 (1H, d, J=8.0 Hz), 5.28-5.37 (2H, m), 7.16 (1H, d, J=8.4 Hz), 7.59 (1H, t, J=8.4 Hz), 7.65 (1H, s), 7.68 (1H, d, J=7.6 Hz), 7.80 (1H, d, J=5.2 Hz), 7.90 (1H, d, J=8.0 Hz), 7.97 (1H, s), 11.8 (1H, brs).
LC-MS MS(EI) for C16H15ClN4O4S2 [M+H]+ (Calcd.: 426.02) Found: 427.2.

Example 168: Synthesis of (2S,3R,4S)-2-(8-((2-iodobenzyl)amino)imidazo[1,2-a]pyrazin-3-yl)tetrahydrothiophene-3,4-diol $^1$H-NMR (DMSO-d$_6$, 400 MHz): δ 2.76 (1H, d, J=10.0 Hz), 3.26 (1H, d, J=11.2 Hz), 4.27 (2H, brs), 4.56 (2H, d, J=6.4 Hz), 4.66 (1H, d, J=7.6 Hz), 5.25 (1H, s), 5.34 (1H, d, J=5.2 Hz), 7.00 (1H, t, J=7.0 Hz), 7.17 (1H, d, J=8.4 Hz), 7.24 (1H, d, J=4.8 Hz), 7.30 (1H, t, J=7.6 Hz), 7.55 (1H, s), 7.68 (1H, d, J=4.4 Hz), 7.86 (1H, d, J=7.2 Hz), 8.06-8.10 (1H, m).
LC-MS MS(EI) for C17H17IN4O2S [M+H]+ (Calcd.: 468.01) Found: 469.2.

Example 169: Synthesis of (2S,3R,4S)-2-(8-((2-fluorophenethyl)amino)imidazo[1,2-a]pyrazin-3-yl)tetrahydrothiophene-3,4-diol $^1$H-NMR (DMSO-d$_6$, 400 MHz): δ 2.72 (1H, dd, J=11.8, 4.2 Hz), 2.94 (2H, t, J=7.0 Hz), 3.20 (1H, dd, J=10.4, 3.6 Hz), 3.65 (2H, q, J=7.3 Hz), 4.21-4.22 (2H, m), 4.60 (1H, d, J=7.6 Hz), 5.20 (1H, d, J=4.0 Hz), 5.29 (1H, d, J=6.4 Hz), 7.06-7.13 (2H, m), 7.19-7.23 (1H, m), 7.27-7.31 (2H, m), 7.43 (1H, s), 7.47-7.48 (1H, m), 7.58 (1H, d, J=4.8 Hz).
LC-MS MS(EI) for C18H19FN4O2S [M+H]+ (Calcd.: 374.12) Found: 375.3.

Example 170: Synthesis of (2S,3R,4S)-2-(8-((4-fluorophenethyl)amino)imidazo[1,2-a]pyrazin-3-yl)tetrahydrothiophene-3,4-diol $^1$H-NMR (DMSO-d$_6$, 400 MHz): δ 2.76 (1H, dd, J=11.2, 1.6 Hz), 2.92 (2H, d, J=7.6 Hz), 3.23 (1H, dd, J=10.8, 4.0 Hz), 3.66 (2H, q, J=7.1 Hz), 4.23-4.26 (2H, m), 4.63 (1H, d, J=8.0 Hz), 5.23 (1H, d, J=4.0 Hz), 5.32 (1H, d, J=6.8 Hz), 7.10 (2H, t, J=8.8 Hz), 7.26-7.32 (3H, m), 7.44-7.47 (2H, m), 7.62 (1H, d, J=4.8 Hz).
LC-MS MS(EI) for C18H19FN4O2S [M+H]+ (Calcd.: 374.12) Found: 375.3.

Example 171: Synthesis of methyl 5-(((3-((2S,3R,4S)-3,4-dihydroxytetrahydrothiophen-2-yl)imidazo[1,2-a]pyrazin-8-yl)amino)methyl)-2-fluorobenzoate $^1$H-NMR (DMSO-d$_6$, 400 MHz): δ 2.76 (1H, dd, J=6.8, 5.6 Hz), 3.23 (1H, dd, J=11.0, 3.8 Hz), 3.83 (3H, s), 4.24-4.25 (2H, m), 4.63-4.67 (3H, m), 5.23 (1H, d, J=3.6 Hz), 5.32 (1H, d, J=6.4 Hz), 7.25-7.29 (2H, m), 7.52 (1H, s), 7.62-7.66 (1H, m), 7.65 (1H, d, J=4.4 Hz), 7.89 (1H, dd, J=7.4, 2.2 Hz), 8.20 (1H, t, J=7.2 Hz).
LC-MS MS(EI) for C19H19FN4O4S [M+H]+ (Calcd.: 418.11) Found: 419.2.

Example 172: Synthesis of (2S,3R,4S)-2-(8-((3-chloro-4-fluorophenethyl)amino)imidazo[1,2-a]pyrazin-3-yl)tetrahydrothiophene-3,4-diol $^1$H-NMR (DMSO-d$_6$, 400 MHz): δ 2.76 (1H, dd, J=10.8, 2.0 Hz), 2.94 (1H, t, J=7.0 Hz), 3.23 (1H, dd, J=11.0, 3.8 Hz), 3.68 (2H, q, J=6.5 Hz), 4.24-4.26 (2H, m), 4.63 (1H, d, J=7.2 Hz), 5.23 (1H, d, J=3.6 Hz), 5.32 (1H, d, J=6.8 Hz), 7.25-7.33 (3H, m), 7.47 (1H, s), 7.49-7.50 (2H, m), 7.62 (1H, d, J=4.8 Hz). *A proton was not observed LC-MS MS(EI) for C18H18ClFN4O2S [M+H]⁺⁺ (Calcd.: 408.08) Found: 409.3.

Example 173: Synthesis of (2S,3R,4S)-2-(8-((3-(dimethylamino)benzyl)amino)imidazo[1,2-a]pyrazin-3-yl)tetrahydrothiophene-3,4-diol ¹H-NMR (DMSO-d₆, 400 MHz): δ 2.76 (1H, d, J=10.8 Hz), 2.85 (6H, s), 3.23 (1H, dd, J=10.4, 3.2 Hz), 4.26 (2H, brs), 4.59 (2H, d, J=6.0 Hz), 4.63 (1H, d, J=7.2 Hz), 5.22 (1H, d, J=3.2 Hz), 5.32 (1H, d, J=6.4 Hz), 6.57 (1H, d, J=8.4 Hz), 6.63 (1H, d, J=7.2 Hz), 6.77 (1H, s), 7.07 (1H, t, J=7.8 Hz), 7.27 (1H, d, J=4.8 Hz), 7.49 (1H, s), 7.62 (1H, d, J=4.8 Hz), 7.87 (1H, t, J=6.0 Hz).
LC-MS MS(EI) for C19H23N5O2S [M+H]⁺⁺ (Calcd.: 385.16) Found: 386.2.

Example 174: Synthesis of (2S,3R,4S)-2-(8-((3-(4-methylpiperazin-1-yl)benzyl)amino)imidazo[1,2-a]pyrazin-3-yl)tetrahydrothiophene-3,4-diol ¹H-NMR (DMSO-d₆, 400 MHz): δ 2.20 (3H, s), 2.41-2.43 (4H, m), 2.76 (1H, dd, J=11.2, 2.0 Hz), 3.07-3.10 (4H, m), 3.23 (1H, dd, J=11.2, 3.6 Hz), 4.25-4.27 (2H, m), 4.60 (2H, d, J=5.6 Hz), 4.63 (1H, d, J=7.6 Hz), 5.23 (1H, d, J=3.2 Hz), 5.32 (1H, d, J=6.4 Hz), 6.76 (2H, t, J=7.0 Hz), 6.97 (1H, s), 7.10 (1H, t, J=7.8 Hz), 7.27 (1H, d, J=4.4 Hz), 7.50 (1H, s), 7.63 (1H, d, J=4.8 Hz), 7.91 (1H, t, J=7.8 Hz).
LC-MS MS(EI) for C22H28N6O2S [M+H]⁺⁺ (Calcd.: 440.20) Found: 441.3.

Example 175: Synthesis of (2S,3R,4S)-2-(8-((2,3-dichlorobenzyl)amino)imidazo[1,2-a]pyrazin-3-yl)tetrahydrothiophene-3, 4-diol ¹H-NMR (DMSO-d₆, 400 MHz): δ 2.76 (1H, d, J=10.0 Hz), 3.26 (1H, d, J=10.0 Hz), 4.27 (2H, brs), 4.66 (1H, d, J=7.2 Hz), 4.73 (2H, d, J=5.6 Hz), 5.25 (1H, d, J=3.2 Hz), 5.34 (1H, d, J=5.6 Hz), 7.24-7.30 (3H, m), 7.52 (1H, d, J=8.0 Hz), 7.56 (1H, s), 7.69 (1H, d, J=4.0 Hz), 8.17 (1H, t, J=6.0 Hz).
LC-MS MS(EI) for C17H16Cl2N4O2S [M+H]⁺⁺ (Calcd.: 410.04) Found: 411.3.

Example 176: Synthesis of (2S,3R,4S)-2-(8-((2,4-dichlorobenzyl)amino)imidazo[1,2-a]pyrazin-3-yl)tetrahydrothiophene-3, 4-diol ¹H-NMR (DMSO-d₆, 400 MHz): δ 2.76 (1H, d, J=10.4 Hz), 3.25 (1H, d, J=10.8 Hz), 4.28 (2H, brs), 4.67 (3H, brs), 5.24 (1H, s), 5.34 (1H, s), 7.25-7.27 (2H, m), 7.32-7.36 (1H, m), 7.55 (1H, s), 7.60 (1H, s), 7.68 (1H, s), 8.12 (1H, brs).
LC-MS MS(EI) for C17H16Cl2N4O2S [M+H]⁺⁺ (Calcd.: 410.04) Found: 411.2.

Example 177: Synthesis of (2S,3R,4S)-2-(8-((2,5-dichlorobenzyl)amino)imidazo[1,2-a]pyrazin-3-yl)tetrahydrothiophene-3, 4-diol ¹H-NMR (DMSO-d₆, 400 MHz): δ 2.77 (1H, dd, J=10.8, 2.0 Hz), 3.25 (1H, d, J=10.8, 4.4 Hz), 4.28 (2H, brs), 4.67 (1H, d, J=8.0 Hz), 4.70 (2H, d, J=6.4 Hz), 5.26 (1H, d, J=4.0 Hz), 5.35 (1H, d, J=6.0 Hz), 7.26 (2H, d, J=3.6 Hz), 7.35 (1H, dd, J=8.4, 2.4 Hz), 7.50 (1H, d, J=8.8 Hz), 7.56 (1H, s), 7.71 (1H, d, J=4.8 Hz), 8.16 (1H, t, J=6.2 Hz).

LC-MS MS(EI) for C17H16Cl2N4O2S [M+H]⁺⁺ (Calcd.: 410.04) Found: 411.3.

Example 178: Synthesis of (2S,3R,4S)-2-(8-((thiophen-2-ylmethyl)amino)imidazo[1,2-a]pyrazin-3-yl)tetrahydrothiophene-3,4-diol ¹H-NMR (DMSO-d₆, 400 MHz): δ 2.76 (1H, d, J=11.6 Hz), 3.24 (1H, dd, J=11.0, 3.4 Hz), 4.26 (2H, brs), 4.64 (1H, d, J=7.6 Hz), 4.81 (2H, d, J=6.0 Hz), 5.23 (1H, d, J=2.8 Hz), 5.33 (1H, d, J=5.6 Hz), 6.93 (1H, t, J=4.0 Hz), 7.01 (1H, s), 7.30-7.33 (2H, m), 7.50 (1H, s), 7.67 (1H, d, J=4.8 Hz), 8.06 (1H, t, J=6.0 Hz).
LC-MS MS(EI) for C15H16N4O2S2 [M+H]⁺⁺ (Calcd.: 348.07) Found: 349.2.

Example 179: Synthesis of (2S,3R,4S)-2-(8-((2-(3-fluorophenyl)cyclopropyl)amino)imidazo[1,2-a]pyrazin-3-yl)tetrahydrothiophene-3,4-diol ¹H-NMR (DMSO-d₆, 400 MHz): δ 1.27-1.32 (1H, m), 1.51-1.56 (1H, m), 2.07-2.12 (1H, m), 1.76 (1H, d, J=10.4 Hz), 3.12-3.16 (1H, m), 3.24 (1H, dd, J=11.0, 2.2 Hz), 4.25 (2H, brs), 4.64 (1H, d, J=7.2 Hz), 5.24 (1H, s), 5.33 (1H, d, J=4.8 Hz), 6.96-7.03 (3H, m), 7.27-7.33 (2H, m), 7.50 (1H, s), 7.67 (1H, d, J=4.8 Hz), 7.89 (1H, d, J=4.0 Hz).
LC-MS MS(EI) for C19H19FN4O2S [M+H]⁺⁺ (Calcd.: 386.12) Found: 387.3.

Example 180: Synthesis of (2S,3R,4S)-2-(8-((2-(3-chlorophenyl)cyclopropyl)amino)imidazo[1,2-a]pyrazin-3-yl)tetrahydrothiophene-3,4-diol ¹H-NMR (DMSO-d₆, 400 MHz): δ 1.25-1.33 (1H, m), 1.52-1.57 (1H, m), 2.06-2.11 (1H, m), 2.76 (1H, d, J=10.8 Hz), 3.11-3.16 (1H, m), 3.25 (1H, dd, J=10.0, 3.6 Hz), 4.25 (2H, brs), 4.64 (1H, d, J=7.6 Hz), 5.25 (1H, s), 5.34 (1H, d, J=5.6 Hz), 7.14 (1H, d, J=8.0 Hz), 7.21-7.25 (2H, m), 7.28-7.31 (2H, m), 7.50 (1H, s), 7.68 (1H, d, J=4.8 Hz), 7.90 (1H, d, J=4.4 Hz).
LC-MS MS(EI) for C19H19ClN4O2S [M+H]⁺⁺ (Calcd.: 402.09) Found: 403.3.

Example 181: Synthesis of (2S,3R,4S)-2-(8-((3-(piperazin-1-yl)benzyl)amino)imidazo[1,2-a]pyrazin-3-yl)tetrahydrothiophene-3,4-diol ¹H-NMR (DMSO-d₆, 400 MHz): δ 2.74-2.80 (5H, m), 2.98-3.00 (4H, m), 3.24 (1H, dd, J=11.2, 4.0 Hz), 4.26 (2H, s), 4.60 (2H, d, J=6.4 Hz), 4.64 (1H, d, J=7.2 Hz), 5.24 (1H, s), 5.34 (1H, d, J=4.8 Hz), 6.74 (2H, d, J=8.0 Hz), 6.95 (1H, s), 7.10 (1H, t, J=7.4 Hz), 7.27 (1H, d, J=4.8 Hz), 7.50 (1H, s), 7.63 (1H, d, J=4.8 Hz), 7.92 (1H, t, J=5.8 Hz).
LC-MS MS(EI) for C21H26N6O2S [M+H]⁺⁺ (Calcd.: 426.18) Found: 427.3.

Example 182: Synthesis of methyl 2-chloro-5-(((3-((2S,3R,4S)-3,4-dihydroxytetrahydrothiophen-2-yl)imidazo[1,2-a]pyrazin-8-yl)amino)methyl)benzoate ¹H-NMR (DMSO-d₆, 400 MHz): δ 2.76 (1H, d, J=9.6 Hz), 3.24 (1H, dd, J=11.0, 4.2 Hz), 3.83 (3H, s), 4.25 (2H, brs), 4.63-4.67 (3H, m), 5.24 (1H, s), 5.33 (1H, d, J=5.6 Hz), 7.25 (1H, d, J=4.4 Hz), 7.48-7.54 (3H, m), 7.66 (1H, d, J=4.8 Hz), 7.79 (1H, s), 8.20 (1H, t, J=6.0 Hz).

LC-MS MS(EI) for C19H19ClN4O4S [M+H]+ (Calcd.: 434.08) Found: 435.2.

Example 183: Synthesis of (2S,3R,4S)-2-(8-((3-chloro-4-fluorobenzyl)amino)imidazo[1,2-a]pyrazin-3-yl)tetrahydrothiophene-3,4-diol $^1$H-NMR (DMSO-d$_6$, 400 MHz): δ 2.76 (1H, d, J=10.8 Hz), 3.24 (1H, dd, J=10.8, 4.0 Hz), 4.25-4.26 (2H, m), 4.62-4.65 (3H, m), 5.23 (1H, d, J=3.6 Hz), 5.33 (1H, d, J=6.4 Hz), 7.27 (1H, d, J=4.8 Hz), 7.30-7.34 (2H, m), 7.52-7.54 (2H, m), 7.66 (1H, d, J=4.4 Hz), 8.15 (1H, t, J=6.4 Hz).
LC-MS MS(EI) for C17H16ClFN4O2S [M+H]+ (Calcd.: 394.07) Found: 395.2.

Example 184: Synthesis of (2S,3R,4S)-2-(8-((3,5-dichlorobenzyl)amino)imidazo[1,2-a]pyrazin-3-yl)tetrahydrothiophene-3, 4-diol $^1$H-NMR (DMSO-d$_6$, 400 MHz): δ 2.76 (1H, d, J=10.0 Hz), 3.24 (1H, dd, J=11.2, 4.0 Hz), 4.24-4.28 (2H, m), 4.64 (3H, d, J=6.4 Hz), 5.24 (1H, d, J=4.0 Hz), 5.33 (1H, d, J=5.6 Hz), 7.27 (1H, d, J=4.8 Hz), 7.38 (2H, s), 7.44 (1H, s), 7.53 (1H, s), 7.68 (1H, d, J=4.4 Hz), 8.19 (1H, t, J=6.4 Hz).
LC-MS MS(EI) for C17H16Cl2N4O2S [M+H]+ (Calcd.: 410.04) Found: 411.3.

Example 185: Synthesis of (2S,3R,4S)-2-(8-((3,4-dichlorobenzyl)amino)imidazo[1,2-a]pyrazin-3-yl)tetrahydrothiophene-3, 4-diol $^1$H-NMR (DMSO-d$_6$, 400 MHz): δ 2.76 (1H, d, J=10.8 Hz), 3.24 (1H, dd, J=11.2, 4.8 Hz), 4.24-4.27 (2H, m), 4.64 (3H, d, J=5.2 Hz), 5.24 (1H, d, J=4.4 Hz), 5.33 (1H, d, J=5.2 Hz), 7.26 (1H, d, J=4.4 Hz), 7.32 (1H, d, J=8.4 Hz), 7.52 (1H, s), 7.55 (1H, d, J=8.4 Hz), 7.58 (1H, s), 7.66 (1H, d, J=4.8 Hz), 8.18 (1H, t, J=7.2 Hz).
LC-MS MS(EI) for C17H16Cl2N4O2S [M+H]+ (Calcd.: 410.04) Found: 411.2.

Example 186: Synthesis of (2S,3R,4S)-2-(8-((2,6-dichlorobenzyl)amino)imidazo[1,2-a]pyrazin-3-yl)tetrahydrothiophene-3, 4-diol $^1$H-NMR (DMSO-d$_6$, 400 MHz): δ 2.73 (1H, dd, J=10.8, 2.4 Hz), 3.24 (1H, dd, J=12.0, 4.8 Hz), 4.23-4.26 (2H, m), 4.64 (1H, d, J=7.2 Hz), 4.88 (2H, d, J=4.8 Hz), 5.23 (1H, d, J=4.0 Hz), 5.33 (1H, d, J=6.0 Hz), 7.34-7.37 (2H, m), 7.41 (1H, t, J=5.0 Hz), 7.47-7.49 (3H, m), 7.69 (1H, d, J=4.4 Hz).
LC-MS MS(EI) for C17H16Cl2N4O2S [M+H]+ (Calcd.: 410.04) Found: 411.3.

Example 187: Synthesis of 5-(((3-((2S,3R,4S)-3,4-dihydroxytetrahydrothiophen-2-yl)imidazo[1,2-a]pyrazin-8-yl)amino)methyl)-2-fluorobenzoic acid 2,2,2-trifluoroacetic acid $^1$H-NMR (DMSO-d$_6$, 400 MHz): 2.76 (1H, d, J=12.0 Hz), 3.24 (1H, d, J=7.6 Hz), 3.42 (2H, brs), 4.26 (2H, s), 4.67 (2H, s), 5.34 (1H, s), 7.24-7.27 (2H, m), 7.56-7.60 (2H, m), 7.69 (1H, s), 7.88 (1H, s), 7.39 (1H, brs), 13.2 (1H, s).
LC-MS MS(EI) for C20H18F4N4O5S [M+H]+ (Calcd.: 404.42) Found: 405.3.

Example 188: Synthesis of 5-(((3-((2S,3R,4S)-3,4-dihydroxytetrahydrothiophen-2-yl)imidazo[1,2-a]pyrazin-8-yl)amino)methyl)-2-fluoro-N,N-dimethyl-benzamide $^1$H-NMR (DMSO-d$_6$, 400 MHz): δ 2.75 (1H, d, J=11.6 Hz), 2.81 (3H, s), 2.97 (3H, s), 3.24 (1H, dd, J=10.2, 4.2 Hz), 4.25-4.26 (2H, m), 4.63-4.66 (3H, m), 5.23 (1H, s), 5.33 (1H, d, J=6.0 Hz), 7.20 (1H, t, J=9.0 Hz), 7.27 (1H, d, J=5.2 Hz), 7.32 (1H, d, J=6.8 Hz), 7.42-7.46 (1H, m), 7.51 (1H, s), 7.65 (1H, d, J=4.8 Hz), 8.13 (1H, t, J=6.0 Hz).
LC-MS MS(EI) for C20H22FN5O3S [M+H]+ (Calcd.: 431.14) Found: 432.2.

Example 189: Synthesis of 2-chloro-5-(((3-((2S,3R,4S)-3,4-dihydroxytetrahydrothiophen-2-yl)imidazo[1,2-a]pyrazin-8-yl)amino)methyl)benzoic acid 2,2,2-trifluoroacetic acid $^1$H-NMR (DMSO-d$_6$, 400 MHz): δ 2.77 (1H, d, J=10.8, Hz), 3.26 (H, dd, J=9.4, 2.6 Hz), 4.24-4.27 (3H, m), 4.67-4.71 (3H, m), 7.29 (1H, d, J=4.8 Hz), 7.49 (2H, s), 7.66 (1H, s), 7.80 (2H, s), 9.01 (1H, brs), 13.46 (1H, brs). A proton was not observed.
LC-MS MS(EI) for C20H18ClF3N4O5S [M+H]+ (Calcd.: 420.07) Found: 421.3.

Example 190: Synthesis of 2-chloro-5-(((3-((2S,3R,4S)-3,4-dihydroxytetrahydrothiophen-2-yl)imidazo[1,2-a]pyrazin-8-yl)amino)methyl)-N,N-dimethyl-benzamide $^1$H-NMR (DMSO-d$_6$, 400 MHz): δ 2.70 (3H, s), 2.71 (1H, d, J=7.2 Hz), 2.93 (3H, s), 3.20 (1H, d, J=11.6 Hz), 4.21 (2H, brs), 4.59-4.62 (3H, m), 5.19 (1H, brs), 5.29 (1H, d, J=7.2 Hz), 7.21-7.23 (2H, m), 7.32-7.39 (2H, m), 7.47 (1H, s), 7.61 (1H, d, J=4.8 Hz), 8.08-8.12 (1H, m).
LC-MS MS(EI) for C20H22ClN5O3S [M+H]+ (Calcd.: 447.11) Found: 448.2.

Example 191: Synthesis of (2S,3R,4S)-2-(8-((3-(1H-tetrazol-5-yl)benzyl)amino)imidazo[1,2-a]pyrazin-3-yl)tetrahydrothiophene-3,4-diol 2,2,2-trifluoroacetic acid $^1$H-NMR (DMSO-d$_6$, 400 MHz): δ 2.73 (1H, d, J=10.4 Hz), 3.22 (1H, dd, J=9.0, 2.2 Hz), 4.20-4.23 (3H, m), 4.65 (2H, d, J=8.0 Hz), 4.79 (3H, s), 7.26 (1H, d, J=5.2 Hz), 7.52-7.54 (2H, m), 7.64 (1H, s), 7.48-7.76 (1H, m), 7.87 (1H, d, J=6.4 Hz), 8.02 (1H, s). *A proton was not observed.
LC-MS MS(EI) for C20H19F3N8O3S [M+H]+ (Calcd.: 410.45) Found: 411.2.

Example 192: Synthesis of (2S,3R,4S)-2-(8-((2,3-difluorophenethyl)amino)imidazo[1,2-a]pyrazin-3-yl)tetrahydrothiophene-3,4-diol $^1$H-NMR (DMSO-d$_6$, 400 MHz): δ 7.63 (1H, d, J=4.8 Hz), 7.57 (1H, t, J=5.6 Hz), 7.47 (1H, s), 7.30 (1H, d, J=4.8 Hz), 7.28-7.22 (1H, m), 7.13-7.11 (2H, m), 5.34 (1H, d, J=4.4 Hz), 5.25 (1H, s), 4.63 (1H, d, J=7.6 Hz), 4.26 (2H, s), 3.71 (2H, q, J=6.4 Hz), 3.23 (1H, dd, J=11.0, 3.8 Hz), 3.02 (2H, t, J=6.8 Hz), 2.76 (1H, d, J=11.2 Hz).
LC-MS MS(EI) for C18H18F2N4O2S [M+H]+ (Calcd.: 392.11) Found: 393.3.

Example 193: Synthesis of (2S,3R,4S)-2-(8-((2,4-difluorophenethyl)amino)imidazo[1,2-a]pyrazin-3-yl)tetrahydrothiophene-3,4-diol $^1$H-NMR (DMSO-d$_6$, 400 MHz): δ 7.62 (1H, d, J=4.5 Hz), 7.54 (1H, t, J=3.0 Hz), 7.47 (1H, s), 7.38-7.34 (1H, m), 7.30 (1H, d, J=4.4 Hz), 7.17 (1H, t, J=9.0 Hz), 7.00 (1H, t, J=8.2 Hz), 5.33 (1H, d, J=5.6 Hz), 5.24 (1H, s), 4.63 (1H, d, J=7.6 Hz), 4.25 (2H, s), 3.30 (2H, q, J=6.3 Hz), 3.23 (1H, dd, J=11.6, 3.2 Hz), 2.95 (2H, t, J=6.6 Hz), 2.75 (1H, d, J=10.8 Hz).
LC-MS MS(EI) for C18H18F2N4O2S [M+H]$^{+\prime}$ (Calcd.: 392.11) Found: 393.3.

Example 194: Synthesis of (2S,3R,4S)-2-(8-((2,5-difluorophenethyl)amino)imidazo[1,2-a]pyrazin-3-yl)tetrahydrothiophene-3,4-diol $^1$H-NMR (DMSO-d$_6$, 400 MHz): δ 7.62 (1H, d, J=4.8 Hz), 7.55 (1H, t, J=5.8 Hz), 7.47 (1H, s), 7.30 (1H, d, J=4.4 Hz), 7.20-7.16 (2H, m), 7.09-7.05 (1H, m), 5.33 (1H, d, J=6.4 Hz), 5.24 (1H, s), 4.63 (1H, d, J=8.0 Hz), 4.26-4.25 (2H, m), 3.71 (2H, q, J=6.5 Hz), 3.23 (1H, dd, J=10.4, 3.6 Hz), 2.97 (2H, t, J=7.0 Hz), 2.76 (1H, d, J=10.8 Hz).
LC-MS MS(EI) for C18H18F2N4O2S [M+H]$^{+\prime}$ (Calcd.: 392.11) Found: 393.3.

Example 195: Synthesis of (2S,3R,4S)-2-(8-((2,6-difluorophenethyl)amino)imidazo[1,2-a]pyrazin-3-yl)tetrahydrothiophene-3,4-diol $^1$H-NMR (DMSO-d$_6$, 400 MHz): δ 7.61 (1H, d, J=4.8 Hz), 7.58 (1H, t, J=6.2 Hz), 7.46 (1H, s), 7.32-7.28 (2H, m), 7.03 (2H, t, J=7.6 Hz), 5.33 (1H, d, J=5.6 Hz), 5.23 (1H, s), 4.63 (1H, d, J=7.6 Hz), 4.26 (2H, s), 3.66 (2H, q, J=6.4 Hz), 3.23 (1H, dd, J=11.4, 3.8 Hz), 3.00 (2H, t, J=6.6 Hz), 2.76 (1H, d, J=12.0 Hz).
LC-MS MS(EI) for C18H18F2N4O2S [M+H]$^{+\prime}$ (Calcd.: 392.11) Found: 393.3.

Example 196: Synthesis of (2S,3R,4S)-2-(8-((3,5-difluorophenethyl)amino)imidazo[1,2-a]pyrazin-3-yl)tetrahydrothiophene-3,4-diol $^1$H-NMR (DMSO-d$_6$, 400 MHz): δ 7.63 (1H, d, J=4.8 Hz), 7.52 (1H, t, J=5.2 Hz), 7.47 (1H, s), 7.31 (1H, d, J=4.8 Hz), 7.05-6.99 (3H, m), 5.33 (1H, d, J=6.0 Hz), 5.23 (1H, s), 4.63 (1H, d, J=7.2 Hz), 4.25 (2H, s), 3.70 (2H, q, J=6.3 Hz), 3.23 (1H, dd, J=4.6, 11.4 Hz), 3.98 (2H, t, J=6.8 Hz), 2.76 (1H, d, J=10.4 Hz).
LC-MS MS(EI) for C18H18F2N4O2S [M+H]$^{+\prime}$ (Calcd.: 392.11) Found: 393.3.

Example 197: Synthesis of (2S,3R,4S)-2-(8-((3,4-difluorophenethyl)amino)imidazo[1,2-a]pyrazin-3-yl)tetrahydrothiophene-3,4-diol $^1$H-NMR (DMSO-d$_6$, 400 MHz): δ 7.62 (1H, d, J=4.8 Hz), 7.50-7.47 (2H, m), 7.35-7.28 (3H, m), 7.08 (1H, brs), 5.33 (1H, d, J=5.6 Hz), 5.24 (1H, s), 4.63 (1H, d, J=8.0 Hz), 4.26-4.25 (2H, m), 3.68 (2H, q, J=6.5 Hz), 3.23 (1H, dd, J=10.6, 3.8 Hz), 2.94 (2H, t, J=7.0 Hz), 2.76 (1H, d, J=10.0 Hz).
LC-MS MS(EI) for C18H18F2N4O2S [M+H]$^{+\prime}$ (Calcd.: 392.11) Found: 393.3.

Example 198: Synthesis of (2S,3R,4S)-2-(8-((4-chloro-3-fluorophenethyl)amino)imidazo[1,2-a]pyrazin-3-yl)tetrahydrothiophene-3,4-diol $^1$H-NMR (DMSO-d$_6$, 400 MHz): δ 7.62 (1H, d, J=4.8 Hz), 7.50-7.45 (3H, m), 7.33-7.31 (2H, m), 7.11 (1H, d, J=8.4 Hz), 5.32 (1H, d, J=6.4 Hz), 5.23 (1H, d, J=3.6 Hz), 4.63 (1H, d, J=8.0 Hz), 4.61-4.25 (2H, m), 3.69 (2H, q, J=6.4 Hz), 3.23 (1H, dd, J=11.6, 4.4 Hz), 3.96 (2H, t, J=7.2 Hz), 2.76 (1H, d, J=10.4 Hz).
LC-MS MS(EI) for C18H18ClFN4O2S [M+H]$^{+\prime}$ (Calcd.: 408.08) Found: 409.3.

Example 199: Synthesis of (2S,3R,4S)-2-(8-((3-chlorobenzyl)thio)imidazo[1,2-a]pyrazin-3-yl)tetrahydrothiophene-3,4-diol $^1$H-NMR (DMSO-d$_6$, 400 MHz): δ 8.30 (1H, d, J=4.4 Hz), 7.81 (1H, d, J=4.4 Hz), 7.70 (1H, s), 7.53 (1H, s), 7.43 (1H, d, J=6.4 Hz), 7.36-7.30 (2H, m), 5.36 (1H, d, J=6.8 Hz), 5.27 (1H, d, J=3.6 Hz), 4.76 (1H, d, J=8.0 Hz), 4.56 (2H, s), 4.27-4.24 (2H, m), 2.98 (1H, dd, J=10.6, 3.8 Hz), 2.77 (1H, d, J=11.2 Hz).
LC-MS MS(EI) for C17H16ClN3O2S2 [M+H]$^{+\prime}$ (Calcd.: 393.04) Found: 394.3.

Example 200: Synthesis of (2S,3R,4S)-2-(8-(((1R,2S)-2-phenylcyclopropyl)amino)imidazo[1,2-a]pyrazin-3-yl)tetrahydrothiophene-3,4-diol $^1$H-NMR (DMSO-d$_6$, 400 MHz): δ 7.86 (1H, d, J=3.6 Hz), 7.67 (1H, d, J=4.8 Hz), 7.50 (1H, s), 7.29-7.25 (3H, m), 7.17 (3H, d, J=6.4 Hz), 5.32 (1H, s), 5.23 (1H, s), 4.64 (1H, d, J=7.8 Hz), 4.26 (2H, s), 3.24 (1H, d, J=9.6 Hz), 3.16-3.11 (1H, m), 2.76 (1H, d, J=10.0 Hz), 2.10-2.06 (1H, m), 1.51-1.46 (1H, m), 1.26-1.21 (1H, m).
LC-MS MS(EI) for C19H20N4O2S [M+H]$^{+\prime}$ (Calcd.: 368.13) Found: 369.3.

Example 201: Synthesis of (2S,3R,4S)-2-(8-((3-chloro-5-fluorobenzyl)amino)imidazo[1,2-a]pyrazin-3-yl)tetrahydrothiophene-3,4-diol $^1$H-NMR (DMSO-d$_6$, 400 MHz): δ 8.19 (1H, t, J=6.6 Hz), 7.68 (1H, d, J=4.8 Hz), 7.53 (1H, s), 7.28-7.25 (3H, m), 7.15 (1H, d, J=10.0 Hz), 5.33 (1H, d, J=6.4 Hz), 5.23 (1H, d, J=3.6 Hz), 4.67-4.65 (3H, m), 4.26 (2H, s), 3.24 (1H, dd, J=10.6, 4.2 Hz), 2.75 (1H, d, J=11.2 Hz).
LC-MS MS(EI) for C17H16ClFN4O2S [M+H]$^{+\prime}$ (Calcd.: 394.07) Found: 395.3.

Example 202: Synthesis of (2S,3R,4S)-2-(8-((3-cyclopropylbenzyl)amino)imidazo[1,2-a]pyrazin-3-yl)tetrahydrothiophene-3,4-diol $^1$H-NMR (DMSO-d$_6$, 400 MHz): δ 7.97 (1H, t, J=6.2 Hz), 7.63 (1H, d, J=4.4 Hz), 7.50 (1H, s), 7.26 (1H, d, J=4.8 Hz), 7.16-7.09 (3H, m), 6.88 (1H, d, J=7.6 Hz), 5.33 (1H, d, J=5.6 Hz), 5.23 (1H, s), 4.65-4.60 (3H, m), 4.26 (2H, s), 3.24 (1H, dd, J=10.6, 3.4 Hz), 2.76 (1H, d, J=10.4 Hz), 1.88-1.82 (1H, m), 0.91 (2H, d, J=8.4 Hz), 0.61 (2H, d, J=4.4 Hz).
LC-MS MS(EI) for C20H22N4O2S [M+H]$^{+\prime}$ (Calcd.: 382.15) Found: 383.3.

Example 203: Synthesis of (2S,3R,4S)-2-(8-(([1,1'-biphenyl]-3-ylmethyl)amino)imidazo[1,2-a]pyrazin-3-yl)tetrahydrothiophene-3,4-diol $^1$H-NMR (DMSO-d$_6$, 400 MHz): δ 8.10 (1H, t, J=6.4 Hz), 7.66-7.60 (4H, m), 7.51-7.44 (4H, m), 7.40-7.33 (3H, m), 7.28 (1H, d, J=4.8 Hz), 5.32 (1H, d, J=6.4 Hz), 5.22 (1H, d, J=3.2 Hz), 4.74 (2H, d, J=6.4 Hz), 4.64 (1H, d, J=7.2 Hz), 4.27-4.23 (2H, m), 3.24 (1H, dd, J=11.0, 4.6 Hz), 2.75 (1H, d, J=11.6 Hz).

LC-MS MS(EI) for C23H22N4O2S [M+H]+' (Calcd.: 418.15) Found: 419.3.

Example 204: Synthesis of (2S,3R,4S)-2-(8-((3-phenoxybenzyl)amino)imidazo[1,2-a]pyrazin-3-yl)tetrahydrothiophene-3,4-diol ¹H-NMR (DMSO-d₆, 400 MHz): δ 8.06 (1H, t, J=6.2 Hz), 7.64 (1H, d, J=4.0 Hz), 7.50 (1H, s), 7.37-7.25 (4H, m), 7.12-7.11 (2H, m), 7.00-6.95 (3H, m), 6.82 (1H, d, J=7.2 Hz), 5.32 (1H, d, J=6.0 Hz), 5.22 (1H, s), 4.64 (3H, d, J=5.6 Hz), 4.26 (2H, s), 3.24 (1H, dd, J=9.8, 2.6 Hz), 2.76 (1H, d, J=9.6 Hz).

LC-MS MS(EI) for C23H22N4O3S [M+H]+' (Calcd.: 434.14) Found: 435.3.

Example 205: Synthesis of methyl 3-(((3-((2S,3R,4S)-3,4-dihydroxytetrahydrothiophen-2-yl)imidazo[1,2-a]pyrazin-8-yl)amino)methyl)benzoate ¹H-NMR (DMSO-d₆, 400 MHz): δ 8.20 (1H, t, J=6.0 Hz), 7.97 (1H, s), 7.80 (1H, d, J=7.2 Hz), 7.65-7.62 (2H, m), 7.52 (1H, s), 7.45 (1H, t, J=7.4 Hz), 7.26 (1H, d, J=4.0 Hz), 5.33 (1H, d, J=5.6 Hz), 5.23 (1H, s), 4.71 (2H, d, J=6.0 Hz), 4.64 (1H, d, J=7.2 Hz), 4.26 (2H, s), 3.82 (3H, s), 2.24 (1H, dd, J=10.4, 4.0 Hz), 2.76 (1H, d, J=10.8 Hz).

LC-MS MS(EI) for C19H20N4O4S [M+H]+' (Calcd.: 400.12) Found: 401.3.

Example 206: Synthesis of (2S,3R,4S)-2-(8-(3-chlorophenethyl)imidazo[1,2-a]pyrazin-3-yl)tetrahydrothiophene-3,4-diol ¹H-NMR (DMSO-d₆, 400 MHz): δ 8.37 (1H, d, J=4.8 Hz), 7.82 (1H, d, J=4.0 Hz), 7.67 (1H, s), 7.35 (1H, s), 7.32-7.28 (1H, m), 7.25-7.23 (2H, m), 5.37 (1H, d, J=6.0 Hz), 5.28 (1H, d, J=3.2 Hz), 4.77 (1H, d, J=7.6 Hz), 4.29-4.27 (2H, m), 3.44 (2H, t, J=7.8 Hz), 3.28 (1H, dd, J=10.4, 3.2 Hz), 3.18 (2H, t, J=8.0 Hz), 2.78 (1H, d, J=10.0 Hz).

LC-MS MS(EI) for C18H18ClN3O2S [M+H]+' (Calcd.: 375.08) Found: 376.3.

Example 207: Synthesis of (2S,3R,4S)-2-(8-(((1R,2R)-2-phenylcyclopropyl)amino)imidazo[1,2-a]pyrazin-3-yl)tetrahydrothiophene-3,4-diol ¹H-NMR (DMSO-d₆, 400 MHz): δ 7.73-7.70 (1H, m), 7.60 (1H, s), 7.23-7.21 (3H, m), 7.13 (2H, t, J=7.4 Hz), 7.05-7.01 (1H, m), 5.32 (2H, brs), 4.61 (1H, d, J=8.4 Hz), 4.24-4.16 (2H, m), 3.24-3.20 (2H, m), 2.75 (1H, d, J=11.2 Hz), 2.42-2.41 (1H, m), 1.65 (1H, s), 1.48-1.46 (1H, m).
*A proton was not observed.

LC-MS MS(EI) for C18H19N5O2S [M+H]+' (Calcd.: 368.13) Found: 369.3.

Example 208: Synthesis of (2S,3R,4S)-2-(8-((5-chloro-2-fluorobenzyl)amino)imidazo[1,2-a]pyrazin-3-yl)tetrahydrothiophene-3,4-diol ¹H-NMR (DMSO-d₆, 400 MHz): δ 8.11 (1H, t, J=6.0 Hz), 7.68 (1H, d, J=4.4 Hz), 7.54 (1H, s), 7.33-7.28 (2H, m), 7.27-7.22 (2H, m), 5.34 (1H, d, J=5.6 Hz), 5.24 (1H, d, J=3.2 Hz), 4.68 (2H, d, J=6.0 Hz), 4.65 (1H, d, J=8.0 Hz), 4.26 (2H, brs), 3.25 (1H, dd, J=11.4, 4.2 Hz), 2.76 (1H, d, J=11.2 Hz).

LC-MS MS(EI) for C17H16ClFN4O2S [M+H]+' (Calcd.: 394.85) Found: 395.3.

Example 209: Synthesis of (2S,3R,4S)-2-(8-(((1S,2R)-2-(3,4-difluorophenyl)cyclopropyl)amino)imidazo[1,2-a]pyrazin-3-yl)tetrahydrothiophene-3,4-diol ¹H-NMR (DMSO-d₆, 400 MHz): δ 7.89 (1H, d, J=4.0 Hz), 7.68 (1H, d, J=4.4 Hz), 7.50 (1H, s), 7.35-7.27 (3H, m), 7.07-7.03 (1H, m), 5.32 (1H, d, J=6.0 Hz), 5.23 (1H, d, J=3.2 Hz), 4.64 (1H, d, J=7.6 Hz), 4.27-4.25 (2H, m), 3.23 (1H, dd, J=10.6, 3.8 Hz), 3.10-3.07 (1H, m), 2.77 (1H, d, J=10.8 Hz), 2.11-2.05 (1H, m), 1.52-1.50 (1H, m), 1.30-1.27 (1H, m).

LC-MS MS(EI) for C19H18F2N4O2S [M+H]+' (Calcd.: 404.11) Found: 405.3.

Example 210: Synthesis of (2S,3R,4S)-2-(8-((3-morpholinobenzyl)amino)imidazo[1,2-a]pyrazin-3-yl)tetrahydrothiophene-3,4-diol ¹H-NMR (DMSO-d₆, 400 MHz): δ 7.92 (1H, t, J=6.4 Hz), 7.63 (1H, d, J=4.8 Hz), 7.47 (1H, s), 7.26 (1H, d, J=4.8 Hz), 7.12 (1H, t, J=7.8 Hz), 6.97 (1H, s), 6.78 (2H, d, J=7.6 Hz), 5.36 (1H, d, J=6.8 Hz), 5.23 (1H, d, J=3.6 Hz), 4.64-4.60 (3H, m), 4.27-4.24 (2H, m), 3.71 (4H, t, J=4.4 Hz), 3.23 (1H, dd, J=12.8, 2.8 Hz), 3.05 (4H, t, J=4.6 Hz), 2.75 (1H, d, J=11.6 Hz).

LC-MS MS(EI) for C21H25N5O3S [M+H]+' (Calcd.: 427.17) Found: 428.3.

Example 211: Synthesis of (2S,3R,4S)-2-(8-((3-fluoro-4-(5-methyloxazol-2-yl)benzyl)amino)imidazo[1,2-a]pyrazin-3-yl)tetrahydrothiophene-3,4-diol ¹H-NMR (DMSO-d₆, 400 MHz): δ 8.20 (1H, t, J=6.2 Hz), 7.88 (1H, t, J=7.8 Hz), 7.67 (1H, d, J=4.8 Hz), 7.54 (1H, s), 7.31-7.27 (3H, m), 7.02 (1H, s), 5.34 (1H, d, J=5.6 Hz), 5.24 (1H, d, J=2.8 Hz), 4.72 (2H, d, J=6.4 Hz), 4.65 (1H, d, J=7.6 Hz), 4.27-4.26 (2H, m), 3.25 (1H, dd, J=11.2, 4.4 Hz), 2.76 (1H, d, J=12.0 Hz), 2.37 (3H, s).

LC-MS MS(EI) for C21H2OFN5O3S [M+H]+, (Calcd.: 441.13) Found: 442.2.

Example 212: Synthesis of (2S,3R,4S)-2-(8-((3-fluoro-4-(5-methylthiazol-2-yl)benzyl)amino)imidazo[1,2-a]pyrazin-3-yl)tetrahydrothiophene-3,4-diol ¹H-NMR (DMSO-d₆, 400 MHz): δ 8.20 (1H, t, J=6.0 Hz), 8.08 (1H, t, J=8.0 Hz), 7.68-7.66 (2H, m), 7.53 (1H, s), 7.33-7.26 (3H, m), 5.34 (1H, d, J=6.0 Hz), 5.24 (1H, d, J=3.6 Hz), 4.71 (2H, d, J=6.4 Hz), 4.65 (1H, d, J=8.0 Hz), 4.28-4.25 (2H, m), 3.24 (1H, dd, J=10.8, 4.0 Hz), 2.76 (1H, d, J=12.4 Hz).

*Protons from CH₃ were overlapped with DMSO peak at 2.5 ppm.

LC-MS MS(EI) for C21H2OFN5O2S2 [M+H]+, (Calcd.: 457.10) Found: 458.2.

Example 213: Synthesis of (2S,3R,4S)-2-(8-((3-fluoro-4-(5-methyl-1,3,4-oxadiazol-2-yl)benzyl)amino)imidazo[1,2-a]pyrazin-3-yl)tetrahydrothiophene-3,4-diol $^1$H-NMR (DMSO-d$_6$, 400 MHz): δ 8.26-8.22 (1H, m), 7.92 (1H, t, J=7.8 Hz), 7.68 (1H, d, J=4.8 Hz), 7.54 (1H, s), 7.39-7.35 (2H, m), 7.26 (1H, d, J=4.0 Hz), 5.34 (1H, d, J=6.4 Hz), 5.25 (1H, s), 4.74 (2H, d, J=6.4 Hz), 4.65 (1H, d, J=8.0 Hz), 4.26-4.24 (2H, m), 3.26-3.24 (1H, m), 2.78-2.75 (1H, m), 2.58 (3H, s).
LC-MS MS(EI) for C20H19FN6O3S [M+H]+, (Calcd.: 442.12) Found: 443.3.

Example 214: Synthesis of (2S,3R,4S)-2-(8-((3-(2-methyl-2H-tetrazol-5-yl)benzyl)amino)imidazo[1,2-a]pyrazin-3-yl)tetrahydrothiophene-3,4-diol $^1$H-NMR (DMSO-d$_6$, 400 MHz): δ 8.23 (1H, t, J=6.0 Hz), 8.06 (1H, s), 7.90 (1H, d, J=7.2 Hz), 7.65 (1H, d, J=4.4 Hz), 7.53-7.46 (3H, m), 7.26 (1H, d, J=4.8 Hz), 5.34 (1H, d, J=6.0 Hz), 5.24 (1H, d, J=3.6 Hz), 4.75 (2H, d, J=6.4 Hz), 4.65 (1H, d, J=7.2 Hz), 4.40 (3H, s), 4.26-4.25 (2H, m), 3.24 (1H, dd, J=10.6, 4.2 Hz), 2.75 (1H, d, J=10.8 Hz).
LC-MS MS(EI) for C19H20N8O2S [M+H]+, (Calcd.: 424.14) Found: 425.2.

Example 215: Synthesis of (2S,3R,4S)-2-(8-(((1S,2R)-2-(3-fluorophenyl)cyclopropyl)amino)imidazo[1,2-a]pyrazin-3-yl)tetrahydrothiophene-3,4-diol $^1$H-NMR (DMSO-d$_6$, 400 MHz): δ 7.90 (1H, d, J=4.4 Hz), 7.68 (1H, d, J=4.8 Hz), 7.50 (1H, s), 7.33-7.28 (2H, m), 7.03-6.96 (3H, m), 5.34 (1H, d, J=6.0 Hz), 5.25 (1H, s), 4.64 (1H, d, J=8.0 Hz), 4.27-4.23 (2H, m), 3.24 (1H, dd, J=11.2, 3.6 Hz), 3.16-3.12 (1H, m), 2.75 (1H, d, J=8.8 Hz), 2.11-2.07 (1H, m), 1.56-1.51 (1H, m), 1.35-1.27 (1H, m).
LC-MS MS(EI) for C19H19FN4O2S [M+H]+, (Calcd.: 386.12) Found: 387.2.

Example 216: Synthesis of (2S,3R,4S)-2-(8-(((1S,2R)-2-(3-chlorophenyl)cyclopropyl)amino)imidazo[1,2-a]pyrazin-3-yl)tetrahydrothiophene-3,4-diol $^1$H-NMR (DMSO-d$_6$, 400 MHz): δ 7.92 (1H, d, J=4.0 Hz), 7.68 (1H, d, J=4.4 Hz), 7.50 (1H, s), 7.32-7.28 (2H, m), 7.25-7.21 (2H, m), 7.15-7.13 (1H, m), 5.35 (1H, d, J=6.0 Hz), 5.26 (1H, s), 4.64 (1H, d, J=7.6 Hz), 4.30-4.20 (2H, m), 3.25-3.23 (1H, m), 3.14 (1H, brs), 2.76 (1H, d, J=8.8 Hz), 2.08 (1H, brs), 1.56-1.53 (1H, m), 1.33-1.29 (1H, m).
LC-MS MS(EI) for C19H19ClN4O2S [M+H]+, (Calcd.: 402.09) Found: 403.2.

Example 217: Synthesis of (2S,3R,4S)-2-(6-chloro-8-((3-chlorobenzyl)amino)imidazo[1,2-a]pyrazin-3-yl)tetrahydrothiophene-3,4-diol

STEP1 Preparation of (S)-2-((tert-butyldimethylsilyl)oxy)-1-((3aR,4S,6aS)-2,2-dimethyltetrahydrothieno[3,4-d][1,3]dioxol-4-yl)ethanol To a solution of (S)-1-((3aR,4S,6aS)-2,2-dimethyltetrahydrothieno[3,4-d][1,3]dioxol-4-yl)ethane-1,2-diol (2.0 g, 9.08 mmol) in DMF (60 mL) was added dropwise TBSCl (1.51 g, 9.99 mmol) and TEA (1.9 ml, 13.62 mmol) at 0° C. The reaction mixture was stirred at room temperature for 15 hours, diluted with EtOAc and washed with water and brine. The separated organic layer was dried over Na$_2$SO$_4$, filtered and concentrated in vacuo. The residue was purified by column chromatography on SiO$_2$ (Hexanes:EtOAc=4:1) to give (S)-2-((tert-butyldimethylsilyl)oxy)-1-((3aR,4S,6aS)-2,2-dimethyltetrahydrothieno[3,4-d][1,3]dioxol-4-yl)ethanol (2.8 g, 93%) as a colorless oil.
$^1$H-NMR (CDCl$_3$, 400 MHz): δ 4.91-4.89 (m, 1H), 4.83 (dd, 1H, J=6.0, 2.0 Hz), 3.86-3.83 (m, 1H), 3.67 (dd, 1H, J=10.4, 6.4 Hz), 3.57 (dd, 1H, J=10.0, 4.8 Hz), 3.39 (dd, 1H, J=3.6, 2.0 Hz), 3.19 (dd, 1H, J=12.4, 5.2 Hz), 2.85 (dd, 1H, J=12.0, 2.0 Hz), 2.46 (d, 1H, J=4.8 Hz), 1.52 (s, 3H), 1.33 (s, 3H), 0.90 (s, 9H), 0.08 (s, 6H).

STEP2 Preparation of tert-butyl((S)-2-chloro-2-((3aR,4R,6aS)-2,2-dimethyltetrahydrothieno[3,4-d][1,3]dioxol-4-yl)ethoxy)dimethylsilane To a solution of (S)-2-((tert-butyldimethylsilyl)oxy)-1-((3aR,4S,6aS)-2,2-dimethyltetrahydrothieno[3,4-d][1,3]dioxol-4-yl)ethanol (2.7 g, 8.07 mmol) in DCM (30 mL) was added MsCl (1.11 g, 9.68 mmol) and TEA (1.69 ml, 12.11 mmol). The reaction mixture was stirred at room temperature for 18 hours, diluted with DCM and washed with water and brine. The separated organic layer was dried over Na$_2$SO$_4$, filtered and concentrated in vacuo. The residue was purified by column chromatography on SiO$_2$ (Hexanes:EtOAc=9:1) to give tert-butyl((S)-2-chloro-2-((3aR,4R,6aS)-2,2-dimethyltetrahydrolthieno[3,4-d][1,3]dioxol-4-yl)ethoxy)dimethylsilane (2.2 g, 84%) as a colorless oil.
$^1$H-NMR (CDCl$_3$, 400 MHz): δ 5.00-4.97 (m, 1H), 4.92-4.91 (m, 1H), 4.21-4.19 (m, 1H), 3.91 (dd, 1H, J=10.4, 4.8 Hz), 3.84-3.74 (m, 2H), 3.33 (dd, 1H, J=12.4, 5.2 Hz), 2.90 (d, 1H, J=12.4 Hz), 1.53 (s, 3H), 1.33 (s, 3H), 0.90 (s, 9H), 0.08 (s, 6H).

STEP3 Preparation of (S)-2-chloro-2-((3aR,4R,6aS)-2,2-dimethyltetrahydrothieno[3,4-d][1,3]dioxol-4-yl)ethanol To a solution of (tert-butyl((S)-2-chloro-2-((3aR,4R,6aS)-2,2-dimethyltetrahydrolthieno[3,4-d][1,3]dioxol-4-yl)ethoxy)dimethylsilane (2.4 g, 6.80 mmol) in THF (30 mL) was added dropwise AcOH (0.82 g, 13.6 mmol) and 1M TBAF (8.84 ml, 8.84 mmol) at 0° C. The reaction mixture was stirred for 3 hours and poured onto water. The mixture was extracted with EtOAc twice. The combined organic layers were dried over Na$_2$SO$_4$, filtered and concentrated in vacuo. The residue was purified by column chromatography on SiO$_2$ (Hexanes:EtOAc=9:1 to 3:1) to give (S)-2-chloro-2-((3aR,4R,6aS)-2,2-dimethyltetrahydrothieno[3,4-d][1,3]dioxol-4-yl)ethanol (1.18 g, 73%) as a colorless oil.
$^1$H-NMR (CDCl$_3$, 400 MHz): δ 4.99 (dt, 1H, J=2.0, 5.6 Hz), 4.86 (dd, 1H, J=5.6, 2.4 Hz), 4.25 (q, 1H, J=5.2 Hz), 3.95-3.81 (m, 2H), 3.72 (dd, 1H, J=1.4, 4.4 Hz), 3.29 (dd, 1H, J=5.6, 12.8 Hz), 2.95 (dd, 1H, J=2.0, 12.8 Hz), 2.19 (t, 1H, J=7.2), 1.52 (s, 3H), 1.33 (s, 3H).

STEP4 Preparation of 6,8-dichloro-3-((3aR,4S,6aS)-2,2-dimethyltetrahydrothieno[3,4-d][1,3]dioxol-4-yl)imidazo[1,2-a]pyrazine COCl$_2$ (2.13 ml, 4.27 mmol) was added dropwise over 15 min to a solution of dimethylsulfoxide (0.39 g, 4.98 mmol) in DCM (30 mL) cooled with a dry ice-acetone bath. To this solution was added a solution of (S)-2-chloro-2-((3aR,4R,6aS)-2,2-dimethyltetrahydrothieno[3,4-d][1,3]dioxol-4-yl)ethanol (0.85 g, 3.56 mmol) over 5 min. The mixture was further stirred at −78° C. for 45 min. TEA (0.26 ml, 1.89 mmol) was added to the solution, stirred at −40° C. for 30 min and allowed to warm up to room temperature. The organic phase was washed with sat. NH$_4$Cl solution and brine, dried over Na$_2$SO$_4$ and filtered. After removal of the solvent, the resulting residue (760 mg) was dissolved in CH$_3$CN. To this solution was added 3,5-dichloropyrazin-2-amine (584 mg, 3.56 mmol), stirred at 85° C. for 16 h and concentrated in vacuo. The residue was purified by column chromatography on SiO$_2$ (Hexanes:EtOAc:DCM=2:1:1) to give 6,8-dichloro-3-((3aR,4S,6aS)-2,2-dimethyltetrahydrothieno[3,4-d][1,3]dioxol-4-yl)imidazo[1,2-a]pyrazine (36 mg, 3%) as a white sticky oil.

$^1$H-NMR (CDCl$_3$, 400 MHz): δ 8.08 (s, 1H), 7.65 (s, 1H), 5.13-5.05 (m, 2H), 4.54 (d, 1H, J=2.4 Hz), 3.13-3.01 (m, 2H), 1.61 (s, 3H), 1.39 (s, 3H).

STEP5 Preparation of 6-chloro-N-(3-chlorobenzyl)-3-((3aR,4S,6aS)-2,2-dimethyltetrahydrothieno[3,4-d][1,3]dioxol-4-yl)imidazo[1,2-a]pyrazin-8-amine A solution of 6,8-dichloro-3-((3aR,4S,6aS)-2,2-dimethyltetrahydrothieno[3,4-d][1,3]dioxol-4-yl)imidazo[1,2-a]pyrazine (44 mg, 0.17 mmol) and (3-chlorophenyl)methanamine (27 mg, 0.19 mmol) in EtOH (6.4 mL) was stirred at room temperature for 24 h and concentrated in vacuo. The residue was purified by column chromatography on SiO$_2$ (MeOH:DCM=1:40) to give 6-chloro-N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (25 mg, 44%) as a white sticky oil.

$^1$H-NMR (CDCl$_3$, 400 MHz): δ 7.46 (s, 1H), 7.38 (s, 1H), 7.27-7.26 (m, 4H), 6.42 (t, 1H, J=6.0 Hz), 5.08-5.01 (m, 2H), 4.78 (d, 1H, J=6.0 Hz), 4.48 (d, 1H, J=2.0 Hz), 3.05 (m, 1H), 1.60 (s, 3H), 1.38 (s, 3H).

STEP6 Preparation of (2S,3R,4S)-2-(6-chloro-8-((3-chlorobenzyl)amino)imidazo[1,2-a]pyrazin-3-yl)tetrahydrothiophene-3,4-diol A solution of 6-chloro-N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (25 mg, 0.055 mmol) and 2N HCl solution (0.5 mL) in THF (2 mL) was stirred at room temperature for 15 h. The reaction mixture was concentrated in vacuo. The residue was diluted with EtOAc, and then 1N NaOH (1 mL) was added to the solution until pH 7. The combined organic layers were dried over Na$_2$SO$_4$, filtered and concentrated in vacuo. The residue was purified by column chromatography on SiO$_2$ (Hexanes:EtOAc=4:1 with 0.5% TEA) to to give (2S,3R,4S)-2-(6-chloro-8-((3-chlorobenzyl)amino)imidazo[1,2-a]pyrazin-3-yl)tetrahydrothiophene-3,4-diol (12 mg, 53%) as a light brown solid.

$^1$H-NMR (CDCl$_3$, 400 MHz): δ 7.81 (s, 1H), 7.59 (s, 1H), 7.45 (s, 1H), 7.35-7.28 (m, 3H), 4.76-4.73 (m, 3H), 4.43-4.40 (m, 1H), 4.34-4.31 (m, 1H), 3.50-3.32 (m, 1H), 2.93-2.90 (m, 1H).

LC-MS MS(EI) for C17H16C12N4O2S [M+H]$^+$ (Calcd.: 410.04) Found: 411.1.

Example 218: Synthesis of (2S,3R,4S)-2-(8-((3-chlorobenzyl)amino)-[1,2,4]triazolo[4,3-a]pyridin-3-yl)tetrahydrothiophene-3,4-diol STEP1 Preparation of 8-bromo-3-((3aR,4S,6aS)-2,2-dimethyltetrahydrothieno[3,4-d][1,3]dioxol-4-yl)-[1,2,4]triazolo[4, 3-a]pyridine To a solution of (3aR,4R,6aS)-2,2-dimethyltetrahydrothieno[3,4-d][1,3]dioxole-4-carbaldehyde (0.3 g, 1.59 mmol) in anhydrous DCM (17 mL) under N$_2$ was added 3-Bromo-2-hydrazinopyridine (0.3 g, 1.59 mmol). The reaction mixture was stirred at room temperature for 30 min, and the disappearance of (3aR,4R,6aS)-2,2-dimethyltetrahydrothieno[3,4-d][1,3]dioxole-4-carbaldehyde was checked with TLC. When about 95% of starting material was disappeared, the reaction mixture was added PhI(OAc)$_2$ (0.77 g, 2.34 mmol). The resulting solution was stirred at room temperature for 3.3 h. The organic phase was washed with sat. NaHCO$_3$ solution and brine, dried over Na$_2$SO$_4$, filtered and concentrated in vacuo. The residue was purified by column chromatography on SiO$_2$ (Hexanes:EtOAc=2:1) to give 8-bromo-3-((3aR,4S,6aS)-2,2-dimethyltetrahydrothieno[3,4-d][1,3]dioxol-4-yl)-[1,2,4]triazolo[4, 3-a]pyridine (383 mg, 54%) as a light orange solid.

$^1$H-NMR (CDCl$_3$, 400 MHz): δ 7.91 (d, J=7.2 Hz, 1H), 7.55 (d, J=7.6 Hz, 1H), 6.80 (t, J=7.2 Hz, 1H), 5.77 (d, J=5.2 Hz, 1H), 5.32-5.30 (m, 1H), 4.60 (s, 1H), 2.96-2.95 (m, 2H), 1.60 (s, 3H), 1.42 (s, 1H).

STEP2 Preparation of N-(3-chlorobenzyl)-3-((3aR,4S,6aS)-2,2-dimethyltetrahydro thieno[3,4-d][1,3]dioxol-4-yl)-[1,2,4]triazolo[4,3-a]pyridin-8-amine To a solution of 8-bromo-3-((3aR,4S,6aS)-2,2-dimethyltetrahydrothieno[3,4-d][1,3]dioxol-4-yl)-[1,2,4]triazolo[4, 3-a]pyridine (150 mg, 0.42 mmol), Pd$_2$dba$_3$ (19 mg, 0.021 mmol), Xantphos (13 mg, 0.023 mmol) and Cs$_2$CO$_3$ (410 mg, 1.26 mmol) in anhydrous Dioxane (8 mL) under N$_2$ was added dropwise 3-chlorobenzylamine (0.06 mL, 0.50 mmol). The reaction mixture was stirred at 110° C. for 18 h and diluted with DCM. The organic solution was filtered through Celite and concentrated in vacuo. The residue was purified by column chromatography on SiO$_2$ (Hexanes:EtOAc=1:1) to give N-(3-chlorobenzyl)-3-((3aR,4S,6aS)-2,2-dimethyltetrahydrothieno[3,4-d][1,3]dioxol-4-yl)-[1,2,4]triazolo[4,3-a]pyridin-8-amine (56 mg, 32%) as a white solid.

$^1$H-NMR (CDCl$_3$, 400 MHz): δ 7.52 (s, 1H), 7.38-7.28 (m, 4H), 6.70 (t, J=7.6 Hz, 1H), 6.00 (d, J=7.6 Hz, 1H), 5.86-5.83 (m, 1H), 5.72 (d, J=5.2 Hz, 1H), 5.32-5.30 (m, 1H), 4.59 (s, 1H), 4.52 (d, J=6.0 Hz, 2H), 3.02-2.93 (m, 2H), 1.69-1.53 (m, 10H), 1.42 (s, 3H).

STEP3 Preparation of (2S,3R,4S)-2-(8-((3-chlorobenzyl)amino)-[1,2,4]triazolo[4,3-a]pyridin-3-yl)tetrahydrothiophene-3,4-diol A solution of N-(3-chlorobenzyl)-3-((3aR,4S,6aS)-2,2-dimethyltetrahydrothieno[3,4-d][1,3]dioxol-4-yl)-[1,2,4]triazolo[4,3-a]pyridin-8-amine (57 mg, 0.14 mmol) in 80% AcOH (32 mL) was refluxed for 2.5 h and concentrated in vacuo. The residue was purified by column chromatography on SiO$_2$ (MeOH:DCM=1:20) to give (2S,3R,4S)-2-(8-((3-chlorobenzyl)amino)-[1,2,4]triazolo[4,3-a]pyridin-3-yl)tetrahydrothiophene-3,4-diol (40 mg, 78%) as a light yellow solid.

$^1$H-NMR (CDCl$_3$, 400 MHz): δ 7.41 (d, J=6.4 Hz, 1H), 7.37 (s, 1H), 6.64 (t, J=7.2 Hz, 1H), 5.98 (d, J=7.6 Hz, 1H), 5.94 (t, J=5.8 Hz, 1H), 5.34 (br, 1H), 5.13 (dd, J=3.2, 8.0 Hz, 1H), 4.87 (d, J=8.4 Hz, 1H), 4.50-5.71 (m, 1H), 4.50 (d, J=5.6 Hz, 1H), 3.64 (br, 1H), 3.29 (dd, J 4.4, 11.6 Hz, 1H), 3.08 (dd, J=2.4, 11.6 Hz, 1H).

LC-MS MS(EI) for C17H17ClN4O2S [M+H]$^+$ (Calcd.: 376.08) Found: 377.1.

Example 219: Synthesis of (2S,3R,4S)-2-(8-((3-chlorobenzyl)amino)imidazo[1,5-a]pyrazin-3-yl)tetrahydrothiophene-3,4-diol

STEP1 Preparation of (3aR,4R,6aS)—N-((3-chloropyrazin-2-yl)methyl)-2,2-dimethyltetrahydrothieno[3,4-d][1,3]dioxole-4-carbothioamide To a solution of (3aR,4R,6aS)-2,2-dimethyltetrahydrothieno[3,4-d][1,3]dioxole-4-carbaldehyde (791 mg, 4.2 mmol) in DMF (5 mL) was added (3-chloropyrazin-2-yl)methanamine 2HCl (1 g, 4.6 mmol), DIPEA (2.2 mL, 12.6 mmol) and sulfur. The reaction mixture was stirred at room temperature for 2 h, diluted with DCM and washed with ice water and brine. The separated organic layer was dried over $Na_2SO_4$, filtered and concentrated in vacuo. The residue was purified by column chromatography on $SiO_2$ (Hexanes:EtOAc:DCM=1:3:1) to give 2-(3-chloropyrazin-2-yl)-1-((3aR,4R,6aS)-2,2-dimethyltetrahydro thieno[3,4-d][1,3]dioxol-4-yl)ethanethione (672 g, 46%) as a brown oil.

$^1$H-NMR (CDCl$_3$, 400 MHz): δ 9.98 (brs, 1H), 8.50 (d, J=2.4 Hz, 1H), 8.39 (d, J=2.4 Hz, 1H), 5.63 (d, J=5.6 Hz, 1H), 5.03-4.98 (m, 3H), 4.33 (s, 1H), 3.22-3.18 (m, 1H), 3.10-2.98 (m, 1H), 1.55 (s, 3H), 1.35 (s, 3H).

STEP2 Preparation of 8-chloro-3-((3aR,4S,6aS)-2,2-dimethyltetrahydrothieno[3,4-d][1,3]dioxol-4-yl)imidazo[1,5-a]pyrazine A solution of 2-(3-chloropyrazin-2-yl)-1-((3aR,4R,6aS)-2,2-dimethyltetrahydrothieno[3,4-d][1,3]dioxol-4-yl)ethanethione (672 mg, 1.94 mmol) and Hg(O$_2$CCF$_3$)$_2$ (837 mg, 1.96 mmol) in 1,4-Dioxane (20 mL) was stirred at room temperature for 2 h and diluted with DCM. The organic solution was filtered through Celite and concentrated in vacuo. The residue was purified by column chromatography on SiO$_2$ (Hexanes:EtOAc=5:1) to give 8-chloro-3-((3aR,4S,6aS)-2,2-dimethyltetrahydrothieno[3,4-d][1,3]dioxol-4-yl)imidazo[1,5-a]pyrazine (292 mg, 48%) as a light yellow solid.

$^1$H-NMR (CDCl$_3$, 400 MHz): δ 7.73 (s, 1H), 7.61 (d, J=4.4 Hz, 1H), 7.41 (d, J=5.2 Hz, 1H), 5.57 (d, J=5.6 Hz, 1H), 5.28-5.26 (m, 1H), 4.58 (s, 1H), 2.99-2.97 (m, 2H), 1.59 (s, 3H), 1.40 (s, 3H).

STEP3 Preparation of N-(3-chlorobenzyl)-3-((3aR,4S,6aS)-2,2-dimethyltetrahydrothieno[3,4-d][1,3]dioxol-4-yl)-[1,2,4]triazolo[4,3-a]pyridin-8-amine A solution of 8-chloro-3-((3aR,4S,6aS)-2,2-dimethyltetrahydrothieno[3,4-d][1,3]dioxol-4-yl)imidazo[1,5-a]pyrazine (40 mg, 0.1 mmol) and (3-chlorophenyl)methanamine (55 mg, 0.4 mmol) and DIPEA (0.08 mL, 0.4 mmol) in CH3CN (1 mL) was stirred at 70° C. for 18 h, diluted with DCM and washed with sat. NH$_4$Cl solution and brine. The separated organic layer was dried over Na$_2$SO$_4$, filtered and concentrated in vacuo. The residue was purified by column chromatography on SiO$_2$ (Hexanes:EtOAc=1:1) to give 2-(3-chloropyrazin-2-yl)-1-((3aR,4R,6aS)-2,2-dimethyltetrahydro thieno[3,4-d][1,3]dioxol-4-yl)ethanethione (672 g, 46%) as a white solid.

$^1$H-NMR (CDCl$_3$, 400 MHz): δ 7.41 (s, 1H), 7.37 (s, 1H), 7.27-7.26 (m, 2H), 7.21-7.17 (m, 2H), 5.53 (d, J=5.6 Hz, 1H), 5.27-5.25 (m, 1H), 5.23-5.19 (m, 1H), 4.78-4.76 (m, 2H), 4.57 (s, 1H), 3.07-3.06 (m, 1H), 2.96-2.93 (m, 1H), 1.59 (s, 3H), 1.39 (s, 3H).

STEP4 Preparation of (2S,3R,4S)-2-(8-((3-chlorobenzyl)amino)imidazo[1,5-a]pyrazin-3-yl)tetrahydrothiophene-3,4-diol A solution of 2-(3-chloropyrazin-2-yl)-1-((3aR,4R,6aS)-2,2-dimethyltetrahydrothieno[3,4-d][1,3]dioxol-4-yl)ethanethione (26 mg, 0.06 mmol) and 2N HCl solution (0.09 mL) in THF (0.5 mL) was stirred at room temperature for 28 h. The reaction mixture was concentrated in vacuo. The residue was diluted with EtOAc, and then 1N NaOH (1 mL) was added to the solution until pH 7. The combined organic layers were dried over Na$_2$SO$_4$, filtered and concentrated in vacuo. The residue was purified by column chromatography on SiO$_2$ (MeOH:DCM=1:15) to to give (2S,3R,4S)-2-(8-((3-chlorobenzyl)amino)imidazo[1,5-a]pyrazin-3-yl)tetrahydrothiophene-3,4-diol (14 mg, 62%) as a white solid.

$^1$H-NMR (CDCl$_3$, 400 MHz): δ 7.41 (d, J=6.4 Hz, 1H), 7.37 (s, 1H), 6.64 (t, J=7.2 Hz, 1H), 5.98 (d, J=7.6 Hz, 1H), 5.94 (t, J=5.8 Hz, 1H), 5.34 (br, 1H), 5.13 (dd, J=3.2, 8.0 Hz, 1H), 4.87 (d, J=8.4 Hz, 1H), 4.50-5.71 (m, 1H), 4.50 (d, J=5.6 Hz, 1H), 3.64 (br, 1H), 3.29 (dd, J 4.4, 11.6 Hz, 1H), 3.08 (dd, J=2.4, 11.6 Hz, 1H).

LC-MS MS(EI) for C17H17ClN4O2S [M+H]$^+$ (Calcd.: 376.08) Found: 377.1.

Example 220: Synthesis of (2S,3R,4S)-2-(6-chloro-8-((3-chlorobenzyl)amino)imidazo[1,2-a]pyridin-3-yl)tetrahydrothiophene-3,4-diol

STEP1 Preparation of (S)-2-((5-chloro-3-nitropyridin-2-yl)amino)-1-((3aR,4S,6aS)-2,2-dimethyltetrahydrothieno[3,4-d][1,3]dioxol-4-yl)ethanol To a solution of (S)-2-amino-1-((3aR,4S,6aS)-2,2-dimethyltetrahydrothieno[3,4-d][1,3]dioxol-4-yl)ethanol (556 mg, 2.54 mmol) in 1,4-dioxane (5 mL) were added 2,5-dichloro-3-nitropyridine (978.64 mg, 5.07 mmol) and TEA (769.65 mg, 7.61 mmol) at room temperature. The reaction mixture was stirred at 110° C. for 18 hours and concentrated in vacuo. The residue was dissolved in DCM and washed with 1N HCl and brine. The organic layer was dried over Na$_2$SO$_4$, filtered and concentrated in vacuo. The residue was purified by column chromatography on SiO$_2$ (Hexanes:EtOAc=3:1) to give (S)-2-((5-chloro-3-nitropyridin-2-yl)amino)-1-((3aR,4S,6aS)-2,2-dimethyltetrahydrothieno[3,4-d][1,3]dioxol-4-yl)ethanol (747 mg, 78%) as a orange oil.

$^1$H-NMR (CDCl$_3$, 400 MHz): δ 8.43 (d, J=2.4 Hz, 2H), 8.33 (d, J=2.4 Hz, 1H), 4.93 (m, 1H), 4.80 (m, 1H), 3.94 (m, 1H), 3.88 (m, 1H), 3.73 (m, 1H), 3.42 (dd, 1H, J=2.4, 5.2 Hz), 3.17 (m, 1H), 2.91 (dd, J=2.0, 12.8 Hz), 1.53 (s, 3H), 1.33 (s, 3H).

STEP2 Preparation of 2-((5-chloro-3-nitropyridin-2-yl)amino)-1-((3aR,4R,6aS)-2,2-dimethyltetrahydrothieno[3,4-d][1, 3]dioxol-4-yl)ethanone To a solution of (S)-2-((5-chloro-3-nitropyridin-2-yl)amino)-1-((3aR,4S,6aS)-2,2-dimethyltetrahydrothieno[3,4-d][1,3]dioxol-4-yl)ethanol (724 mg, 1.93 mmol) in DCM (13 mL) was added Dess-Martin (980.48 mg, 2.31 mmol) at 0° C. The reaction mixture was stirred room temperature for 1 hour, diluted with DCM and washed with 1N NaOH and brine. The separated organic layer was dried over Na$_2$SO$_4$, filtered and concentrated in vacuo. The residue was purified by column chromatography on SiO$_2$ (Hexanes:EtOAc=5:1) to give 2-((5-chloro-3-nitropyridin-2-yl)amino)-1-((3aR,4R, 6aS)-2,2-dimethyltetrahydrothieno[3,4-d][1,3]dioxol-4-yl)ethanone (586 mg, 81%) as a yellow solid.

¹H-NMR (CDCl₃, 400 MHz): δ 8.50 (brs, 1H), 8.44 (d, J=2.0 Hz, 1H), 8.34 (d, J=2.0 Hz, 1H), 4.99 (m, 2H), 4.80 (dd, J=5.2 Hz, 19.2 Hz, 1H), 4.45 (dd, J=4.8 Hz, 12.8 Hz, 1H), 4.00 (s, 1H), 2.90 (m, 3H), 1.51 (s, 3H), 1.33 (s, 3H).

STEP3 Preparation of 6-chloro-3-((3aR,4S,6aS)-2,2-dimethyltetrahydrothieno[3,4-d][1,3]dioxol-4-yl)-8-nitroimidazo[1,2-a]pyridine To a solution of 2-((5-chloro-3-nitropyridin-2-yl)amino)-1-((3aR,4R,6aS)-2,2-dimethyltetrahydro thieno[3,4-d][1,3]dioxol-4-yl)ethanone (586 mg, 1.57 mmol) in toluene (10 mL) were added pyridine (1.49 g, 18.81 mmol) followed by TFA (1.25 g, 10.97 mmol) at 0° C. After being stirred for 30 min at room temperature, the mixture was cooled to 0° C. and then TFAA (2.3 g, 10.97 mmol) was added to it. The resulting reaction mixture was stirred at room temperature for 3 hours. After concentration in vacuo, the residue was dissolved in DCM, washed with water and brine, dried over Na₂SO₄, filtered and concentrated in vacuo. The residue was purified by column chromatography on SiO₂ (Hexanes:EtOAc=2:1) to give 6-chloro-3-((3aR,4S,6aS)-2,2-dimethyltetrahydrothieno[3,4-d][1,3]dioxol-4-yl)-8-nitroimidazo[1,2-a]pyridine (280 mg, 60%) as a yellow solid.

¹H-NMR (CDCl₃, 400 MHz): δ 8.41 (d, J=1.6 Hz, 1H), 8.34 (d, J=1.6 Hz, 1H), 7.64 (s, 1H), 5.13 (m, 2H), 4.57 (s, 1H), 4.12 (q, J=7.2 Hz, 1H), 3.10-2.98 (m, 2H), 1.61 (s, 3H), 1.41 (s, 3H).

STEP4 Preparation of 6-chloro-3-((3aR,4S,6aS)-2,2-dimethyltetrahydrothieno[3,4-d][1,3]dioxol-4-yl)imidazo[1,2-a]pyridin-8-amine To a solution of 6-chloro-3-((3aR,4S,6aS)-2,2-dimethyltetrahydrothieno[3,4-d][1,3]dioxol-4-yl)-8-nitroimidazo[1,2-a]pyridine (170 mg, 0.48 mmol) in MeOH (5 mL) were added NH₄Cl (217.28 mg, 4.06 mmol) and Fe (133.42 mg, 2.39 mmol). The reaction mixture was refluxed for 3 hour and cooled to r.t. The organic solution was filtered through Celite and concentrated in vacuo to give 6-chloro-3-((3aR,4S,6aS)-2,2-dimethyltetrahydrothieno[3,4-d][1,3]dioxol-4-yl)imidazo[1,2-a]pyridin-8-amine (145 mg, 93%) as a dark brown solid, which used in the next step without purification.

¹H-NMR (CDCl₃, 400 MHz): δ 7.57 (d, J=1.6 Hz, 1H), 7.31 (s, 1H), 6.44 (s, 1H), 5.10 (m, 2H), 4.78 (brs, 2H), 4.53 (s, 1H), 3.06 (d, J=2.8H, 2H), 1.62 (s, 3H), 1.41 (s, 3H).

STEP5 Preparation of N-(3-chlorobenzyl)-3-((3aR,4S,6aS)-2,2-dimethyltetrahydro thieno[3,4-d][1,3]dioxol-4-yl)imidazo[1,2-a]pyrazin-8-amine A solution of 6-chloro-3-((3aR,4S,6aS)-2,2-dimethyltetrahydrothieno[3,4-d][1,3]dioxol-4-yl)imidazo[1,2-a]pyridin-8-amine (62 mg, 0.19 mmol) in MeOH (3 mL) was added 3-chlorobenzaldehyde (33.44 mg, 0.24 mmol) and ZnCl₂ (45.39 mg, 0.33 mmol). The reaction mixture was stirred at room temperature for 1 h, whereupon NaBH₃CN (14.95 mg, 0.24 mmol) was added in one portion. The reaction mixture was refluxed for 15 h, cooled to r.t and concentrated in vacuo. The residue was purified by column chromatography on SiO₂ (Hexanes:EtOAc=1:1) to give N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (30 mg, 35%) as a yellow solid.

¹H-NMR (CDCl₃, 400 MHz): δ 8.20 (d, J=3.2 Hz, 1H), 8.07 (s, 4H), 7.46 (d, J=1.6 Hz, 1H), 7.34 (s, 1H), 6.04 (s, 1H), 5.07 (d, J=1.2 Hz, 2H), 3.85 (m, 3H), 3.01 (d, J=2.4H, 2H), 1.58 (s, 3H), 1.37 (s, 3H).

STEP6 Preparation of (2S,3R,4S)-2-(6-chloro-8-((3-chlorobenzyl)amino)imidazo[1,2-a]pyridin-3-yl)tetrahydrothiophene-3,4-diol A solution of N-(3-chlorobenzyl)-3-((3aR,4S,6aS)-2,2-dimethyltetrahydrothieno[3,4-d][1,3]dioxol-4-yl)imidazo[1,2-a]pyrazin-8-amine (30 mg, 0.067 mmol) and 2N HCl solution (0.09 mL) in THF (1.3 mL) was stirred at 50° C. for 18 h. The reaction mixture was concentrated in vacuo. The residue was diluted with EtOAc, and then 1N NaOH (1 mL) was added to the solution until pH 7. The combined organic layers were dried over Na₂SO₄, filtered and concentrated in vacuo. The residue was purified by column chromatography on SiO₂ (MeOH:DCM=1:20) to to give (2S,3R,4S)-2-(6-chloro-8-((3-chlorobenzyl)amino)imidazo[1,2-a]pyridin-3-yl)tetrahydrothiophene-3,4-diol (12 mg, 44%) as a white solid.

¹H-NMR (DMSO-d₆, 400 MHz): δ 7.76 (s, 1H) 7.48 (s, 1H), 7.44 (s, 1H), 7.35 (m, 4H), 6.00 (s, 1H), 5.35 (d, J=6.4 Hz, 1H), 5.19 (d, J=4.0 Hz, 1H), 4.64 (d, J=7.6 Hz, 1H), 4.50 (d, J=6.4 Hz, 2H), 4.23 (m, 2H), 3.20 (dd, J=4.8 Hz, 10.8 Hz, 1H), 2.76 (dd, J=3.2 Hz, 10.0 Hz, 1H).

LC-MS MS(EI) for C18H17C12N3O2S [M+H]⁺ (Calcd.: 409.04) Found: 410.1.

Example 221: Synthesis of (2S,3R,4S)-2-(8-((3-chlorobenzyl)amino)imidazo[1,2-a]pyridin-3-yl)tetrahydrothiophene-3,4-diol ¹H-NMR (DMSO-d₆, 400 MHz): δ 7.59 (d, J=6.8 Hz, 1H), 7.47 (s, 2H), 7.34-7.33 (m, 2H), 7.28-7.27 (m, 1H), 6.88-6.86 (m, 1H), 6.68-6.64 (m, 1H), 5.97 (d, J=7.6 Hz, 1H), 5.30 (d, J=6.4 Hz, 1H), 5.21 (d, J=4.0 Hz, 1H), 4.64 (d, J=7.6 Hz, 1H), 4.48 (d, J=6.4 Hz, 2H), 4.28-4.27 (m, 2H), 3.22-3.18 (m, 1H), 2.78-2.75 (m, 1H).

LC-MS MS(EI) for C18H18ClN3O2S [M+H]+, (Calcd.: 375.08) Found: 376.1.

Example 222: Synthesis of (1R,2S,3S)-3-(8-((3-chlorobenzyl)amino)imidazo[1,2-a]pyrazin-3-yl)cyclopentane-1,2-diol STEP1 Preparation of (3aR,4S,6aR)-2,2-dimethyl-4,6a-dihydro-3aH-cyclopenta[d][1,3]dioxol-4-yl methyl carbonate To a solution of (3aS,4S,6aR)-2,2-dimethyl-4,6a-dihydro-3aH-cyclopenta[d][1,3]dioxol-4-ol (8.86 g, 56.7 mmol) in DCM (189 mL) was added pyridine (6.87 mL, 85 mmol) at 0° C. The mixture was stirred at 0° C. for 1 hour. After addition of DMAP (2.77 g, 22.7 mmol) and methyl chloroformate (17.6 mL, 227 mmol), the reaction mixture was slowly warmed to room temperature and stirred for 3 hours. The reaction mixture was washed with water and brine, dried over Na2SO4, filtered and concentrated in vacuo. The residue was purified by column chromatography on SiO₂ (Hexanes:EtOAc=4:1) to give (3aR,4S,6aR)-2,2-dimethyl-4,6a-dihydro-3aH-cyclopenta[d][1,3]dioxol-4-yl methyl carbonate (10.3 g, 85%) as a yellow oil.

¹H-NMR (CDCl₃, 400 MHz): δ 6.10 (1H, d, J=5.6 Hz), 5.91 (1H, d, J=4.8 Hz), 5.30 (1H, d, J=5.2 Hz), 5.03 (1H, d, J=5.2 Hz), 4.92 (1H, t, J=5.8 Hz), 3.83 (3H, s), 1.40 (3H, s), 1.38 (3H, s).

STEP2 Preparation of (3aS,4R,6aR)-2,2-dimethyl-4-vinyl-4,6a-dihydro-3aH-cyclopenta[d][1,3]dioxole To a solution of (3aR,4S,6aR)-2,2-dimethyl-4,6a-dihydro-3aH-cyclopenta[d][1,3]dioxol-4-yl methyl carbonate (8.00 g, 37.3 mmol) in dry THF (187 mL) were added CuCN (1.00 g, 11.2 mmol) followed by vinylmagnesium bromide (1 M in THF, 93.0 mL, 93.0 mmol) at −10° C. The reaction mixture was stirred for 10 min at that temperature, quenched with saturated aq. NH4Cl and extracted with ether. The separated organic layer was dried over Na2SO4, filtered and concentrated in vacuo. The residue was purified by column chromatography on SiO2 (Hexanes:EtOAc=8:1) to give (3aS,4R,6aR)-2,2-dimethyl-4-vinyl-4,6a-dihydro-3aH-cyclopenta[d][1,3]dioxole (3.86 g, 62%) as a yellow oil.
¹H-NMR (CDCl₃, 400 MHz): δ 5.87-5.75 (3H, m), 5.17 (1H, d, J=5.2 Hz), 5.08-5.04 (2H, m), 4.45 (1H, d, J=5.6 Hz), 3.45 (1H, d, J=7.2 Hz), 1.43 (3H, s), 1.35 (3H, s).

STEP3 Preparation of (3aS,4S,6aR)-2,2-dimethyl-4-(oxiran-2-yl)-4,6a-dihydro-3aH-cyclopenta[d][1,3]dioxole To a solution of (3aS,4R,6aR)-2,2-dimethyl-4-vinyl-4,6a-dihydro-3aH-cyclopenta[d][1,3]dioxole (3.86 g, 23.2 mmol) in DCM (232 mL) was added mCPBA (50 wt %, 8.82 g, 25.5 mmol) at 0° C. The reaction mixture was stirred at room temperature for 24 hours and washed with 1 N aq. NaOH. The separated organic layer was dried over Na2SO4, filtered and concentrated in vacuo. The residue was purified by column chromatography on SiO2 (Hexanes:EtOAc=4:1) to give (3aS,4S,6aR)-2,2-dimethyl-4-(oxiran-2-yl)-4,6a-dihydro-3 aH-cyclopenta[d][1,3]dioxole (3.08 g, 72%) as a yellow solid.
¹H-NMR (CDCl₃, 400 MHz): δ 5.93-5.91 (1H, m), 5.75-5.74 (1H, m), 5.17 (1H, d, J=5.2 Hz), 4.65 (0.6H, d, J=6.0 Hz), 4.60 (0.4H, d, J=5.6 Hz), 2.97-2.88 (2H, m), 2.76 (1H, t, J=4.0 Hz), 2.57-2.55 (1H, m), 1.42 (3H, s), 1.36 (3H, s).

STEP4 Preparation of (R)-2-amino-1-((3aS,4S,6aR)-2,2-dimethyl-4,6a-dihydro-3aH-cyclopenta[d][1,3]dioxol-4-yl)ethanol A mixture of (3aS,4S,6aR)-2,2-dimethyl-4-(oxiran-2-yl)-4,6a-dihydro-3aH-cyclopenta[d][1,3]dioxole (3.08 g, 16.9 mmol) and NH4OH (26.3 mL, 169 mmol) in EtOH (169 mL) was stirred at 60° C. for 24 hours. The reaction mixture was cooled to room temperature and concentrated in vacuo to give (R)-2-amino-1-((3aS,4S,6aR)-2,2-dimethyl-4,6a-dihydro-3aH-cyclopenta[d][1,3]dioxol-4-yl)ethanol (2.40 g, 71%) as a yellow oil, which was used for the next step without further purification.
¹H-NMR (CDCl₃, 400 MHz): δ 5.96-5.92 (1H, m), 5.81 (0.6H, d, J=3.2 Hz), 5.75 (0.4H, d, J=4.4 Hz), 5.14 (1H, brs), 4.71 (0.4H, d, J=6.0 Hz), 4.59 (0.6H, d, J=6.0 Hz), 3.61-3.59 (1H, m), 3.44-3.43 (1H, m), 2.96-2.85 (2H, m), 2.74-2.69 (0.4H, m), 2.63-2.57 (0.6H, m), 1.42 (3H, s), 1.35 (3H, s). *NH2 proton peak was not observed.

STEP5 Preparation of (R)-2-amino-1-((3aS,4S,6aR)-2,2-dimethyltetrahydro-3aH-cyclopenta[d][1,3]dioxol-4-yl)ethanol A suspension of (R)-2-amino-1-((3aS,4S,6aR)-2,2-dimethyl-4,6a-dihydro-3aH-cyclopenta[d][1,3]dioxol-4-yl)ethanol (3.30 g, 16.56 mmol) and Pd/C (5 wt %, 1.76 g, 16.6 mmol) in MeOH (166 mL) was stirred at room temperature for 2 hours under H2 atmosphere (balloon). The reaction mixture was filtered through a Celite pad, and the filtrate was concentrated in vacuo to give (R)-2-amino-1-((3aS,4S,6aR)-2,2-dimethyltetrahydro-3aH-cyclopenta[d][1,3]dioxol-4-yl)ethanol (2.60 g, 78%) as a brown oil, which was used for the next step without further purification.
¹H-NMR (CDCl₃, 400 MHz): δ 4.65 (1H, s), 4.36 (1H, brs), 3.95-3.82 (1H, m), 3.27-3.18 (1H, m), 3.05-2.99 (1H, m), 2.08-1.90 (3H, m), 1.80 (1H, brs), 1.67 (1H, brs), 1.46 (3H, s), 1.29 (3H, s). *NH2 and OH proton peaks were not observed.

STEP6 Preparation of (R)-2-((3-chloropyrazin-2-yl)amino)-1-((3aS,4S,6aR)-2,2-dimethyltetrahydro-3aH-cyclopenta[d][1,3]dioxol-4-yl)ethanol A mixture of (R)-2-amino-1-((3aS,4S,6aR)-2,2-dimethyltetrahydro-3aH-cyclopenta[d][1,3]dioxol-4-yl)ethanol (2.6 g, 12.9 mmol), 2,3-dichloropyrazine (4.03 mL, 38.8 mmol) and TEA (0.517 mL, 3.73 mmol) in dioxane (43 mL) was stirred at 100° C. for 18 hours. The reaction mixture was cooled to room temperature and concentrated in vacuo. The residue was dissolved in DCM and washed with water and brine. The separated organic layer was dried over Na2SO4, filtered and concentrated in vacuo. The residue was purified by column chromatography on SiO2 (Hexanes:EtOAc=1:1) to give (R)-2-((3-chloropyrazin-2-yl)amino)-1-((3aS,4S,6aR)-2,2-dimethyltetrahydro-3aH-cyclopenta[d][1,3]dioxol-4-yl)ethanol (1.03 g, 25%) as a yellow oil.
¹H-NMR (CDCl₃, 400 MHz): δ 8.02-8.00 (1H, m), 5.56 (1H, d, J=2.4 Hz), 6.81-6.78 (0.6H, m), 6.72-6.68 (0.4H, m), 5.01 (0.4H, d, J=6.4 Hz), 4.95 (0.6H, d, J=4.8 Hz), 4.62-4.55 (1H, m), 4.39-4.38 (1H, m), 3.53-3.49 (1H, m), 3.28-3.21 (2H, m), 1.91 (1H, brs), 1.91-1.76 (2H, m), 1.66-1.60 (2H, m), 1.33 (3H, s), 1.20 (3H, s).

STEP7 Preparation of 2-((3-chloropyrazin-2-yl)amino)-1-((3aS,4R,6aR)-2,2-dimethyltetrahydro-3aH-cyclopenta[d][1,3]dioxol-4-yl)ethanone To a solution of (R)-2-((3-chloropyrazin-2-yl)amino)-1-((3aS,4S,6aR)-2,2-dimethyltetrahydro-3aH-cyclopenta[d][1,3]dioxol-4-yl)ethanol (360 mg, 1.147 mmol) and TEA (792 mL, 5.71 mmol) in dry DMSO (11 mL) was added SO3.TEA (312 mg, 1.72 mmol) at 0° C. The reaction mixture was stirred room temperature for 1 hour, quenched with water and extracted with EtOAc. The separated organic layer was dried over Na2SO4, filtered and concentrated in vacuo. The residue was purified by column chromatography on SiO2 (Hexanes:EtOAc=3:1) to afford 2-((3-chloropyrazin-2-yl)amino)-1-((3aS,4R,6aR)-2,2-dimethyltetrahydro-3aH-cyclopenta[d][1,3]dioxol-4-yl)ethanone (270 mg, 75%) as a white solid.
¹H-NMR (CDCl₃, 400 MHz): δ 7.92 (1H, d, J=2.4 Hz), 7.64 (1H, d, J=2.4 Hz), 5.92 (1H, brs), 4.81-4.79 (1H, m), 4.75-4.72 (1H, m), 4.47 (1H, dd, J=19.8, 5.0 Hz), 4.31 (1H, dd, J=19.8, 4.6 Hz), 3.17 (1H, d, J=7.6 Hz), 2.26-2.16 (1H, m), 1.90-1.82 (2H, m), 1.77-1.69 (1H, m), 1.47 (3H, s), 1.32 (3H, s).

STEP8 Preparation of 8-chloro-3-((3aS,4S,6aR)-2,2-dimethyltetrahydro-3aH-cyclopenta[d][1,3]dioxol-4-yl)imidazo[1,2-a]pyrazine To a solution of 2-((3-chloropyrazin-2-yl)amino)-1-((3aS,4R,6aR)-2,2-dimethyltetrahydro-3aH-cyclopenta[d][1,3]dioxol-4-yl)ethanone (270 mg, 0.866 mmol) in toluene (5.8 mL) were added pyridine (0.839 mL, 10.4 mmol) and TFA (0.467 mL, 6.06 mmol) at 0° C. The mixture was stirred for 30 min at room temperature. After addition of TFAA (0.855 mL, 6.06 mmol) at 0° C., the reaction mixture was stirred at room temperature for 3 hours and concentrated in vacuo. The residue was diluted with DCM, washed with water and brine, dried over Na2SO4, filtered and concentrated in vacuo. The residue was purified by column chromatography on SiO2 (Hexanes:EtOAc=1:1) to give 8-chloro-3-((3aS,4S,6aR)-2,2-dimethyltetrahydro-3aH-cyclopenta[d][1,3]dioxol-4-yl)imidazo[1, 2-a]pyrazine (90.0 mg, 35%) as a white solid.

$^1$H-NMR (CDCl$_3$, 400 MHz): δ 8.12 (1H, d, J=4.0 Hz), 7.76 (1H, d, J=4.8 Hz), 7.56 (1H, s), 4.81 (1H, s), 4.59 (1H, d, J=4.0 Hz), 3.47 (1H, brs), 2.48-2.42 (1H, m), 2.10-2.00 (3H, m), 1.58 (3H, s), 1.34 (3H, s).

STEP9 Preparation of N-(3-chlorobenzyl)-3-((3aS, 4S,6aR)-2,2-dimethyltetrahydro-3aH-cyclopenta[d] [1,3]dioxol-4-yl) imidazo[1,2-a]pyrazin-8-amine A mixture of 8-chloro-3-((3aS,4S,6aR)-2,2-dimethyltetrahydro-3aH-cyclopenta[d][1,3]dioxol-4-yl)imidazo[1, 2-a] pyrazine (35.0 mg, 0.119 mmol), (3-chlorophenyl)methanamine (20.0 mg, 0.143 mmol) and DIPEA (52.0 µL, 0.298 mmol) in i-BuOH (1.2 mL) was subjected to microwave irradiation at 170° C. for 2 hours. The reaction mixture was cooled to room temperature and concentrated in vacuo. The residue was diluted with EtOAc and washed with water and brine. The separated organic layer was dried over Na2SO4, filtered and concentrated in vacuo. The residue was purified by column chromatography on NH—SiO2 (Hexanes:EtOAc=1:1) to give N-(3-chlorobenzyl)-3-((3aS,4S,6aR)-2,2-dimethyltetrahydro-3aH-cyclopenta[d][1,3]dioxol-4-yl) imidazo[1,2-a]pyrazin-8-amine (40.0 mg, 84%) as a white solid.

$^1$H-NMR (CDCl$_3$, 400 MHz): δ 7.45 (1H, d, J=5.2 Hz), 7.41 (1H, d, J=4.8 Hz), 7.34 (1H, s), 7.33 (1H, s), 7.28-7.21 (2H, m), 7.17 (1H, s), 6.24 (1H, brs), 4.78 (3H, d, J=6.4 Hz), 4.65 (1H, d, J=6.0 Hz), 3.86 (1H, s), 3.44 (1H, d, J=6.8 Hz), 2.38 (1H, brs), 2.0-1.80 (2H, m), 1.55 (3H, s), 1.34 (3H, s).

STEP10 Preparation of (1R,2S,3S)-3-(8-((3-chlorobenzyl)amino)imidazo[1,2-a]pyrazin-3-yl)cyclopentane-1,2-diol A solution of N-(3-chlorobenzyl)-3-((3aS,4S,6aR)-2,2-dimethyltetrahydro-3aH-cyclopenta[d][1,3]dioxol-4-yl) imidazo[1,2-a]pyrazin-8-amine (40.0 mg, 0.100 mmol) in 80% TFA (1.00 mL, 0.100 mmol) was stirred at room temperature for 30 min. After concentration in vacuo, the residue was diluted with DCM, and then TEA was added to the solution until pH 7. The mixture was stirred at room temperature for 20 min and concentrated in vacuo. The residue was purified by column chromatography on NH—SiO2 (EtOAc:MeOH=10:1) to give (1R,2S,3S)-3-(8-((3-chlorobenzyl)amino)imidazo[1,2-a]pyrazin-3-yl)cyclopentane-1,2-diol (11.0 mg, 30%) as a white solid.

$^1$H-NMR (CDCl$_3$, 400 MHz): δ 8.06 (1H, t, J=6.6 Hz), 7.69 (1H, d, J=4.4 Hz), 7.40-7.38 (2H, m), 7.34-7.30 (3H, m), 7.21 (1H, d, J=4.4 Hz), 4.85 (1H, d, J=6.4 Hz), 4.65 (2H, d, J=6.8 Hz), 4.60 (1H, d, J=3.6 Hz), 3.94 (1H, brs), 3.90-3.80 (1H, m), 2.25-2.15 (1H, m), 2.00-1.90 (1H, m), 1.70-1.60 (2H, m). *OH proton peak would be overlabed with H2O peak at 3.33 ppm.

LC-MS MS(EI) for C18H19ClN4O2 [M+H]+, (Calcd.: 358.12) Found: 359.2.

Example 223: Synthesis of (1R,2S,3S)-3-(8-((3,5-dichlorobenzyl)amino)imidazo[1,2-a]pyrazin-3-yl) cyclopentane-1,2-diol $^1$H-NMR (DMSO-d$_6$, 400 MHz): δ 8.12 (1H, t, J=7.6 Hz), 7.71 (1H, d, J=4.8 Hz), 7.44-7.37 (4H, m), 7.21 (1H, d, J=4.0 Hz), 4.85 (1H, d, J=6.8 Hz), 4.64 (2H, d, J=6.0 Hz), 4.59 (1H, d, J=4.0 Hz), 4.04-4.02 (1H, m), 3.94-3.84 (1H, m), 3.33-3.31 (1H, m), 2.21-2.20 (1H, m), 1.99-1.98 (1H, m), 1.65-1.61 (2H, m).

LC-MS MS(EI) for C18H18Cl2N4O2 [M+H]+, (Calcd.: 392.08) Found: 393.2.

Example 224: Synthesis of (1R,2S,3S)-3-(8-((2,5-dichlorobenzyl)amino)imidazo[1,2-a]pyrazin-3-yl) cyclopentane-1,2-diol $^1$H-NMR (DMSO-d$_6$, 400 MHz): δ 8.08 (1H, t, J=7.6 Hz), 7.74 (1H, d, J=4.4 Hz), 7.50 (1H, d, J=8.8 Hz), 7.44 (1H, s), 7.35 (1H, d, J=6.0 Hz), 7.26 (1H, s), 7.21 (1H, d, J=4.4 Hz), 4.86 (1H, d, J=6.0 Hz), 4.69 (2H, d, J=5.6 Hz), 4.60 (1H, d, J=2.8 Hz), 3.95-3.94 (1H, m), 3.91-3.88 (1H, m), 3.35-3.33 (1H, m), 2.21-2.20 (1H, m), 1.99-1.98 (1H, m), 1.65-1.61 (2H, m).

LC-MS MS(EI) for C18H18Cl2N4O2 [M+H]+, (Calcd.: 392.08) Found: 393.2.

Example 225: Synthesis of (1R,2S,3S)-3-(8-((5-chloro-2-fluorobenzyl)amino)imidazo[1,2-a]pyrazin-3-yl)cyclopentane-1,2-diol $^1$H-NMR (DMSO-d$_6$, 400 MHz): δ 8.03 (1H, t, J=6.8 Hz), 7.72 (1H, d, J=4.8 Hz), 7.42 (1H, s), 7.33-7.31 (2H, m), 7.26-7.21 (2H, m), 4.85 (1H, d, J=6.4 Hz), 4.68 (2H, d, J=6.0 Hz), 4.59 (1H, d, J=3.6 Hz), 3.95-3.94 (1H, m), 3.89-3.86 (1H, m), 2.22-2.20 (1H, m), 1.99-1.98 (1H, m), 1.66-1.63 (2H, m). *A proton would be overlapped with H$_2$O peak at 3.33 ppm.

LC-MS MS(EI) for C18H18ClFN4O2 [M+H]+, (Calcd.: 376.11) Found: 377.2.

Example 226: Synthesis of (1R,2S,3S)-3-(8-((4-fluorophenethyl)amino)imidazo[1,2-a]pyrazin-3-yl) cyclopentane-1,2-diol $^1$H-NMR (DMSO-d$_6$, 400 MHz): δ 7.65 (1H, d, J=4.8 Hz), 7.37-7.34 (2H, m), 7.30-7.25 (3H, m), 7.10 (2H, t, J=9.0 Hz), 4.83 (1H, d, J=6.8 Hz), 4.59 (1H, d, J=3.6 Hz), 3.94-3.92 (1H, m), 3.88-3.83 (1H, m), 3.66 (2H, q, J=6.6 Hz), 3.33-3.27 (1H, m), 2.92 (2H, t, J=7.4 Hz), 2.25-2.16 (1H, m), 1.97-1.91 (1H, m), 1.68-1.59 (2H, m).

LC-MS MS(EI) for C19H21FN4O2 [M+H]+, (Calcd.: 356.16) Found: 357.3.

Example 227: Synthesis of (1R,2S,3S)-3-(8-((3-fluorophenethyl)amino)imidazo[1,2-a]pyrazin-3-yl) cyclopentane-1,2-diol $^1$H-NMR (DMSO-d$_6$, 400 MHz): δ 7.66 (1H, d, J=4.8 Hz), 7.38-7.29 (3H, m), 7.26 (1H, d, J=4.8 Hz), 7.10-7.08 (2H, m), 7.01 (1H, t, J=8.4 Hz), 4.83 (1H, d, J=6.8 Hz), 4.59 (1H, d, J=4.0 Hz), 3.94-3.93 (1H, m), 3.88-3.83 (1H, m), 3.69 (2H, q, J=6.4 Hz), 3.33-3.27 (1H, m), 2.96 (2H, t, J=7.0 Hz), 2.20-2.16 (1H, m), 2.03-1.91 (1H, m), 1.67-1.58 (2H, m).

LC-MS MS(EI) for C19H21FN4O2 [M+H]+, (Calcd.: 356.16) Found: 357.3.

Example 228: Synthesis of (1R,2S,3S)-3-(8-((3,4-difluorophenethyl)amino)imidazo[1,2-a]pyrazin-3-yl)cyclopentane-1,2-diol $^1$H-NMR (DMSO-d$_6$, 400 MHz): δ 7.66 (1H, d, J=4.8 Hz), 7.39 (1H, t, J=5.4 Hz), 7.34-7.29 (3H, m), 7.25 (1H, d, J=4.4 Hz), 7.11-7.05 (1H, m), 4.83 (1H, d, J=6.8 Hz), 4.59 (1H, d, J=4.0 Hz), 3.94-3.93 (1H, m), 3.88-3.83 (1H, m), 3.65 (2H, q, J=6.8 Hz), 3.33-3.27 (1H, m), 2.93 (2H, t, J=7.0 Hz), 2.21-2.16 (1H, m), 1.97-1.90 (1H, m), 1.66-1.55 (2H, m).

LC-MS MS(EI) for C19H20F2N4O2 [M+H]+, (Calcd.: 374.16) Found: 375.2.

Example 229: Synthesis of (1R,2S,3S)-3-(8-((3-chloro-4-fluorophenethyl)amino)imidazo[1,2-a]pyrazin-3-yl)cyclopentane-1,2-diol $^1$H-NMR (DMSO-d$_6$, 400 MHz): δ 7.66 (1H, d, J=4.8 Hz), 7.48 (1H, d, J=6.4 Hz), 7.40 (1H, t, J=5.8 Hz), 7.34 (1H, s), 7.30 (2H, t, J=9.0 Hz), 7.25-7.24 (1H, m), 4.82 (1H, d, J=6.0 Hz), 4.58 (1H, d, J=4.0 Hz), 3.94-3.93 (1H, m), 3.88-3.85 (1H, m), 3.68 (2H, q, J=7.0 Hz), 2.33-2.27 (1H, m), 2.93 (2H, d, J=6.8 Hz), 2.21-2.16 (1H, m), 2.00-1.91 (1H, m), 1.67-1.63 (2H, m).

LC-MS MS(EI) for C19H20ClFN4O2 [M+H]+, (Calcd.: 390.13) Found: 391.2.

Example 230: Synthesis of (1R,2S,3S)-3-(8-(((1S,2R)-2-phenylcyclopropyl)amino)imidazo[1,2-a]pyrazin-3-yl)cyclopentane-1,2-diol $^1$H-NMR (DMSO-d$_6$, 400 MHz): δ 7.76 (1H, d, J=3.2 Hz), 7.70 (1H, d, J=4.0 Hz), 7.37 (1H, s), 7.29-7.23 (3H, m), 7.17 (3H, d, J=6.8 Hz), 4.84 (1H, d, J=7.6 Hz), 4.59 (1H, s), 3.94 (1H, s), 3.86-3.84 (1H, m), 3.33-3.30 (1H, m), 3.12-3.11 (1H, m), 2.23-2.16 (1H, m), 2.09-2.02 (1H, m), 2.00-1.93 (1H, m), 1.68-1.60 (2H, m), 1.49-1.47 (1H, m), 1.24-1.21 (1H, m).

LC-MS MS(EI) for C$_{20}$H$_{22}$N$_4$O$_2$ [M+H]+, (Calcd.: 350.17) Found: 351.3.

Example 231: Synthesis of (1R,2S,3S)-3-(8-((4-chloro-3-fluorophenethyl)amino)imidazo[1,2-a]pyrazin-3-yl)cyclopentane-1,2-diol $^1$H-NMR (DMSO-d$_6$, 400 MHz): δ δ 7.66 (1H, d, J=5.4 Hz), 7.45 (1H, t, J=8.0 Hz), 7.41 (1H, t, J=6.6 Hz), 7.34-7.31 (2H, m), 7.25 (1H, d, J=4.8 Hz), 7.11 (1H, d, J=7.2 Hz), 4.83 (1H, d, J=7.2 Hz), 4.58 (1H, d, J=4.0 Hz), 3.94-3.93 (1H, m), 3.88-3.85 (1H, m), 3.68 (2H, q, J=7.0 Hz), 2.33-2.27 (1H, m), 2.96 (2H, d, J=7.0 Hz), 2.23-1.18 (1H, m), 2.00-1.81 (1H, m), 1.69-1.52 (2H, m).

LC-MS MS(EI) for C19H20ClFN4O2 [M+H]+, (Calcd.: 390.13) Found: 391.3.

Example 232: Synthesis of (1R,2S,3 S)-3-(8-((3-chlorobenzyl)amino)-[1,2,4]triazolo[4,3-a]pyrazin-3-yl)cyclopentane-1,2-diol STEP1 Preparation of (R)-1-((3aS,4S,6aR)-2,2-dimethyl-4,6a-dihydro-3aH-cyclopenta[d][1,3]dioxol-4-yl)ethane-1,2-diol A mixture of (3aS,4S,6aR)-2,2-dimethyl-4-(oxiran-2-yl)-4,6a-dihydro-3 aH-cyclopenta[d][1,3]dioxole (4.41 g, 24.2 mmol), water (0.87 mL) and DMF (0.94 mL) was heated at 110° C. for 18 hours. After concentration in vacuo, the residue was purified by column chromatography on SiO$_2$ (Hexanes:EtOAc=1:3 to EtOAc only) to give (R)-1-((3aS,4S,6aR)-2,2-dimethyl-4,6a-dihydro-3aH-cyclopenta[d][1,3]dioxol-4-yl)ethane-1,2-diol (3.86 g, 80%) as a colorless oil.

$^1$H-NMR (CDCl$_3$, 400 MHz): δ 5.98 (0.6H, d, J=5.6 Hz), 5.93 (0.4H, d, J=5.6 Hz), 5.81 (0.6H, d, J=3.6 Hz), 5.74 (0.4H, d, J=4.0 Hz), 5.15 (1H, d, J=5.6 Hz), 4.72 (0.4H, d, J=6.0 Hz), 4.60 (0.6H, d, J=5.2 Hz), 3.84-3.54 (3H, m), 2.98 (0.6H, s), 2.90 (0.4H, s), 2.30 (0.4H, s), 2.07-2.05 (1H, m), 1.98 (0.6H, s), 1.42 (3H, s), 1.36 (3H, s).

STEP2 Preparation of (R)-1-((3aS,4S,6aR)-2,2-dimethyltetrahydro-3aH-cyclopenta[d][1,3]dioxol-4-yl)ethane-1,2-diol A suspension of (R)-1-((3aS,4S,6aR)-2,2-dimethyl-4,6a-dihydro-3aH-cyclopenta[d][1,3]dioxol-4-yl)ethane-1,2-diol (3.86 g, 19.3 mmol) and Pd/C (10 wt %, 2.05 g, 1.93 mmol) in MeOH (193 mL) was stirred at room temperature for 2 hours under H2 atmosphere (balloon). The reaction mixture was filtered through a Celite pad, and the filtrate was concentrated in vacuo to give (R)-1-((3aS,4S,6aR)-2,2-dimethyltetrahydro-3aH-cyclopenta[d][1,3]dioxol-4-yl)ethane-1,2-diol (3.48 g, 89%) as a colorless oil, which was used for the next step without further purification.

$^1$H-NMR (CDCl$_3$, 400 MHz): δ 4.65-4.60 (1.5H, m), 4.37-4.34 (0.5H, m), 3.77-3.72 (1H, m), 3.63-3.56 (2H, m), 2.21-1.90 (5H, m), 1.89-1.77 (1H, m), 1.65-1.63 (1H, m), 1.48 (3H, s), 1.32 and 1.30 (3H, s+s).

STEP3 Preparation of (3aS,4R,6aR)-2,2-dimethyltetrahydro-3aH-cyclopenta[d][1,3]dioxole-4-carbaldehyde A suspension of sodium periodate (5.52 g, 25.8 mmol) and SiO2 (ca 10 g) in DCM (167 mL) and water (5.5 mL) was stirred at room temperature for 30 min and cooled to 0° C. After addition of a solution of (R)-1-((3aS,4S,6aR)-2,2-dimethyltetrahydro-3aH-cyclopenta[d][1,3]dioxol-4-yl)ethane-1,2-diol (3.48 g, 17.2 mmol) in DCM (5.0 mL) at 0° C., the reaction mixture was stirred at room temperature for 2 hours. An insoluble solid was filtered off through a Celite pad. The filtrate was concentrated in vacuo. The residue was purified by column chromatography on SiO2 (Hexanes:EtOAc=5:1) to give (3aS,4R,6aR)-2,2-dimethyltetrahydro-3aH-cyclopenta[d][1,3]dioxole-4-carbaldehyde (1.81 g, 62%) as a yellow solid.

$^1$H-NMR (CDCl$_3$, 400 MHz): δ 9.69 (1H, s), 4.94 (1H, d, J=5.2 Hz), 4.70 (1H, d, J=5.4 Hz), 2.98 (1H, d, J=8.0 Hz), 2.13-2.03 (1H, m), 1.97 (1H, dd, J=12.8, 6.8 Hz), 1.88 (1H, dd, J=14.0, 6.0 Hz), 1.49-1.39 (4H, m), 1.32 (3H, s).

STEP4 Preparation of 8-chloro-3-((3aS,4S,6aR)-2,2-dimethyltetrahydro-3aH-cyclopenta[d][1,3]dioxol-4-yl)-[1,2,4]triazolo[4,3-a]pyrazine A mixture of (3aS,4R,6aR)-2,2-dimethyltetrahydro-3aH-cyclopenta[d][1,3]dioxole-4-carbaldehyde (1.81 g, 10.6 mmol) and 2-chloro-3-hydrazinylpyrazine (1.85 g, 12.8 mmol) in DCM (106 mL) was stirred at room temperature for 1 hour and cooled to 0° C. After addition of PhI(OAc)2 (5.14 g, 15.9 mmol) at 0° C., the reaction mixture was stirred at room temperature for 3 hours, and then washed with saturated aq. NaHCO3 and brine. The separated organic layer was dried over Na2SO4, filtered and concentrated in vacuo. The residue was purified by column chromatography on NH—SiO2 (Hexanes:EtOAc=3:1) to give 8-chloro-3-((3aS,4S,6aR)-2,2-dimethyltetrahydro-3aH-cyclopenta[d][1,3]dioxol-4-yl)-[1,2,4]triazolo[4,3-a]pyrazine (1.36 g, 43%) as a yellow solid.

$^1$H-NMR (CDCl$_3$, 400 MHz): δ 7.97 (1H, d, J=4.4 Hz), 7.72 (1H, d, J=4.4 Hz), 4.98-4.93 (2H, m), 3.59 (1H, d, J=6.0 Hz), 2.51-2.41 (1H, m), 2.14-1.99 (3H, m), 1.56 (3H, s), 1.36 (3H, s).

STEP5 Preparation of N-(3-chlorobenzyl)-3-((3aS,4S,6aR)-2,2-dimethyltetrahydro-3aH-cyclopenta[d][1,3]dioxol-4-yl)-[1,2,4]triazolo[4,3-a]pyrazin-8-amine A mixture of 8-chloro-3-((3aS,4S,6aR)-2,2-dimethyltetrahydro-3aH-cyclopenta[d][1,3]dioxol-4-yl)-[1,2,4]triazolo[4,3-a]pyrazine (50.0 mg, 0.170 mmol), (3-chlorophenyl)methanamine (36.0 mg, 0.254 mmol) and DIPEA (89.0 μL, 0.506 mmol) in i-BuOH (1.5 mL) was subjected to microwave irradiation at 170° C. for 2 hours. The reaction mixture was cooled to room temperature, diluted with EtOAc and washed with water and brine. The separated organic layer was dried over Na2SO4, filtered and concentrated in vacuo. The residue was purified by column chromatography on NH—SiO2 (Hexanes:EtOAc=3:1) to give N-(3-chlorobenzyl)-3-((3aS,4S,6aR)-2,2-dimethyltetrahydro-3aH-cyclopenta[d][1,3]dioxol-4-yl)-[1,2,4]triazolo[4,3-a]pyrazin-8-amine (45.0 mg, 66%) as a yellow solid.

$^1$H-NMR (CDCl$_3$, 400 MHz): δ 7.39 (1H, s), 7.36 (1H, d, J=5.6 Hz), 7.32 (1H, d, J=4.8 Hz), 7.26-7.20 (3H, m), 6.68 (1H, brs), 5.03 (1H, d, J=5.2 Hz), 4.92-4.91 (1H, m), 4.82 (1H, d, J=5.6 Hz), 3.86 (1H, s), 3.54 (1H, d, J=6.4 Hz), 2.42-2.38 (1H, m), 2.05-1.97 (3H, m), 1.54 (3H, s), 1.36 (3H, s).

STEP6 Preparation of (1R,2S,3S)-3-(8-((3-chlorobenzyl)amino)-[1,2,4]triazolo[4,3-a]pyrazin-3-yl)cyclopentane-1,2-diol A solution of N-(3-chlorobenzyl)-3-((3aS,4S,6aR)-2,2-dimethyltetrahydro-3aH-cyclopenta[d][1,3]dioxol-4-yl)-[1,2,4]triazolo[4,3-a]pyrazin-8-amine (45.0 mg, 0.113 mmol) in 80% TFA (1.00 mL, 1.00 mmol) was stirred at room temperature for 20 min. After concentration in vacuo, the residue was purified by column chromatography on NH—SiO2 (EtOAc:MeOH=10:1) to give (1R,2S,3S)-3-(8-((3-chlorobenzyl)amino)-[1,2,4]triazolo[4,3-a]pyrazin-3-yl)cyclopentane-1,2-diol (28.0 mg, 69%) as a white solid.

$^1$H-NMR (DMSO-d$_6$, 400 MHz): δ 8.71 (1H, t, J=6.2 Hz), 7.72 (1H, d, J=5.2 Hz), 7.40 (1H, s), 7.35-7.27 (3H, m), 7.21 (1H, d, J=4.5 Hz), 4.95 (1H, d, J=6.4 Hz), 4.68-4.66 (3H, m), 4.06-3.98 (2H, m), 3.52 (1H, q, J=8.5 Hz), 2.21-2.20 (1H, m), 2.08-1.98 (2H, m), 1.71-1.68 (1H, m).

LC-MS MS(EI) for C17H18ClN5O2 [M+H]+, (Calcd.: 359.11) Found: 360.3.

Example 233: Synthesis of (1R,2S,3S)-3-(8-((3,5-dichlorobenzyl)amino)-[1,2,4]triazolo[4,3-a]pyrazin-3-yl)cyclopentane-1, 2-diol $^1$H-NMR (DMSO-d$_6$, 400 MHz): δ 8.78-8.70 (1H, m), 7.74 (1H, d, J=4.4 Hz), 7.46 (1H, s), 7.40 (2H, s), 7.22 (1H, d, J=4.8 Hz), 4.95 (1H, d, J=6.4 Hz), 4.70-4.60 (3H, m), 4.03-3.99 (2H, m), 3.56-3.50 (1H, m), 2.25-2.15 (1H, m), 2.08-1.99 (2H, m), 1.69 (1H, brs).

LC-MS MS(EI) for C17H17Cl2N5O2 [M+H]+, (Calcd.: 393.08) Found: 394.2.

Example 234: Synthesis of (1R,2S,3S)-3-(8-((2,5-dichlorobenzyl)amino)-[1,2,4]triazolo[4,3-a]pyrazin-3-yl)cyclopentane-1, 2-diol $^1$H-NMR (DMSO-d$_6$, 400 MHz): δ 7.70 (1H, t, J=7.6 Hz), 7.76 (1H, d, J=5.2 Hz), 7.51 (1H, d, J=8.8 Hz), 7.36 (1H, d, J=8.4 Hz), 7.31 (1H, s), 7.22 (1H, d, J=4.8 Hz), 4.97 (1H, d, J=6.8 Hz), 4.70 (3H, dd, J=15.8, 4.6 Hz), 4.05-4.00 (2H, m), 3.54 (1H, q, J=8.8 Hz), 2.28-2.21 (1H, m), 2.12-1.96 (2H, m), 1.70-1.65 (1H, m).

LC-MS MS(EI) for C17H17Cl2N5O2 [M+H]+, (Calcd.: 393.08) Found: 394.2.

Example 235: Synthesis of (1R,2S,3S)-3-(8-((5-chloro-2-fluorobenzyl)amino)-[1,2,4]triazolo[4,3-a]pyrazin-3-yl)cyclopentane-1,2-diol $^1$H-NMR (DMSO-d$_6$, 400 MHz): δ 8.68 (1H, t, J=7.2 Hz), 7.74 (1H, d, J=4.8 Hz), 7.37-7.35 (2H, m), 7.27-7.22 (2H, m), 4.96 (1H, d, J=6.8 Hz), 4.69 (3H, dd, J=15.8, 4.6 Hz), 4.04-4.00 (2H, m), 3.53 (1H, q, J=8.1 Hz), 2.22-2.20 (1H, m), 2.09-1.99 (2H, m), 1.70-1.66 (1H, m).

LC-MS MS(EI) for C17H17ClFN5O2 [M+H]+, (Calcd.: 377.11) Found: 378.2.

Example 236: Synthesis of (1R,2S,3S)-3-(8-((4-fluorophenethyl)amino)-[1,2,4]triazolo[4,3-a]pyrazin-3-yl)cyclopentane-1,2-diol $^1$H-NMR (DMSO-d$_6$, 400 MHz): δ 8.08-8.02 (1H, m), 7.64 (1H, d, J=4.4 Hz), 7.26-7.21 (3H, m), 7.06 (2H, t, J=8.6 Hz), 4.91 (1H, d, J=7.2 Hz), 4.62 (1H, d, J=6.4 Hz), 4.00-3.90 (2H, m), 3.70-3.60 (2H, m), 3.48-3.43 (1H, m), 2.89 (2H, t, J=7.2 Hz), 2.20-2.10 (1H, m), 2.00-1.90 (2H, m), 1.70-1.60 (1H, m).

LC-MS MS(EI) for C18H20FN5O2 [M+H]+, (Calcd.: 357.16) Found: 358.3.

Example 237: Synthesis of (1R,2S,3S)-3-(8-((3-fluorophenethyl)amino)-[1,2,4]triazolo[4,3-a]pyrazin-3-yl)cyclopentane-1,2-diol $^1$H-NMR (DMSO-d$_6$, 400 MHz): δ 8.12 (1H, t, J=6.0 Hz), 7.69 (1H, d, J=4.4 Hz), 7.34-7.29 (1H, m), 7.25 (1H, d, J=4.4 Hz), 7.12-7.08 (2H, m), 7.01 (1H, t, J=8.0 Hz), 4.94 (1H, d, J=6.0 Hz), 4.66 (1H, d, J=3.6 Hz), 4.08-3.98 (2H, m), 3.72-3.70 (2H, m), 3.51 (1H, q, J=8.4 Hz), 2.98 (2H, t, J=6.8 Hz), 2.22-2.18 (1H, m), 2.08-1.98 (2H, m), 1.69-1.66 (1H, m).

LC-MS MS(EI) for C18H20FN5O2 [M+H]+, (Calcd.: 357.16) Found: 358.3.

Example 238: Synthesis of (1R,2S,3S)-3-(8-((3,4-difluorophenethyl)amino)-[1,2,4]triazolo[4,3-a]pyrazin-3-yl)cyclopentane-1,2-diol $^1$H-NMR (DMSO-d$_6$, 400 MHz): δ 8.14-8.08 (1H, m), 7.69 (1H, d, J=4.8 Hz), 7.26-7.28 (2H, m), 7.25 (1H, d, J=4.8 Hz), 7.10-7.06 (1H, m), 4.94 (1H, d, J=6.4 Hz), 4.66 (1H, d, J=3.2 Hz), 4.03-3.98 (2H, m), 3.75-3.65 (2H, m), 3.52-3.48 (1H, m), 2.95 (2H, t, J=7.2 Hz), 2.25-2.15 (1H, m), 2.10-1.95 (2H, m), 1.70-1.60 (1H, m).

LC-MS MS(EI) for C18H19F2N5O2 [M+H]+, (Calcd.: 375.15) Found: 376.3.

Example 239: Synthesis of (1R,2S,3S)-3-(8-((3-chloro-4-fluorophenethyl)amino)-[1,2,4]triazolo[4,3-a]pyrazin-3-yl)cyclopentane-1,2-diol $^1$H-NMR (DMSO-d$_6$, 400 MHz): δ 8.12 (1H, t, J=5.8 Hz), 7.69 (1H, d, J=4.4 Hz), 7.49 (1H, d, J=6.0 Hz), 7.33-7.24 (3H, m), 4.94 (1H, d, J=6.4 Hz), 4.66 (1H, d, J=3.6 Hz), 4.03-3.98 (2H, m), 3.71-3.70 (2H, m), 3.51 (1H, q, J=6.9 Hz), 2.95 (2H, t, J=7.0 Hz), 2.19-2.17 (1H, m), 2.01-1.98 (2H, m), 1.69-1.65 (1H, m).
LC-MS MS(EI) for C18H19ClFN5O2 [M+H]+, (Calcd.: 391.12) Found: 392.3.

Example 240: Synthesis of (1R,2S,3S)-3-(8-(((1S,2R)-2-phenylcyclopropyl)amino)-[1,2,4]triazolo[4,3-a]pyrazin-3-yl)cyclo pentane-1,2-diol $^1$H-NMR (DMSO-d$_6$, 400 MHz): δ 8.47 (1H, d, J=4.0 Hz), 7.73 (1H, d, J=4.4 Hz), 7.30-7.24 (3H, m), 7.18 (3H, d, J=6.8 Hz), 4.95 (1H, d, J=6.4 Hz), 4.68 (1H, s), 4.04-3.98 (2H, m), 3.52 (1H, q, J=8.5 Hz), 3.17-3.16 (1H, m), 2.22-2.20 (1H, m), 2.13-2.12 (1H, m), 2.04-1.99 (2H, m), 1.69-1.66 (1H, m), 1.52-1.51 (1H, m), 1.26 (1H, q, J=3.3 Hz).
LC-MS MS(EI) for C$_{19}$H$_{21}$N$_5$O$_2$ [M+H]+, (Calcd.: 351.17) Found: 352.3.

Example 241: Synthesis of (1R,2S,3S)-3-(8-((4-chloro-3-fluorophenethyl)amino)-[1,2,4]triazolo[4,3-a]pyrazin-3-yl)cyclopentane-1,2-diol $^1$H-NMR (DMSO-d$_6$, 400 MHz): δ 8.13 (1H, t, J=6.0 Hz), 7.69 (1H, d, J=4.4 Hz), 7.47 (1H, t, J=8.0 Hz), 7.33 (1H, d, J=10.8 Hz), 7.25 (1H, d, J=4.4 Hz), 7.12 (1H, d, J=8.4 Hz), 4.94 (1H, d, J=6.4 Hz), 4.66 (1H, d, J=3.6 Hz), 4.06-3.98 (2H, m), 3.73-3.71 (2H, m), 3.51 (1H, q, J=8.6 Hz), 2.97 (2H, t, J=6.8 Hz), 2.24-2.15 (1H, m), 2.05-1.97 (2H, m), 1.68-1.66 (1H, m).
LC-MS MS(EI) for C18H19ClFN5O2 [M+H]+, (Calcd.: 391.12) Found: 392.3.

EVALUATION EXAMPLES

Evaluation Example 1: Assay for Binding Affinity for Adenosine Receptors

The adenosine derivatives according to embodiments of the present disclosure were assayed for binding affinity for human A1, A2a and A3 adenosine receptors as follows:
CHO cell membrane homogenates (40 μg protein), in which A1 adenosine receptors were expressed, are incubated for 60 min at 22° C. with 1 nM [3H]CCPA in the absence or presence of the test compound in a buffer containing 50 mM Tris-HCl (pH 7.4), 5 mM MgCl$_2$, 1 mM EDTA, 2 UI/ml ADA, 1 g/ml Leupeptin, 1 M Pepstatin and 10 μg/ml Trypsin inhibitor. Nonspecific binding is determined in the presence of 10 μM CPA. Following incubation, the derivatives according to embodiments of the present disclosure are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is CPA, which is tested in each experiment at several concentrations to obtain a competition curve from which its IC50 is calculated.

HEK-293 cell membrane homogenates (40 μg protein), in which A2a adenosine receptors were expressed, are incubated for 120 min at 22° C. with 6 nM [3H]CGS 21680 in the absence or presence of the test compound in a buffer containing 50 mM Tris-HCl (pH 7.4), 10 mM MgCl$_2$ and 2 UI/ml ADA. Nonspecific binding is determined in the presence of 10 μM NECA. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is NECA, which is tested in each experiment at several concentrations to obtain a competition curve from which its IC50 is calculated.

HEK-293 cell membrane homogenates (32 μg protein), in which A3 adenosine receptors were expressed, are incubated for 120 min at 22° C. with 0.15 nM [125I]AB-MECA in the absence or presence of the test compound in a buffer containing 50 mM Tris-HCl (pH 7.4), 5 mM MgCl$_2$, 1 mM EDTA and 2 UI/ml ADA. Nonspecific binding is determined in the presence of 1 μM IB-MECA. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is IB-MECA, which is tested in each experiment at several concentrations to obtain a competition curve from which its IC50 is calculated.

The standard for each marking is shown in Table 1 below.

TABLE 1

| Ki | Marking |
| --- | --- |
| <10 nM | ++++ |
| 10 nM~100 nM | +++ |
| 100 nM~1 uM | ++ |
| 1 uM~10 uM | + |
| >10 uM | − |

Example number the compounds synthesized in the examples and Ki values for binding affinity are summarized in Table 2 below.

TABLE 2

| | | Ki | | |
| --- | --- | --- | --- | --- |
| Compound (Example) No. | | A1(uM) | A2a(uM) | A3(nM) |
| Compound 1 | Example 1 | − | − | +++ |
| Compound 5 | Example 5 | − | − | ++ |
| Compound 6 | Example 6 | − | − | ++++ |
| Compound 7 | Example 7 | − | − | ++ |
| Compound 9 | Example 9 | − | − | +++ |
| Compound 11 | Example 11 | − | − | +++ |
| Compound 12 | Example 12 | − | − | +++ |

TABLE 2-continued

| Compound (Example) No. | | Ki | | |
|---|---|---|---|---|
| | | A1(uM) | A2a(uM) | A3(nM) |
| Compound 13 | Example 13 | – | – | ++ |
| Compound 17 | Example 17 | – | – | ++++ |
| Compound 24 | Example 24 | – | – | +++ |
| Compound 25 | Example 25 | – | + | +++ |
| Compound 26 | Example 26 | – | – | +++ |
| Compound 30 | Example 30 | + | + | ++ |
| Compound 32 | Example 32 | – | – | ++ |
| Compound 34 | Example 34 | – | – | – |
| Compound 35 | Example 35 | – | – | – |
| Compound 39 | Example 39 | – | – | – |
| Compound 40 | Example 40 | – | – | ++ |
| Compound 43 | Example 43 | – | – | +++ |
| Compound 44 | Example 44 | – | – | ++ |
| Compound 45 | Example 45 | – | – | – |
| Compound 46 | Example 46 | – | – | ++ |
| Compound 47 | Example 47 | – | – | ++ |
| Compound 48 | Example 48 | – | – | ++ |
| Compound 50 | Example 50 | – | – | +++ |
| Compound 55 | Example 55 | – | – | ++++ |
| Compound 56 | Example 56 | – | – | ++++ |
| Compound 62 | Example 62 | – | – | ++ |
| Compound 64 | Example 64 | – | – | +++ |
| Compound 93 | Example 93 | – | – | + |
| Compound 109 | Example 109 | – | + | +++ |
| Compound 112 | Example 112 | – | – | ++ |
| Compound 113 | Example 113 | – | – | ++ |
| Compound 115 | Example 115 | – | – | ++ |
| Compound 118 | Example 118 | – | – | – |
| Compound 119 | Example 119 | – | – | – |
| Compound 120 | Example 120 | – | – | ++ |
| Compound 121 | Example 121 | – | – | +++ |
| Compound 122 | Example 122 | – | – | +++ |
| Compound 123 | Example 123 | – | – | +++ |
| Compound 124 | Example 124 | – | – | +++ |
| Compound 125 | Example 125 | – | – | ++ |
| Compound 126 | Example 126 | – | – | ++ |
| Compound 127 | Example 127 | – | – | +++ |
| Compound 128 | Example 128 | – | – | +++ |
| Compound 129 | Example 129 | – | – | ++ |
| Compound 132 | Example 132 | + | + | ++++ |
| Compound 145 | Example 145 | – | + | +++ |
| Compound 146 | Example 146 | – | – | ++ |
| Compound 147 | Example 147 | – | – | ++ |
| Compound 149 | Example 149 | – | + | +++ |
| Compound 155 | Example 155 | – | – | – |
| Compound 158 | Example 158 | – | – | – |
| Compound 159 | Example 159 | + | – | + |
| Compound 160 | Example 160 | – | + | ++ |
| Compound 161 | Example 161 | – | + | + |
| Compound 162 | Example 162 | – | – | +++ |
| Compound 163 | Example 163 | – | + | + |
| Compound 164 | Example 164 | – | – | ++ |
| Compound 167 | Example 167 | – | – | N.C |
| Compound 168 | Example 168 | – | – | ++ |
| Compound 169 | Example 169 | – | – | +++ |
| Compound 170 | Example 170 | – | – | ++++ |
| Compound 177 | Example 177 | – | + | ++++ |
| Compound 184 | Example 184 | – | + | ++++ |
| Compound 210 | Example 210 | – | + | +++ |
| Compound 211 | Example 211 | – | – | ++ |
| Compound 212 | Example 212 | – | – | N.C |
| Compound 213 | Example 213 | – | – | ++ |
| Compound 214 | Example 214 | – | – | ++ |

Evaluation Example 2: Assay for Calcium Flux for Adenosine Receptors

FLIPR (Fluorescent Imaging Plate Reader) assays were conducted to profile the compounds according to embodiments of the present disclosure for agonist and antagonist activities on A3 receptor.

Coupling of the A3AR to Gq leading to a stimulation of intracellular calcium mobilization. The Calcium mobilization was monitored by FLIPR assay, a functional response can be measured using calcium-sensitive dyes and a fluorescence plate reader.

Test compounds were dissolved in dimethylsulphoxide (DMSO), and ultimately prepared in GPCR Profiler® Assay Buffer (Eurofins Discovery services) to concentrations that were three-fold higher than the final assay concentration. Similarly, vehicle controls and positive controls were prepared to ensure all assays were properly controlled. And final DMSO concentration was below 0.5% required.

All wells were prepared using GPCRProfiler® Assay Buffer. The GPCRProfiler® Assay Buffer was a modified Hanks Balanced Salt Solution (HBSS) where HBSS was supplemented to contain 20 mM HEPES and 2.5 mM Probenecid at pH7.4.

FLIPR assay was performed using ChemiScreen A3 Adenosine Receptor stable cell line, (Eurofins, Cat no. HTS052C), which cloned human A3 receptor expressing ChemiScreen cells were constructed by stable transfection of Chem-3 cells with A3.

Cell culture was performed using a 384 well Black clear bottom plate and incubation in humidified atmosphere containing 5% CO2 incubator at 37° C. On the day of assay, cells were loaded with GPCRProfiler® Assay Buffer.

Concentration-response curves were generated for the A3AR reference agonist (NECA) and reference antagonist (VUF5574) testing so EC50 & EC80 concentrations could be determined.

The agonist assay was conducted on a FLIPRTETRA instrument where the test compounds, vehicle controls, and reference agonist (NECA) were added to the assay plate after a fluorescence/luminescence baseline was established. The agonist assay was a total of 180 seconds and was used to assess each compound's ability to activate each GPCR assayed.

Antagonist assay using EC80 potency values determined during the agonist assay, all pre-incubated test compound wells were challenged with EC80 concentration of reference agonist (NECA) after establishment of a fluorescence/luminescence baseline. The antagonist assay was conducted using the same assay plate that was used for the agonist assay. The antagonist assay was conducted on a FLIPRTETRA instrument where vehicle controls and EC80 concentration of reference agonist (NECA) were added to appropriate wells. The antagonist assay was a total of 180 seconds and was used to assess each compound's ability to inhibit each GPCR assayed.

The compounds according to embodiments of the present disclosure were plated in duplicate for each concentration assayed.

The standard for each marking is shown in Table 3 below.

TABLE 3

| IC50 | Marking |
|---|---|
| <10 nM | ++++ |
| 10 nM~100 nM | +++ |
| 100 nM~1 uM | ++ |
| 1 uM~10 uM | + |
| >10 uM | – |

Example number the compounds synthesized in the examples and IC50 markings are summarized in Table 4 below.

TABLE 4

| Compound No. | IC50 |
|---|---|
| Compound 1 | +++ |
| Compound 2 | ++ |
| Compound 3 | − |
| Compound 4 | − |
| Compound 5 | ++ |
| Compound 6 | +++ |
| Compound 7 | ++ |
| Compound 8 | ++ |
| Compound 9 | +++ |
| Compound 10 | ++ |
| Compound 11 | +++ |
| Compound 12 | +++ |
| Compound 13 | ++ |
| Compound 14 | ++ |
| Compound 15 | + |
| Compound 16 | + |
| Compound 17 | ++ |
| Compound 18 | − |
| Compound 19 | − |
| Compound 20 | − |
| Compound 21 | − |
| Compound 22 | − |
| Compound 23 | − |
| Compound 24 | + |
| Compound 25 | + |
| Compound 26 | ++ |
| Compound 27 | + |
| Compound 28 | − |
| Compound 29 | + |
| Compound 30 | ++ |
| Compound 31 | + |
| Compound 32 | + |
| Compound 33 | − |
| Compound 34 | − |
| Compound 35 | − |
| Compound 36 | + |
| Compound 37 | − |
| Compound 38 | − |
| Compound 39 | + |
| Compound 40 | ++ |
| Compound 41 | − |
| Compound 42 | − |
| Compound 43 | ++++ |
| Compound 44 | +++ |
| Compound 45 | + |
| Compound 46 | ++ |
| Compound 47 | ++ |
| Compound 48 | − |
| Compound 49 | − |
| Compound 50 | +++ |
| Compound 51 | − |
| Compound 52 | − |
| Compound 53 | − |
| Compound 54 | − |
| Compound 55 | +++ |
| Compound 56 | ++++ |
| Compound 57 | − |
| Compound 58 | +++ |
| Compound 59 | +++ |
| Compound 60 | − |
| Compound 61 | ++ |
| Compound 62 | +++ |
| Compound 63 | +++ |
| Compound 64 | ++++ |
| Compound 65 | +++ |
| Compound 66 | − |
| Compound 67 | ++ |
| Compound 68 | − |
| Compound 69 | +++ |
| Compound 70 | +++ |
| Compound 71 | +++ |
| Compound 72 | − |
| Compound 73 | +++ |
| Compound 74 | +++ |
| Compound 75 | +++ |
| Compound 76 | +++ |
| Compound 77 | − |
| Compound 78 | +++ |
| Compound 79 | − |
| Compound 80 | +++ |
| Compound 81 | +++ |
| Compound 82 | ++++ |
| Compound 83 | +++ |
| Compound 84 | +++ |
| Compound 85 | ++++ |
| Compound 86 | +++ |
| Compound 87 | ++ |
| Compound 88 | − |
| Compound 89 | − |
| Compound 90 | ++ |
| Compound 91 | − |
| Compound 92 | − |
| Compound 109 | − |
| Compound 110 | − |
| Compound 111 | − |
| Compound 112 | − |
| Compound 113 | ++ |
| Compound 114 | +++ |
| Compound 115 | +++ |
| Compound 116 | +++ |
| Compound 117 | +++ |
| Compound 118 | +++ |
| Compound 119 | ++++ |
| Compound 120 | +++ |
| Compound 121 | ++++ |
| Compound 122 | +++ |
| Compound 123 | +++ |
| Compound 124 | +++ |
| Compound 125 | +++ |
| Compound 126 | − |
| Compound 127 | + |
| Compound 128 | ++ |
| Compound 129 | ++ |
| Compound 130 | + |
| Compound 131 | ++ |
| Compound 132 | − |
| Compound 133 | + |
| Compound 134 | − |
| Compound 135 | − |
| Compound 136 | ++ |
| Compound 137 | +++ |
| Compound 138 | ++ |
| Compound 139 | ++ |
| Compound 140 | +++ |
| Compound 141 | ++ |
| Compound 142 | +++ |
| Compound 143 | ++++ |
| Compound 144 | ++ |
| Compound 145 | +++ |
| Compound 146 | + |
| Compound 147 | + |
| Compound 148 | +++ |
| Compound 149 | − |
| Compound 150 | − |
| Compound 151 | + |
| Compound 152 | + |
| Compound 153 | + |
| Compound 154 | − |
| Compound 155 | + |
| Compound 156 | ++ |
| Compound 157 | ++ |
| Compound 158 | − |
| Compound 159 | − |
| Compound 160 | − |
| Compound 161 | ++ |
| Compound 162 | + |
| Compound 163 | ++ |
| Compound 164 | ++ |
| Compound 165 | +++ |
| Compound 166 | − |
| Compound 167 | ++ |
| Compound 168 | ++ |
| Compound 169 | + |
| Compound 170 | + |
| Compound 171 | − |
| Compound 172 | |

TABLE 4-continued

| Compound No. | IC50 |
|---|---|
| Compound 173 | ++ |
| Compound 174 | - |
| Compound 175 | ++ |
| Compound 176 | +++ |
| Compound 177 | ++ |
| Compound 178 | +++ |
| Compound 179 | +++ |
| Compound 180 | ++ |
| Compound 181 | ++ |
| Compound 182 | +++ |
| Compound 183 | - |
| Compound 184 | +++ |
| Compound 185 | +++ |
| Compound 186 | +++ |
| Compound 187 | +++ |
| Compound 188 | +++ |
| Compound 189 | +++ |
| Compound 190 | +++ |
| Compound 191 | +++ |
| Compound 192 | ++++ |
| Compound 193 | +++ |
| Compound 194 | +++ |
| Compound 195 | +++ |
| Compound 196 | ++ |
| Compound 197 | +++ |
| Compound 198 | +++ |
| Compound 199 | ++++ |
| Compound 200 | +++ |
| Compound 201 | ++ |
| Compound 202 | - |
| Compound 203 | +++ |
| Compound 204 | +++ |
| Compound 205 | +++ |
| Compound 206 | - |
| Compound 207 | +++ |
| Compound 208 | ++++ |
| Compound 209 | +++ |
| Compound 210 | +++ |
| Compound 211 | +++ |
| Compound 212 | - |
| Compound 213 | +++ |
| Compound 214 | ++++ |
| Compound 215 | ++++ |
| Compound 216 | ++++ |
| Compound 217 | ++++ |
| Compound 218 | ++ |
| Compound 219 | - |
| Compound 220 | - |
| Compound 221 | - |
| Compound 222 | +++ |
| Compound 223 | +++ |
| Compound 224 | +++ |
| Compound 225 | +++ |
| Compound 226 | +++ |
| Compound 227 | - |
| Compound 228 | +++ |
| Compound 229 | +++ |
| Compound 230 | +++ |
| Compound 231 | +++ |
| Compound 232 | - |
| Compound 233 | +++ |
| Compound 234 | +++ |
| Compound 235 | +++ |
| Compound 236 | +++ |
| Compound 237 | +++ |
| Compound 238 | +++ |
| Compound 239 | +++ |
| Compound 240 | +++ |
| Compound 241 | +++ |

As shown in Tables 2 and 4, the compounds according to embodiments of the present disclosure were effective in antagonizing the A3 adenosine receptor. In particular, the compounds of the present disclosure did not or little bind the A1 and A2 receptor, which means that the compounds are very selective in binding or inhibiting the A3 adenosine receptor.

Evaluation Example 3: Evaluation with Rabbits

New Zealand white rabbits were maintained under 12-hr light-dark illumination cycle and allowed unrestricted access to food and water. All procedures conformed to The Catholic Institute for Visual Science College of Medicine. Rabbits were anesthetized with Zoletil 50 (VIRBAC, France) and xylazine (Rompun®, Bayer AG, Germany) for the IOP measurements.

IOP was monitored with TonoVet®, a highly reliable electro physiologic approach that has been extensively validated and used in previous studies. Data reported were obtained from one eye of each rabbit studied. Mean values of IOP were calculated by averaging 3-5 min of data acquired at 3 Hz before and after drug application. Thus, each mean was obtained from ~540 to 900 measurements.

Test compounds were applied topically in 10-μl drops with an Eppendorf pipette at 250 uM. The agents were initially dissolved in Cremophor RH40 and then added to a NaOH solution containing benzalkonium chloride to enhance corneal permeability. The final droplet solution contained the drugs at the stated concentrations together with 3% Cremophor RH40 and 0.005% benzalkonium chloride at an osmolality of 270-280 mOsm. Control NaOH solution (0.1% NaCl) contained benzalkonium.

The results are shown in Table 5 below.

TABLE 5

| | | 0 week | 1 weeks | 3 weeks |
|---|---|---|---|---|
| Compound 1 | IOP(mmHg) | 31.0 | 28.67 | 18.00 |
| | Percent(%) | 100 | 92.47 | 58.06 |
| Compound 2 | IOP(mmHg) | 30.0 | 23.40 | 13.00 |
| | Percent(%) | 100 | 77.99 | 43.35 |
| Vehicle | IOP(mmHg) | 30.00 | 30.00 | 30.2 |
| | Percent(%) | 100 | 100.02 | 100.69 |

As shown in Table 5 above, the compounds of the present disclosure were effective in decreasing Intraocular Pressure (TOP). Thus, the compounds are useful in ameliorating, preventing or treating glaucoma or glaucoma-related ocular diseases.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A compound of Formula I or a pharmaceutically acceptable salt thereof,

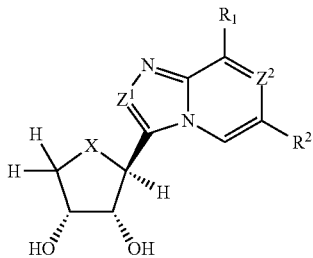

Formula I wherein:
X is sulfur or oxygen;
$Z^1$ and $Z^2$ are the same or different, and are each independently nitrogen or CH;
$R^1$ is halogen, $NR^3R^4$, $NR^3NR^3R^4$, $CR^3R^4R^5$, $OR^3$ or $SR^3$, wherein said $R^3$, $R^4$, and $R^5$ are each independently H, C1-6 alkyl, substituted C1-6 alkyl, C3-7 cycloalkyl, substituted C3-7 cycloalkyl, aryl, substituted aryl, heteroaryl, substituted heteroaryl, heterocycle, substituted heterocycle, heterocycloalkyl, substituted heterocycloalkyl, C2-6 alkynyl optionally substituted with aryl or heteroaryl, —C(=O)—C1-6 alkyl, —S(O)n-C1-6 alkyl, substituted —C(=O)— C1-6 alkyl, or substituted —S(O)n-C1-6 alkyl, and said n is 0, 1, or 2, and
$R^2$ is H or halogen.

2. The compound of Formula I or a pharmaceutically acceptable salt thereof according to claim 1, wherein $R^1$ is $NR^3R^4$ or $CR^3R^4R^5$, wherein said $R^3$, $R^4$, and $R^5$ are each independently H, C1-6 alkyl, substituted C1-6 alkyl, C3-7 cycloalkyl, substituted C3-7 cycloalkyl, aryl, substituted aryl, heteroaryl, substituted heteroaryl, heterocycle, substituted heterocycle, heterocycloalkyl, substituted heterocycloalkyl, or C2-6 alkynyl optionally substituted with aryl or heteroaryl.

3. The compound of Formula I or a pharmaceutically acceptable salt thereof according to claim 1, wherein the compound of Formula 1 selected from the group consisting of:
(2S,3R,4S)-2-(8-((3-chlorobenzyl)amino)-[1,2,4]triazolo[4,3-a]pyrazine-3-yl)tetrahydrothiophene-3,4-diol (Compound 1),
(2S,3R,4S)-2-(8-(methylamino)-[1,2,4]triazolo[4,3-a]pyrazin-3-yl)tetrahydrothiophene-3,4-diol (Compound 2),
(2S,3R,4S)-2-(8-(benzylamino)-[1,2,4]triazolo[4,3-a]pyrazin-3-yl)tetrahydrothiophene-3,4-diol (Compound 5),
(2S,3R,4S)-2-(8-((3-iodobenzyl)amino)-[1,2,4]triazolo[4,3-a]pyrazin-3-yl)tetrahydrothiophene-3,4-diol (Compound 6),
(2S,3R,4S)-2-(8-((cyclopropylmethyl)amino)-[1,2,4]triazolo[4,3-a]pyrazin-3-yl)tetrahydrothiophene-3,4-diol (Compound 7),
(2S,3R,4S)-2-(8-(cyclobutylamino)-[1,2,4]triazolo[4,3-a]pyrazin-3-yl)tetrahydrothiophene-3,4-diol (Compound 8),
(2S,3R,4S)-2-(8-((3-trifluoromethyl)benzyl)amino)-[1,2,4]triazolo[4,3-a]pyrazin-3-yl)tetrahydrothiophene-3,4-diol (Compound 9),
(2S,3R,4S)-2-(8-((thiophen-3-ylmethyl)amino)-[1,2,4]triazolo[4,3-a]pyrazin-3-yl)tetrahydrothiophene-3,4-diol (Compound 10),
(2S,3R,4S)-2-(8-(phenethylamino)-[1,2,4]triazolo[4,3-a]pyrazin-3-yl)tetrahydrothiophene-3,4-diol (Compound 11),
(2S,3R,4S)-2-(8-((3-methylbenzyl)amino)-[1,2,4]triazolo[4,3-a]pyrazin-3-yl)tetrahydrothiophene-3,4-diol (Compound 12),
(2S,3R,4S)-2-(8-((3-fluorobenzyl)amino)-[1,2,4]triazolo[4,3-a]pyrazin-3-yl)tetrahydrothiophene-3,4-diol (Compound 13),
(2S,3R,4S)-2-(8-((3-(trifluoromethoxy)benzyl)amino)-[1,2,4]triazolo[4,3-a]pyrazin-3-yl)tetrahydrothiophene-3,4-diol (Compound 14),
(2S,3R,4S)-2-(8-((3-methoxybenzyl)amino)-[1,2,4]triazolo[4,3-a]pyrazin-3-yl)tetrahydrothiophene-3,4-diol (Compound 15)
3-(((3-((2S,3R,4S)-3,4-dihydroxytetrahydrothiophen-2-yl)-[1,2,4]triazolo[4,3-a]pyrazin-8-yl)amino)methyl)benzonitrile (Compound 16),
(2S,3R,4S)-2-(8-((3-bromobenzyl)amino)-[1,2,4]triazolo[4,3-a]pyrazin-3-yl)tetrahydrothiophene-3,4-diol (Compound 17),
(2S,3R,4S)-2-(8-((3-chlorophenethyl)amino)-[1,2,4]triazolo[4,3-a]pyrazin-3-yl)tetrahydrothiophene-3,4-diol (Compound 24),
(2S,3R,4S)-2-(8-((3-bromophenethyl)amino)-[1,2,4]triazolo[4,3-a]pyrazin-3-yl)tetrahydrothiophene-3,4-diol (Compound 25),
(2S,3R,4S)-2-(8-((3-fluorophenethyl)amino)-[1,2,4]triazolo[4,3-a]pyrazin-3-yl)tetrahydrothiophene-3,4-diol (Compound 26),
(2S,3R,4S)-2-(8-((2-phenylcyclopropyl)amino)-[1,2,4]triazolo[4,3-a]pyrazin-3-yl)tetrahydrothiophene-3,4-diol (Compound 27),
(2S,3R,4S)-2-(8-((1-(3-chlorophenyl)cyclopropyl)amino)-[1,2,4]triazolo[4,3-a]pyrazin-3-yl)tetrahydrothiophene-3,4-diol (Compound 29),
(2S,3R,4S)-2-(8-((3-chlorophenyl)ethynyl)-[1,2,4]triazolo[4,3-a]pyrazin-3-yl)tetrahydrothiophene-3,4-diol (Compound 30),
(2S,3R,4S)-2-(8-(cyclopropylamino)-[1,2,4]triazolo[4,3-a]pyrazin-3-yl)tetrahydrothiophene-3,4-diol (Compound 31),
(2S,3R,4S)-2-(8-(isopentylamino)-[1,2,4]triazolo[4,3-a]pyrazin-3-yl)tetrahydrothiophene-3,4-diol (Compound 32),
(2S,3R,4S)-2-(8-((imidazo[1,2-a]pyridin-2-ylmethyl)amino)-[1,2,4]triazolo[4,3-a]pyrazin-3-yl)tetrahydrothiophene-3,4-diol (Compound 36),
(2S,3R,4R)-2-(8-((3-chlorophenethyl)amino)-[1,2,4]triazolo[4,3-a]pyrazin-3-yl)tetrahydrofuran-3,4-diol (Compound 39),
4-(((3-((2S,3R,4S)-3,4-dihydroxytetrahydrothiophen-2-yl)-[1,2,4]triazolo[4,3-a]pyrazin-8-yl)amino)methyl)-2-fluoro-N-methylbenzamide (Compound 40),
(2S,3R,4S)-2-(8-(((1 S,2R)-2-phenylcyclopropyl)amino)-[1,2,4]triazolo[4,3-a]pyrazin-3-yl)tetrahydrothiophene-3,4-diol (Compound 43),
2-chloro-4-(((3-((2S,3R,4S)-3,4-dihydroxytetrahydrothiophen-2-yl)-[1,2,4]triazolo[4,3-a]pyrazin-8-yl)amino)methyl)-N-methylbenzamide (Compound 44),
(2S,3R,4S)-2-(8-(((S)-1-(3-chlorophenyl)ethyl)amino)-[1,2,4]triazolo[4,3-a]pyrazin-3-yl)tetrahydrothiophene-3,4-diol (Compound 45), (2S,3R,4S)-2-(8-(((R)-1-(3-chlorophenyl)ethyl)amino)-[1,2,4]triazolo[4,3-a]pyrazin-3-yl)tetrahydrothiophene-3,4-diol (Compound 46), (2S,3R,4S)-2-(8-((2-chlorobenzyl)amino)-[1,2,4]triazolo[4,3-a]pyrazin-3-yl)tetrahydrothiophene-3,4-diol (Compound 47), (2S,3R,4S)-2-(8-(2-fluorophenethyl)amino)-[1,2,4]triazolo[4,3-a]pyrazin-3-yl)tetrahydrothiophene-3,4-diol (Compound 50), (2S,3R,4S)-2-(8-((3,5-dichlorobenzyl)amino)-[1,2,4]triazolo[4,3-a]pyrazin-3-yl)tetrahydrothiophene-3,4-diol (Compound 55), (2S,3R,4S)-2-(8-((2,5-dichlorobenzyl)amino)-[1,2,4]triazolo[4,3-a]pyrazin-3-yl)tetrahydrothiophene-3,4-diol (Compound 56), (2S,3R,4S)-2-(8-((2,3-dichlorobenzyl)amino)-[1,2,4]triazolo[4,3-a]pyrazin-3-yl)tetrahydrothiophene-3,4-diol (Compound 58), (2S,3R,4S)-2-(8-((3,4-dichlorobenzyl)amino)-[1,2,4]triazolo[4,3-a]pyrazin-3-yl)tetrahydrothiophene-3,4-diol (Compound 59), methyl2-chloro-5-(((3-((2S,3R,4S)-3,4-dihydroxytetrahydro thiophen-2-yl)-[1,2,4]triazolo[4,3-a]pyrazin-8-yl)amino)methyl)benzoate (Compound 61), (2S,3R,4S)-2-(8-((2-iodobenzyl)amino)-[1,2,4]triazolo[4,3-a]pyrazin-3-yl)tetrahydrothiophene-3,4-diol (Compound 62), (2S,3R,4S)-2-(8-((3-chloro-4-fluorophenethyl)amino)-[1,2,4]triazolo[4,3-a]pyrazin-3-yl)tetrahydrothiophene-3,4-diol (Compound 63), (2S,3R,4S)-2-(8-(4-fluorophenethyl)amino)-[1,2,4]triazolo[4,3-a]pyrazin-3-yl)tetrahydrothiophene-3,4-diol (Compound 64), (2S,3R,4S)-2-(8-((3-chloro-4-fluorobenzyl)amino)-[1,2,4]triazolo[4,3-a]pyrazin-3-yl)tetrahydrothiophene-3,4-diol (Compound 65), (2S,3R,4S)-2-(8-((3-(4-methylpiperazin-1-yl)benzyl)amino)-[1,2,4]triazolo[4,3-a]pyrazin-3-yl)tetrahydrothiophene-3,4-diol (Compound 67), (2S,3R,4S)-2-(8-((3-(1H-tetrazol-5-yl)benzyl)amino)-[1,2,4]triazolo[4,3-a]pyrazin-3-yl)tetrahydrothiophene-3,4-diol (Compound 69), (2S,3R,4S)-2-(8-((2-(3-fluorophenyl)cyclopropyl)amino)-[1,2,4]triazolo[4,3-a]pyrazin-3-yl)tetrahydrothiophene-3,4-diol (Compound 70), (2S,3R,4S)-2-(8-((2-(3-chlorophenyl)cyclopropyl)amino)-[1,2,4]triazolo[4,3-a]pyrazin-3-yl)tetrahydrothiophene-3,4-diol (Compound 71), (2S,3R,4S)-2-(8-((2,3-difluorophenethyl)amino)-[1,2,4]triazolo[4,3-a]pyrazin-3-yl)tetrahydrothiophene-3,4-diol (Compound 73), (2S,3R,4S)-2-(8-((2,4-difluorophenethyl)amino)-[1,2,4]triazolo[4,3-a]pyrazin-3-yl)tetrahydrothiophene-3,4-diol (Compound 74), (2S,3R,4S)-2-(8-(((1R,2R)-2-phenylcyclopropyl)amino)-[1,2,4]triazolo[4,3-a]pyrazin-3-yl)tetrahydrothiophene-3,4-diol (Compound 75), (2S,3R,4S)-2-(8-((2,5-difluorophenethyl)amino)-[1,2,4]triazolo[4,3-a]pyrazin-3-yl)tetrahydrothiophene-3,4-diol (Compound 76), (2S,3R,4S)-2-(8-((4-chloro-3-fluorophenethyl)amino)-[1,2,4]triazolo[4,3-a]pyrazin-3-yl)tetrahydrothiophene-3,4-diol (Compound 78), (2S,3R,4S)-2-(8-((3-(piperazin-1-yl)benzyl)amino)-[1,2,4]triazolo[4,3-a]pyrazin-3-yl)tetrahydrothiophene-3,4-diol (Compound 80), (2S,3R,4S)-2-(8-((2,6-difluorophenethyl)amino)-[1,2,4]triazolo[4,3-a]pyrazin-3-yl)tetrahydrothiophene-3,4-diol (Compound 81), (2S,3R,4S)-2-(8-((3,4-difluorophenethyl)amino)-[1,2,4]triazolo[4,3-a]pyrazin-3-yl)tetrahydrothiophene-3,4-diol (Compound 82), (2S,3R,4S)-2-(8-((3,5-difluorophenethyl)amino)-[1,2,4]triazolo[4,3-a]pyrazin-3-yl)tetrahydrothiophene-3,4-diol (Compound 83), (2S,3R,4S)-2-(8-(((1 S,2R)-2-(3,4-difluorophenyl)cyclopropyl)amino)-[1,2,4]triazolo[4,3-a]pyrazin-3-yl)tetrahydrothiophene-3,4-diol (Compound 84), (2S,3R,4S)-2-(8-((5-chloro-2-fluorobenzyl)amino)-[1,2,4]triazolo[4,3-a]pyrazin-3-yl)tetrahydrothiophene-3,4-diol (Compound 85), (2S,3R,4S)-2-(8-((3-chloro-5-fluorobenzyl)amino)-[1,2,4]triazolo[4,3-a]pyrazin-3-yl)tetrahydrothiophene-3,4-diol (Compound 86), (2S,3R,4S)-2-(8-((3-cyclopropylbenzyl)amino)-[1,2,4]triazolo[4,3-a]pyrazin-3-yl)tetrahydrothiophene-3,4-diol (Compound 87), methyl3-(((3-((2S,3R,4S)-3,4-dihydroxytetrahydrothiophen-2-yl)-[1,2,4]triazolo[4,3-a]pyrazin-8-yl)amino)methyl)benzoate (Compound 90), (2S,3R,4S)-2-(8-((3-fluoro-4-(5-methyl-1,3,4-thiadiazol-2-yl)benzyl)amino)-[1,2,4]triazolo[4,3-a]pyrazin-3-yl)tetrahydrothiophene-3,4-diol (Compound 97), (2S,3R,4S)-2-(8-(((1S,2R)-2-(3-fluorophenyl)cyclopropyl)amino)-[1,2,4]triazolo[4,3-a]pyrazin-3-yl)tetrahydrothiophene-3,4-diol (Compound 98), (2S,3R,4S)-2-(8-(((1S,2R)-2-(3-chlorophenyl)cyclopropyl)amino)-[1,2,4]triazolo[4,3-a]pyrazin-3-yl)tetrahydrothiophene-3,4-diol (Compound 99), (2S,3R,4S)-2-(6-chloro-8-((3-chlorobenzyl)amino)-[1,2,4]triazolo[4,3-a]pyrazin-3-yl)tetrahydrothiophene-3,4-diol (Compound 100), (2S,3R,4S)-2-(6-chloro-8-((2,5-dichlorobenzyl)amino)-[1,2,4]triazolo[4,3-a]pyrazin-3-yl)tetrahydrothiophene-3,4-diol (Compound 101), (2S,3R,4S)-2-(6-chloro-8-((3,5-dichlorobenzyl)amino)-[1,2,4]triazolo[4,3-a]pyrazin-3-yl)tetrahydrothiophene-3,4-diol (Compound 102), (2S,3R,4S)-2-(6-chloro-8-((5-chloro-2-fluorobenzyl)amino)-[1,2,4]triazolo[4,3-a]pyrazin-3-yl)tetrahydrothiophene-3,4-diol (Compound 103), (2S,3R,4S)-2-(6-chloro-8-((4-fluorophenethyl)amino)-[1,2,4]triazolo[4,3-a]pyrazin-3-yl)tetrahydrothiophene-3,4-diol (Compound 104), (2S,3R,4S)-2-(6-chloro-8-((3-fluorophenethyl)amino)-[1,2,4]triazolo[4,3-a]pyrazin-3-yl)tetrahydrothiophene-3,4-diol (Compound 105), (2S,3R,4S)-2-(6-chloro-8-((3,4-difluorophenethyl)amino)-[1,2,4]triazolo[4,3-a]pyrazin-3-yl)tetrahydrothiophene-3,4-diol (Compound 106), (2S,3R,4S)-2-(6-chloro-8-((4-chloro-3-fluorophenethyl)amino)-[1,2,4]triazolo[4,3-a]pyrazin-3-yl)tetrahydrothiophene-3,4-diol (Compound 107), (2S,3R,4S)-2-(6-chloro-8-(((1S,2R)-2-phenylcyclopropyl)amino)-[1,2,4]triazolo[4,3-a]pyrazin-3-yl)tetrahydrothiophene-3,4-diol (Compound 108), (2S,3R,4S)-2-(8-((3-chlorobenzyl)amino)imidazo[1,2-a]pyrazin-3-yl)tetrahydrothiophene-3,4-diol (Compound 109), (2S,3R,4S)-2-(8-(methylamino)imidazo[1,2-a]pyrazin-3-yl)tetrahydrothiophene-3,4-diol (Compound 111), (2S,3R,4S)-2-(8-((cyclopropylmethyl)amino)imidazo[1,2-a]pyrazin-3-yl)tetrahydrothiophene-3,4-diol (Compound 112), (2S,3R,4S)-2-(8-(cyclobutylamino)imidazo[1,2-a]pyrazin-3-yl)tetrahydrothiophene-3,4-diol (Compound 113), (2S,3R,4S)-2-(8-(cyclopropylamino)imidazo[1,2-a]pyrazin-3-yl)tetrahydrothiophene-3,4-diol (Compound 114), (2S,3R,4S)-2-(8-(isopentylamino)imidazo[1,2-a]pyrazin-3-yl)tetrahydrothiophene-3,4-diol (Compound 115), (2S,3R,4S)-2-(8-(piperidin-1-yl)imidazo[1,2-a]pyrazin-3-yl)tetrahydrothiophene-3,4-diol (Compound 117), (2S,3R,4S)-2-(8-(benzylamino)imidazo[1,2-a]pyrazin-3-yl)tetrahydrothiophene-3,4-diol (Compound 120), (2S,3R,4S)-2-(8-((3-methylbenzyl)amino)imidazo[1,2-a]pyrazin-3-yl)tetrahydrothiophene-3,4-diol (Compound 121), (2S,3R,4S)-2-(8-((3-fluorobenzyl)amino)imidazo[1,2-a]pyrazin-3-yl)tetrahydrothiophene-3,4-diol (Compound 122), (2S,3R,4S)-2-(8-((3-(trifluoromethyl)benzyl)amino)imidazo[1,2-a]pyrazin-3-yl)tetrahydrothiophene-3,4-diol (Compound 123), (2S,3R,4S)-2-(8-((3-iodobenzyl)amino)imidazo[1,2-a]pyrazin-3-yl)tetrahydrothiophene-3,4-diol (Compound 124), 4-(((3-((2S,3R,4S)-3,4-dihydroxytetrahydrothiophen-2-yl)imidazo[1,2-a]pyrazin-8-yl)amino)methyl)-2-fluoro-N-methylbenzamide (Compound 125), 2-chloro-4-(((3-((2S,3R,4S)-3,4-dihydroxytetrahydrothiophen-2-yl)imidazo[1,2-a]pyrazin-8-yl)amino)methyl)-N-methylbenzamide (Compound 126), (2S,3R,4S)-2-(8-((3-fluorophenethyl)amino)imidazo[1,2-a]pyrazin-3-yl)tetrahydrothiophene-3,4-diol (Compound 127), (2S,3R,4S)-2-(8-(phenethylamino)imidazo[1,2-a]pyrazin-3-yl)tetrahydrothiophene-3,4-diol (Compound 128), (2S,3R,4S)-2-(8-(2-phenylcyclopropyl)amino)imidazo[1,2-a]pyrazin-3-yl)tetrahydrothiophene-3,4-diol (Compound 129), (2S,3R,4S)-2-(8-((thiophen-3-ylmethyl)amino)imidazo[1,2-a]pyrazin-3-yl)tetrahydrothiophene-3,4-diol (Compound 130), (2S,3R,4S)-2-(8-((furan-3-ylmethyl)amino)imidazo[1,2-a]pyrazin-3-yl)tetrahydrothiophene-3,4-diol (Compound 131), (2S,3R,4S)-2-(8-((3-bromobenzyl)amino)imidazo[1,2-a]pyrazin-3-yl)tetrahydrothiophene-3,4-diol (Compound 132), (2S,3R,4S)-2-(8-((pyridin-3-ylmethyl)amino)imidazo[1,2-a]pyrazin-3-yl)tetrahydrothiophene-3,4-diol (Compound 135), (2S,3R,4S)-2-(8-((pyridin-4-ylmethyl)amino)imidazo[1,2-a]pyrazin-3-yl)tetrahydrothiophene-3,4-diol (Compound 136), (2S,3R,4S)-2-(8-((3-methoxybenzyl)amino)imidazo[1,2-a]pyrazin-3-yl)tetrahydrothiophene-3,4-diol (Compound 137), (2S,3R,4S)-2-(8-((cyclohexylmethyl)amino)imidazo[1,2-a]pyrazin-3-yl)tetrahydrothiophene-3,4-diol (Compound 139), (2S,3R,4S)-2-(8-((3-(trifluoromethoxy)benzyl)amino)imidazo[1,2-a]pyrazin-3-yl)tetrahydrothiophene-3,4-diol (Compound 140), 3-(((3-((2S,3R,4S)-3,4-dihydroxytetrahydrothiophen-2-yl)imidazo[1,2-a]pyrazin-8-yl)amino)methyl)benzonitrile (Compound 141), (2S,3R,4S)-2-(8-((pyrimidin-4-ylmethyl)amino)imidazo[1,2-a]pyrazin-3-yl)tetrahydrothiophene-3,4-diol (Compound 145), (2S,3R,4S)-2-(8-((3-chlorophenethyl)amino)imidazo[1,2-a]pyrazin-3-yl)tetrahydrothiophene-3,4-diol (Compound 146), (2S,3R,4S)-2-(8-((thiazol-4-ylmethyl)amino)imidazo[1,2-a]pyrazin-3-yl)tetrahydrothiophene-3,4-diol (Compound 147), (2S,3R,4S)-2-(8-((thiazol-2-ylmethyl)amino)imidazo[1,2-a]pyrazin-3-yl)tetrahydrothiophene-3,4-diol (Compound 148), (2S,3R,4S)-2-(8-((3-bromophenethyl)amino)imidazo[1,2-a]pyrazin-3-yl)tetrahydrothiophene-3,4-diol (Compound 149), (2S,3R,4S)-2-(8-((1-(3-chlorophenyl)cyclopropyl)amino)imidazo[1,2-a]pyrazin-3-yl)tetrahydrothiophene-3,4-diol (Compound 151), (2S,3R,4S)-2-(8-((2-(3-chlorophenyl)propan-2-yl)amino)imidazo[1,2-a]pyrazin-3-yl)tetrahydrothiophene-3,4-diol (Compound 152), (2S,3R,4S)-2-(8-(((1H-benzo[d]imidazol-2-yl)methyl)amino)imidazo[1,2-a]pyrazin-3-yl)tetrahydrothiophene-3,4-diol hydrochloride (Compound 153), (2S,3R,4S)-2-(8-((2-(piperidin-1-yl)ethyl)amino)imidazo[1,2-a]pyrazin-3-yl)tetrahydrothiophene-3,4-diol (Compound 154), (2S,3R,4S)-2-(8-((thiazol-5-ylmethyl)amino)imidazo[1,2-a]pyrazin-3-yl)tetrahydrothiophene-3,4-diol (Compound 157), (2S,3R,4S)-2-(8-((3-chlorophenyl)ethynyl)imidazo[1,2-a]pyrazin-3-yl)tetrahydrothiophene-3,4-diol (Compound 159), (2S,3R,4S)-2-(8-(((R)-1-(3-chlorophenyl)ethyl)amino)imidazo[1,2-a]pyrazin-3-yl)tetrahydrothiophene-3,4-diol (Compound 160), (2S,3R,4S)-2-(8-(((S)-1-(3-chlorophenyl)ethyl)amino)imidazo[1,2-a]pyrazin-3-yl)tetrahydrothiophene-3,4-diol (Compound 161), (2S,3R,4S)-2-(8-(((1S,2R)-2-phenylcyclopropyl)amino)imidazo[1,2-a]pyrazin-3-yl)tetrahydrothiophene-3,4-diol (Compound 162), (2S,3R,4S)-2-(8-((2-chlorobenzyl)amino)imidazo[1,2-a]pyrazin-3-yl)tetrahydrothiophene-3,4-diol (Compound 163), (2S,3R,4S)-2-(8-((4-chlorobenzyl)amino)imidazo[1,2-a]pyrazin-3-yl)tetrahydrothiophene-3,4-diol (Compound 164), (2S,3R,4S)-2-(8-((4-iodobenzyl)amino)imidazo[1,2-a]pyrazin-3-yl)tetrahydrothiophene-3,4-diol (Compound 165), (2S,3R,4S)-2-(8-(((1H-indol-5-yl)methyl)amino)imidazo[1,2-a]pyrazin-3-yl)tetrahydrothiophene-3,4-diol (Compound 166), (2S,3R,4S)-2-(8-((2-iodobenzyl)amino)imidazo[1,2-a]pyrazin-3-yl)tetrahydrothiophene-3,4-diol (Compound 168), (2S,3R,4S)-2-(8-((2-fluorophenethyl)amino)imidazo[1,2-a]pyrazin-3-yl)tetrahydrothiophene-3,4-diol (Compound 169), (2S,3R,4S)-2-(8-((4-fluorophenethyl)amino)imidazo[1,2-a]pyrazin-3-yl)tetrahydrothiophene-3,4-diol (Compound 170), Methyl 5-(((3-((2S,3R,4S)-3,4-dihydroxytetrahydrothiophen-2-yl)imidazo[1,2-a]pyrazin-8-yl)amino)methyl)-2-fluorobenzoate (Compound 171), (2S,3R,4S)-2-(8-((3-chloro-4-fluorophenethyl)amino)imidazo[1,2-a]pyrazin-3-yl)tetrahydrothiophene-3,4-diol (Compound 172), (2S,3R,4S)-2-(8-((3-(dimethylamino)benzyl)amino)imidazo[1,2-a]pyrazin-3-yl)tetrahydrothiophene-3,4-diol (Compound 173), (2S,3R,4S)-2-(8-((3-(4-methylpiperazin-1-yl)benzyl)amino)imidazo[1,2-a]pyrazin-3-yl)tetrahydrothiophene-3,4-diol (Compound 174), (2S,3R,4S)-2-(8-((2,3-dichlorobenzyl)amino)imidazo[1,2-a]pyrazin-3-yl)tetrahydrothiophene-3,4-diol (Compound 175), (2S,3R,4S)-2-(8-((2,4-dichlorobenzyl)amino)imidazo[1,2-a]pyrazin-3-yl)tetrahydrothiophene-3,4-diol (Compound 176), (2S,3R,4S)-2-(8-((2,5-dichlorobenzyl)amino)imidazo[1,2-a]pyrazin-3-yl)tetrahydrothiophene-3,4-diol (Compound 177), (2S,3R,4S)-2-(8-((thiophen-2-ylmethyl)amino)imidazo[1,2-a]pyrazin-3-yl)tetrahydrothiophene-3,4-diol (Compound 178), (2S,3R,4S)-2-(8-((2-(3-fluorophenyl)cyclopropyl)amino)imidazo[1,2-a]pyrazin-3-yl)tetrahydrothiophene-3,4-diol (Compound 179), (2S,3R,4S)-2-(8-((2-(3-chlorophenyl)cyclopropyl)amino)imidazo[1,2-a]pyrazin-3-yl)tetrahydrothiophene-3,4-diol (Compound 180), (2S,3R,4S)-2-(8-((3-(piperazin-1-yl)benzyl)amino)imidazo[1,2-a]pyrazin-3-yl)tetrahydrothiophene-3,4-diol (Compound 181), methyl 2-chloro-5-(((3-((2S,3R,4S)-3,4-dihydroxytetrahydrothiophen-2-yl)imidazo[1,2-a]pyrazin-8-yl)amino)methyl)benzoate (Compound 182), (2S,3R,4S)-2-(8-((3-chloro-4-fluorobenzyl)amino)imidazo[1,2-a]pyrazin-3-yl)tetrahydrothiophene-3,4-diol (Compound 183), (2S,3R,4S)-2-(8-((3,5-dichlorobenzyl)amino)imidazo[1,2-a]pyrazin-3-yl)tetrahydrothiophene-3,4-diol (Compound 184), (2S,3R,4S)-2-(8-((3,4-dichlorobenzyl)amino)imidazo[1,2-a]pyrazin-3-yl)tetrahydrothiophene-3,4-diol (Compound 185), (2S,3R,4S)-2-(8-((2,6-dichlorobenzyl)amino)imidazo[1,2-a]pyrazin-3-yl)tetrahydrothiophene-3,4-diol (Compound 186), (2S,3R,4S)-2-(8-((3-(1H-tetrazol-5-yl)benzyl)amino)imidazo[1,2-a]pyrazin-3-yl)tetrahydrothiophene-3,4-diol 2,2,2-trifluoroacetic acid (Compound 191), (2S,3R,4S)-2-(8-((2,3-difluorophenethyl)amino)imidazo[1,2-a]pyrazin-3-yl)tetrahydrothiophene-3,4-diol (Compound 192), (2S,3R,4S)-2-(8-((2,4-difluorophenethyl)amino)imidazo[1,2-a]pyrazin-3-yl)tetrahydrothiophene-3,4-diol (Compound 193), (2S,3R,4S)-2-(8-((2,5-difluorophenethyl)amino)imidazo[1,2-a]pyrazin-3-yl)tetrahydrothiophene-3,4-diol (Compound 194), (2S,3R,4S)-2-(8-((2,6-difluorophenethyl)amino)imidazo[1,2-a]pyrazin-3-yl)tetrahydrothiophene-3,4-diol (Compound 195), (2S,3R,4S)-2-(8-((3,5-difluorophenethyl)amino)imidazo[1,2-a]pyrazin-3-yl)tetrahydrothiophene-3,4-diol (Compound 196), (2S,3R,4S)-2-(8-((3,4-difluorophenethyl)amino)imidazo[1,2-a]pyrazin-3-yl)tetrahydrothiophene-3,4-diol (Compound 197), (2S,3R,4S)-2-(8-((4-chloro-3-fluorophenethyl)amino)imidazo[1,2-a]pyrazin-3-yl)tetrahydrothiophene-3,4-diol (Compound 198), (2S,3R,4S)-2-(8-(((1R,2S)-2-phenylcyclopropyl)amino)imidazo[1,2-a]pyrazin-3-yl)tetrahydrothiophene-3,4-diol (Compound 200), (2S,3R,4S)-2-(8-((3-chloro-5-fluorobenzyl)amino)imidazo[1,2-a]pyrazin-3-yl)tetrahydrothiophene-3,4-diol (Compound 201), (2S,3R,4S)-2-(8-((3-cyclopropylbenzyl)amino)imidazo[1,2-a]pyrazin-3-yl)tetrahydrothiophene-3,4-diol (Compound 202), (2S,3R,4S)-2-(8-(([1,1'-biphenyl]-3-ylmethyl)amino)imidazo[1,2-a]pyrazin-3-yl)tetrahydrothiophene-3,4-diol (Compound 203), (2S,3R,4S)-2-(8-((3-phenoxybenzyl)amino)imidazo[1,2-a]pyrazin-3-yl)tetrahydrothiophene-3,4-diol (Compound 204), methyl3-(((3-((2S,3R,4S)-3,4-dihydroxytetrahydrothiophen-2-yl)imidazo[1,2-a]pyrazin-8-yl)amino)methyl)benzoate (Compound 205), (2S,3R,4S)-2-(8-(((1R,2R)-2-phenylcyclopropyl)amino)imidazo[1,2-a]pyrazin-3-yl)tetrahydrothiophene-3,4-diol (Compound 207), (2S,3R,4S)-2-(8-((5-chloro-2-fluorobenzyl)amino)imidazo[1,2-a]pyrazin-3-yl)tetrahydrothiophene-3,4-diol (Compound 208), (2S,3R,4S)-2-(8-(((1S,2R)-2-(3,4-difluorophenyl)cyclopropyl)amino) imidazo[1,2-a]pyrazin-3-yl)tetrahydrothiophene-3,4-diol Compound 209), (2S,3R,4S)-2-(8-((3-morpholinobenzyl)amino)imidazo[1,2-a]pyrazin-3-yl)tetrahydrothiophene-3,4-diol (Compound 210), (2S,3R,4S)-2-(8-((3-fluoro-4-(5-methyloxazol-2-yl)benzyl)amino)imidazo[1,2-a]pyrazin-3-yl)tetrahydrothiophene-3,4-diol (Compound 211), (2S,3R,4S)-2-(8-((3-fluoro-4-(5-methyl-1,3,4-oxadiazol-2-yl)benzyl)amino)imidazo[1,2-a]pyrazin-3-yl)tetrahydrothiophene-3,4-diol (Compound 213), (2S,3R,4S)-2-(8-((3-(2-methyl-2H-tetrazol-5-yl)benzyl)amino)imidazo[1,2-a]pyrazin-3-yl)tetrahydrothiophene-3,4-diol (Compound 214), (2S,3R,4S)-2-(8-(((1S,2R)-2-(3-fluorophenyl)cyclopropyl)amino)imidazo[1,2-a]pyrazin-3-yl)tetrahydrothiophene-3,4-diol (Compound 215), (2S,3R,4S)-2-(8-(((1S,2R)-2-(3-chlorophenyl)cyclopropyl)amino)imidazo[1,2-a]pyrazin-3-yl)tetrahydrothiophene-3,4-diol (Compound 216), (2S,3R,4S)-2-(6-chloro-8-((3-chlorobenzyl)amino)imidazo[1,2-a]pyrazin-3-yl)tetrahydrothiophene-3,4-diol (Compound 217), and (2S,3R,4S)-2-(8-((3-chlorobenzyl)amino)-[1,2,4]triazolo[4,3-a]pyridin-3-yl)tetrahydrothiophene-3,4-diol (Compound 218).

4. The compound of Formula I or a pharmaceutically acceptable salt thereof according to claim 3, wherein the compound of Formula I is selected from the group consisting of:

(2S,3R,4S)-2-(8-((3-chlorobenzyl)amino)-[1,2,4]triazolo[4,3-a]pyrazine-3-yl)tetrahydrothiophene-3,4-diol (Compound 1), (2S,3R,4S)-2-(8-((3-iodobenzyl)amino)-[1,2,4]triazolo[4,3-a]pyrazin-3-yl)tetrahydrothiophene-3,4-diol (Compound 6), (2S,3R,4S)-2-(8-((3-(trifluoromethyl)benzyl)amino)-[1,2,4]triazolo[4,3-a]pyrazin-3-yl)tetrahydrothiophene-3,4-diol (Compound 9), (2S,3R,4S)-2-(8-(phenethylamino)-[1,2,4]triazolo[4,3-a]pyrazin-3-yl)tetrahydrothiophene-3,4-diol (Compound 11), (2S,3R,4S)-2-(8-((3-methylbenzyl)amino)-[1,2,4]triazolo[4,3-a]pyrazin-3-yl)tetrahydrothiophene-3,4-diol (Compound 12), (2S,3R,4S)-2-(8-(((1 S,2R)-2-phenylcyclopropyl)amino)-[1,2,4]triazolo[4,3-a]pyrazin-3-yl)tetrahydrothiophene-3,4-diol (Compound 43), 2-chloro-4-(((3-((2S,3R,4S)-3,4-dihydroxytetrahydrothiophen-2-yl)-[1,2,4]triazolo[4,3-a]pyrazin-8-yl)amino)methyl)-N-methylbenzamide (Compound 44), (2S,3R,4S)-2-(8-((2-fluorophenethyl)amino)-[1,2,4]triazolo[4,3-a]pyrazin-3-yl)tetrahydrothiophene-3,4-diol (Compound 50), (2S,3R,4S)-2-(8-((3,5-dichlorobenzyl)amino)-[1,2,4]triazolo[4,3-a]pyrazin-3-yl)tetrahydrothiophene-3,4-diol (Compound 55), (2S,3R,4S)-2-(8-((2,5-dichlorobenzyl)amino)-[1,2,4]triazolo[4,3-a]pyrazin-3-yl)tetrahydrothiophene-3,4-diol (Compound 56), (2S,3R,4S)-2-(8-((2,3-dichlorobenzyl)amino)-[1,2,4]triazolo[4,3-a]pyrazin-3-yl)tetrahydrothiophene-3,4-diol (Compound 58), (2S,3R,4S)-2-(8-((3,4-dichlorobenzyl)amino)-[1,2,4]triazolo[4,3-a]pyrazin-3-yl)tetrahydrothiophene-3,4-diol (Compound 59), (2S,3R,4S)-2-(8-((2-iodobenzyl)amino)-[1,2,4]triazolo[4,3-a]pyrazin-3-yl)tetrahydrothiophene-3,4-diol (Compound 62), (2S,3R,4S)-2-(8-((3-chloro-4-fluorophenethyl)amino)-[1,2,4]triazolo[4,3-a]pyrazin-3-yl)tetrahydrothiophene-3,4-diol (Compound 63), (2S,3R,4S)-2-(8-((4-fluorophenethyl)amino)-[1,2,4]triazolo[4,3-a]pyrazin-3-yl)tetrahydrothiophene-3,4-diol (Compound 64), (2S,3R,4S)-2-(8-((3-chloro-4-fluorobenzyl)amino)-[1,2,4]triazolo[4,3-a]pyrazin-3-yl)tetrahydrothiophene-3,4-diol (Compound 65), (2S,3R,4S)-2-(8-((3-(1H-tetrazol-5-yl)benzyl)amino)-[1,2,4]triazolo[4,3-a]pyrazin-3-yl)tetrahydrothiophene-3,4-diol (Compound 69), (2S,3R,4S)-2-(8-((2-(3-fluorophenyl)cyclopropyl)amino)-[1,2,4]triazolo[4,3-a]pyrazin-3-yl)tetrahydrothiophene-3,4-diol (Compound 70), (2S,3R,4S)-2-(8-((2-(3-chlorophenyl)cyclopropyl)amino)-[1,2,4]triazolo[4,3-a]pyrazin-3-yl)tetrahydrothiophene-3,4-diol (Compound 71), (2S,3R,4S)-2-(8-((2,3-difluorophenethyl)amino)-[1,2,4]triazolo[4,3-a]pyrazin-3-yl)tetrahydrothiophene-3,4-diol (Compound 73), (2S,3R,4S)-2-(8-((2,4-difluorophenethyl)amino)-[1,2,4]triazolo[4,3-a]pyrazin-3-yl)tetrahydrothiophene-3,4-diol (Compound 74), (2S,3R,4S)-2-(8-(((1R,2R)-2-phenylcyclopropyl)amino)-[1,2,4]triazolo[4,3-a]pyrazin-3-yl)tetrahydrothiophene-3,4-diol (Compound 75), (2S,3R,4S)-2-(8-((2,5-difluorophenethyl)amino)-[1,2,4]triazolo[4,3-a]pyrazin-3-yl)tetrahydrothiophene-3,4-diol (Compound 76), (2S,3R,4S)-2-(8-((4-chloro-3-fluorophenethyl)amino)-[1,2,4]triazolo[4,3-a]pyrazin-3-yl)tetrahydrothiophene-3,4-diol (Compound 78), (2S,3R,4S)-2-(8-((3-(piperazin-1-yl)benzyl)amino)-[1,2,4]triazolo[4,3-a]pyrazin-3-yl)tetrahydrothiophene-3,4-diol (Compound 80), (2S,3R,4S)-2-(8-((2,6-difluorophenethyl)amino)-[1,2,4]triazolo[4,3-a]pyrazin-3-yl)tetrahydrothiophene-3,4-diol (Compound 81), (2S,3R,4S)-2-(8-((3,4-difluorophenethyl)amino)-[1,2,4]triazolo[4,3-a]pyrazin-3-yl)tetrahydrothiophene-3,4-diol (Compound 82), (2S,3R,4S)-2-(8-((3,5-difluorophenethyl)amino)-[1,2,4]triazolo[4,3-a]pyrazin-3-yl)tetrahydrothiophene-3,4-diol (Compound 83), (2S,3R,4S)-2-(8-(((1 S,2R)-2-(3,4-difluorophenyl)cyclopropyl)amino)-[1,2,4]triazolo[4,3-a]pyrazin-3-yl)tetrahydrothiophene-3,4-diol (Compound 84), (2S,3R,4S)-2-(8-((5-chloro-2-fluorobenzyl)amino)-[1,2,4]triazolo[4,3-a]pyrazin-3-yl)tetrahydrothiophene-3,4-diol (Compound 85), (2S,3R,4S)-2-(8-((3-chloro-5-fluorobenzyl)amino)-[1,2,4]triazolo[4,3-a]pyrazin-3-yl)tetrahydrothiophene-3,4-diol (Compound 86), (2S,3R,4S)-2-(8-(((1S,2R)-2-(3-fluorophenyl)cyclopropyl)amino)-[1,2,4]triazolo[4,3-a]pyrazin-3-yl)tetrahydrothiophene-3,4-diol (Compound 98), (2S,3R,4S)-2-(8-(((1S,2R)-2-(3-chlorophenyl)cyclopropyl)amino)-[1,2,4]triazolo[4,3-a]pyrazin-3-yl)tetrahydrothiophene-3,4-diol (Compound 99), (2S,3R,4S)-2-(6-chloro-8-((3-chlorobenzyl)amino)-[1,2,4]triazolo[4,3-a]pyrazin-3-yl)tetrahydrothiophene-3,4-diol (Compound 100), (2S,3R,4S)-2-(6-chloro-8-((2,5-dichlorobenzyl)amino)-[1,2,4]triazolo[4,3-a]pyrazin-3-yl)tetrahydrothiophene-3,4-diol (Compound 101), (2S,3R,4S)-2-(6-chloro-8-((3,5-dichlorobenzyl)amino)-[1,2,4]triazolo[4,3-a]pyrazin-3-yl)tetrahydrothiophene-3,4-diol (Compound 102), (2S,3R,4S)-2-(6-chloro-8-((5-chloro-2-fluorobenzyl)amino)-[1,2,4]triazolo[4,3-a]pyrazin-3-yl)tetrahydrothiophene-3,4-diol (Compound 103), (2S,3R,4S)-2-(6-chloro-8-((4-fluorophenethyl)amino)-[1,2,4]triazolo[4,3-a]pyrazin-3-yl)tetrahydrothiophene-3,4-diol (Compound 104), (2S,3R,4S)-2-(6-chloro-8-((3-fluorophenethyl)amino)-[1,2,4]triazolo[4,3-a]pyrazin-3-yl)tetrahydrothiophene-3,4-diol (Compound 105), (2S,3R,4S)-2-(6-chloro-8-((3,4-difluorophenethyl)amino)-[1,2,4]triazolo[4,3-a]pyrazin-3-yl)tetrahydrothiophene-3,4-diol (Compound 106), (2S,3R,4S)-2-(6-chloro-8-((4-chloro-3-fluorophenethyl)amino)-[1,2,4]triazolo[4,3-a]pyrazin-3-yl)tetrahydrothiophene-3,4-diol (Compound 107), (2S,3R,4S)-2-(6-chloro-8-(((1S,2R)-2-phenylcyclopropyl)amino)-[1,2,4]triazolo[4,3-a]pyrazin-3-yl)tetrahydrothiophene-3,4-diol (Compound 108), (2S,3R,4S)-2-(8-((3-chlorobenzyl)amino)imidazo[1,2-a]pyrazin-3-yl)tetrahydrothiophene-3,4-diol (Compound 109), (2S,3R,4S)-2-(8-((3-methylbenzyl)amino)imidazo[1,2-a]pyrazin-3-yl)tetrahydrothiophene-3,4-diol (Compound 121), (2S,3R,4S)-2-(8-((3-iodobenzyl)amino)imidazo[1,2-a]pyrazin-3-yl)tetrahydrothiophene-3,4-diol (Compound 124), 2-chloro-4-(((3-((2S,3R,4S)-3,4-dihydroxytetrahydrothiophen-2-yl)imidazo[1,2-a]pyrazin-8-yl)amino)methyl)-N-methylbenzamide (Compound 126), (2S,3R,4S)-2-(8-((3-fluorophenethyl)amino)imidazo[1,2-a]pyrazin-3-yl)tetrahydrothiophene-3,4-diol (Compound 127), (2S,3R,4S)-2-(8-((2-phenylcyclopropyl)amino)imidazo[1,2-a]pyrazin-3-yl)tetrahydrothiophene-3,4-diol (Compound 129), (2S,3R,4S)-2-(8-((3-bromobenzyl)amino)imidazo[1,2-a]pyrazin-3-yl)tetrahydrothiophene-3,4-diol (Compound 132), (2S,3R,4S)-2-(8-((3-bromophenethyl)amino)imidazo[1,2-a]pyrazin-3-yl)tetrahydrothiophene-3,4-diol (Compound 149), (2S,3R,4S)-2-(8-(((R)-1-(3-chlorophenyl)ethyl)amino)imidazo[1,2-a]pyrazin-3-yl)tetrahydrothiophene-3,4-diol (Compound 160), (2S,3R,4S)-2-(8-(((1S,2R)-2-phenylcyclopropyl)amino)imidazo[1,2-a]pyrazin-3-yl)tetrahydrothiophene-3,4-diol (Compound 162), (2S,3R,4S)-2-(8-((2-chlorobenzyl)amino)imidazo[1,2-a]pyrazin-3-yl)tetrahydrothiophene-3,4-diol (Compound 163), (2S,3R,4S)-2-(8-(((1H-indol-5-yl)methyl)amino)imidazo[1,2-a]pyrazin-3-yl)tetrahydrothiophene-3,4-diol (Compound 166), (2S,3R,4S)-2-(8-((2-iodobenzyl)amino)imidazo[1,2-a]pyrazin-3-yl)tetrahydrothiophene-3,4-diol (Compound 168), (2S,3R,4S)-2-(8-((2-fluorophenethyl)amino)imidazo[1,2-a]pyrazin-3-yl)tetrahydrothiophene-3,4-diol (Compound 169), (2S,3R,4S)-2-(8-((4-fluorophenethyl)amino)imidazo[1,2-a]pyrazin-3-yl)tetrahydrothiophene-3,4-diol (Compound 170), methyl 5-(((3-((2S,3R,4S)-3,4-dihydroxytetrahydrothiophen-2-yl)imidazo[1,2-a]pyrazin-8-yl)amino)methyl)-2-fluorobenzoate (Compound 171), (2S,3R,4S)-2-(8-((3-chloro-4-fluorophenethyl)amino)imidazo[1,2-a]pyrazin-3-yl)tetrahydrothiophene-3,4-diol (Compound 172), (2S,3R,4S)-2-(8-((3-(dimethylamino)benzyl)amino)imidazo[1,2-a]pyrazin-3-yl)tetrahydrothiophene-3,4-diol (Compound 173), (2S,3R,4S)-2-(8-((3-(4-methylpiperazin-1-yl)benzyl)amino)imidazo[1,2-a]pyrazin-3-yl)tetrahydrothiophene-3,4-diol (Compound 174), (2S,3R,4S)-2-(8-((2,3-dichlorobenzyl)amino)imidazo[1,2-a]pyrazin-3-yl)tetrahydrothiophene-3,4-diol (Compound 175), (2S,3R,4S)-2-(8-((2,4-dichlorobenzyl)amino)imidazo[1,2-a]pyrazin-3-yl)tetrahydrothiophene-3,4-diol (Compound 176), (2S,3R,4S)-2-(8-((2,5-dichlorobenzyl)amino)imidazo[1,2-a]pyrazin-3-yl)tetrahydrothiophene-3,4-diol (Compound 177), (2S,3R,4S)-2-(8-(((thiophen-2-yl)methyl)amino)imidazo[1,2-a]pyrazin-3-yl)tetrahydrothiophene-3,4-diol (Compound 178), (2S,3R,4S)-2-(8-((2-(3-fluorophenyl)cyclopropyl)amino)imidazo[1,2-a]pyrazin-3-yl)tetrahydrothiophene-3,4-diol (Compound 179), (2S,3R,4S)-2-(8-((2-(3-chlorophenyl)cyclopropyl)amino)imidazo[1,2-a]pyrazin-3-yl)tetrahydrothiophene-3,4-diol (Compound 180), methyl 2-chloro-5-(((3-((2S,3R,4S)-3,4-dihydroxytetrahydrothiophen-2-yl)imidazo[1,2-a]pyrazin-8-yl)amino)methyl)benzoate (Compound 182), (2S,3R,4S)-2-(8-((3-chloro-4-fluorobenzyl)amino)imidazo[1,2-a]pyrazin-3-yl)tetrahydrothiophene-3,4-diol (Compound 183), (2S,3R,4S)-2-(8-((3,5-dichlorobenzyl)amino)imidazo[1,2-a]pyrazin-3-yl)tetrahydrothiophene-3,4-diol (Compound 184), (2S,3R,4S)-2-(8-((3,4-dichlorobenzyl)amino)imidazo[1,2-a]pyrazin-3-yl)tetrahydrothiophene-3,4-diol (Compound 185), (2S,3R,4S)-2-(8-((2,3-difluorophenethyl)amino)imidazo[1,2-a]pyrazin-3-yl)tetrahydrothiophene-3,4-diol (Compound 192), (2S,3R,4S)-2-(8-((2,4-difluorophenethyl)amino)imidazo[1,2-a]pyrazin-3-yl)tetrahydrothiophene-3,4-diol (Compound 193), (2S,3R,4S)-2-(8-((2,5-difluorophenethyl)amino)imidazo[1,2-a]pyrazin-3-yl)tetrahydrothiophene-3,4-diol (Compound 194), (2S,3R,4S)-2-(8-((2,6-difluorophenethyl)amino)imidazo[1,2-a]pyrazin-3-yl)tetrahydrothiophene-3,4-diol (Compound 195), (2S,3R,4S)-2-(8-((3,5-difluorophenethyl)amino)imidazo[1,2-a]pyrazin-3-yl)tetrahydrothiophene-3,4-diol (Compound 196), (2S,3R,4S)-2-(8-((3,4-difluorophenethyl)amino)imidazo[1,2-a]pyrazin-3-yl)tetrahydrothiophene-3,4-diol (Compound 197), (2S,3R,4S)-2-(8-((4-chloro-3-fluorophenethyl)amino)imidazo[1,2-a]pyrazin-3-yl)tetrahydrothiophene-3,4-diol (Compound 198), (2S,3R,4S)-2-(8-(((1R,2S)-2-phenylcyclopropyl)amino)imidazo[1,2-a]pyrazin-3-yl)tetrahydrothiophene-3,4-diol (Compound 200), (2S,3R,4S)-2-(8-((3-chloro-5-fluorobenzyl)amino)imidazo[1,2-a]pyrazin-3-yl)tetrahydrothiophene-3,4-diol (Compound 201), (2S,3R,4S)-2-(8-((3-cyclopropylbenzyl)amino)imidazo[1,2-a]pyrazin-3-yl)tetrahydrothiophene-3,4-diol (Compound 202), (2S,3R,4S)-2-(8-(([1,1'-biphenyl]-3-ylmethyl)amino)imidazo[1,2-a]pyrazin-3-yl)tetrahydrothiophene-3,4-diol (Compound 203), (2S,3R,4S)-2-(8-((3-phenoxybenzyl)amino)imidazo[1,2-a]pyrazin-3-yl)tetrahydrothiophene-3,4-diol (Compound 204), methyl 3-(((3-((2S,3R,4S)-3,4-dihydroxytetrahydrothiophen-2-yl)imidazo[1,2-a]pyrazin-8-yl)amino)methyl)benzoate (Compound 205), (2S,3R,4S)-2-(8-(((1R,2R)-2-phenylcyclopropyl)amino)imidazo[1,2-a]pyrazin-3-yl)tetrahydrothiophene-3,4-diol (Compound 207), (2S,3R,4S)-2-(8-((5-chloro-2-fluorobenzyl)amino)imidazo[1,2-a]pyrazin-3-yl)tetrahydrothiophene-3,4-diol (Compound 208), (2S,3R,4S)-2-(8-(((1S,2R)-2-(3,4-difluorophenyl)cyclopropyl)amino) imidazo[1,2-a]pyrazin-3-yl)tetrahydrothiophene-3,4-diol Compound 209), (2S,3R,4S)-2-(8-((3-morpholinobenzyl)amino)imidazo[1,2-a]pyrazin-3-yl)tetrahydrothiophene-3,4-diol (Compound 210), (2S,3R,4S)-2-(8-((3-fluoro-4-(5-methyloxazol-2-yl)benzyl)amino)imidazo[1,2-a]pyrazin-3-yl)tetrahydrothiophene-3,4-diol (Compound 211), (2S,3R,4S)-2-(8-((3-fluoro-4-(5-methyl-1,3,4-oxadiazol-2-yl)benzyl)amino)imidazo[1,2-a]pyrazin-3-yl)tetrahydrothiophene-3,4-diol (Compound 213), (2S,3R,4S)-2-(8-((3-(2-methyl-2H-tetrazol-5-yl)benzyl)amino)imidazo[1,2-a]pyrazin-3-yl)tetrahydrothiophene-3,4-diol (Compound 214), (2S,3R,4S)-2-(8-(((1S,2R)-2-(3-fluorophenyl)cyclopropyl)amino)imidazo[1,2-a]pyrazin-3-yl)tetrahydrothiophene-3,4-diol (Compound 215), (2S,3R,4S)-2-(8-(((1S,2R)-2-(3-chlorophenyl)cyclopropyl)amino)imidazo[1,2-a]pyrazin-3-yl)tetrahydrothiophene-3,4-diol (Compound 216), and (2S,3R,4S)-2-(6-chloro-8-((3-chlorobenzyl)amino)imidazo[1,2-a]pyrazin-3-yl)tetrahydrothiophene-3,4-diol (Compound 217).

5. A pharmaceutical composition comprising a therapeutically effective amount of the compound of Formula I or a pharmaceutically acceptable salt thereof according to claim 1, and a pharmaceutically acceptable carrier, excipient or diluent.

6. A pharmaceutical composition comprising a therapeutically effective amount of the compound of Formula I or a pharmaceutically acceptable salt thereof according to claim 3, and a pharmaceutically acceptable carrier, excipient or diluent.

7. A method for preventing, ameliorating or treating a condition comprising administering to a subject in need thereof a therapeutically effective amount of the compound of Formula I or a pharmaceutically acceptable salt thereof according claim 1, wherein the condition is selected from the group consisting of glaucoma or glaucoma-related ocular disorders.

8. The method according to claim 7, wherein the condition is glaucoma.

9. The method according to claim 7, wherein the subject is a human.

10. A method for preventing, ameliorating or treating a condition comprising administering to a subject in need thereof a therapeutically effective amount of the compound of Formula I or a pharmaceutically acceptable salt thereof according to claim 3, wherein the condition is selected from the group consisting of glaucoma or glaucoma-related ocular disorders.

11. The method according to claim 10, wherein the condition is glaucoma.

12. The method according to claim 10, wherein the subject is a human.

13. A method for antagonizing an A3 adenosine receptor comprising contacting the cells with an effective amount of the compound of Formula I or a pharmaceutically acceptable salt thereof according to claim 1.

\* \* \* \* \*